United States Patent
Karsenty et al.

(10) Patent No.: US 9,746,463 B2
(45) Date of Patent: Aug. 29, 2017

(54) UNDERCARBOXYLATED/UNCARBOXYLATED OSTEOCALCIN INCREASES BETA-CELL PROLIFERATION, INSULIN SECRETION, INSULIN SENSITIVITY, GLUCOSE TOLERANCE AND DECREASES FAT MASS

(71) Applicant: THE TRUSTEES OF COLUMBIA UNIVERSITY IN THE CITY OF NEW YORK, New York, NY (US)

(72) Inventors: Gerard Karsenty, New York, NY (US); Patricia F. Ducy, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 75 days.

(21) Appl. No.: 14/032,008

(22) Filed: Sep. 19, 2013

(65) Prior Publication Data
US 2014/0128320 A1    May 8, 2014

Related U.S. Application Data

(62) Division of application No. 12/441,045, filed as application No. PCT/US2007/020029 on Sep. 13, 2007, now abandoned.

(60) Provisional application No. 60/844,203, filed on Sep. 13, 2006, provisional application No. 60/870,604, filed on Dec. 18, 2006, provisional application No. 60/909,712, filed on Apr. 2, 2007, provisional application No. 60/945,081, filed on Jun. 19, 2007.

(51) Int. Cl.
| | |
|---|---|
| *A61K 38/16* | (2006.01) |
| *G01N 33/543* | (2006.01) |
| *A61K 38/39* | (2006.01) |
| *A61K 47/48* | (2006.01) |
| *G01N 33/50* | (2006.01) |

(52) U.S. Cl.
CPC ....... *G01N 33/54306* (2013.01); *A61K 38/16* (2013.01); *A61K 38/39* (2013.01); *A61K 47/48215* (2013.01); *G01N 33/502* (2013.01); *G01N 33/5008* (2013.01); *G01N 33/5023* (2013.01); *G01N 33/5038* (2013.01); *G01N 33/5088* (2013.01); *G01N 2333/78* (2013.01); *G01N 2333/916* (2013.01); *G01N 2333/988* (2013.01)

(58) Field of Classification Search
None
See application file for complete search history.

(56) References Cited

U.S. PATENT DOCUMENTS

| | | | |
|---|---|---|---|
| 5,164,483 A | 11/1992 | Kurihara | |
| 6,004,765 A | 12/1999 | Delmas | |
| 6,967,081 B1 | 11/2005 | Kakonen | |
| 2003/0138844 A1 | 7/2003 | Stenflo | |
| 2003/0204063 A1 | 10/2003 | Gravel et al. | |
| 2004/0002442 A1 | 1/2004 | Pan et al. | |
| 2004/0082018 A1* | 4/2004 | Ekema et al. | ............... 435/7.21 |
| 2005/0084877 A1 | 4/2005 | Plowman | |
| 2005/0186636 A1 | 8/2005 | Yang | |
| 2005/0208054 A1 | 9/2005 | Czech | |

FOREIGN PATENT DOCUMENTS

| | | | |
|---|---|---|---|
| DE | 3842498 A1 | 6/1989 | |
| EP | 0401705 A2 | 12/1990 | |
| EP | 0557663 A1 | 9/1993 | |
| EP | 0834740 A1 * | 4/1998 | ............ G01N 33/53 |
| EP | 1618893 A1 | 1/2006 | |
| EP | 1621210 | 2/2006 | |
| JP | 3-20226 A | 1/1991 | |
| JP | 2005-232150 A | 9/2005 | |
| JP | 2005-232151 A | 9/2005 | |
| WO | 03033699 A1 | 4/2003 | |
| WO | 2004039332 A1 | 5/2004 | |

OTHER PUBLICATIONS

Ferron et al., "An ELISA-based method to quantify osteocalcin carboxylation in mice", Biochem Biophys Res Commun, 2010, pp. 691-696.*
Takara Bio Inc., "Monoclonal Antibody to Undercarboxylated Osteocalcin, M171", 2012, pp. 1-2.*
Yeap, "Osteocalcin: An Endocrine Link Between Bone and Glucose Metabolism", Expert Rev Endocrinol Metab, 2011, pp. 177-185.*
Shea et al., "g-carboxylation of osteocalcin and insulin resistance in older man and women", Am. J. Clin. Nutr., 2009, pp. 1230-1235.*
Kanazawa et al., "Serum undercarboxylated osteocalcin was inversely associated with plasmas glucose level and fat mass in type 2 diabetes mellitus", Osteoporos Int, 2011, pp. 187-194.*
Polgreen et al., "Association of Osteocalcin With Obesity, Insulin Resistance, and Cardiovascular Risk Factors in Young Adults", Obesity, 2012, pp. 2194-2201.*
Akin, O. et al., "Evaluatuion of bone turnover in postmenopausal patients with type 2 diabetes mellitus using biochemical markers and mone mineral density measurements", Gynecol Endocrinal (2003), vol. 17, pp. 19-29.
Berkner, K.L., "The vitamin K-dependent carboxylase", (2000) Annu Rev Nutr, vol. 130, pp. 1877-1880.
Boskey, A. L. et al., "Fourier transform infrared microspectroscopic analysis of bones of osteocalcin-deficient mice provides insight into the function of osteocalcin", Elsevier (1998) vol. 23, No. 3, pp. 187-196.
Brecher, G. et al.,"The Brain Lesion of Goldthioglucose Obesity", J. Exp Med. (1965), vol. 121, pp. 395-401.

(Continued)

*Primary Examiner* — Lianko Garyu
(74) *Attorney, Agent, or Firm* — Andrews Kurth Kenyon LLP

(57) ABSTRACT

The present invention relates to methods and compositions for treating and diagnosing disorders related to energy metabolism and the OST-PTP signaling pathway involving gamma-carboxylase, osteocalcin and adiponectin. Such disorders include, but are not limited to, metabolic syndrome, glucose intolerance, diabetes types 1 and 2, atherosclerosis and obesity.

1 Claim, 58 Drawing Sheets

(56) References Cited

OTHER PUBLICATIONS

Cantini, F. et al., "Serum osteocalcin and diabetes mellitus. A study of 98 patients", Minerva Med. (1992) vol. 83 (3), pp. 129-133.
Chengalvala, Murty V. et al., "Biochemical Characterization of Osto-Testicular Tyrosine Phosphatase and Its Functional Significance in Rat Primary Osteoblasts", Biochemistry (2001), vol. 40, pp. 814-821.
Corral, David A. et al., "Dissociation between bone resorption and bone formation in osteopenic transgenic mice", Natl. Acad. Sci. USA (1998), vol. 95, pp. 13835-13840.
Cousin, W. et al., Cloning of HOST-PTP: the only example of a protein-tyrosine- . . . , Biochem Biophys Res Commun, (2004), vol. 321, pp. 259-265.
Dacquin, R. et al, "Knock-in of nuclear localised beta-galactosidase reveals that the tyrosine . . . ", Dev Dyn (2004), vol. 229, pp. 826-834.
Dacquin, R. et al., "Mouse alpha1(I)-collagen promoter is best known promoter to drive efficient Cre . . . ", Dev Dyn (2002), vol. 224, pp. 245-251.
Desbois, C. et al., "Osteocalcin Cluster: Implications for functional studies", Journal of Cellular Biochemistry, (1995) vol. 57, pp. 379-383.
Ducy, P. et al., "Leptin inhibits bone formation through a hypothalamic relay: a central control of bone mass", Cell (2000a), vol. 100, pp. 197-207.
Ducy, P. et al., "Increased bone formation in osteocalcin-deficient mice", Nature (1996) vol. 382, pp. 448-452.
Ducy, P., et al., "The osteoblast: A sophisticated fibroblast under central surveillance" Science (2000b) vol. 289, pp. 1501-1504.
Flint, A. J. et al., "Development of "substrate-trapping" mutants", Proc Natl Acad Sci USA (1997), vol. 94, pp. 1680-1685.
Friedman, J.M. et al., "Leptin and the regulation of body weight in mammals", Nature (1998), vol. 395, pp. 763-770.
Harada, S. et al., "Control of osteoblast function and regulation of bone mass", (2003), Nature, vol. 423, pp. 349-355.
Hauschka, P. V. et al., "Ostocalcin and matrix Gla protein: vitamin K-dependent proteins in bone", Physiol Rev (1989) vol. 69, pp. 990-1047.
Herman, M. A., et al., "Glucose transport and sensing in the maintenance of glucose homeostasis and metabolic harmony", J Clin Invest (2006), vol. 116, pp. 1767-1775.
Kadowaki, T. et al., "Adiponectin and adiponectin receptors", Endocr Rev (2005) vol. 26, pp. 439-451.
Karsenty, G. "Convergance between bone and energy homeostases: Leptin regulation of bone mass", Cell Metab (2006) vol. 4, pp. 341-348.
Kasuga, M. "Insulin resistance and pancreatic beta-cell failure", J Clin invest (2006), vol. 116, pp. 1756-1760.
Kushner, J.A. et al., "Cyclins D2 and D1 are essential for postnatal pancreatic beta-cell growth", Mol Cell Biol (2005), vol. 25, pp. 3752-3762.
Lee, Na Kyang, et al., "Endocrine Regulation of Energy Metabolism by the Skeleton", Cell (2007), vol. 130, pp. 456-469.
Le May, C. et al., "Estrogens protect pancreatic beta-cells from apoptosis and prevent insulin-deficient diabetes . . . " Proc Natl Acad Sci USA (2006), vol. 103, pp. 9232-9237.
Lu, Haufei. et al., "Diabetes interferes with the Bone Formation by Affecting the Expression of Transcription Factors that Regulate Osteoblast Differentiation", Endocrinology (2003) vol. 144, pp. 346-352.
Luo, G. et al., The matrix Gla protein gene is a marker of the chondrogenesis cell lineage during mouse development, Journal of Bone and Mineral Research (1995) vol. 10, No. 2, pp. 325-383.
Maeda, N. et al., "Diet-induced insulin resistance in mice lacking adiponectin/ACRP30", Nat Med (2002) vol. 8, pp. 731-737.
Mauro, L.J. et al., "Identification of a hormonally regulated protein tyrosine phosphatase associated with bone and testicu", J Biol Chem, (1994) vol. 269, pp. 30659-30667.

Mauvais-Jarvis, F. et al., "Reduced expression of the murine p85alpha subunit of phosphoinositide 3-kinase improves insulin sign", (2002), J Clin Invest vol. 109, pp. 141-149.
Mauvais-Jarvis, F. et al., "A model to explore the interaction between muscle insulin resistance and beta-cell dysfunction in the de". Diabetes (2000) vol. 49, pp. 2126-2134.
Murshed, M. et al., "Extracellular matrix mineralizatin is regulated locally; different roles of two gla-containing proteins", J Cell Biol (2004), vol. 165, pp. 625-630.
Poser, James W. et al., "Isolation and Sequence of the Vitamin K-dependent Protein from Human Bone", (1980), vol. 255, No. 18, pp. 8685-8691.
Price, P. A., "Gla-containing proteins of bone" Connect Tissue Res (1989), vol. 21, pp. 51-57; discussion 57-60.
Rosato, M. T. et al., "Bone turnover and insulin-like growth factor I levels increase after improved glycemic control", Calcif Tissue Int (1998) vol. 63, pp. 107-111.
Spiegelman, B.M. et al., Obesity and the regulation of energy balance. Cell (2001), vol. 104, pp. 531-543.
Steppan, C.M. et al., "The hormone resistin links obesity to diabetes", Nature (2001) vol. 409, pp. 307-312.
Stromstedt, Per-Erik et al., "The Glucocorticoid recepteor Binds to a Sequence Overlapping the TATA Box of the Human Osteocalcin: a Potential Mechanism for Negative Regulation", Molecular and Cellular Biology (1991), vol. 11, No. 6, pp. 3379-3383.
Takayanagi, H., "Osteoimmunology: the integrated understanding of the bone and immume systems", (2006). Nat Rev Genet In press.
Takeda, S., et al., "Leptin regulates bone formation via the sympathetic nervous system", Cell (2002), vol. 111, pp. 305-317.
Teitelbaum, S.L. et al., "Genetic regulation of osteoclast development and function", Nat Rev Genet (2URAKAWA, I. et al., Klotho converts canonical FGF receptor into a specific receptor for FGF23. Nature (2003), vol. 4, pp. 638-649.
Urakawa, I. et al., "Klotho converts canonical FGF receptor into a specific receptor for FGF23", Nature (2006) vol. 444, pp. 770-774.
Wang, Dong et al., "Bone-targeting macromolecular therapeutics", Advanced Drug Delivery Reviews (2005), vol. 57, pp. 1049-1076.
Watanabe, M. et al., "Bile acids induce energy expenditure by promoting intracellular thyroid hormone activation", Nature (2006) vol. 439, pp. 484-489.
Wexler, Lewis, M.D., et al., "Coronary Artery Calcification: Pathophysiology, Epidemiology, Imaging Methods, and Clinical Implications", Circulation (1996), vol. 94, pp. 1175-1192.
Wheeler, Marie A. et al., "Transcriptional Activation of the Tyrosine Phosphatase Gene, OST-PTP, During Osteoblast Differentiation", JCB (2002), vol. 87, pp. 363-376.
Xiao, Guozhi et al., "Cooperative interactions between Activating Transcription Factor 4 and Runx2/Cbfa1 Stimulate Osteoblast-specific Osteocalcin Gene Expression", JBC (2005), vol. 280, No. 35, pp. 30689-30696.
Yamauchi, T. et al, "The Fat-derived hormone adiponectin reverses insulin resistance associated with both lipoatrophy and obesity". Nat Med (2001), vol. 7, pp. 941-946.
Zacchigna, L. et al., "Emilin 1 links TGF-beta maturation to blood pressure homeostasis", Cell (2006), vol. 124, pp. 929-942.
Horiuchi, T., et al., "Impaired gamma carboxylation of osteocalcin in elderly women with type II diabetes mellitus: relationship between increase in undercarboxylated osteocalcin levels and low bone mineral density", J. of Bone and Mineral Metabolism, (2004) vol. 22, pp. 236-240.
Paolisso, G. et al., "Effects of simvastatin and atorvastatin administration on insulin resistance and respiratory quotient in aged dyslipidemic non-insulin dependent diabetic patients", Atherosclerosis (200), vol. 150, pp. 121-127.
Paniagua, J.A. et al., "Cerivastatin Improves Insulin Sensitivity and Isulin Secretion in Early-State Obese Type 2 Diabetes", Diabetes (2002), vol. 51, pp. 2596-2603.
Cingözbay, B. et al., "Effects of Fluvastatin Treatment on Insulin Sensitivity in Patients with Hyperlipidaemia", Journal of International Medical Research (2002), vol. 30, pp. 21-25.
Kurohara, M. et al., "Controlling diabetes on NOD mouse by administering warfarin" (Kobe University Graduate School of Medical Research Department, Geriatric Internal Medicine), Japan

(56) References Cited

OTHER PUBLICATIONS

Immunological Society—Congress Records (2004), vol. 34, p. 81. Abstract # 1-E-W7-21-P (English translation).

Kurohara, M. et al., "Occurrence control of diabetes on NOD mouse by administering low-capacity warfarin" ((Kobe University Graduate School of Medical Research Department, Geriatric Internal Medicine). Diabetes (2005), vol. 48, pp. S-50. Abstract #1-3-4 (English translation).

Hinoi, E., et al., "The sympathetic tone mediates leptin's inhibition of insulin secretion by modulating osteocalcin bioactivity", J. Cell Biol. (2008), vol. 183:7, pp. 1235-1242.

Yang, D., et al., "Identification of the ice-binding surface on a type III antifreeze protein with a "flatness function" algorithm", J. Biophysical (1998), vol. 74, pp. 2142-2151.

Gundberg, C.M. et al., "Vitamin K Status and Bone Health: An Analysis of Methods for Determination of Undercarboxylated Osteocalcin", J. of Clinical Endocrinology and Metabolism (1998), vol. 83:9, pp. 3258-3266.

Lee, Allison Jane et al., "Measurement of Osteocalcin," Ann. Clin. Biochem., vol. 37, pp. 432-446, 2000.

Schoon, E.J. et al., "Low Serum and Bone Vitamin K Status in Patients . . . ," Gut, vol. 48, pp. 473-477, 2001.

Pedrazzoni, M. et al., "Osteocalcin Levels in Diabetic Subjects," Calcified Tissue International, vol. 45, pp. 331-336, 1989.

Jéquier, E., "Pathways to Obesity," International Journal of Obesity, vol. 26, Suppl 2, pp. S12-S17, 2002.

Racette, Susan B. et al., "Obesity: Overview of Prevalence, Etiology, and Treatment," Physical Therapy, vol. 83, pp. 276-288, Mar. 2003.

Zimmet, P. et al., "Etiology of the Metabolic Syndrome: . . . ," Ann. N.Y. Acad. of Sci., pp. 25-44, 1999.

Adeghate, Ernest et al., "An Update on the Etiology and Epidemiology of Diabetes Mellitus," Ann. N.Y. Acad. Sci., vol. 1084, pp. 1-29, 2006.

\* cited by examiner

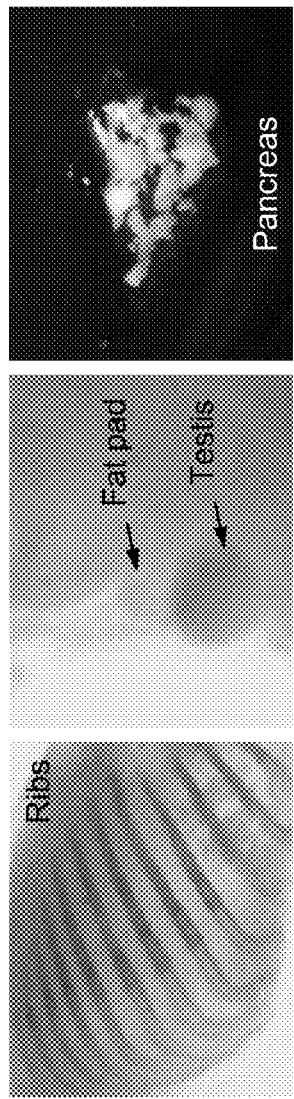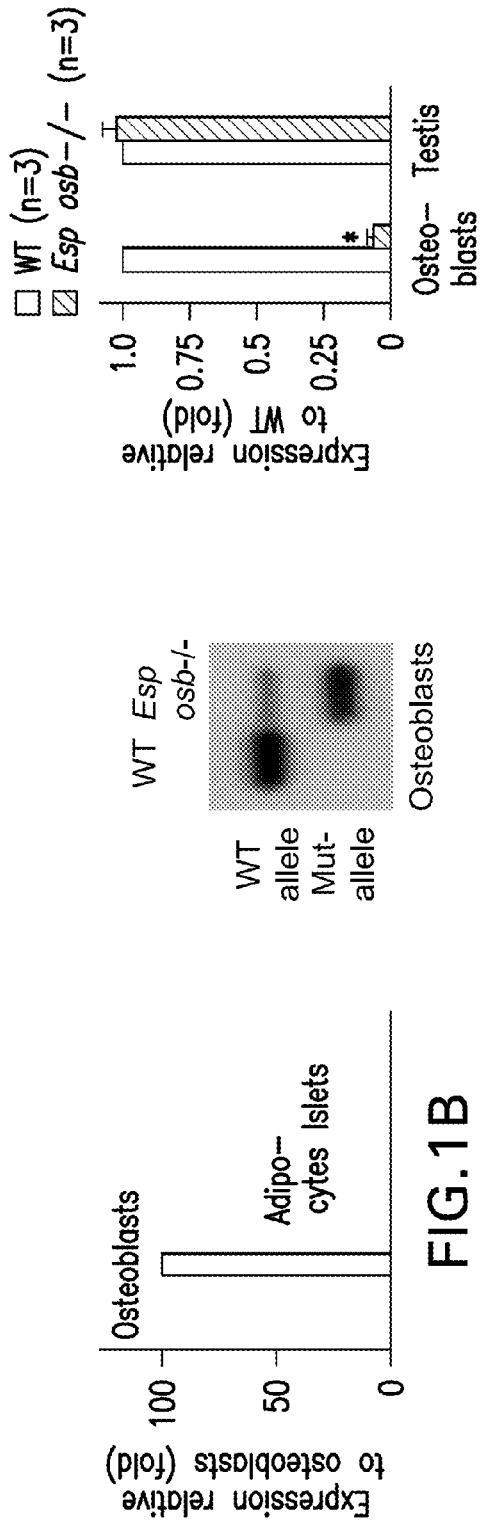

FIG. 1E
| Geno-Type | No | % of Total |
|---|---|---|
| +/+ | 28 | 26.1 |
| +/- | 60 | 56.2 |
| -/- | 19 | 17.7 |
FIG. 1F
| | No. of pups at birth | No. of pups after weaning | Survival rate (%) |
|---|---|---|---|
| +/- +/- | 41 | 37 | 90 |
| -/- +/- | 39 | 34 | 87 |
| +/- -/- | 42 | 32 | 75 |
| -/- -/- | 33 | 21 | 64 |
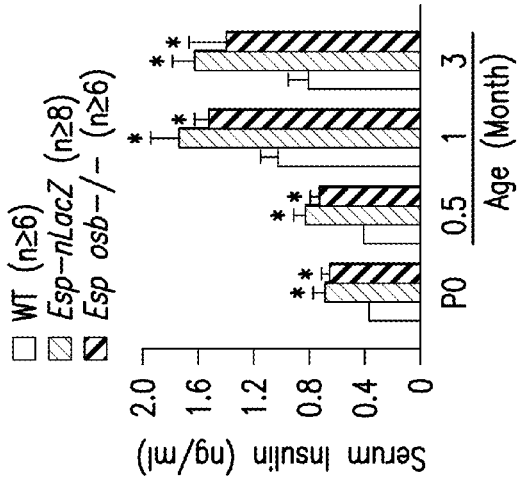
FIG. 1G
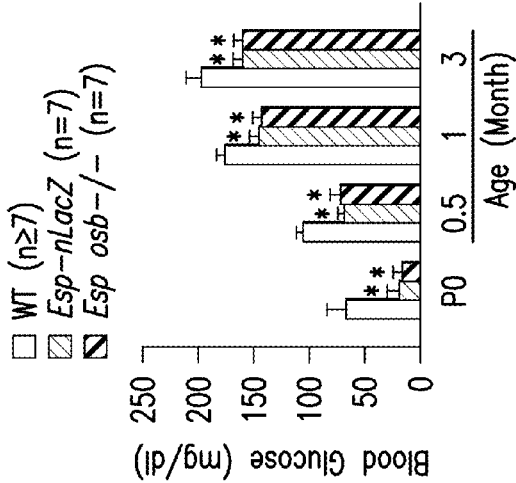
FIG. 1H

| | WT | α1(I)-*Esp* |
|---|---|---|
| Islet No/mm² | 0.54 ± 0.05 | 0.22 ± 0.04* |
| β-cell area (%) | 0.90 ± 0.32 | 0.47 ± 0.28* |
| β-cell mass (mg) | 1.0 ± 0.04 | 0.7 ± 0.01* |
| Ki67-pos. Cell (%) | 1.6 ± 0.1 | 1.1 ± 0.1* |

| | WT (n≥6) | α1(I)-*Esp* (n≥6) |
|---|---|---|
| Blood Glucose (mg/dl) | 152.1 ± 8.9 | 202.6 ± 6.6* |
| Serum Insulin (ng/ml) | 0.9 ± 0.14 | 0.63 ± 0.01* |
| Adiponectin (ng/ml) | 15.8 ± 1.8 | 11.6 ± 1.4* |

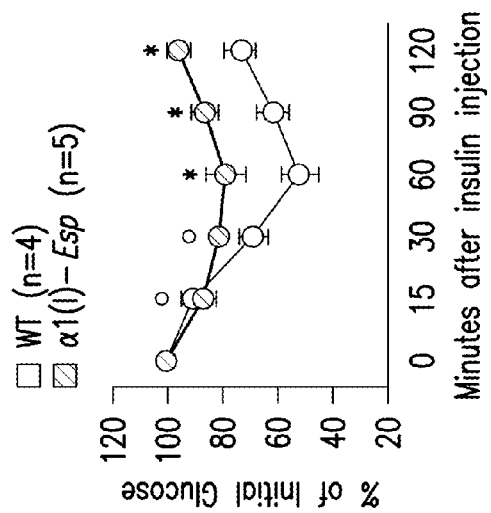
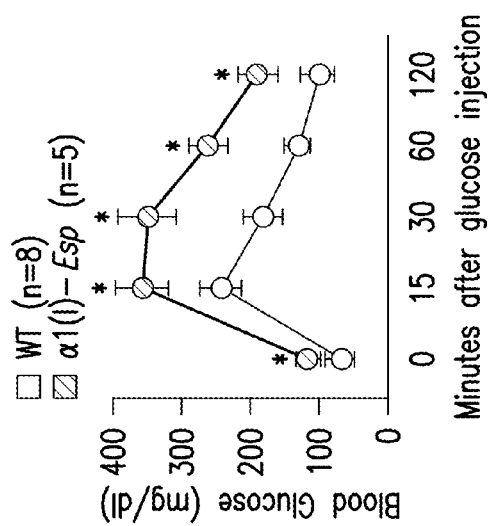
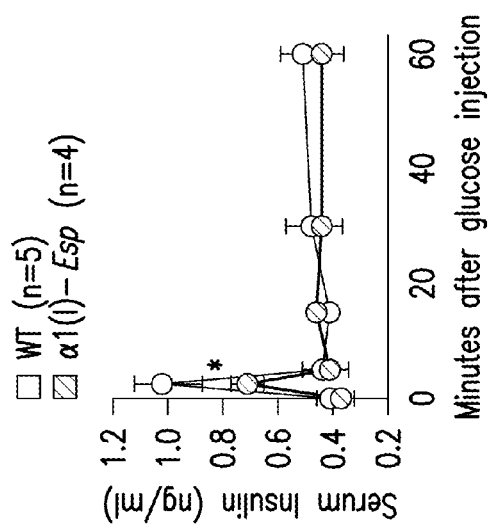
FIG. 4E
FIG. 4D
FIG. 4C

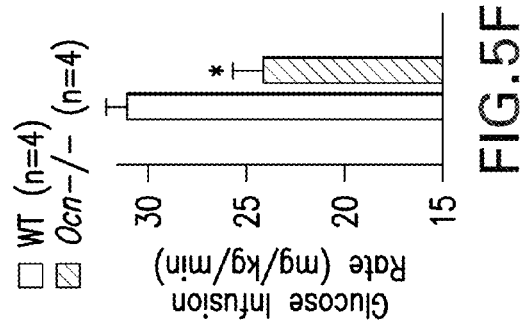
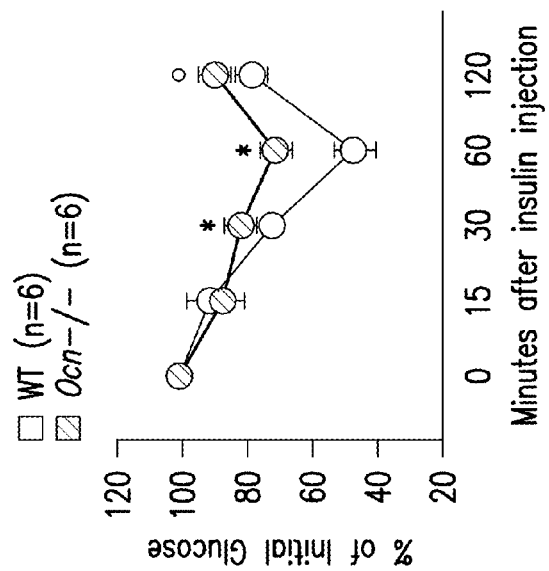
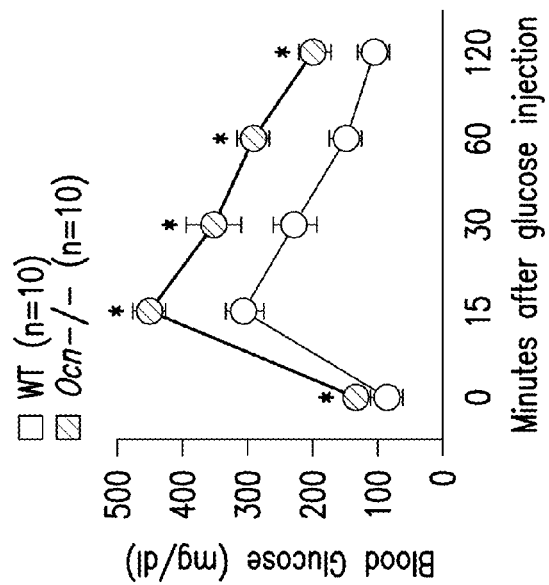
FIG. 5F
FIG. 5E
FIG. 5D

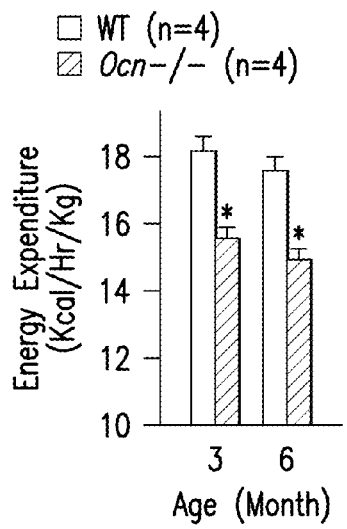
FIG.5G
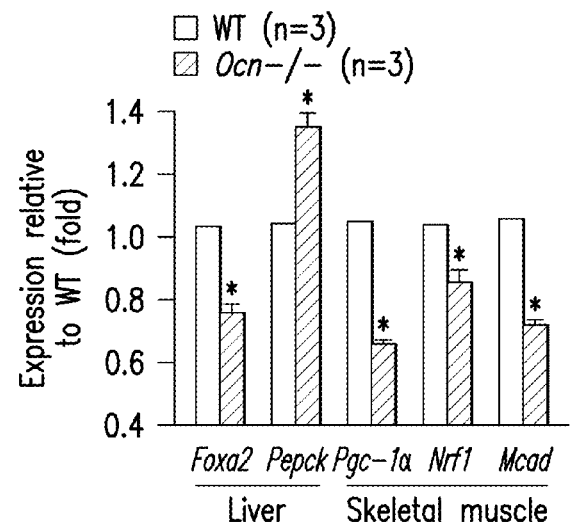
FIG.5H
| | WT | Ocn-/- |
|---|---|---|
| Islet No./mm² | 0.47 ±0.09 | 0.25 ±0.11* |
| β-cell area(%) | 0.66 ±0.05 | 0.36 ±0.03* |
| β-cell mass (mg) | 0.8 ±0.1 | 0.4 ±0.1* |
| Insulin content (ng/mg pancreas) | 73.2 ±2.9 | 50.5 ±4.1* |
| Ki67 positive cells (%) | 2.1 ±0.2 | 1.2 ±0.2°(P5) |
| | 2.1 ±0.4 | 1.1 ±0.1°(3M) |
FIG.5I

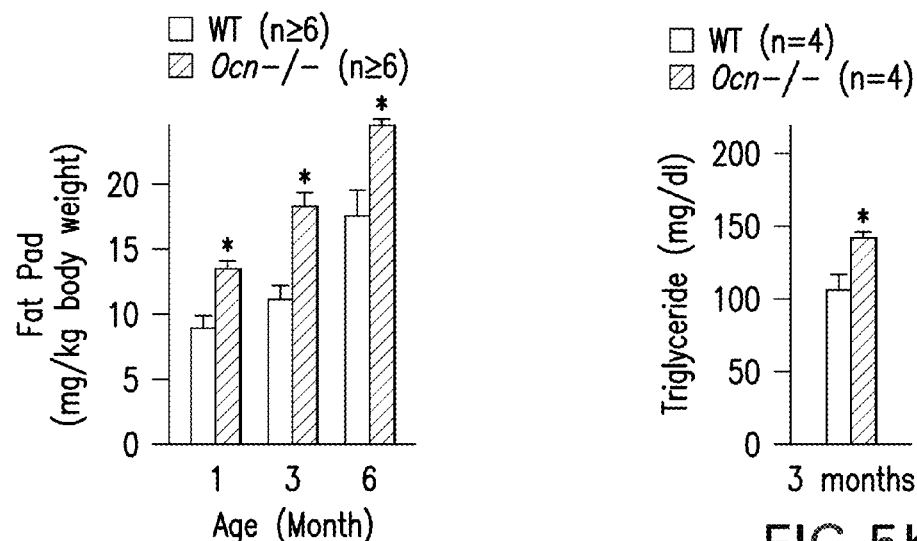
FIG.5J
FIG.5K
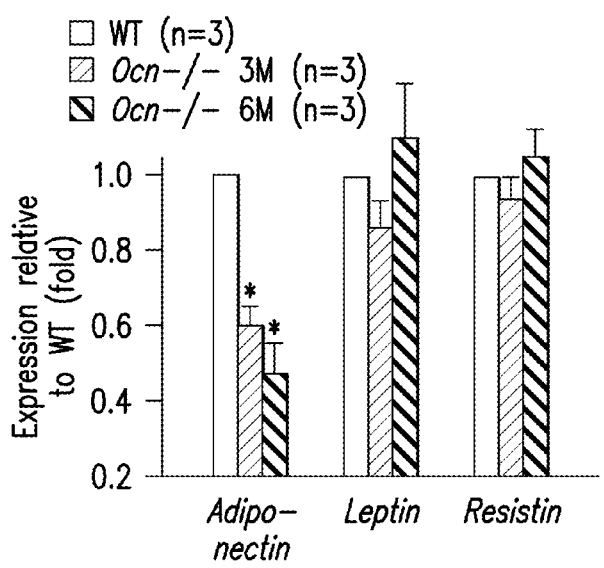
FIG.5L
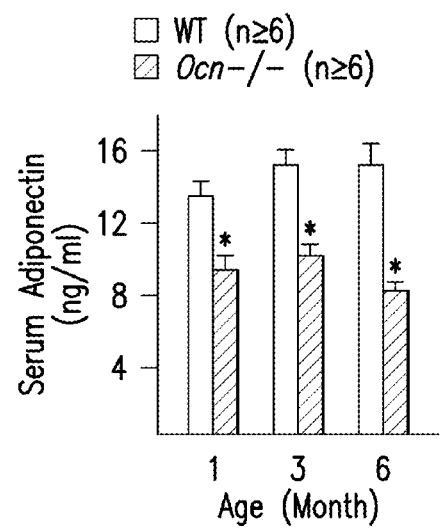
FIG.5M

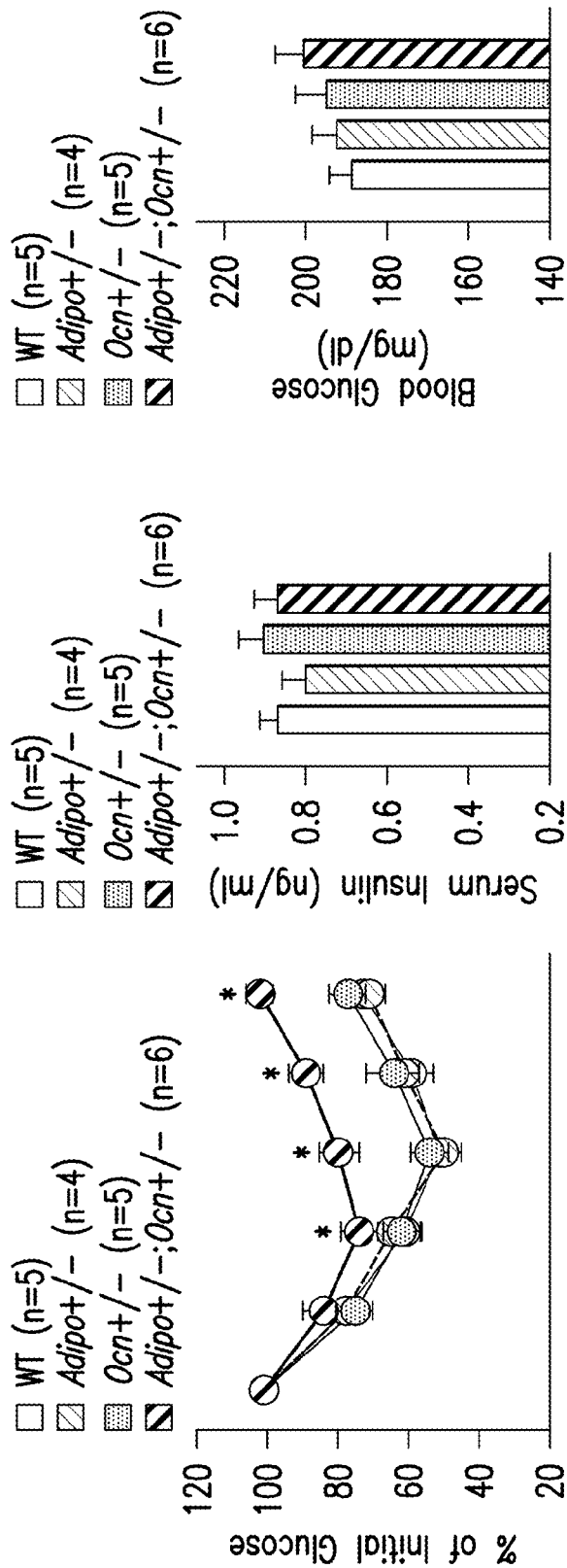

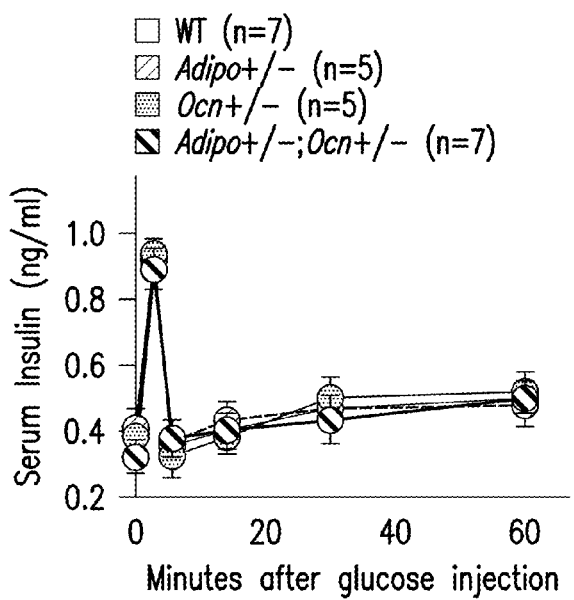
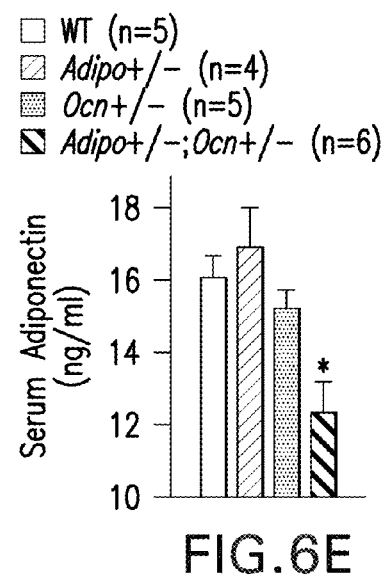
FIG.6D
FIG.6E

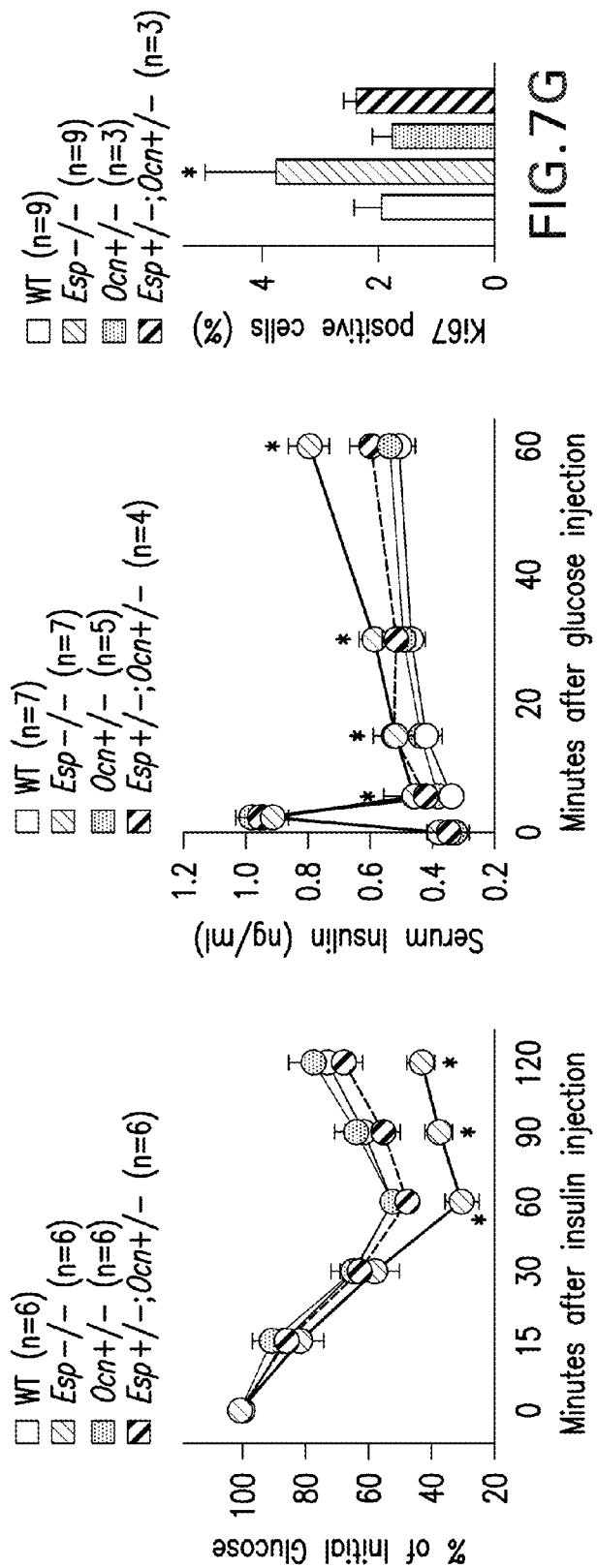

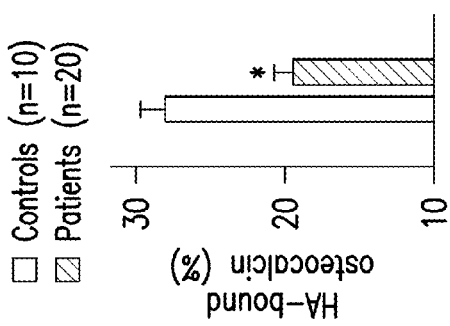
FIG. 7M
| | Control (n=10) | Patients (n=20) |
|---|---|---|
| Age (year) | 41 ± 9 | 40 ± 14 |
| Weight (kg) | 57 ± 6 | 112 ± 21* |
| BMI (kg/m²) | 20.5 ± 1.3 | 38.7 ± 5.9* |
| Insulin (pM) | 40.2 ± 21.1 | 80.5 ± 34.1* |
| Glucose (mmol/l) | 5.2 ± 1.1 | 5.5 ± 1.1 |
| Osteocalcin (ng/ml) | 6.3 ± 3.6 | 6.0 ± 3.0 |
FIG. 7N
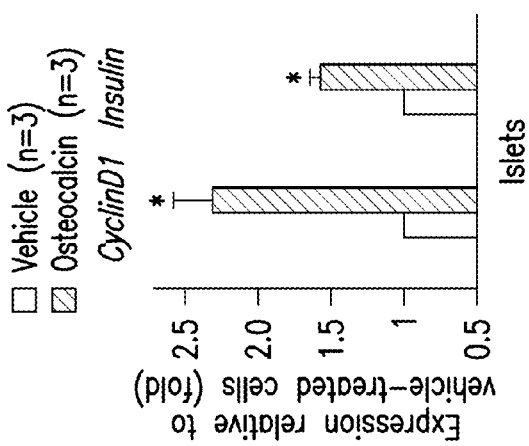
FIG. 7L

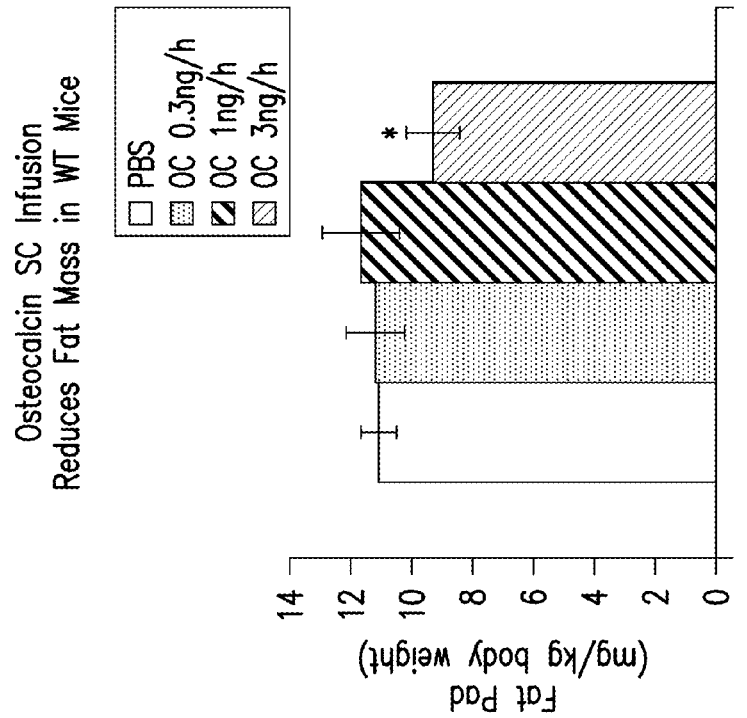
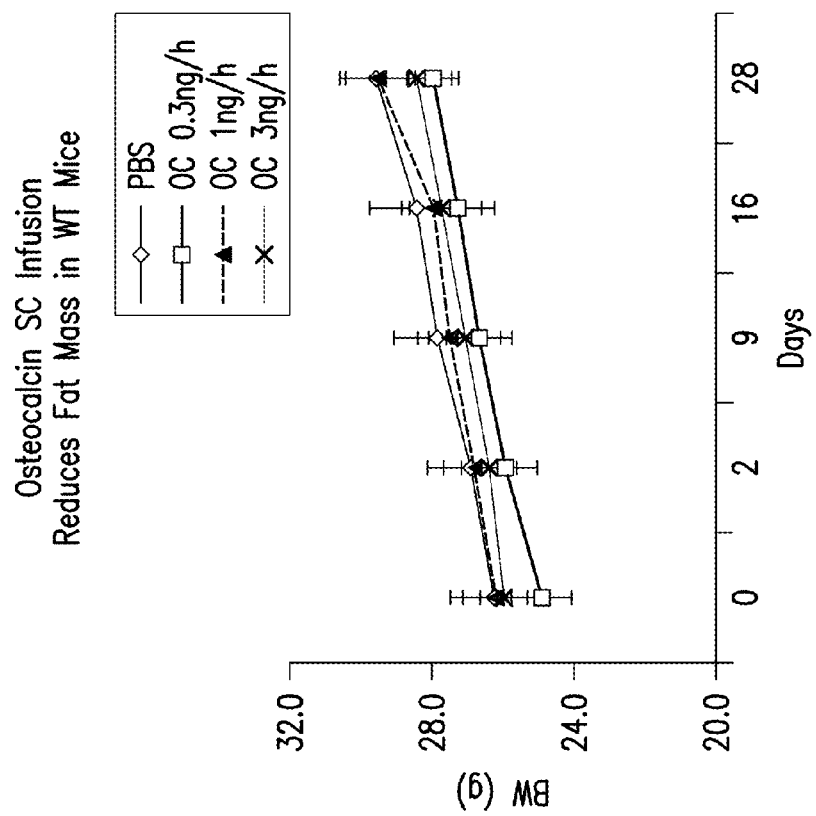
FIG. 13B
FIG. 13A

FIG.21

|  | WT (n≥8) | Esp−/− (n≥8) |
|---|---|---|
| Tibial length (P0) (mm) | 7.5 ±0.5 | 7.4 ±0.8 |
| Femoral length (1M) (mm) | 12.9 ±1.7 | 13.1 ±1.5 |

WT    Esp-nLacZ    WT    Esp$_{osb-/-}$

|  | WT (n≥8) | Esp−/− (n≥8) |
|---|---|---|
| BV/TV | 16.5 ±1.5 | 16.0 ±1.8 |
| N.ob/B.Pm | 19.9 ±1.7 | 19.3 ±1.5 |
| Dpd/creat. | 18.5 ±2.5 | 18.9 ±1.7 |

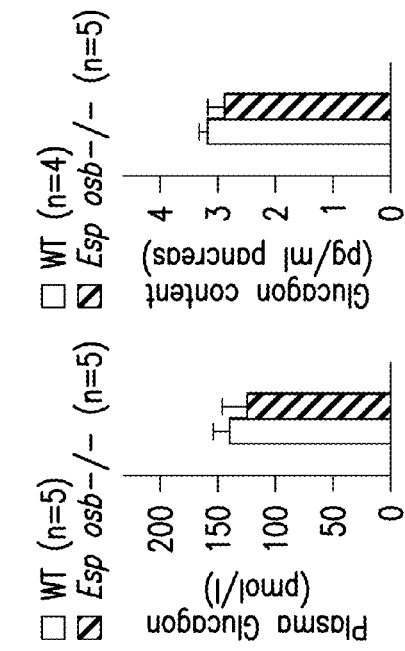
FIG. 23A
FIG. 23B
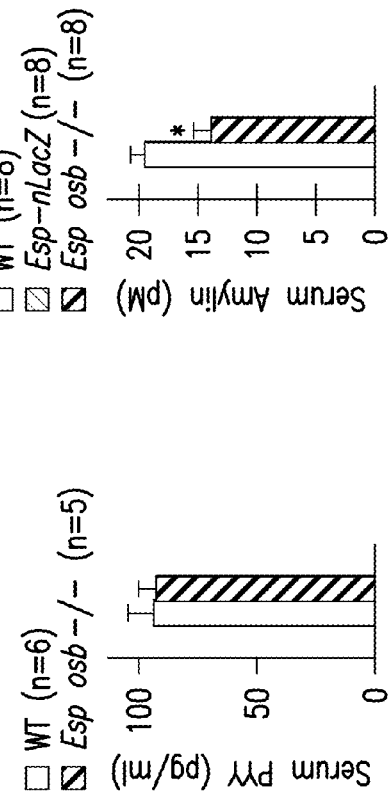
FIG. 23D
FIG. 23E
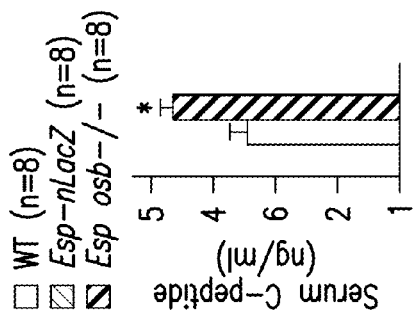
FIG. 23C
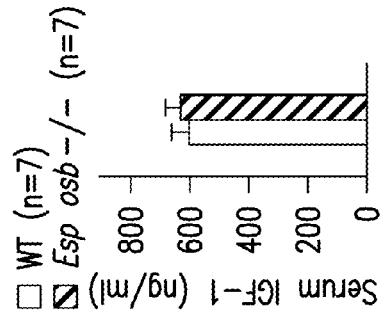

UNDERCARBOXYLATED/UNCARBOXYLATED OSTEOCALCIN INCREASES BETA-CELL PROLIFERATION, INSULIN SECRETION, INSULIN SENSITIVITY, GLUCOSE TOLERANCE AND DECREASES FAT MASS

This application claims the benefit of U.S. Provisional Patent Applications No. 60/844,203 filed Sep. 13, 2006; 60/870,604 filed Dec. 18, 2006; 60/909,712 filed Apr. 2, 2007; and 60/945,081 filed Jun. 19, 2007; the contents of which are hereby incorporated by reference as if set forth fully herein.

This invention was made with Government support under Grant No. PHS 398/2590 (Rev. 09/04, Reissued 4/2006). The Government has certain rights in the invention.

FIELD OF THE INVENTION

The present invention relates to methods and compositions for treating, preventing and diagnosing disorders related to energy metabolism and the OST-PTP signaling pathway, which involves gamma-carboxylase, osteocalcin and adiponectin. Such disorders include, but are not limited to, metabolic syndrome, glucose intolerance, diabetes types 1 and 2, atherosclerosis and obesity.

BACKGROUND OF THE INVENTION

The prevailing research paradigm in bone biology is that differentiation and functions of the two bone-specific cell types, osteoblasts and osteoclasts, are determined by secreted molecules that can either be cytokines acting locally, or hormones acting systemically (Harada and Rodan, 2003; Takayanagi, 2006; Teitelbaum and Ross, 2003). Applicants have discovered a previously unknown genetic pathway related to energy metabolism and occurring in osteoblasts in which decreased activity of OST-PTP leads to decreased activity of gamma-carboxylase, which in turn leads to increased secretion of undercarboxylated/uncarboxylated osteocalcin from the osteoblasts, with beneficial effects on glucose homeostasis.

OST-PTP is the protein encoded by the Esp gene. The Esp gene was originally named for embryonic stem (ES) cell phosphatase and it has also been called the Ptpry gene in mice. (Lee et al, 1996, Mech Dev 59: 153-164). OST-PTP is a receptor-like protein osteotesticular protein tyrosine phosphatase as well as fragments and variants thereof OST-PTP is a large, 1711 amino-acid long protein that includes three distinct domains. OST-PTP has a 1068 amino-acid long extracellular domain containing multiple fibronectin type III repeats.

Esp expression is restricted to ES cells, the gonads and the skeleton. In the gonads, Esp is specifically expressed in Sertoli cells of the testis and coelomic epithelial cells of the ovaries. During development, Esp is initially expressed in the apical ectodermal ridge of the limbs. Later during embryonic development and after birth, its expression becomes restricted to pre-osteoblasts and osteoblasts (i.e., Runx2-positive cells) of the perichondrium and periosteum. Because of its bone and testicular localization, the gene product of Esp is often referred to as osteoblast testicular protein tyrosine phosphatase (OST-PTP).

Osteocalcin, one of the very few osteoblast-specific proteins, has several features of a hormone. Ducy et. al. demonstrated that mineralized bone from aging osteocalcin-deficient mice was two times thicker than that of wild-type. It was shown that the absence of osteocalcin led to an increase in bone formation without impairing bone resorption and did not affect mineralization. Multiple immunoreactive forms of human osteocalcin have been discovered in circulation (Garnero et al. J Bone Miner Res 1994; 9:255-4) and also in urine (Taylor et al. J. Clin. Endocrin. Metab. 1990; 70:467-72). Fragments of human osteocalcin can be produced either during osteoclastic degradation of bone matrix or as the result of the catabolic breakdown of the circulating protein after synthesis by osteoblasts.

Metabolic syndrome is a combination of medical disorders that increase the risk of cardiovascular disease and diabetes. Some of the symptoms of metabolic syndrome include: fasting hyperglycemia, high blood pressure, decreased HDL cholesterol, elevated triglycerides, and elevated uric acid levels.

The experiments described herein provide the first evidence that the skeleton is an endocrine regulator of energy metabolism and thereby determines, in part, the onset and severity of metabolic syndrome or type 2 diabetes, as well as the risk of developing these disorders. The experiments described herein establish that the skeleton makes and secretes undercarboxylated osteocalcin which acts as a hormone regulating energy metabolism. Described herein is a previously unknown genetic pathway relating to energy metabolism and occurring in osteoblasts in which decreased activity of OST-PTP leads to decreased activity of gamma-carboxylase, which in turn leads to increased secretion of undercarboxylated osteocalcin from the osteoblasts, with beneficial effects on glucose homeostasis.

SUMMARY OF THE INVENTION

The present invention provides pharmaceutical compositions comprising an agent that modulates energy metabolism and the OST-PTP signaling pathway, wherein the agent reduces OST-PTP phosphorylase activity, reduces gamma-carboxylase activity, or increases undercarboxylated/uncarboxylated osteocalcin, wherein the pharmaceutical compositions comprise the agent in an amount that produces an effect selected from the group consisting of an increase in glucose tolerance, an increase in insulin production, an increase insulin sensitivity, an increase in pancreatic beta-cell proliferation, an increase in adiponectin serum level, a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, and a decrease in the thickness of arterial plaque.

In certain embodiments, the pharmaceutical compositions comprise the agent in an amount effective to treat or prevent a disorder selected from the group consisting of metabolic syndrome, glucose intolerance, type 1 diabetes, type 2 diabetes, atherosclerosis, and obesity. In certain embodiments, the agent inhibits the expression or activity of OST-PTP or gamma-carboxylase, inhibits phosphorylation of gamma-carboxylase, increases the level of undercarboxylated or uncarboxylated osteocalcin, inhibits carboxylation of osteocalcin, decarboxylates osteocalcin. In certain embodiments, the agent is selected from the group consisting of a small molecule, an antibody, a nucleic acid and a biologically active fragment or variant thereof.

In certain embodiments, the agent is undercarboxylated/uncarboxylated osteocalcin. In certain embodiments, at least one of the glutamic acids in the undercarboxylated/uncarboxylated osteocalcin at the positions corresponding to positions 17, 21 and 24 of mature human osteocalcin is not carboxylated. In certain embodiments, all three of the glutamic acids in the undercarboxylated/uncarboxylated osteocalcin at the positions corresponding to positions 17, 21 and 24 of mature human osteocalcin are not carboxylated.

In certain embodiments, the undercarboxylated/uncarboxylated osteocalcin is a preparation of undercarboxylated/uncarboxylated osteocalcin in which more than about 20% of the total Glu residues at the positions corresponding to positions 17, 21 and 24 of mature human mature human osteocalcin in the preparation are not carboxylated. In certain embodiments, the undercarboxylated/uncarboxylated osteocalcin shares at least 80% amino acid sequence identity with mature human osteocalcin when the undercarboxylated/uncarboxylated osteocalcin and mature human osteocalcin are aligned for maximum sequence homology.

In certain embodiments, the undercarboxylated/uncarboxylated osteocalcin is a polypeptide selected from the group consisting of:
  (a) a fragment comprising mature human osteocalcin missing the last 10 amino acids from the C-terminal end;
  (b) a fragment comprising mature human osteocalcin missing the first 10 amino acids from the N-terminal end;
  (c) a fragment comprising amino acids 62-90 of SEQ ID NO:2;
  (d) a fragment comprising amino acids 1-36 of mature human osteocalcin; and
  (e) variants of the above.

In certain embodiments, the pharmaceutical composition comprises a small molecule selected from the group consisting of warfarin, beta-blockers, statins, vitamin K inhibitors and biologically active fragments or variants thereof. In a preferred embodiment, the small molecule is warfarin. In another preferred embodiment, the agent is a small molecule that increases the activity or expression of osteocalcin or adiponectin.

In certain embodiments, the pharmaceutical composition comprises an antibody or antibody fragment that binds to OST-PTP or gamma-carboxylase. Preferably, the antibody or antibody fragment is a monoclonal antibody. In certain embodiments, the antibody or antibody fragment binds to the extracellular domain of OST-PTP. In preferred embodiments, the OST-PTP is human OST-PTP. In certain embodiments, the OST-PTP is the mouse OST-PTP of SEQ ID NO:19 or an OST-PTP having an amino acid sequence that is substantially homologous or identical to SEQ ID NO:19. In certain embodiments, the OST-PTP is an OST-PTP having an amino acid sequence that is at least 70% homologous or identical to SEQ ID NO:19.

In certain embodiments, the pharmaceutical composition comprises a nucleic acid that inhibits the expression or activity of OST-PTP or gamma-carboxylase. In certain embodiments, the nucleic acid is an antisense oligonucleotide or a siRNA. In certain embodiments, the nucleic acid is an isolated nucleic acid that is selected from the group consisting of an antisense DNA, antisense RNA, and small interfering RNA, which nucleic acid is sufficiently complementary to SEQ ID NO:18 or a sequence that is substantially homologous or identical to SEQ ID NO:18 to permit specific hybridization to SEQ ID NO:18 or the sequence that is substantially homologous or identical to SEQ ID NO:18, and wherein the hybridization prevents or reduces expression of OST-PTP in osteoblasts.

In certain embodiments, the pharmaceutical composition comprises an agent that increases the level of serum insulin.

In certain embodiments, the pharmaceutical composition comprises about 1 mg to about 750 mg of the agent. In certain embodiments, the pharmaceutical composition comprises an agent that is formulated into a controlled release preparation. In certain embodiments, the pharmaceutical composition comprises an agent that is chemically modified to prolong its half life in the human body.

In certain embodiments, the pharmaceutical composition comprises an anti-coagulant, a vasodilator, a drug used to treat atherosclerosis, a drug used to treat diabetes, a vitamin K inhibitor, a statin, or a beta blocker.

The present invention also provides a pharmaceutical composition comprising an undercarboxylated osteocalcin polypeptide comprising an amino acid sequence (SEQ ID NO: 23)
YLYQWLGAPVPYPDPLX$_1$PRRX$_2$VCX$_3$LNPDCDELADHIGFQEAYRRFY
GPV wherein
  $X_1$, $X_2$ and $X_3$ are each independently selected from an amino acid or amino acid analog, with the proviso that if $X_1$, $X_2$ and $X_3$ are each glutamic acid, then $X_1$ is not carboxylated, or less than 50 percent of $X_2$ is carboxylated, and/or less than 50 percent of $X_3$ is carboxylated, or said osteocalcin polypeptide comprises an amino acid sequence that is different from SEQ. ID. NO:23 at 1 to 7 positions other than $X_1$, $X_2$ and $X_3$; and
  wherein said amino acid sequence can include one amide backbone substitutions.

In certain embodiments, the osteocalcin polypeptide of SEQ. ID. NO:23 is a fusion protein. In certain embodiments, the arginine at position 43 of SEQ. ID. NO:23 is replaced with an amino acid or amino acid analog that reduces susceptibility of the osteocalcin polypeptide to proteolytic degradation. In certain embodiments, the arginine at position 44 of SEQ. ID. NO:23 is replaced with β-dimethyl-arginine. In certain embodiments, the osteocalcin polypeptide is a retroenantiomer of uncarboxylated human osteocalcin (1-49).

The present invention also provides a method of modulating a pathway related to energy metabolism and the OST-PTP signaling pathway comprising administering an agent that reduces OST-PTP phosphorylase activity, reduces gamma-carboxylase activity, or increases undercarboxylated/uncarboxylated osteocalcin, wherein the agent is administered in an amount that produces an effect selected from the group consisting of an increase in glucose tolerance, an increase in insulin production, an increase insulin sensitivity, an increase in pancreatic beta-cell proliferation, an increase in adiponectin serum level, a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, and a decrease in the thickness of arterial plaque. In certain embodiments, the agent is administered in an amount effective to treat or prevent a disorder selected from the group consisting of metabolic syndrome, glucose intolerance, type 1 diabetes, type 2 diabetes, atherosclerosis, and obesity.

In certain embodiments, the method comprises administering the agent in an amount effective to treat or prevent a disorder selected from the group consisting of metabolic syndrome, glucose intolerance, type 1 diabetes, type 2 diabetes, atherosclerosis, and obesity. In certain embodiments, the agent inhibits the expression or activity of OST-PTP or gamma-carboxylase, inhibits phosphorylation of gamma-carboxylase, increases the level of undercarboxylated or uncarboxylated osteocalcin, inhibits carboxylation of osteocalcin, decarboxylates osteocalcin. In certain embodiments, the agent is selected from the group consisting of a small molecule, an antibody, a nucleic acid and a biologically active fragment or variant thereof.

In certain embodiments, the agent is undercarboxylated/uncarboxylated osteocalcin. In certain embodiments, at least one of the glutamic acids in the undercarboxylated/uncarboxylated osteocalcin at the positions corresponding to positions 17, 21 and 24 of mature human osteocalcin is not carboxylated. In certain embodiments, all three of the glutamic acids in the undercarboxylated/uncarboxylated osteocalcin at the positions corresponding to positions 17, 21 and 24 of mature human osteocalcin are not carboxylated. In certain embodiments, the present invention provides methods of administering undercarboxylated/uncarboxylated osteocalcin to increase insulin production.

In certain embodiments, the undercarboxylated/uncarboxylated osteocalcin is a preparation of undercarboxylated/uncarboxylated osteocalcin in which more than about 20% of the total Glu residues at the positions corresponding to positions 17, 21 and 24 of mature human mature human osteocalcin in the preparation are not carboxylated. In certain embodiments, the undercarboxylated/uncarboxylated osteocalcin shares at least 80% amino acid sequence identity with mature human osteocalcin when the undercarboxylated/uncarboxylated osteocalcin and mature human osteocalcin are aligned for maximum sequence homology.

In certain embodiments, the undercarboxylated/uncarboxylated osteocalcin is a polypeptide selected from the group consisting of:
(a) a fragment comprising mature human osteocalcin missing the last 10 amino acids from the C-terminal end;
(b) a fragment comprising mature human osteocalcin missing the first 10 amino acids from the N-terminal end;
(c) a fragment comprising amino acids 62-90 of SEQ ID NO:2;
(d) a fragment comprising amino acids 1-36 of mature human osteocalcin; and
(e) variants of the above.

In certain embodiments, the agent is a small molecule that inhibits the expression or activity of OST-PTP or gamma-carboxylase. In certain embodiments, the agent is a small molecule selected from the group consisting of warfarin, beta-blockers, statins, vitamin K inhibitors and biologically active fragments or variants thereof. In a preferred embodiment, the small molecule is warfarin. In another preferred embodiment, the agent is a small molecule that increases the activity or expression of osteocalcin or adiponectin.

In certain embodiments, agent is an antibody or antibody fragment that binds to OST-PTP or gamma-carboxylase. Preferably, the antibody or antibody fragment is a monoclonal antibody. In certain embodiments, the antibody or antibody fragment binds to the extracellular domain of OST-PTP. In preferred embodiments, the OST-PTP is human OST-PTP. In certain embodiments, the OST-PTP is the mouse OST-PTP of SEQ ID NO:19 or an OST-PTP having an amino acid sequence that is substantially homologous or identical to SEQ ID NO:19. In certain embodiments, the OST-PTP is an OST-PTP having an amino acid sequence that is at least 70% homologous or identical to SEQ ID NO:19.

In certain embodiments, the agent is a nucleic acid that inhibits the expression or activity of OST-PTP or gamma-carboxylase. In certain embodiments, the nucleic acid is an antisense oligonucleotide or a siRNA. In certain embodiments, the nucleic acid is an isolated nucleic acid that is selected from the group consisting of an antisense DNA, antisense RNA, and small interfering RNA, which nucleic acid is sufficiently complementary to SEQ ID NO:18 or a sequence that is substantially homologous or identical to SEQ ID NO:18 to permit specific hybridization to SEQ ID NO:18 or the sequence that is substantially homologous or identical to SEQ ID NO:18, and wherein the hybridization prevents or reduces expression of OST-PTP in osteoblasts.

In certain embodiments, the methods of the present invention are carried out by administering about 1 mg to about 750 mg of the agent. In certain embodiments, the agent that is formulated into a controlled release preparation. In certain embodiments, the agent is chemically modified to prolong its half life in the human body. In certain embodiments, the agent is co-administered with an anti-coagulant, a vasodilator, a drug used to treat atherosclerosis, a drug used to treat diabetes, a vitamin K inhibitor, a statin, or a beta blocker.

The present invention also provides a method of diagnosing a patient at risk of developing a disease related to energy metabolism and the OST-PTP signaling pathway comprising (i) determining the ratio of undercarboxylated/uncarboxylated osteocalcin to total osteocalcin in a biological sample from the patient; and (ii) comparing the ratio to a standard ratio; wherein, if the patient ratio is lower than the standard ratio, the patient is at risk of developing a disease related to the OST-PTP signaling pathway.

In certain embodiments, the disease related to the OST-PTP signaling pathway is selected from the group consisting of metabolic syndrome, glucose intolerance, type 1 diabetes, type 2 diabetes, atherosclerosis, and obesity. In certain embodiments, disease related to the OST-PTP signaling is characterized by decreased insulin production, decreased insulin sensitivity, decreased glucose tolerance and/or increased fat mass.

In certain embodiments, the biological sample is blood.

In certain embodiments of the diagnostic method described above, the standard ratio is 5%-10%, 10%-15%, 15%-20%, 20%-25%, 25%-30%, or 30%-35%.

The present invention provides a use of an agent that modulates energy metabolism and the OST-PTP signaling pathway and reduces OST-PTP phosphorylase activity, reduces gamma-carboxylase activity, or increases undercarboxylated/uncarboxylated osteocalcin, in an amount that produces an effect selected from the group consisting of an increase in glucose tolerance, an increase in insulin production, an increase insulin sensitivity, an increase in pancreatic beta-cell proliferation, an increase in adiponectin serum level, a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, and a decrease in the thickness of arterial plaque, as a medicament.

In certain embodiments, the agent is used to treat or prevent a disorder selected from the group consisting of metabolic syndrome, glucose intolerance, type 1 diabetes, type 2 diabetes, atherosclerosis, and obesity.

In certain embodiments, the agent inhibits phosphorylation of gamma-carboxylase. In certain embodiments, the agent increases the level of uncarboxylated osteocalcin. In certain embodiments, the agent inhibits carboxylation of osteocalcin. In certain embodiments, the agent decarboxylates osteocalcin.

In certain embodiments, the agent is undercarboxylated/uncarboxylated osteocalcin. In certain embodiments, the undercarboxylated/uncarboxylated osteocalcin increases insulin production. In certain embodiments, at least one of the glutamic acids in the undercarboxylated/uncarboxylated osteocalcin at the positions corresponding to positions 17, 21 and 24 of mature human osteocalcin is not carboxylated. In certain embodiments, all three of the glutamic acids in the undercarboxylated/uncarboxylated osteocalcin at the positions corresponding to positions 17, 21 and 24 of mature human osteocalcin are not carboxylated. In certain embodiments, the undercarboxylated/uncarboxylated osteocalcin is a preparation of undercarboxylated/uncarboxylated osteocalcin in which more than about 20% of the total Glu residues at the positions corresponding to positions 17, 21 and 24 of mature human mature human osteocalcin in the preparation are not carboxylated. In certain embodiments, the undercarboxylated/uncarboxylated osteocalcin shares at least 80% amino acid sequence identity with mature human osteocalcin when the undercarboxylated/uncarboxylated osteocalcin and mature human osteocalcin are aligned for maximum sequence homology.

In certain embodiments, the undercarboxylated/uncarboxylated osteocalcin is a polypeptide selected from the group consisting of:
(a) a fragment comprising mature human osteocalcin missing the last 10 amino acids from the C-terminal end;
(b) a fragment comprising mature human osteocalcin missing the first 10 amino acids from the N-terminal end;
(c) a fragment comprising amino acids 62-90 of SEQ ID NO:2;
(d) a fragment comprising amino acids 1-36 of mature human osteocalcin; and
(e) variants of the above.

In certain embodiments, the agent is selected from the group consisting of a small molecule, an antibody, a nucleic acid and a biologically active fragment or variant thereof.

In certain embodiments, the agent is a small molecule that inhibits the expression or activity of OST-PTP or gamma-carboxylase. In certain embodiments, the agent is a small molecule selected from the group consisting of warfarin, beta-blockers, statins, vitamin K inhibitors and biologically active fragments or variants thereof. In a preferred embodiment, the small molecule is warfarin. In another preferred embodiment, the agent is a small molecule that increases the activity or expression of osteocalcin or adiponectin.

In certain embodiments, agent is an antibody or antibody fragment that binds to OST-PTP or gamma-carboxylase. Preferably, the antibody or antibody fragment is a monoclonal antibody. In certain embodiments, the antibody or antibody fragment binds to the extracellular domain of OST-PTP. In preferred embodiments, the OST-PTP is human OST-PTP. In certain embodiments, the OST-PTP is the mouse OST-PTP of SEQ ID NO:19 or an OST-PTP having an amino acid sequence that is substantially homologous or identical to SEQ ID NO:19. In certain embodiments, the OST-PTP is an OST-PTP having an amino acid sequence that is at least 70% homologous or identical to SEQ ID NO:19.

In certain embodiments, the agent is a nucleic acid that inhibits the expression or activity of OST-PTP or gamma-carboxylase. In certain embodiments, the nucleic acid is an antisense oligonucleotide or a siRNA. In certain embodiments, the nucleic acid is an isolated nucleic acid that is selected from the group consisting of an antisense DNA, antisense RNA, and small interfering RNA, which nucleic acid is sufficiently complementary to SEQ ID NO:18 or a sequence that is substantially homologous or identical to SEQ ID NO:18 to permit specific hybridization to SEQ ID NO:18 or the sequence that is substantially homologous or identical to SEQ ID NO:18, and wherein the hybridization prevents or reduces expression of OST-PTP in osteoblasts.

In certain embodiments, about 750 mg of the agent is used as a medicament. In certain embodiments, the agent is formulated into a controlled release preparation. In certain embodiments, the agent is chemically modified to prolong its half life in the human body. In certain embodiments, the agent is co-administered with an anti-coagulant, a vasodilator, a drug used to treat atherosclerosis, a drug used to treat diabetes, a vitamin K inhibitor, a statin, or a beta blocker.

The present invention provides the use of an undercarboxylated osteocalcin polypeptide, or mimetic thereof, in the manufacture of a medicament for treatment of a metabolic condition.

The present invention also provides the use of an agent that modulates energy metabolism and the OST-PTP signaling pathway and reduces OST-PTP phosphorylase activity, reduces gamma-carboxylase activity, or increases undercarboxylated/uncarboxylated osteocalcin, in an amount that produces an effect selected from the group consisting of an increase in glucose tolerance, an increase in insulin production, an increase insulin sensitivity, an increase in pancreatic beta-cell proliferation, an increase in adiponectin serum level, a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, and a decrease in the thickness of arterial plaque, for the manufacture of a medicament for the treatment or prevention of a disorder selected from the group consisting of metabolic syndrome, glucose intolerance, type 1 diabetes, type 2 diabetes, atherosclerosis, and obesity.

BRIEF DESCRIPTION OF THE FIGURES

FIG. 1A-M. Increased insulin secretion and beta-cell proliferation in Esp−/− mice. (FIG. 1A) LacZ-stained tissues from newborn Esp−/− mice demonstrating Esp locus activity in bone and testis but not in pancreas or fat pads. (FIG. 1B) Expression of Esp in osteoblasts, adipocytes, and pancreatic islets by real-time PCR in 1-month-old mice. (FIG. 1C) Southern blot analysis showing efficient recombination at the Esp locus in osteoblasts of Esposb−/− mice. (FIG. 1D) Using real-time PCR Esp expression is 90% decreased in osteoblasts but not altered in testis of Esposb−/− mice. (FIG. 1E) Decreased percentage at weaning of Esp−/− pups born from crosses between Esp+/− mice. (FIG. 1F) Lower survival at birth and at weaning of Esp−/− pups born from Esp+/− and Esp−/− mothers. (FIG. 1G and FIG. 1H) Blood glucose levels (FIG. 1G) and serum insulin levels (FIG. 1H) in WT and Esp−/− newborn before feeding (P0) or after random feeding at indicated ages. (FIGS. 1I-J) GSIS (FIG. 1I) and GTT (FIG. 1J) test in 1-month-old WT and Esp−/− mice. (FIG. 1K) H&E staining, insulin immunostaining, and insulin/Ki67 double immunostaining showing larger islets and increased beta-cell proliferation in pancreas of WT and 1-month-old Esp−/− mice. Arrowheads indicate islets, and arrows point at Ki67-positive cells. Scale bars are 100 mm except in upper panels, where they are 800 mm. Histomorphometric comparisons of islet number, size, and beta-cell mass between 1-month-old WT and Esp−/− mice (lowest panel). (FIG. 1L) Pancreas insulin content in 1-month-old WT and Esp−/− mice. (FIG. 1M) Quantification of the number of Ki67-immunoreactive cells in pancreatic islets of P5 and 1-month-old WT and Esp−/− mice. All panels except (FIG. 1I) and (FIG. 1J), °p<0.05 and *p<0.01 versus WT (Student's t test). (FIG. 1I and FIG. 1J) °p<0.05 versus WT and *p % 0.001 versus WT (ANOVA followed by post hoc analysis).

(FIG. 2A) ITT. (FIG. 2N) Expression of adiponectin target genes in tissues of WT and Esp−/− mice. In (FIG. 2A), °p<0.05 versus WT and *p % 0.001 versus WT (ANOVA followed by post hoc analysis); in (FIG. 2B)-(FIG. 2N), *p<0.01 versus WT (Student's t test).

FIGS. 3A-F) Food intake per day (FIG. 3A), body weight curve (FIG. 3B), fat pad mass (FIG. 3C), serum triglyceride levels (FIG. 3D), GTT (FIG. 3E), and ITT (FIG. 3F) in 4-month-old WT and Esp−/− mice 3 months after GTG or vehicle injection. (FIG. 3N) Urinary glucose assays in 1-month-old WT and Esp−/− mice 8 days after STZ injection. In (FIGs. 3A)-(F), (FIG. 3J), and (FIG. 3K): a, WT versus Esp−/−; b, WT+GTG (or STZ) versus WT+vehicle; c, WT+GTG (or STZ) versus Esp−/−+ GTG (or STZ); d, Esp−/−+GTG (or STZ) versus Esp−/−+ vehicle. In (FIG. 3G)-(I) and (FIG. 3M), *p<0.05 WT versus Esp−/−. In (FIG. 3A), (FIG. 3C), (FIG. 3D), (FIG. 3J), and (FIG. 3K), Student's t test, p<0.05 for a-d; in (FIG. 3B), (FIG. 3E)-(I), (FIG. 3L), and (FIG. 3M), ANOVA followed by post hoc analysis when number of groups >2, p % 0.001 for a-d.

FIG. 4A-J Osteoblasts Secrete a Factor Regulating Insulin and Adiponectin Expression. FIGS. 4A-E) All experiments compare 1-month-oldWT and a1(I)-Esp mice. (FIG. 4A) Insulin immunostaining (upper panel) and histomorphometric comparisons of islet number, size, beta-cell mass, and Ki67-immunoreactive cells in pancreas (lower panel). Scale bars are 100 mm. (FIG. 4B) Blood glucose and serum insulin/adiponectin levels. (FIG. C) GSIS test. (FIG. D) GTT. (FIG. E) ITT. (FIG. 4F) Expression of Insulin and Glucagon in WT islets cocultured with fibroblasts or osteoblasts. (FIG. 4G) Expression of Adiponectin and Leptin in WT adipocytes cocultured with fibroblasts or osteoblasts. (FIG. 4H) Expression of Insulin and Adiponectin in Esp−/− indicated cells cocultured with fibroblasts or osteoblasts. (FIGS. 4I and J) Expression of Insulin (FIG. 4I) and Adiponectin (FIG. 4J) in WT indicated cells cocultured with or without osteoblasts in presence of a filter preventing cell-cell contact or in presence of conditioned medium (CM) collected from osteoblast cultures. (FIGS. 4A, B, and F-J) *p<0.05 versus WT (Student's t test); (FIGS. 4C-E) °p<0.05 versus WT and *p % 0.001 versus WT (ANOVA).

(FIG. 5A) Blood glucose levels after random feeding. (FIG. 5D) GTT. (FIG. 5E) ITT. (FIG. 5F) Glucose infusion rate during hyperinsulinemic-euglycemic clamp. (FIG. 5G) Energy expenditure. (FIG. 5H) Expression of insulin target genes by real-time PCR. (FIG. 5I) Histomorphometric comparisons of islet numbers, islet size, beta-cell mass, insulin content in pancreas, and Ki67 immunoreactive cells in pancreatic islets. P5, 5-day-old pups; 3M, 3-month-old mice. (FIG. 5J) Fat pad mass (fat pad weight over body weight). (FIG. 5K) Serum triglyceride levels after an overnight fast. (FIG. 5L and M) serum levels (FIG. 5L) and gene expression (FIG. 5M) of adiponectin. FIGS. 5A, B, F-R: *p<0.05 vs WT (Student's t test); FIGS. 5C-E, S and T, °p<0.01 vs WT and *p<0.001 vs WT (ANOVA). Results are given as means±SD except in FIG. 5F where means±SEM are shown.

FIG. 6A-E. Osteocalcin Regulates Insulin Sensitivity via Adiponectin. (FIGS. 6A-E) Comparison between 6-week-old WT, Adiponectin+/− (Adipo+/−), Osteocalcin+/− (Ocn+/−), and Ocn+/−; Adipo+/− mice. (FIG. 6A) ITT. (FIG. 6B) Insulin serum levels. (FIG. 6C) Blood glucose levels. (FIG. 6D) GSIS test. (FIG. 6E) Adiponectin serum levels. In (FIG. 6A) and (FIG. 6D), *p % 0.001 versus WT (ANOVA followed by post hoc analysis); in (FIG. 6B), (FIG. 6C), and (FIG. 6E), *p<0.05 versus WT (Student's t test).

FIG. 7A-O. Esp−/− Mice Are a Model of Increased Osteocalcin Bioactivity. (FIGS. 7A-G) Comparison between 6-week-old WT, Esp−/, Ocn+/−, and Esp−/−; Ocn+/− mice. (FIG. 7A) Blood glucose levels. (FIG. 7B) Serum insulin levels. (FIG. 7C) Serum adiponectin levels. (FIG. 7D) GTT. (FIG. 7E) ITT. (FIG. 7F) GSIS test. (FIG. 7G) Quantification of the number of Ki67-immunoreactive cells in pancreatic islets. (FIG. 7L) Expression of Insulin and Cyclin D1 in WT islets cultured in presence of 0.3 ng/ml of bacterially produced uncarboxylated osteocalcin or vehicle. (FIG. 7M) Metabolic parameters and total serum osteocalcin levels in control and obese patients. (FIG. 7N-O) Quantification of carboxylated osteocalcin (HA-bound osteocalcin) in control and obese patients. In (FIGS. 7A)-(C) and (FIGS. G)-(L): *$p<0.05$ versus WT (Student's t test); in (FIG. D)-(F), °$p<0.05$ versus WT and *p % 0.001 versus WT (ANOVA followed by post hoc analysis).

FIG. 13A-B. Osteocalcin subcutaneous infusion decreases fat mass in wt mice. (FIG. 13A) Indicated doses of recombinant osteocalcin or PBS were infused subcutaneously for 28 days in wt mice. Body weight was recorded at indicated days. (FIG. 13B) Gonadal fat pad mass was measured after 28 days.

FIG. 21. A diagram showing the high degree of conserved amino acid sequence homology of osteocalcin among species. The sequence labeled "g" is SEQ ID NO:26; the sequence labeled "human" is SEQ ID NO:27; the sequence labeled "monkey" is SEQ ID NO:28; the sequence labeled "cow" is SEQ ID NO:29; the sequence labeled "sheep" is SEQ ID NO:30; the sequence labeled "bat" is SEQ ID NO:31; the sequence labeled "dog" is SEQ ID NO:32; the sequence labeled "cat" is SEQ ID NO:33; the sequence labeled "rabbit" is SEQ ID NO:34; the sequence labeled "wallaby" is SEQ ID NO:35; the sequence labeled "t" is SEQ ID NO:36; the sequence labeled "mouse" is SEQ ID NO:37; the sequence labeled "nopus" is SEQ ID NO:38; the sequence labeled "nu" is SEQ ID NO:39; the sequence labeled "chicken" is SEQ ID NO:40; the sequence labeled "rp" is SEQ ID NO:41; the sequence labeled "traodon" is SEQ ID NO:42; the sequence labeled "gu" is SEQ ID NO:43; the sequence labeled "egill" is SEQ ID NO:44; the sequence labeled "abream" is SEQ ID NO:45; the sequence labeled "swordfish" is SEQ ID NO:46.

(FIG. 22A) Targeting construct for conditional inactivation of Esp. White boxes, exons encoding the phosphatase domain of OST-PTP; grey triangles, LoxP sites; black bars, 5' and 3' external probes; S, Sac1; EV, EcoRV. (FIG. 22B) PCR genotyping of Esposb−/− mice. WT and floxed allele (Fl) yield 280-bp and 350-bp products, respectively. 1(I) collagen-Cre (1(I)-Cre)) transgenic mice (TG) harbor a transgene-specific band. (FIGS. 22C-D) Similar body weight gain (FIG. 22C) and linear growth (FIG. 22D) in WT and Esp−/− mice. P0, newborn; 1M, 1 month (FIG. 22E) Alizarin red/alcian blue staining of skeletons of newborn WT and Esp−/− mice. Mice were dissected, fixed in 95% ethanol, and stained in alcian blue and alizarin red as previously described (Ducy et al., 1996). There is no overt defect in mineralization that could explain the perinatal death of mutant pups. (FIG. 22F) Bone histomorphometry of 2 month-old WT and Esp−/− mice. BV/TV, bone volume per Total tissue volume (%); N.ob/B.Pm, number of osteoblasts per bone perimeter (mm−1); Dpd/Creat. Relative levels of deoxypyridinolone crosslinks, a marker of bone resorption.

FIG. 23A-K. (FIGS. 23A-E) Comparison of 1 month-old WT and Esp−/− mice. Serum levels of C-peptide (FIG. 23A), serum Glucagon level (left) and glucagons content in pancreas (right) (FIG. 23B) and serum levels of IGF-1 (FIG. 23C), PYY (FIG. 23D), and amylin (FIG. 23E) in Esp−/− mice. (FIG. 23F) Ratio of muscle mass over body mass calculated by proton magnetic resonance spectroscopy (1H-MRS) in 10 week-old WT and Esp−/− mice. (FIG. 23G) Representative images of proton 1H-MRS of 10 week-old WT and Esp−/− mice. (FIG. 23H) Food intake per day in 1 month- and 3 month-old Esp−/− and WT mice. (FIG. 23I and J) Comparison of expression level by real time PCR (FIG. 23I) and of serum levels (FIG. 23J) of TNF-(left) and IL-6 (right) in 1 month-old Esp−/− and WT mice. (FIG. 23K) Serum leptin (left) and resistin (right) levels in 1 month-old Esp−/− and WT mice. In all panels data represent the means±SD of experiments. *, P<0.01 (t-test).

(FIGS. 25A-D) Analysis of Runx2 (FIG. 25A), Osteocalcin (FIG. 25B), adiponectin (FIG. 25C), and Leptin (FIG. 25D) expression by real time PCR in indicated cells 4 h after co-culture of osteoblasts with adipocytes or islets.

(FIG. 26A) In situ hybridization analysis of osteocalcin and Esp expression in pancreas of 18.5 dpc embryos. Neither gene is expressed in pancreas. Insulin expression was used as a positive control. Hematoxylin-eosin staining of adjacent sections was used to assess tissue integrity. (FIG. 26B) Real time PCR analysis of osteocalcin expression in osteoblasts, adipocytes, and pancreatic islets collected from 1 month-old WT mice. Osteocalcin is not expressed in adipocytes or islets.

(FIGS. 27A-B) Real-time PCR analysis of osteocalcin expression (FIG. 27A) and osteocalcin serum levels (FIG. 27B) in 1 month-old WT, Esp−/− and alpha1(I) Esp mice. (FIG. 27C) Analysis of the purity of bacterially produced osteocalcin by SDS-PAGE stained with Coomassie blue.

(FIG. 28A) Schematic representation of the transgene used to overexpress adiponectin (Adipo) in mice. (FIG. 28B) PCR genotyping of SAP-Adipo transgenic mice. (FIG. 28C) Adiponectin serum levels in 3 distinct SAP-Adipo transgenic lines at 1 month of age. (FIG. 28D) Fat pad mass in WT and SAP-Adipo transgenic mice at 3 month of age. (FIG. 28E) Serum insulin levels in WT and SAP-Adipo transgenic mice at 3 month of age. (FIG. 28F) Insulin tolerance test in WT and SAP-Adipo transgenic mice at 3 month of age.

(FIGS. 29A-B) Blood glucose levels after fasting (FIG. 29A) or random feeding (FIG. 29B) in SAP-insulin transgenic and wt mice. (FIG. 29C) Serum levels of triglycerides in WT and SAP-insulin transgenic mice. (FIG. 29D) Serum levels of free fatty acids in WT and SAP-insulin transgenic mice. (FIG. 29E) Fat pad mass in WT and SAP-insulin transgenic mice. (FIG. 29F) Glucose tolerance test in WT and SAP-insulin transgenic mice. (FIG. 29G) Food intake in WT and SAP-insulin transgenic mice.

DETAILED DESCRIPTION OF THE INVENTION

Figure 1I:
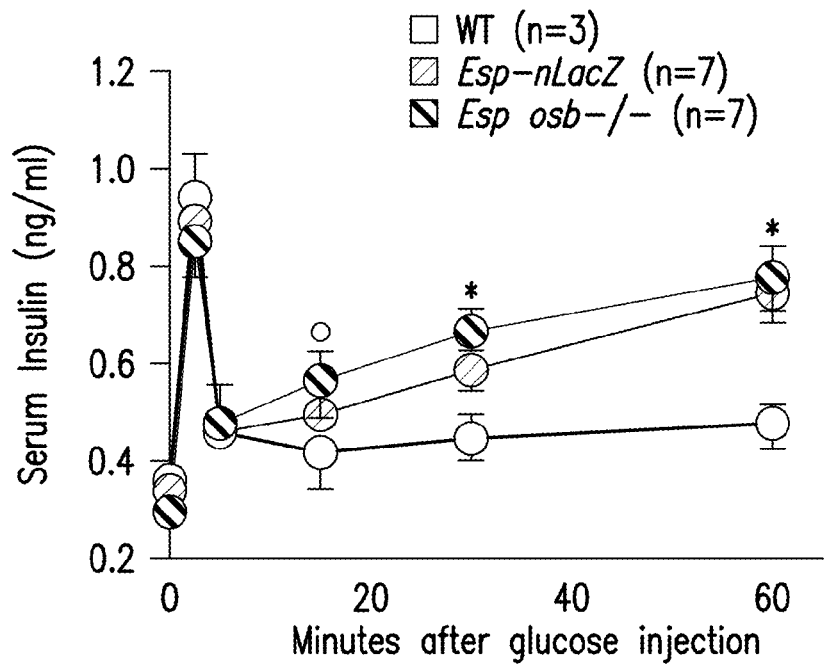

The present invention is based in part on the discovery that undercarboxylated/uncarboxylated osteocalcin secreted by osteoblasts in bone is responsible for regulating various aspects of energy metabolism. For example, it increases pancreatic beta-cell proliferation, insulin secretion, insulin sensitivity, glucose tolerance, and serum adiponectin and decreases weight gain and fat mass. It also reduces the pathological effects of atherosclerosis. Therefore, certain aspects of the invention are directed to the therapeutic use of undercarboxylated/uncarboxylated osteocalcin, fragments and variants thereof, to treat or prevent metabolic syndrome, type 1 and type 2 diabetes, atherosclerosis and obesity.

The present invention is also based on the discovery that gamma-carboxylase carboxylates osteocalcin, thereby inactivating osteocalcin. Such inactivation of osteocalcin decreases pancreatic beta-cell proliferation, insulin secretion, insulin sensitivity, glucose tolerance, and serum adiponectin and increases weight gain and fat mass. It also increases the pathological effects of atherosclerosis. Therefore, certain aspects of the invention are directed to the therapeutic use of agents that inhibit the activity of gamma-carboxylase, to treat or prevent metabolic syndrome, type 1 and type 2 diabetes, atherosclerosis and obesity.

The present invention is further based on the discovery that OST-PTP activates gamma-carboxylase through dephosphorylation. As indicated above, activation of gamma-carboxylase leads to inactivation of osteocalcin. Such inactivation of osteocalcin decreases pancreatic beta-cell proliferation, insulin secretion, insulin sensitivity, glucose tolerance, and serum adiponectin and increases weight gain and fat mass. It also it increases the pathological effects of atherosclerosis. Therefore certain aspects of the invention are directed to the therapeutic use of agents that inhibit the activity of OST-PTP, to treat or prevent metabolic syndrome, type 1 and type 2 diabetes, atherosclerosis and obesity.

The present invention is also based on the discovery that undercarboxylated/uncarboxylated osteocalcin increases the level of adiponectin expression, resulting in increased insulin sensitivity, glucose tolerance, and decreased weight gain and fat mass. It also reduces the pathological effects of atherosclerosis. Therefore, certain aspects of the invention are directed to the therapeutic use of undercarboxylated/ uncarboxylated osteocalcin to regulate the expression of adiponectin, to treat or prevent metabolic syndrome, type 1 and type 2 diabetes, atherosclerosis and obesity.

The present invention thus relates to methods and compositions for treating and diagnosing disorders related to the OST-PTP signaling pathway involving gamma-carboxylase, osteocalcin and adiponectin. Such disorders include, but are not limited to, metabolic syndrome, glucose intolerance, diabetes types 1 and 2, atherosclerosis and obesity. The invention is based on the discovery that OST-PTP dephosphorylates gamma-carboxylase, thereby leading to activation of gamma-carboxylase. Activation of gamma-carboxylase results in carboxylation of osteocalcin, which, as demonstrated herein, leads to symptoms associated with metabolic syndrome, diabetes types 1 and 2, atherosclerosis and obesity.

Other aspects of the invention are directed to diagnostic methods based on detection of decreased levels of undercarboxylated/uncarboxylated osteocalcin, which is found to be associated with metabolic syndrome, type 1 and type 2 diabetes, atherosclerosis and obesity. In one aspect, the method of diagnosing a disease, including metabolic syndrome, diabetes types 1 and 2, atherosclerosis and obesity, in a patient comprises (i) determining a patient level of undercarboxylated/uncarboxylated osteocalcin in a biological sample taken from the patient (ii) comparing the patient level of undercarboxylated/uncarboxylated osteocalcin and a control level of undercarboxylated/uncarboxylated osteocalcin, and (iii) if the patient level is significantly lower than the control level, then the patient is diagnosed as having, or being at risk for, the disease, including metabolic syndrome, diabetes types 1 and 2, atherosclerosis and obesity.

Other aspects of the invention are directed to diagnostic methods based on detection of decreased ratios of undercarboxylated/uncarboxylated vs carboxylated osteocalcin. Such ratios are found to be associated with metabolic syndrome, type 1 and type 2 diabetes, atherosclerosis and obesity. In one aspect, the method of diagnosing a disease, including metabolic syndrome, diabetes types 1 and 2, atherosclerosis and obesity, in a patient comprises (i) determining a patient ratio of undercarboxylated/uncarboxylated vs carboxylated osteocalcin in a biological sample taken from the patient (ii) comparing the patient ratio of undercarboxylated/uncarboxylated vs carboxylated osteocalcin and a control ratio of undercarboxylated/uncarboxylated vs carboxylated osteocalcin, and (iii) if the patient ratio is significantly lower than the control ratio, then the patient is diagnosed has having, or being at risk for, the disease, including metabolic syndrome, diabetes types 1 and 2, atherosclerosis and obesity.

Other aspects of the invention are directed to methods for diagnosing a patient at risk of developing a disease, including metabolic syndrome, glucose intolerance, impaired pancreatic beta-cell proliferation, impaired insulin secretion, impaired insulin sensitivity, atherosclerosis and obesity, by determining the patient level of, or level of activity of, OST-PTP and/or gamma-carboxylase, wherein increases in said levels, as compared to controls, indicates a patient is at risk of developing the disease.

Pharmaceutical Compositions of the Invention

The present invention provides pharmaceutical compositions comprising an agent for modulating the OST-PTP signaling pathway, which as disclosed herein involves gamma-carboxylase and osteocalcin, or for treating or preventing disorders related to the OST-PTP signaling pathway. In particular embodiments, the agent inhibits OST-PTP phosphorylase activity, reduces gamma-carboxylase activity, and/or increases undercarboxylated/uncarboxylated osteocalcin. In particular embodiments, the agent decarboxylates osteocalcin. The agent may be selected from the group consisting of small molecules, polypeptides, antibodies, and nucleic acids. The pharmaceutical compositions of the invention provide an amount of the agent effective to treat or prevent a disorder associated with the OST-PTP signaling pathway. In certain embodiments, a pharmaceutical composition provides an amount of the agent effective to treat or prevent metabolic syndrome or a component thereof, diabetes type 1, diabetes type 2, atherosclerosis, or obesity in a subject. In other embodiments, the composition provides an amount of the agent effective to treat or prevent a disease characterized by decreased insulin production, decreased insulin sensitivity, and decreased glucose tolerance or increased fat mass The pharmaceutical compositions of the invention may function to increase serum osteocalcin levels (preferably undercarboxylated or uncarboxylated osteocalcin), serum adiponectin levels and/or serum insulin levels. The pharmaceutical compositions may also increase glucose tolerance, increase insulin sensitivity, and/or increase pancreatic beta-cell proliferation. Other beneficial effects may include a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, a decrease in the thickness of arterial plaque, a reduction in clinical events such as heart attack, angina, or stroke, and a decrease in hypertension.

In particular embodiments of the invention, therapeutic agents that may be administered include undercarboxylated osteocalcin; uncarboxylated osteocalcin; or inhibitors that reduce the expression or activity of gamma-carboxylase or OST-PTP (e.g., antibodies, small molecules, antisense nucleic acids or siRNA). The pharmaceutical agents may also include agents that decarboxylate osteocalcin.

The therapeutic agents are generally administered in an amount sufficient to treat or prevent metabolic syndrome, obesity, diabetes type 1 and 2 and atherosclerosis in a subject. The therapeutic agents may also be administered to reduce fat mass in a subject.

Biologically active fragments or variants of the therapeutic agents are also within the scope of the present invention. By "biologically active" is meant capable of modulating the OST-PTP signaling pathway involving gamma-carboxylase, osteocalcin and adiponectin. As described herein, "biologically active" means reducing the expression of OST-PTP or its ability to dephosphorylate gamma-carboxylase and reducing the expression of gamma-carboxylase or its ability to carboxylate osteocalcin, or decarboxylating carboxylated osteocalcin thereby leading to increased levels of undercarboxylated/uncarboxylated osteocalcin, insulin and adiponectin. "Biologically active" also means capable of causing at least one effect selected from the group consisting of increasing pancreatic beta-cell proliferation, increasing insulin secretion, increasing insulin sensitivity, increasing glucose tolerance, decreasing weight gain, decreasing fat mass, weight loss, increasing serum adiponectin, a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, a decrease in the thickness of arterial plaque, a reduction in clinical events such as heart attack, angina, or stroke, and a decrease in hypertension. Fragments and variants are described below. The screens or assays described below may be used to identify, or assay, biologically active fragments and variants of the therapeutic agents of the invention, as well as other agents.

Compositions Comprising Undercarboxylated Osteocalcin

In a specific embodiment of the invention, pharmaceutical compositions comprising osteocalcin, particularly undercarboxylated or uncarboxylated osteocalcin, are provided.

Osteocalcin, one of the very few osteoblast-specific proteins, has several features of a hormone. For instance, it is synthesized as a pre-pro-molecule and is secreted in the general circulation (Hauschka et al., 1989; Price, 1989). Because of their exquisite cell-specific expression, the osteocalcin genes have been intensively studied to identify osteoblast-specific transcription factors and to define the molecular bases of bone physiology (Ducy et al., 2000b; Harada and Rodan, 2003).

Osteocalcin is the most abundant non-collagenous protein found associated with the mineralized bone matrix and it is currently being used as a biological marker for clinical assessment of bone turnover. Osteocalcin is a small (46-50 residue) bone specific protein that contains 3 gamma-carboxylated glutamic acid residues in its primary structure. The name osteocalcin (osteo, Greek for bone; Calc, Latin for lime salts; in, protein) derives from the protein's ability to bind $Ca^{2+}$ and its abundance in bone. Osteocalcin undergoes a peculiar post-translational modification whereby glutamic acid residues are carboxylated to form gamma-carboxyglutamic acid (Gla) residues; hence osteocalcin's other name, bone Gla protein (Hauschka et al., 1989). Gla residues usually confer on proteins high affinity for mineral ions, yet loss- and gain-of function experiments until now have failed to identify a function for osteocalcin in extracellular matrix mineralization in vivo (Ducy et al., 1996; Murshed et al., 2004).

Osteocalcin is a vitamin K-dependent calcium binding protein (Price et al. (1976) Proc. Natl. Acad. Sci. 73:3373-375). Mature human osteocalcin contains 49 amino acids with a predicted molecular mass of 5,800 kDa (Poser et al. (1980) The Journal of Biological Chemistry, Vol 255, No. 18, pp. 8685-8691). Osteocalcin is synthesized primarily by osteoblasts and ondontoblasts and comprises 15 to 20% of the non-collagenous protein of bone. Poser et al. (1980) J. Biol. Chem. 255:8685-8691 showed that mature osteocalcin contains three carboxyglutamic acid residues which are formed by post-translational vitamin K-dependent modification of glutamic acid residues. The carboxylated Gla residues are at positions 17, 21 and 24 of mouse and human mature osteocalcin. Some human osteocalcin has been shown to contain only 2 Gla residues. Poser, J. W. & Price, P. A. (1979) A Method for Decarboxylation of γ-Carboxyglutamic Acid in Proteins. J. Biol. Chem. 254, 431-436.

The conformation of decarboxylated (or uncarboxylated or undercarboxylated) osteocalcin lies somewhere between the random coil and helical form. Thus, in solution the peptide occurs as a flexible structure and a single conformation cannot be defined for it (Atkinson et al. Eur. J. Biochem. 1995; 232:515-21). Peptide bonds between arginine residues 19 and 20 and between residues 43 and 44 are susceptible to tryptic hydrolysis, leading to peptides 1-19, 20-43, 45-49, 1-43, and 20-49 which may be the main products of human osteocalcin breakdown in the circulation (Farrugia and Melick, Calcif Tissue Int 1986; 39:234-8, Hellman et al. J Bone Miner Res 1996; 11:1165-75 and Garnero et al. J Bone Miner Res 1994; 9:255-4).

Conformational study of osteocalcin by circular dichroism (CD) has shown the existence of alpha-helical conformation in osteocalcin and that addition of $Ca^{2+}$ induces higher helical content. Two-dimensional nuclear magnetic resonance (NMR) studies of osteocalcin in solution, while structurally inconclusive, revealed that the calcium-free protein was effectively unstructured except for the turn required by the disulfide bridge between Cys23 and Cys29. All the proline residues (Hyp9, Pro11, Pro13, Pro15, and Pro27) were in the trans conformation. Beta-turns are present in the region of Tyr12, Asp14 and Asn26. The hydrophobic core of the molecule is composed of the side chains of Leu2, Leu32, Val36 and Tyr42. The calcium-induced helix is extremely rigid due to, in part, the hydrophobic stabilization of the helical domain by the C-terminal domain.

Osteocalcin in solution binds $Ca^{2+}$ with a dissociation constant ranging from 0.5 to 3 mM, with a stoichiometry of between 2 and 5 mol $Ca^{2+}$/mol protein, and to hydroxyapatite (Kd. approximately equal to $10^{-7}$ M). It appears that the Gla residues in osteocalcin are important for its affinity toward $Ca^{2+}$. Binding of $Ca^{2+}$ induces normal osteocalcin to adopt the alpha-helical conformation; however, thermally decarboxylated osteocalcin showed higher alpha-helical content than normal osteocalcin and the calcium induced alpha-helical formation was lost. Decarboxylated osteocalcin also lost its specific binding to hydroxyapatite, which is consistent with the results showing that uncarboxylated osteocalcin is the secreted bone hormone. When bound to hydroxyapatite, the Gla residues are protected from thermal decarboxylation. Furthermore, osteocalcin synthesized in animals treated with warfarin, which inhibits the formation of Gla, failed to bind to bone. Furthermore, hydroxyapatite competition studies demonstrated that prothrombin (10 Gla/molecule) and decarboxylated osteocalcin fail to compete with $^{125}$I-labeled osteocalcin bound to hydroxyapatite. Combining all the information discussed above, a structural model has been constructed. This model consists of two antiparallel alpha-helical domains. The Gla residues are spaced about 5.4 angstroms apart on one of the helices, which is similar to the interatomic lattice spacing of $Ca^{2+}$ in the x-y plane of hydroxyapatite. It was therefore predicted that the Gla residues in osteocalcin bind to the (001) plane of the hydroxyapatite lattice.

"Osteocalcin" also known as Bone Gla Protein or BGP, refers to a small vitamin K-dependent calcium binding protein (Price et al. (1976) Proc. Natl. Acad. Sci. 73:3373-5) which is highly conserved among animal species. "Osteocalcin" includes both carboxylated, uncarboxylated and undercarboxylated forms as well as fragments and variants thereof as described herein.

"Undercarboxylated osteocalcin" means osteocalcin in which one or more of the Glu residues at positions Glu17, Glu21 and Glu24 of the amino acid sequence of the mature human osteocalcin having 49 amino acids, or at the positions corresponding to Glu17, Glu21 and Glu24 in other forms of osteocalcin, are not carboxylated. Undercarboxylated osteocalcin includes uncarboxylated osteocalcin, i.e., osteocalcin in which all three of the glutamic acid residues at positions 17, 21, and 24 are not carboxylated. Recombinant osteocalcin expressed in bacteria is uncarboxylated because bacteria do not have gamma-carboxylase. Preparations of osteocalcin are considered to be "undercarboxylated osteocalcin" if more than about 10% of the total Glu residues at positions Glu17, Glu21 and Glu24 (taken together) in mature osteocalcin (or the corresponding Glu residues in other forms) of the preparation are not carboxylated. In particular preparations of undercarboxylated osteocalcin, more than about 20%, 30%, 40%, 50%, 60%, 70%, 80%, 90%, 95%, or 100% of the total Glu residues at positions Glu17, Glu21 and Glu24 in mature osteocalcin (or the corresponding Glu residues in other forms) of the preparation are not carboxylated. In particularly preferred embodiments, essentially all of the Glu residues at positions Glu17, Glu21 and Glu24 in mature osteocalcin (or the corresponding Glu residues in other forms) of the preparation are not carboxylated.

Human osteocalcin cDNA (SEQ ID NO:1) encodes a mature osteocalcin protein represented by the last 49 amino acids of SEQ ID NO:2 (i.e., positions 52-100) with a predicted molecular mass of 5,800 kDa (Poser et al., (1980) The Journal of Biological Chemistry, Vol 255, No. 18, pp. 8685-8691). SEQ ID NO:2 is the pre-pro-sequence of human osteocalcin and mature human osteocalcin is the processed product of SEQ ID NO:2. In this application, the amino acid positions of mature human osteocalcin are referred to. It will be understood that the amino acid positions of mature human osteocalcin correspond to those of SEQ ID NO:2 as follows: position 1 of mature human osteocalcin corresponds to position 52 of SEQ ID NO:2; position 2 of mature human osteocalcin corresponds to position 53 of SEQ ID NO:2, etc. In particular, positions 17, 21, and 24 of mature human osteocalcin correspond to positions 68, 72, and 75, respectively, of SEQ ID NO:2.

When positions in two amino acid sequences correspond, it is meant that the two positions align with each other when the two amino acid sequences are aligned with one another to provide maximum homology between them. This same concept of correspondence also applies to nucleic acids.

For example, in the two amino acid sequences AGLYST-VLMGRPS and GLVSTVLMGN, positions 2-11 of the first sequence correspond to positions 1-10 of the second sequence, respectively. Thus, position 2 of the first sequence corresponds to position 1 of the second sequence; position 4 of the first sequence corresponds to position 3 of the second sequence; etc. It should be noted that a position in one sequence may correspond to a position in another sequence, even if the positions in the two sequence are not occupied by the same amino acid.

Osteocalcin is synthesized primarily by osteoblasts and ondontoblasts. "Osteocalcin" includes the mature protein and further includes biologically active fragments derived from full-length osteocalcin (SEQ ID NO:2) or the mature protein, including various domains, as well as variants as described herein.

In an embodiment of the invention, the pharmaceutical compositions of the invention comprise a mammalian uncarboxylated osteocalcin. In a preferred embodiment of the invention, the compositions of the invention comprise human osteocalcin having the amino acid sequence of SEQ ID NO:2, or portions thereof, and encoded for by the nucleic acid of SEQ ID NO:1, or portions thereof, or the compositions of the invention may comprise one or more of the human osteocalcin fragments described herein.

In a specific embodiment, the present invention provides pharmaceutical compositions comprising human undercarboxylated osteocalcin which does not contain a carboxylated glutamic acid at one or more of positions corresponding to positions 17, 21 and 24 of mature human osteocalcin. A preferred form of osteocalcin for use in the present invention is mature human osteocalcin wherein at least one of the glutamic acid residues at positions 17, 21, and 24 is not carboxylated. Preferably, all three of the glutamic acid residues at positions 17, 21, and 24 are not carboxylated. The amino acid sequence of mature human osteocalcin is shown in SEQ. ID. NO: 25.

The invention also includes the use of polypeptide fragments of osteocalcin. Fragments can be derived from the full-length, naturally occurring amino acid sequence of osteocalcin (e.g., SEQ. ID. NO:2). Fragments may also be derived from mature osteocalcin. The invention also encompasses fragments of the variants of osteocalcin described herein. A fragment can comprise an amino acid sequence of any length that is biologically active.

Preferred fragments of osteocalcin include fragments containing Glu17, Glu21 and Glu24 of the mature protein. Also preferred are fragments of the mature protein missing the last 10 amino acids from the C-terminal end of the mature protein. Also preferred are fragments missing the first 10 amino acids from the N-terminal end of the mature protein. Also preferred is a fragment of the mature protein missing both the last 10 amino acids from the C-terminal end and the first 10 amino acids from the N-terminal end. Such a fragment comprises amino acids 62-90 of SEQ ID NO:2.

Other preferred fragments of osteocalcin for the pharmaceutical compositions of the invention described herein include polypeptides comprising, consisting of, or consisting essentially of, the following sequences of amino acids:
positions 1-19 of mature human osteocalcin
positions 20-43 of mature human osteocalcin
positions 20-49 of mature human osteocalcin
positions 1-43 of mature human osteocalcin
positions 1-42 of mature human osteocalcin
positions 1-41 of mature human osteocalcin
positions 1-40 of mature human osteocalcin
positions 1-39 of mature human osteocalcin
positions 1-38 of mature human osteocalcin
positions 1-37 of mature human osteocalcin
positions 1-36 of mature human osteocalcin
positions 1-35 of mature human osteocalcin
positions 1-34 of mature human osteocalcin
positions 1-33 of mature human osteocalcin
positions 1-32 of mature human osteocalcin
positions 1-31 of mature human osteocalcin
positions 1-30 of mature human osteocalcin
positions 1-29 of mature human osteocalcin
positions 2-49 of mature human osteocalcin
positions 2-45 of mature human osteocalcin
positions 2-40 of mature human osteocalcin
positions 2-35 of mature human osteocalcin
positions 2-30 of mature human osteocalcin
positions 2-25 of mature human osteocalcin
positions 2-20 of mature human osteocalcin
positions 4-49 of mature human osteocalcin
positions 4-45 of mature human osteocalcin
positions 4-40 of mature human osteocalcin
positions 4-35 of mature human osteocalcin
positions 4-30 of mature human osteocalcin
positions 4-25 of mature human osteocalcin
positions 4-20 of mature human osteocalcin
positions 8-49 of mature human osteocalcin
positions 8-45 of mature human osteocalcin
positions 8-40 of mature human osteocalcin
positions 8-35 of mature human osteocalcin
positions 8-30 of mature human osteocalcin
positions 8-25 of mature human osteocalcin
positions 8-20 of mature human osteocalcin
positions 10-49 of mature human osteocalcin
positions 10-45 of mature human osteocalcin
positions 10-40 of mature human osteocalcin positions 10-35 of mature human osteocalcin
positions 10-30 of mature human osteocalcin
positions 10-25 of mature human osteocalcin
positions 10-20 of mature human osteocalcin
positions 7-30 of mature human osteocalcin
positions 7-25 of mature human osteocalcin
positions 7-23 of mature human osteocalcin
positions 7-21 of mature human osteocalcin
positions 7-19 of mature human osteocalcin
positions 7-17 of mature human osteocalcin
positions 8-30 of mature human osteocalcin
positions 8-25 of mature human osteocalcin
positions 8-23 of mature human osteocalcin
positions 8-21 of mature human osteocalcin
positions 8-19 of mature human osteocalcin
positions 8-17 of mature human osteocalcin
positions 9-30 of mature human osteocalcin
positions 9-25 of mature human osteocalcin
positions 9-23 of mature human osteocalcin
positions 9-21 of mature human osteocalcin
positions 9-19 of mature human osteocalcin
positions 9-17 of mature human osteocalcin Especially preferred is a fragment comprising positions 1-36 of mature human osteocalcin. Another preferred fragment is a fragment comprising positions 20-49 of mature human osteocalcin. Other fragments can be designed to contain Pro13 to Tyr76 or Pro 13 to Asn26 of mature human osteocalcin. Additionally, fragments containing the cysteine residues at positions 23 and 29 of mature human osteocalcin, and capable of forming a disulfide bond between those two cysteines, are useful.

Fragments can be discrete (not fused to other amino acids or polypeptides) or can be within a larger polypeptide. Further, several fragments can be comprised within a single larger polypeptide. In one embodiment, a fragment designed for expression in a host can have heterologous pre- and pro-polypeptide regions fused to the amino terminus of the osteocalcin fragment and/or an additional region fused to the carboxyl terminus of the fragment.

Also provided for use in the compositions and methods of the present invention are variants of the osteocalcin and osteocalcin fragments described above.

"Variants" refers to osteocalcin peptides that contain modifications in their amino acid sequences such as one or more amino acid substitutions, additions, deletions and/or insertions but that are still biologically active. In some instances, the antigenic and/or immunogenic properties of the variants are not substantially altered, relative to the corresponding peptide from which the variant was derived. Such modifications may be readily introduced using standard mutagenesis techniques, such as oligonucleotide directed site-specific mutagenesis as taught, for example, by Adelman et al. (DNA, 2:183, 1983) or by chemical synthesis. Variants and fragments are not mutally exclusive terms. Fragments also include peptides that may contain one or more amino acid substitutions, additions, deletions and/or insertions such that the fragments are still biologically active.

One particular type of variant that is within the scope of the present invention is a variant in which one of more of the positions corresponding to positions 17, 21 and 24 of mature human osteocalcin is occupied by an amino acid that is not glutamic acid. In some embodiments, the amino acid that is not glutamic acid is also not aspartic acid. Such variants are versions of undercarboxylated osteocalcin because at least one of the three positions corresponding to positions 17, 21 and 24 of mature human osteocalcin is not carboxylated glutamic acid, since at least one of those positions is not occupied by glutamic acid.

In particular embodiments, the present invention provides osteocalcin variants comprising the amino acid sequence (SEQ. ID. NO: 23)
YLYQWLGAPV PYPDPLX$_1$PRR X$_2$VCX$_3$LNPDCD ELADHIGFQE

AYRRFYGPV wherein
X$_1$, X$_2$ and X$_3$ are each independently selected from an amino acid or amino acid analog, with the proviso that if X$_1$, X$_2$ and X$_3$ are each glutamic acid, then X$_1$ is not carboxylated, or less than 50 percent of X$_2$ is carboxylated, and/or less than 50 percent of X$_3$ is carboxylated.

In certain embodiments, the osteocalcin variants comprise an amino acid sequence that is different from SEQ. ID. NO: 23 at 1 to 7 positions other than X$_1$, X$_2$ and X$_3$.

In other embodiments, the osteocalcin variants comprise an amino acid sequence that includes one or more amide backbone substitutions.

Fully functional variants typically contain only conservative variation or variation in non-critical residues or in non-critical regions. Functional variants can also contain substitutions of similar amino acids, which results in no change, or an insignificant change, in function. Alternatively, such substitutions may positively or negatively affect function to some degree. The activity of such functional osteocalcin variants can be determined using assays such as those described herein.

Variants can be naturally-occurring or can be made by recombinant means, or chemical synthesis, to provide useful and novel characteristics for undercarboxylated/uncarboxylated osteocalcin. For example, the variant osteocalcin polypeptides may have reduced immunogenicity, increased serum half-life, increase bioavailability and/or increased potency. In particular embodiments, serum half-life is increased by substituting one or more of the native Arg residues at positions 19, 20, 43, and 44 of mature osteocalcin with another amino acid or an amino acid analog, e.g., β-dimethyl-arginine. Such substitutions can be combined with the other changes in the native amino acid sequence of osteocalcin described herein.

Provided for use in the pharmaceutical compositions and methods of the present invention are variants that are also derivatives of the osteocalcin and osteocalcin fragments described above. Derivatization is a technique used in chemistry which transforms a chemical compound into a product of similar chemical structure, called derivative. Generally, a specific functional group of the compound participates in the derivatization reaction and transforms the educt to a derivate of deviating reactivity, solubility, boiling point, melting point, aggregate state, functional activity, or chemical composition. Resulting new chemical properties can be used for quantification or separation of the educt or can be used to optimize the compound as a therapeutic agent. The well-known techniques for derivatization can be applied to the above-described osteocalcin and osteocalcin fragments. Thus, derivatives of the osteocalcin and osteocalcin fragments described above will contain amino acids that have been chemically modified in some way so that they differ from the natural amino acids.

Provided also are osteocalcin mimetics. "Mimetic" refers to a synthetic chemical compound that has substantially the same structural and functional characteristics of a naturally or non-naturally occurring polypeptide, and includes, for instance, polypeptide- and polynucleotide-like polymers having modified backbones, side chains, and/or bases. Peptide mimetics are commonly used in the pharmaceutical industry as non-peptide drugs with properties analogous to those of the template peptide. Generally, mimetics are structurally similar (i.e., have the same shape) to a paradigm polypeptide that has a biological or pharmacological activity, but one or more polypeptide linkages are replaced. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

By way of example, example, Cho et al., 1993, Science 261:1303-5 discloses an "unnatural biopolymer" consisting of chiral aminocarbonate monomers substituted with a variety of side chains, synthesis of a library of such polymers, and screening for binding affinity to a monoclonal antibody. Similarly, Cho et al, 1998, J. Am. Chem. Soc. discloses libraries of linear and cyclic oligocarbamate libraries and screening for binding to the integrin GPIIb/IIIa. Simon et al., Proc. Natl. Acad. Sci. 89:9367-71 discloses a polymer consisting of N-substituted glycines ("peptoids") with diverse side chains. Schumacher et al, 1996, Science 271: 1854-7 discloses D-peptide ligands specific for Src homology domain 3 (SH3 domain) by screening phage libraries of L-peptides against a proteins (SH3) synthesized with D-amino acids and then synthesizing a selected L-peptide using D-amino acids. Brody et al., 1999, Mol. Diagn. 4: 381-8 describes generation and screening of hundreds to thousands of aptamers.

A particular type of osteocalcin variant within the scope of the invention is an osteocalcin mimetic in which one or more backbone amides is replaced by a different chemical structure or in which one or more amino acids are replaced by an amino acid analog. In a particular embodiment, the osteocalcin mimetic is a retroenantiomer of uncarboxylated human osteocalcin.

Osteocalcin, as well as its fragments and variants, is optionally produced by chemical synthesis or recombinant methods and may be produced as a modified osteocalcin molecule (i.e., osteocalcin fragments or variants) as described herein. Osteocalcin polypeptides can be produced by any conventional means (Houghten, R. A. (1985) Proc. Natl. Acad. Sci. USA 82:5131-5135). Simultaneous multiple peptide synthesis is described in U.S. Pat. No. 4,631,211 and can also be used. When produced recombinantly, osteocalcin may be produced as a fusion protein, e.g., a GST-osteocalcin fusion protein.

Undercarboxylated/uncarboxylated osteocalcin molecules that fall within the scope of the invention include proteins substantially homologous to human osteocalcin including proteins derived from another organism, i.e., an ortholog. One particular ortholog is mouse osteocalcin. Mouse osteocalcin gene 1 cDNA is SEQ ID NO:3; mouse osteocalcin gene 2 cDNA is SEQ ID NO:4; the amino acid sequence of mouse osteocalcin gene 1 and gene 2 is SEQ ID NO:5.

As used herein, two proteins are substantially homologous, or identical, when their amino acid sequences are at least about 70-75%, typically at least about 80-85%, and most typically at least about 90-95%, 97%, 98% or 99% or more homologous. "Homology" between two amino acid sequences or nucleic acid sequences can be determined by using the alogorithms disclosed herein. These algorithms can also be used to determine percent identity between two amino acid sequences or nucleic acid sequences.

In a specific embodiment of the invention, the undercarboxylated/uncarboxylated osteocalcin is a osteocalcin molecule sharing at least 80% homology with the human osteocalcin of SEQ ID:2 or a portion of SEQ ID:2 that is at least 8 amino acids long. In another embodiment of the invention, the undercarboxylated/uncarboxylated osteocalcin is a osteocalcin molecule sharing at least 80% amino acid sequence identity with the human osteocalcin of SEQ ID:2 or a portion of SEQ ID:2 that is at least 8 amino acids long. Homologous sequences include those sequences that are substantially identical. In preferred embodiments, the homology or identity is over the entire length of mature human osteocalcin.

To determine the percent homology or percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). Preferably, the length of a reference sequence aligned for comparison purposes is at least 30%, preferably at least 40%, more preferably at least 50%, even more preferably at least 60%, and even more preferably at least 70%, 80%, or 90% or more of the length of the sequence that the reference sequence is compared to. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but which have sufficient similarity so as to perform one or more of the same functions performed by undercarboxylated/uncarboxylated osteocalcin. Similarity is determined by considering conserved amino acid substitutions. Such substitutions are those that substitute a given amino acid in a polypeptide by another amino acid of like characteristics. Conservative substitutions are likely to be phenotypically silent. Guidance concerning which amino acid changes are likely to be phenotypically silent is found in Bowie et al., Science 247:1306-1310 (1990).

Examples of conservative substitutions are the replacements, one for another, among the hydrophobic amino acids Ala, Val, Leu, and Ile; interchange of the hydroxyl residues Ser and Thr; exchange of the acidic residues Asp and Glu; substitution between the amide residues Asn and Gln; exchange of the basic residues Lys, His and Arg; replacements among the aromatic residues Phe, Trp and Tyr; exchange of the polar residues Gln and Asn; and exchange of the small residues Ala, Ser, Thr, Met, and Gly.

The comparison of sequences and determination of percent identity and homology between two osteocalcin polypeptides can be accomplished using a mathematical algorithm. For example, Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H G., eds., Humana Press, New Jersey, 1994; Sequence Analysis in Molecular Biology, van Heinje, G., Academic Press, 1987; and Sequence Analysis Primer, Gribskov, M. and Devereux, J., eds., M Stockton Press, New York, 1991. A non-limiting example of such a mathematical algorithm is described in Karlin et al. (1993) Proc. Natl. Acad. Sci. USA 90:5873-5877.

The percent identity or homology between two osteocalcin amino acid sequences may be determined using the Needleman et al. (1970) (.I Mol. Biol. 48:444-453) algorithm. Another non-limiting example of a mathematical algorithm that may be utilized for the comparison of sequences is the algorithm of Myers and Miller, CABIOS (1989).

A substantially homologous osteocalcin, according to the present invention, may also be a polypeptide encoded by a nucleic acid sequence capable of hybridizing to the human osteocalcin nucleic acid sequence under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encoding a functionally equivalent gene product; or under less stringent conditions, such as moderately stringent conditions, e.g., washing in 0.2×SSC/0.1% SDS at 42° C. (Ausubel et al., 1989 supra), yet which still encodes a biologically active undercarboxylated/uncarboxylated osteocalcin.

A substantially homologous osteocalcin, according to the present invention, may also be a polypeptide encoded by a nucleic acid sequence capable of hybridizing to a sequence having at least 70-75%, typically at least about 80-85%, and most typically at least about 90-95%, 97%, 98% or 99% identity to the human osteocalcin nucleic acid sequence, under stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encoding a functionally equivalent gene product; or under less stringent conditions, such as moderately stringent conditions, e.g., washing in 0.2×SSC/0.1% SDS at 42° C. (Ausubel et al., 1989 supra), yet which still encodes a biologically active undercarboxylated/uncarboxylated osteocalcin.

It will be understood that a biologically active fragment or variant of human osteocalcin may contain a different number of amino acids than native human osteocalcin. Accordingly, the position number of the amino acid residues corresponding to positions 17, 21 and 24 of mature human osteocalcin may differ in the fragment or variant. One skilled in the art would easily recognize such corresponding positions from a comparison of the amino acid sequence of the fragment or variant with the amino acid sequence of mature human osteocalcin.

Peptides corresponding to fusion proteins in which full length osteocalcin, mature osteocalcin, or an osteocalcin fragment or variant is fused to an unrelated protein or polypeptide are also within the scope of the invention and can be designed on the basis of the osteocalcin nucleotide and amino acid sequences disclosed herein. Such fusion proteins include fusions to an enzyme, fluorescent protein, or luminescent protein which provides a marker function. In a preferred embodiment of the invention, the fusion protein comprises fusion to a polypeptide capable of targeting the osteocalcin to a particular target cell or location in the body. For example, osteocalcin polypeptide sequences may be fused to a ligand molecule capable of targeting the fusion protein to a cell expressing the receptor for said ligand. Osteocalcin can also be made as part of a chimeric protein for drug screening or use in making recombinant protein. These comprise an osteocalcin peptide sequence operatively linked to a heterologous peptide having an amino acid sequence not substantially homologous to the osteocalcin. "Operatively linked" in this context indicates that the osteocalcin peptide and the heterologous peptide are fused in-frame. The heterologous peptide can be fused to the N-terminus or C-terminus of osteocalcin or can be internally located. In one embodiment, the fusion protein does not affect osteocalcin function. For example, the fusion protein can be a GST-fusion protein in which the osteocalcin sequences are fused to the N- or C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant osteocalcin. In certain host cells (e.g., mammalian host cells), expression and/or secretion of a protein can be increased by using a heterologous signal sequence. Therefore, the fusion protein may contain a heterologous signal sequence at its N-terminus.

EP-A 0 464 533 discloses fusion proteins comprising various portions of immunoglobulin constant regions (Fc regions). The Fc region is useful in therapy and diagnosis and thus results, for example, in improved pharmacokinetic properties (EP-A 0 232 262). In drug discovery, for example, human proteins have been fused with Fc regions for the purpose of high-throughput screening assays to identify antagonists (Bennett et al. (1995) J. Mol. Recog. 8:52-58 (1995) and Johanson et al. J. Biol. Chem. 270:9459-9471). Thus, various embodiments of this invention also utilize soluble fusion proteins containing an osteocalcin polypeptide and various portions of the constant regions of heavy or light chains of immunoglobulins of various subclasses (e.g., IgG, IgM, 1gA, IgE, 1gB). Preferred as immunoglobulin is the constant part of the heavy chain of human IgG, particularly IgG1, where fusion takes place at the hinge region. For some uses, it is desirable to remove the Fc region after the fusion protein has been used for its intended purpose, e.g., when the fusion protein is to be used as antigen for immunizations. In a particular embodiment, the Fc part can be removed in a simple way by a cleavage sequence, which is also incorporated and can be cleaved, e.g., with factor Xa.

A chimeric or fusion protein can be produced by standard recombinant DNA techniques. For example, DNA fragments coding for the different protein sequences can be ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) Current Protocols in Molecular Biology). Moreover, many expression vectors are commercially available that already encode a fusion moiety (e.g., a GST protein). An osteocalcin-encoding nucleic acid can be cloned into such an expression vector such that the fusion moiety is linked in-frame to osteocalcin.

Chimeric osteocalcin proteins can be produced in which one or more functional sites are derived from a different isoform, or from another osteocalcin molecule from another species. Sites also could be derived from osteocalcin-related proteins that occur in the mammalian genome but which have not yet been discovered or characterized.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described below.

Accordingly, the osteocalcin polypeptides of the present invention also encompass derivatives which contain a substituted amino acid residue that is not one encoded by the genetic code, in which a substituent group is included, in which the mature polypeptide is fused with another compound, such as a compound to increase the half-life of the polypeptide (for example, polyethylene glycol), or in which the additional amino acids are fused to the osteocalcin polypeptide, such as a leader or secretory sequence or a sequence for purification of the osteocalcin polypeptide or a pro-protein sequence.

Undercarboxylated/uncarboxylated osteocalcin can be modified according to known methods in medicinal chemistry to increase its stability, half-life, uptake or efficacy. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

In a specific embodiment of the invention, modifications may be made to the osteocalcin to reduce susceptibility to proteolysis at residue ARG43 as a means for increasing serum half life. Such modifications include, for example, the use of retroenantio isomers, D-amino acids, or other amino acid analogs.

Acylation of the N-terminal amino group can be accomplished using a hydrophilic compound, such as hydroorotic acid or the like, or by reaction with a suitable isocyanate, such as methylisocyanate or isopropylisocyanate, to create a urea moiety at the N-terminus. Other agents can also be N-terminally linked that will increase the duration of action of the osteocalcin derivative as known in this art.

Reductive amination is the process by which ammonia is condensed with aldehydes or ketones to form imines which are subsequently reduced to amines. Reductive amination is a useful method for conjugating undercarboxylated/uncarboxylated osteocalcin and its fragments or variants to PEG. Covalent linkage of poly(ethylene glycol) (PEG) to undercarboxylated/uncarboxylated osteocalcin and its fragments and variants may result in conjugates with increased water solubility, altered bioavailability, pharmacokinetics, immunogenic properties, and biological activities. See, e.g., Bentley et al., J. Pharm. Sci. 1998 November; 87(11):1446-9.

Several particularly common modifications that may be applied to undercarboxylated/uncarboxylated osteocalcin and its fragments and variants such as glycosylation, lipid attachment, sulfation, hydroxylation and ADP-ribosylation are described in most basic texts, such as Proteins—Structure and Molecular Properties, 2nd ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (1990) Meth. Enzymol. 182: 626-646) and Rattan et al. (1992) Ann. NY: Acad. Sci. 663:48-62.

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in the undercarboxylated/uncarboxylated osteocalcin and its fragments and variants, including the peptide backbone, the amino acid side-chains and the amino or carboxyl termini. Blockage of the amino or carboxyl group in a polypeptide, or both, by a covalent modification, is common in naturally-occurring and synthetic polypeptides and may be applied to the undercarboxylated/uncarboxylated osteocalcin or its fragments and variants of the present invention. For instance, the amino terminal residue of polypeptides made in E. coli, prior to proteolytic processing, almost invariably will be N-formylmethionine. Thus, undercarboxylated/uncarboxylated osteocalcin and its fragments and variants with N-formylmethionine as the amino terminal residue are within the scope of the present invention.

A brief description of various protein modifications that come within the scope of this invention are set forth in the table below:

TABLE 1

| Protein Modification | Description |
|---|---|
| Acetylation | Acetylation of N-terminus or ε-lysines. Introducing an acetyl group into a protein, specifically, the substitution of an acetyl group for an active hydrogen atom.<br>A reaction involving the replacement of the hydrogen atom of a hydroxyl group with an acetyl group ($CH_3CO$) yields a specific ester, the acetate. Acetic anhydride is commonly used as an acetylating agent, which reacts with free hydroxyl groups.<br>Acylation may facilitate addition of other functional groups.<br>A common reaction is acylation of e.g., conserved lysine residues with a biotin appendage. |

TABLE 1-continued

| Protein Modification | Description |
| --- | --- |
| ADP-ribosylation | Covalently linking proteins or other compounds via an arginine-specific reaction. |
| Alkylation | Alkylation is the transfer of an alkyl group from one molecule to another. The alkyl group may be transferred as an alkyl carbocation, a free radical or a carbanion (or their equivalents). Alkylation is accomplished by using certain functional groups such as alkyl electrophiles, alkyl nucleophiles or sometimes alkyl radicals or carbene acceptors. A common example is methylation (usually at a lysine or arginine residue). |
| Amidation | Reductive animation of the N-terminus. Methods for amidation of insulin are described in U.S. Pat. No. 4,489,159. |
| Carbamylation | Nigen et al. describes a method of carbamylating hemoglobin. |
| Citrullination | Citrullination involves the addition of citrulline amino acids to the arginine residues of a protein, which is catalyzed by peptidylarginine deaminase enzymes (PADs). This generally converts a positively charged arginine into a neutral citrulline residue, which may affect the hydrophobicity of the protein (and can lead to unfolding). |
| Condensation of amines with aspartate or glutamate | Such reactions, may be used, e.g., to attach a peptide to other proteins labels. |
| Covalent attachment of flavin | Flavin mononucleotide (FAD) may be covalently attached to serine and/or threonine residues. May be used, e.g., as a light-activated tag. |
| Covalent attachment of heme moiety | A heme moiety is generally a prosthetic group that consists of an iron atom contained in the center of a large heterocyclic organic ring, which is referred to as a porphyrin. The heme moiety may be used, e.g., as a tag for the peptide. |
| Attachment of a nucleotide or nucleotide derivative | May be used as a tag or as a basis for further derivatising a peptide. |
| Cross-linking | Cross-linking is a method of covalently joining two proteins. Cross-linkers contain reactive ends to specific functional groups (primary amines, sulfhydryls, etc.) on proteins or other molecules. Several chemical groups may be targets for reactions in proteins and peptides. For example, Ethylene glycol bis[succinimidylsuccinate, Bis[2-(succinimidooxycarbonyloxy)ethyl]sulfone, and Bis[sulfosuccinimidyl] suberate link amines to amines. |
| Cyclization | For example, cyclization of amino acids to create optimized delivery forms that are resistant to, e.g., aminopeptidases (e.g., formation of pyroglutamate, a cyclized form of glutamic acid). |
| Disulfide bond formation | Disulfide bonds in proteins are formed by thiol-disulfide exchange reactions, particularly between cysteine residues (e.g., formation of cystine). |
| Demethylation | See, e.g., U.S. Pat. No. 4,250,088 (Process for demethylating lignin). |
| Formylation | The addition of a formyl group to, e.g., the N-terminus of a protein. See, e.g., U.S. Pat. Nos. 4,059,589, 4,801,742, and 6,350,902. |
| Glycylation | The covalent linkage of one to more than 40 glycine residues to the tubulin C-terminal tail. |
| Glycosylation | Glycosylation may be used to add saccharides (or polysaccharides) to the hydroxy oxygen atoms of serine and threonine side chains (which is also known as O-linked Glycosylation). Glycosylation may also be used to add saccharides (or polysaccharides) to the amide nitrogen of asparagine side chains (which is also known as N-linked Glycosylation), e.g., via oligosaccharyl transferase. |
| GPI anchor formation | The addition of glycosylphosphatidylinositol to the C-terminus of a protein. GPI anchor formation involves the addition of a hydrophobic phosphatidylinositol group - linked through a carbohydrate containing linker (e.g., glucosamine and mannose linked to phosphoryl ethanolamine residue) - to the C-terminal amino acid of a protein. |

TABLE 1-continued

| Protein Modification | Description |
| --- | --- |
| Hydroxylation | Chemical process that introduces one or more hydroxyl groups (—OH) into a protein (or radical). Hydroxylation reactions are typically catalyzed by hydroxylases. Proline is the principal residue to be hydroxylated in proteins, which occurs at the $C^{\gamma}$ atom, forming hydroxyproline (Hyp). In some cases, proline may be hydroxylated at its $C^{\beta}$ atom. Lysine may also be hydroxylated on its $C^{\delta}$ atom, forming hydroxylysine (Hyl). These three reactions are catalyzed by large, multi-subunit enzymes known as prolyl 4-hydroxylase, prolyl 3-hydroxylase and lysyl 5-hydroxylase, respectively. These reactions require iron (as well as molecular oxygen and α-ketoglutarate) to carry out the oxidation, and use ascorbic acid to return the iron to its reduced state. |
| Iodination | See, e.g., U.S. Pat. No. 6,303,326 for a disclosure of an enzyme that is capable of iodinating proteins. U.S. Pat. No. 4,448,764 discloses, e.g., a reagent that may be used to iodinate proteins. |
| ISGylation | Covalently linking a peptide to the ISG15 (Interferon-Stimulated Gene 15) protein, for, e.g., modulating immune response. |
| Methylation | Reductive methylation of protein amino acids with formaldehyde and sodium cyanoborohydride has been shown to provide up to 25% yield of N-cyanomethyl (—CH$_2$CN) product. The addition of metal ions, such as Ni$^{2+}$, which complex with free cyanide ions, improves reductive methylation yields by suppressing by-product formation. The N-cyanomethyl group itself, produced in good yield when cyanide ion replaces cyanoborohydride, may have some value as a reversible modifier of amino groups in proteins. (Gidley et al.) Methylation may occur at the arginine and lysine residues of a protein, as well as the N- and C-terminus thereof. |
| Myristoylation | Myristoylation involves the covalent attachment of a myristoyl group (a derivative of myristic acid), via an amide bond, to the alpha-amino group of an N-terminal glycine residue. This addition is catalyzed by the N-myristoyltransferase enzyme. |
| Oxidation | Oxidation of cysteines. Oxidation of N-terminal Serine or Threonine residues (followed by hydrazine or aminooxy condensations). Oxidation of glycosylations (followed by hydrazine or aminooxy condensations). |
| Palmitoylation | Palmitoylation is the attachment of fatty acids, such as palmitic acid, to cysteine residues of proteins. Palmitoylation increases the hydrophobicity of a protein. |
| (Poly)glutamylation | Polyglutamylation occurs at the glutamate residues of a protein. Specifically, the gamma-carboxy group of a glutamate will form a peptide-like bond with the amino group of a free glutamate whose alpha-carboxy group may be extended into a polyglutamate chain. The glutamylation reaction is catalyzed by a glutamylase enzyme (or removed by a deglutamylase enzyme). Polyglutamylation has been carried out at the C-terminus of proteins to add up to about six glutamate residues. Using such a reaction, Tubulin and other proteins can be covalently linked to glutamic acid residues. |
| Phosphopantetheinylation | The addition of a 4'-phosphopantetheinyl group. |
| Phosphorylation | A process for phosphorylation of a protein or peptide by contacting a protein or peptide with phosphoric acid in the presence of a non-aqueous apolar organic solvent and contacting the resultant solution with a dehydrating agent is disclosed e.g., in U.S. Pat. No. 4,534,894. Insulin products are described to be amenable to this process. See, e.g., U.S. Pat. No. 4,534,894. Typically, phosphorylation occurs at the serine, threonine, and tyrosine residues of a protein. |
| Prenylation | Prenylation (or isoprenylation or lipidation) is the addition of hydrophobic molecules to a protein. Protein prenylation involves the transfer of either a farnesyl (linear grouping of three isoprene units) or a geranyl-geranyl moiety to C-terminal cysteine(s) of the target protein. |
| Proteolytic Processing | Processing, e.g., cleavage of a protein at a peptide bond. |
| Selenoylation | The exchange of, e.g., a sulfur atom in the peptide for selenium, using a selenium donor, such as selenophosphate. |

TABLE 1-continued

| Protein Modification | Description |
| --- | --- |
| Sulfation | Processes for sulfating hydroxyl moieties, particularly tertiary amines, are described in, e.g., U.S. Pat. No. 6,452,035. A process for sulphation of a protein or peptide by contacting the protein or peptide with sulphuric acid in the presence of a non-aqueous apolar organic solvent and contacting the resultant solution with a dehydrating agent is disclosed. Insulin products are described to be amenable to this process. See, e.g., U.S. Pat. No. 4,534,894. |
| SUMOylation | Covalently linking a peptide a SUMO (small ubiquitin-related Modifier) protein, for, e.g., stabilizing the peptide. |
| Transglutamination | Covalently linking other protein(s) or chemical groups (e.g., PEG) via a bridge at glutamine residues |
| tRNA-mediated addition of amino acids (e.g., arginylation) | For example, the site-specific modification (insertion) of an amino acid analog into a peptide. |
| Ubiquitination | The small peptide ubiquitin is covalently linked to, e.g., lysine residues of a protein. The ubiquitin-proteasome system can be used to carryout such reaction. See, e.g., U.S. 2007-0059731. |

To practice the methods of the invention, it may be desirable to recombinantly express the osteocalcin protein. The cDNA sequence and deduced amino acid sequence of human osteocalcin is represented in SEQ ID NO:1 and SEQ ID NO:2. Osteocalcin nucleotide sequences may be isolated using a variety of different methods known to those skilled in the art. For example, a cDNA library constructed using RNA from a tissue known to express osteocalcin can be screened using a labeled osteocalcin probe. Alternatively, a genomic library may be screened to derive nucleic acid molecules encoding the osteocalcin protein. Further, osteocalcin nucleic acid sequences may be derived by performing a polymerase chain reaction (PCR) using two oligonucleotide primers designed on the basis of known osteocalcin nucleotide sequences. The template for the reaction may be cDNA obtained by reverse transcription of mRNA prepared from cell lines or tissue known to express osteocalcin.

While the osteocalcin polypeptides and peptides can be chemically synthesized (e.g., see Creighton, 1983, Proteins: Structures and Molecular Principles, W.H. Freeman & Co., N.Y.), large polypeptides derived from osteocalcin and the full length osteocalcin itself may be advantageously produced by recombinant DNA technology using techniques well known in the art for expressing a nucleic acid. Such methods can be used to construct expression vectors containing the osteocalcin nucleotide sequences and appropriate transcriptional and translational control signals. These methods include, for example, in vitro recombinant DNA techniques, synthetic techniques, and in vivo genetic recombination. (See, for example, the techniques described in Sambrook et al., 1989, supra, and Ausubel et al., 1989, supra).

A variety of host-expression vector systems may be utilized to express the osteocalcin nucleotide sequences. In a preferred embodiment, the osteocalcin peptide or polypeptide is secreted and may be recovered from the culture media.

Appropriate expression systems can be chosen to ensure that the correct modification, processing and subcellular localization of the osteocalcin protein occurs. To this end, bacterial host cells are preferred for expression of osteocalcin, as such cells are unable to carboxylate osteocalcin.

The isolated osteocalcin can be purified from cells that naturally express it, e.g., osteoblasts, or purified from cells that naturally express it but have been modified to overproduce osteocalcin, e.g., purified from cells that have been altered to express it (recombinant), synthesized using known protein synthesis methods, or by modifying cells that naturally encode osteocalcin to express it. In a particular embodiment, a recombinant cell has been manipulated to activate expression of the endogenous osteocalcin gene. For example, WO 99/15650 and WO 00/49162 describe a method of expressing endogenous genes termed random activation of gene expression (RAGE), which can be used to activate or increase expression of endogenous osteocalcin. The RAGE methodology involves non-homologous recombination of a regulatory sequence to activate expression of a downstream endogenous gene. Alternatively, WO 94/12650, WO 95/31560, WO 96/29411, U.S. Pat. No. 5,733,761 and U.S. Pat. No. 6,270,985 describe a method of increasing expression of an endogenous gene that involves homologous recombination of a DNA construct that includes a targeting sequence, a regulatory sequence, an exon, and a splice-donor site. Upon homologous recombination, a downstream endogenous gene is expressed. The methods of expressing endogenous genes described in the forgoing patents are hereby expressly incorporated by reference.

Compositions Comprising Adiponectin and Undercarboxylated/Uncarboxylated Osteocalcin In a specific embodiment of the invention, pharmaceutical compositions comprising adiponectin and undercarboxylated/uncarboxylated osteocalcin or biologically active undercarboxylated/uncarboxylated osteocalcin fragments or variants may be administered to a patient in need of such administration. In an embodiment of the invention, the adiponectin is a mammalian adiponectin. In a preferred embodiment of the invention, the pharmaceutical compositions of the invention comprise human adiponectin. The cDNA sequence of human adiponectin is shown in SEQ ID NO:6. The amino acid sequence of human adiponectin is shown in SEQ ID NO:7.

In another aspect of the present invention, biologically active adiponectin fragments or variants together with undercarboxylated/uncarboxylated osteocalcin or biologically active undercarboxylated/uncarboxylated osteocalcin fragments in a pharmaceutical composition can be used in the treatment methods of the present invention. Adiponectin fragments or variants encompass the kinds of changes in the native sequence of adiponectin that are described above for osteocalcin and can be produced by the same methods that are described above for producing osteocalcin fragments and variants.

Compositions Comprising Inhibitors of Gamma-Carboxylase and/or OST-PTP

In another embodiment of the invention, the pharmaceutical compositions of the invention comprise an inhibitor that reduces the expression or activity of gamma-carboxylase or OST-PTP. Preferably, the biological activity of gamma-carboxylase or OST-PTP (as previously described) is inhibited. The inhibitors may be antibodies (monoclonal or polyclonal) or fragments of antibodies, small molecules, polypeptides or proteins, or nucleic acids (e.g., antisense DNA or RNA, siRNA).

In certain embodiments, the inhibitors reduce the activity of OST-PTP having the amino acid sequence of SEQ ID NO:19. In other embodiments, the inhibitors reduce the activity of an OST-PTP having an amino acid sequence that is substantially homologous or identical, as previously described to the amino acid sequence of SEQ ID NO:19.

In certain embodiments, the inhibitors reduce the activity of gamma-carboxylase having the amino acid sequence of SEQ ID NO:11. In other embodiments, the inhibitors reduce the activity of an gamma-carboxylase having an amino acid sequence that is substantially homologous or identical, as previously described to the amino acid sequence.

Small Molecule Inhibitors of OST-PTP and Gamma-Carboxylase

In certain embodiments, the agent is a small molecule. By "small molecule" is meant organic compounds of molecular weight of more than 100 and less than about 2,500 daltons, and preferably less than 500 daltons. Such small molecules inhibit the biological activity of OST-PTP or gamma-carboxylase.

The inhibitors may comprise agents that act as inhibitors of vitamin K, beta blockers, statins, and/or thiol-specific inhibitors that function to increase serum adiponectin, serum insulin and/or serum osteocalcin levels, preferably undercarboxylated/uncarboxylated osteocalcin. The agents may also increase glucose tolerance, increase insulin sensitivity, increase beta-cell proliferation, and/or cause other effects of biologically active agents as previously described.

Warfarin and other vitamin K inhibitors, including coumadin and other derivatives, beta-blockers, statins, and fragments and modifications thereof, may be administered to patients who would benefit from inhibition of gamma-carboxylase. In a specific embodiment of the invention, the small molecule warfarin may be used to inhibit the activity of gamma-carboxylase. Warfarin derivatives are exemplified by acenocoumarol, phenprocoumon and phenindione. Warfarin and other coumadin derivatives block vitamin K-dependent gamma-carboxylation, thus increasing the level of undercarboxylated/uncarboxylated osteocalcin.

Beta blockers are used to treat high blood pressure (hypertension), congestive heart failure (CHF), abnormal heart rhythms (arrhythmias), and chest pain (angina). Beta blockers are sometimes used in heart attack patients to prevent future heart attacks. There are 2 main beta receptors: beta 1 and beta 2. Some beta blockers are selective, which means that they block beta 1 receptors more than they block beta 2 receptors. Beta 1 receptors are responsible for heart rate and the strength of the heartbeat. Nonselective beta blockers block both beta 1 and beta 2 receptors. Beta 2 receptors are responsible for the function of smooth muscles; they are also the only beta receptors expressed by osteoblasts. Non-limiting examples of beta blockers include sotalol, timolol, esmolol, carteolol, carvedilol, nadolol, propranolol, betaxolol, penbutolol, metoprolol, labetalol, acebutolol, atenolol, metoprolol, labetalol, pindolol, and bisoprolol.

Statins are further exemplified by atorvastatin, cerivastatin, fluvastatin, lovastatin, mevastatin, pitavastatin, pravastatin, rosuvastatin, and simvastatin. Non-limiting examples of beta-blockers include sotalol, carvedilol, metroprolol. Other small molecules can be identified using the screens and assays disclosed herein.

Other inhibitors include thiol specific inhibitors of gamma-carboxylase. Cys and His residues of gamma carboxylase are implicated in the carboxylase mechanism of gamma carboxylase, and it is observed that the enzyme is inhibited by thiol-specific inhibitors, such as N-ethylmaleimide (NEM) and mercurials such as p-hydroxymurcuribenzoate (pHMB). Additional non-limiting examples of these inhibitors include 5,5-dithiobis-(2-nitrobenzoic acid) (DTNB), 2-nitro-5-thiocyanobenzoic acid (NTCB), iodoacetamide (IA), N-phenylmaleimide (PheM), N-(1-pyrenyl) maleimide (PyrM), naphthalene-1,5-dimaleimide (NDM), N,N'-(1,2-phenylene) dimaleimide (oPDM), N,N'-1,4-phenylene dimaleimide (pPDM), N,N'-1,3-phenylene dimaleimide (mPDM), 1,1-(methylenedi-4,1-phenylene)bismaleimide (BM), 4-(N-maleimido)phenyltrimethylammonium (MPTM), N,N'-bis(3-maleimidopropionyl)-2-hydroxy-1,3-propanediamine (BMP), N-succinimidyl 3-(2-pyridyldithio) propionate, diethyl pyrocarbonate, p-chloromercuribenzene sulphonic acid and thiosulfinates. These inhibitors may also be provided as conjugate or derivative, such as with, e.g., BSA or aminodextran.

Antibody Inhibitors of OST-PTP and Gamma-Carboxylase

The present invention also provides compositions comprising an antibody or antibodies, as well as biologically active fragments or variants thereof, that are capable of binding to an epitope of OST-PTP or gamma-carboxylase polypeptides. An antibody against OST-PTP that decreases its activity can be used therapeutically. In certain embodiments, the antibody against OST-PTP binds to the extracellular domain of OST-PTP.

In certain embodiments, the antibody against OST-PTP binds to an epitope in the mouse OST-PTP of SEQ ID NO:19 or an OST-PTP having an amino acid sequence that is substantially homologous or identical to SEQ ID NO:19. In other embodiments, the antibody against OST-PTP binds to an epitope in an OST-PTP having an amino acid sequence that is at least 70% homologous or identical to SEQ ID NO:19.

Human OST-PTP can be obtained by isolating the human ortholog of mouse OST-PTP (SEQ ID NO:18) (or rat OST-PTP; SEQ ID NO:24) by methods known in the art. For example, one could prepare a cDNA library from human osteoblasts and identify human OST-PTP cDNA by hybridizing the cDNA clones from the library to a mouse probe. The mouse probe could be based on a portion of mouse OST-PTP (SEQ ID NO:18). Alternatively, PCR, using primers based on the mouse sequence, can be used to obtain the human OST-PTP gene.

Gamma-carboxylase is an intracellular protein, so antibodies or fragments of antibodies against it are preferably used therapeutically when combined with technologies for delivering the antibodies, fragments or variants into the interior of target cells expressing gamma-carboxylase, e.g., osteoblasts. Antibodies, fragments or variants against gamma-carboxylase can also be used diagnostically or in drug screening assays. Antibodies or antibody fragments or variants against osteocalcin and adiponectin similarly can be used with technologies for delivering the antibodies or fragments into the interior of target cells and can also be used in diagnostics and drug screening assays.

In a particular embodiment, the present invention provides antibodies, fragments or variants of antibodies that recognize an epitope in OST-PTP that includes the amino acid at position 1316 of mouse OST-PTP or the corresponding position of human OST-PTP. In certain embodiments, these antibodies, fragments or variants of antibodies block or inhibit the ability of OST-PTP to activate gamma-carboxylase. In certain embodiments, use of these antibodies or fragments results in OST-PTP losing 50%, 60%, 70%, 80%, 90%, 95%, or essentially all of its ability to activate gamma-carboxylase.

The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids. The terms "antibody" and "antibodies" include polyclonal antibodies, monoclonal antibodies, humanized or chimeric antibodies, single chain Fv antibody fragments, Fab fragments, and F(ab')$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful in the present invention.

Antibody fragments that have specific binding affinity for the polypeptide of interest (e.g., OST-PTP or gamma-carboxylase) can be generated by known techniques. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. See, for example, Huse et al. (1989) Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Once produced, antibodies or fragments thereof can be tested for recognition of the target polypeptide by standard immunoassay methods including, for example, enzyme-linked immunosorbent assay (ELISA) or radioimmunoassay assay (RIA). See, Short Protocols in Molecular Biology eds. Ausubel et al., Green Publishing Associates and John Wiley & Sons (1992).

The immunoassays, immunohistochemistry, RIA, IRMAs used herein are based on the generation of various antibodies, including those that specifically bind to osteocalcin, OST-PTP, gamma-carboxylase, adiponectin, vitamin K, or their fragments or variants. Antibodies and methods of using antibodies to quantitate the amount of osteocalcin, in particular, in a sample are also described in Hosoda et al. (U.S. Pat. No. 5,681,707). Hosoda et al. disclose antibodies that bind to the N-terminal 20 amino acids, or the C-terminal 14 amino acids of osteocalcin. Anti-OST-PTP antibodies are commercially available.

In one embodiment, antibodies against OST-PTP or gamma-carboxylase that reduce its activity are useful in the treatment of a patient having a disorder related to the OST-PTP pathway. Such disorders include metabolic syndrome, glucose intolerance, diabetes types 1 and 2, atherosclerosis and obesity. Such disorders are characterized by decreased insulin production, decreased insulin sensitivity, decreased glucose tolerance and/or increased fat mass.

Nucleic Acid Inhibitors of OST-PTP and Gamma-Carboxylase

Other embodiments of the present invention are directed to the use of antisense nucleic acids or small interfering RNA (siRNA) to reduce or inhibit expression and hence the biological acitivity of proteins or peptides, particularly OST-PTP and gamma-carboxylase. The cDNA sequences encoding OST-PTP and gamma-carboxylase are set forth below. Based on these known sequences, antisense DNA or RNA that hybridize sufficiently to the respective gene or mRNA encoding OST-PTP and gamma-carboxylase to turn off or reduce expression can be readily designed and engineered, using methods known in the art.

In a specific embodiment of the invention, antisense or siRNA molecules for use in the present invention are those that bind under stringent conditions to the human gamma-carboxylase nucleic sequence of SEQ ID NO:10. In yet another embodiment of the invention, the antisense or siRNA molecules are those that that bind under stringent conditions to the OST-PTP nucleic acid sequence of SEQ ID NO:18, or sequences that are substantially homologous to SEQ ID NO:18. In other embodiments, the antisense or siRNA molecules bind under stringent conditions to sequences that are substantially homologous or identical to SEQ ID NO:18.

Antisense-RNA and anti-sense DNA have been used therapeutically in mammals to treat various diseases. See for example Agrawal, S, and Zhao, Q. (1998) Curr. Opin. Chemical Biol. Vol. 2, 519-528; Agrawal, S. and Zhang, R. (1997) CIBA Found. Symp. Vol. 209, 60-78; and Zhao, Q, et al., (1998), Antisense Nucleic Acid Drug Dev. Vol 8, 451-458; the entire contents of which are hereby incorporated by reference as if fully set forth herein. Antisense oligodeoxyribonucleotides (antisense-DNA), oligoribonucleotides (antisense-RNA), and other polymeric antisense compounds (e.g., oligonucleotides composed of naturally-occurring nucleobases, sugars and covalent internucleoside linkages and non-naturally-occurring portions which function similarly) can base pair with a gene or its transcript. An antisense PS-oligodeoxyribonucleotide for treatment of cytomegalovirus retinitis in AIDS patients is the first antisense oligodeoxyribonucleotide approved for human use in the US. Anderson, K. O., et al., (1996) Antimicrobiol. Agents Chemother. Vol. 40, 2004-2011, and U.S. Pat. No. 6,828,151 by Borchers, et al., entitled "Antisense modulation of hematopoietic cell protein tyrosine kinase expression," describe methods for making and using antisense nucleic acids and their formulation, the entire contents of which are hereby incorporated by reference as if fully set forth herein.

Methods of making antisense nucleic acids are well known in the art. Further provided are methods of modulating the expression of OST-PTP and gamma-carboxylase genes and mRNA in cells or tissues by contacting the cells or tissues with one or more of the antisense compounds or compositions of the invention. As used herein, the terms "target nucleic acid" encompass DNA encoding OST-PTP or gamma-carboxylase and RNA (including pre-mRNA and mRNA) transcribed from such DNA. The specific hybridization of a nucleic acid oligomeric compound with its target nucleic acid interferes with the normal function of the target nucleic acid. This modulation of function of a target nucleic acid by compounds which specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, and catalytic activity which may be engaged in or facilitated by the RNA. The overall effect of such interference with target nucleic acid function is modulation of the expression of the protein encoded by the DNA or RNA. In the context of the present invention, "modulation" means reducing or inhibiting in the expression of the gene or mRNA for OST-PTP and/or gamma-carboxylase. DNA is the preferred antisense nucleic acid.

The targeting process includes determination of a site or sites within the target DNA or RNA encoding the OST-PTP and/or gamma-carboxylase for the antisense interaction to occur such that the desired inhibitory effect is achieved. Within the context of the present invention, a preferred intragenic site is the region encompassing the translation initiation or termination codon of the open reading frame (ORF) of the mRNA for OST-PTP or gamma-carboxylase, preferably human OST-PTP or gamma-carboxylase. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine in eukaryotes. It is also known in the art that eukaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene. Routine experimentation will determine the optimal sequence of the antisense or siRNA.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, nucleic acids are chosen which are sufficiently complementary to the target, i.e., hybridize sufficiently well and with sufficient specificity, to give the desired effect of inhibiting gene expression and transcription or mRNA translation.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of a nucleic acid is capable of hydrogen bonding with a nucleotide at the same position of a DNA or RNA molecule, then the nucleic acid and the DNA or RNA are considered to be complementary to each other at that position. The nucleic acid and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the nucleic acid and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of function, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense nucleic acids have been employed as therapeutic moieties in the treatment of disease states in animals and man. Antisense nucleic acid drugs, including ribozymes, have been safely and effectively administered to humans and numerous clinical trials are presently underway. It is thus established that nucleic acids can be useful therapeutic modalities that can be configured to be useful in treatment regimes for treatment of cells, tissues and animals, especially humans, for example to regulate expression of OST-PTP and gamma-carboxylase.

Nucleic acids in the context of this invention includes "oligonucleotides," which refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense nucleic acids are a preferred form of antisense compound, the present invention comprehends other oligomeric antisense compounds, including but not limited to oligonucleotide mimetics. The antisense compounds in accordance with this invention preferably comprise from about 8 to about 50 nucleobases (i.e., from about 8 to about 50 linked nucleosides). Particularly preferred antisense compounds are antisense nucleic acids comprising from about 12 to about 30 nucleobases. Antisense compounds include ribozymes, external guide sequence (EGS) nucleic acids (oligozymes), and other short catalytic RNAs or catalytic nucleic acids which hybridize to the target nucleic acid and modulate its expression.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare nucleic acids such as the phosphorothioates and alkylated derivatives.

The antisense compounds of the present invention can be utilized for diagnostics, therapeutics, and prophylaxis and as research reagents and kits. For therapeutics, an animal, preferably a human, suspected of having a disease or disorder such as metabolic syndrome, glucose intolerance, diabetes, atherosclerosis, and/or obesity, which can be treated by modulating the expression of gamma-carboxylase or OST-PTP, is treated by administering antisense compounds in accordance with this invention. The compounds of the invention can be utilized in pharmaceutical compositions by adding an effective amount of an antisense compound to a suitable pharmaceutically acceptable diluent or carrier. The antisense compounds and methods of the invention are useful prophylactically, e.g., to prevent or delay the appearance of metabolic syndrome, glucose intolerance, diabetes, atherosclerosis or obesity. The antisense compounds and methods of the invention are also useful to retard the progression of metabolic syndrome, glucose intolerance, diabetes, atherosclerosis or obesity.

The present invention also includes pharmaceutical compositions and formulations which include the antisense compounds of the invention that are administered to return the level of serum insulin in diabetic patients (for example) to normal.

US Patent Application 2004/0023390 (the entire contents of which are hereby incorporated by reference as if fully set forth herein) teaches that double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shut-down of protein synthesis and even cell death through apoptosis. Recent work shows that RNA fragments are the sequence-specific mediators of RNAi (Elbashir et al., 2001). Interference of gene expression by these small interfering RNA (siRNA) is now recognized as a naturally occurring strategy for silencing genes in *C. elegans, Drosophila*, plants, and in mouse embryonic stem cells, oocytes and early embryos (Cogoni et al., 1994; Baulcombe, 1996; Kennerdell, 1998; Timmons, 1998; Waterhouse et al., 1998; Wianny and Zernicka-Goetz, 2000; Yang et al., 2001; Svoboda et al., 2000).

In mammalian cell culture, a siRNA-mediated reduction in gene expression has been accomplished by transfecting cells with synthetic RNA nucleic acids (Caplan et al., 2001; Elbashir et al., 2001). The 2004/0023390 application, the entire contents of which are hereby incorporated by reference as if fully set forth herein, provides exemplary methods using a viral vector containing an expression cassette containing a pol II promoter operably-linked to a nucleic acid sequence encoding a small interfering RNA molecule (siRNA) targeted against a gene of interest.

As used herein RNAi is the process of RNA interference. A typical mRNA produces approximately 5,000 copies of a protein. RNAi is a process that interferes with or significantly reduces the number of protein copies made by an mRNA, preferably encoding OST-PTP or gamma-carboxylase. For example, a double-stranded short interfering RNA (siRNA) molecule is engineered to complement and match the protein-encoding nucleotide sequence of the target mRNA to be interfered with. Following intracellular delivery, the siRNA molecule associates with an RNA-induced silencing complex (RISC). The siRNA-associated RISC binds the target mRNA (such as mRNA encoding gamma-carboxylase and OST-PTP) through a base-pairing interaction and degrades it. The RISC remains capable of degrading additional copies of the targeted mRNA. Other forms of RNA can be used such as short hairpin RNA and longer RNA molecules. Longer molecules cause cell death, for example by instigating apoptosis and inducing an interferon response. Cell death was the major hurdle to achieving RNAi in mammals because dsRNAs longer than 30 nucleotides activated defense mechanisms that resulted in nonspecific degradation of RNA transcripts and a general shut-down of the host cell. Using from about 20 to about 29 nucleotide siRNAs to mediate gene-specific suppression in mammalian cells has apparently overcome this obstacle. These siRNAs are long enough to cause gene suppression but not of a length that induces an interferon response. In a specific embodiment of the invention, the targets of gene suppression are the OST-PTP gene and the gene for gamma-carboxylase. siRNA molecules useful in the present invention include those sequences that bind under stringent conditions to the human gamma-carboxylase gene of SEQ ID:10 or the OST-PTP gene of SEQ ID NO:18. siRNA molecules useful in the present invention also include those sequences that bind under stringent conditions to nucleic acids that are 80%, 85%, 90%, or 95% homologous to SEQ ID NO:18.

Co-Administration of the Therapeutic Agents of the Present Invention and Other Drugs The undercarboxylated/uncarboxylated osteocalcin and inhibitors of OST-PTP and gamma-carboxylase described herein may be co-administered to a patient with other drugs such as anti-coagulants, vasodilators, drugs used to treat atherosclerosis, drugs used to treat glucose intolerance, drugs used to treat diabetes, vitamin K inhibitors, statins, beta blockers, and other drugs used to treat diseases associated with disorders related to the OST-PTP signaling pathway, including, but not limited to metabolic syndrome, glucose intolerance, type 1 or type 2 diabetes, atherosclerosis, and obesity in amounts effective to provide therapeutic benefit of the drug in the combination therapy. The combination may provide increased, additive, or synergistic effect. The co-administration of the undercarboxylated/uncarboxylated osteocalcin, inhibitors of OST-PTP, inhibitors of gamma-carboxylase and the other drugs may be done by administration of separate pharmaceutical compositions or the undercarboxylated/uncarboxylated osteocalcin, inhibitors of OST-PTP, inhibitors of gamma-carboxylase and the other drugs may be present in a single pharmaceutical composition.

Anticoagulants useful in the invention are exemplified by vitamin K antagonists, heparin and derivatives of heparin, and direct thrombin inhibitors. Vitamin K antagonists are exemplified by warfarin (also known under the brand names COUMADIN® (warfarin), JANTOVEN® (warfarin), MAREVAN® (warfarin), and WARAN® (warfarin)), warfarin derivatives, acenocoumarol, phenprocoumon as well as phenindione. Heparin and derivatives of heparin are exemplified by low molecular weight heparin and fondaparinux. Direct thrombin inhibitors are exemplified by argatroban, lepirudin, bivalirudin and ximelagatran.

Vasodilators are useful in the present invention. Vasodilators are exemplified by adenosine, amyl nitrite and other nitrites, L-arginine, atrial natriuretic peptide (ANP), bradykinin, ethanol, endothelium-derived hyperpolarizing factor (EDHF), histamine, complement proteins C3a, C4a and C5a, niacin (nicotinic acid), nitric oxide, glyceryl trinitrate (commonly known as nitroglycerin), isosorbide mononitrate & isosorbide dinitrate, pentaerythritol tetranitrate (PETN), sodium nitroprusside, PDE5 inhibitors, sildenafil, tadalafil, vardenafil, platelet activating factor (PAF), prostacyclin ($PGI_2$) as well as other prostaglandins, tetrahydrocannabinol (THC), theobromine, and papaverine.

Drugs used to treat atherosclerosis are useful in the present invention. Drugs used to treat atherosclerosis are exemplified by statins, scilostazol, benzothiazepines, phenylalkylamines, dihydropyridines, epoprostenol, vitamin B3, and aspirin. Statins are further exemplified by atorvastatin, cerivastatin, fluvastatin, lovastatin, mevastatin, pitavastatin, pravastatin, rosuvastatin, and simvastatin. Benzothiazepines are exemplified by diltiazem. Phenylalkylamines are exemplified by verapamil. Dihydropyridines are exemplified by amlodipine, felodipine, isradipine, lacidipine, lercanidipine, nicardipine, nifedipine, nimodipine, nisoldipine, and nitrendipine.

Drugs useful in the treatment of diabetes include, but are not limited to, sulfonylureas, meglitinides, D-Phenylalanine Derivatives (nateglinides), biguanides, thiazolidinediones, alpha-glucose inhibitors, Dipeptidyl peptidase 4 (DPP4) inhibitors, insulins (preferably human recombinant insulin) and incretins.

Sulfonylureas are exemplified by glimepiride, glyburide, chlorpropamide, acetohexamide, glipizide, tolbutamide, and tolazamide. Meglitinides are exemplified by Repaglinide. D-Phenylalanine Derivatives are exemplified by nateglinide. Biguanides are exemplified by metformin and metformin hydrochloride. Thiazolidinediones are exemplified by pioglitazone and rosiglitazone. Alpha-glucose inhibitors are exemplified by miglitol and acarbose. Dipeptidyl peptidase 4 (DPP4) inhibitors are exemplified by vildagliptin, sitagliptin and saxagliptin.

Generally, there are six categories of insulins: rapid-acting, short-acting, intermediate acting, long acting, very long acting, and premixed. Incretins are a type of gastrointestinal hormone that cause an increase in the amount of insulin released from the beta-cells of the islets of Langerhans after eating, even before blood glucose levels become elevated. Incretins are exemplified by glucagon-like peptide-1 (GLP-1) and Gastric inhibitory peptide (aka glucose-dependent Insulinotropic peptide or GIP).

Beta blockers are used to treat high blood pressure (hypertension), congestive heart failure (CHF), abnormal heart rhythms (arrhythmias), and chest pain (angina). Beta blockers are sometimes used in heart attack patients to prevent future heart attacks. Beta blockers work by blocking the effects of the hormone epinephrine, also known as adrenaline. As a result, the heart beats more slowly and with less force, thereby reducing blood pressure. Beta blockers also help blood vessels relax and open up to improve blood flow. Beta blockers also block the impulses that can cause an arrhythmia. There are 2 main beta receptors: beta 1 and beta 2. Some beta blockers are selective, which means that they block beta 1 receptors more than they block beta 2 receptors. Beta 1 receptors are responsible for heart rate and the strength of the heartbeat. Nonselective beta blockers block both beta 1 and beta 2 receptors. Beta 2 receptors are responsible for the function of smooth muscles; they are also the only beta receptors expressed by osteoblasts. Brand Names and generic claims of beta blockers commonly used in the United States are: Betapace (sotalol), Blocadren (timolol), Brevibloc (esmolol), Cartrol (carteolol), Coreg (carvedilol), Corgard (nadolol), Inderal (propranolol), Inderal-LA (propranolol), Kerlone (betaxolol), Levatol (penbutolol), Lopressor (metoprolol), Normodyne (labetalol), Sectral (acebutolol), Tenormin (atenolol), Toprol-XL (metoprolol), Trandate (labetalol), Visken (pindolol), Zebeta (bisoprolol). Commonly Used Brand Names in Canada are: Apo-Atenolol (atenolol), Apo-Metoprolol (metoprolol), Apo-Propranolol (propranolol), Apo-Timol (timolol), Betaloc (metoprolol), Blocadren (timolol), Corgard (nadolol), Inderal (propranolol), Lopressor (metoprolol), Monitan (acebutolol), Novo-Atenol (atenolol), Novometoprol (metoprolol), Novo-Pindol (pindolol), Novo-Timol (timolol), Sectral (acebutolol), Sotacor (sotalol), Tenormin (atenolol), Trandate (labetalol), Trasicor (oxprenolol), Visken (pindolol).

Pharmaceutical Compositions and Administration

The present invention encompasses the use of the polypeptides, nucleic acids, antibodies, small molecules and other therapeutic agents described herein formulated in pharmaceutical compositions to administer to a subject. The therapeutic agents (also referred to as "active compounds") can be incorporated into pharmaceutical compositions suitable for administration to a subject, e.g., a human. Such compositions typically comprise the polypeptides, nucleic acids, antibodies, small molecules and a pharmaceutically acceptable carrier. Preferably, such compositions are non-pyrogenic when administered to humans.

The pharmaceutical compositions of the invention are administered in an amount sufficient to modulate the OST-PTP signaling pathway involving gamma-carboxylase, osteocalcin, insulin and adiponectin.

As used herein the language "pharmaceutically acceptable carrier" is intended to include any and all solvents, binders, diluents, disintegrants, lubricants, dispersion media, coatings, antibacterial and antifungal agents, isotonic and absorption delaying agents, and the like, compatible with pharmaceutical administration. The use of such media and agents for pharmaceutically active substances is well known in the art. As long as any conventional media or agent is compatible with the active compound, such media can be used in the compositions of the invention. Supplementary active compounds or therapeutic agents can also be incorporated into the compositions. A pharmaceutical composition of the invention is formulated to be compatible with its intended route of administration. Examples of routes of administration include parenteral, e.g., intravenous, intradermal, intranasal, subcutaneous, oral, inhalation, transdermal (topical), transmucosal, and rectal administration.

The term "administer" is used in its broadest sense and includes any method of introducing the compositions of the present invention into a subject. This includes producing polypeptides or polynucleotides in vivo as by transcription or translation of polynucleotides that have been exogenously introduced into a subject. Thus, polypeptides or nucleic acids produced in the subject from the exogenous compositions are encompassed in the term "administer."

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamine tetra acetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where the therapeutic agents are water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., undercarboxylated/uncarboxylated osteocalcin protein or anti-OST-PTP antibody) in the required amount in an appropriate solvent with one or a combination of the ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. Depending on the specific conditions being treated, pharmaceutical compositions of the present invention for treatment of atherosclerosis or the other elements of metabolic syndrome can be formulated and administered systemically or locally. Techniques for formulation and administration can be found in "Remington: The Science and Practice of Pharmacy" ($20^{th}$ edition, Gennaro (ed.) and Gennaro, Lippincott, Williams & Wilkins, 2000). For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL® (sodium starch glycolate), or corn starch; a lubricant such as magnesium stearate or STEROTES® (magnesium stearate); a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

If appropriate, the compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to particular cells with, e.g., monoclonal antibodies) can also be used as pharmaceutically acceptable carriers. These can be prepared according to methods known to those skilled in the art, for example, as described in U.S. Pat. No. 4,522,811.

It is especially advantageous to formulate oral or parenteral compositions in unit dosage form for ease of administration and uniformity of dosage. "Unit dosage form" as used herein refers to physically discrete units suited as unitary dosages for the subject to be treated; each unit containing a predetermined quantity of active compound calculated to produce the desired therapeutic effect in association with the required pharmaceutical carrier. The specification for the unit dosage forms of the invention are dictated by and directly dependent on the unique characteristics of the active compound and the particular therapeutic effect to be achieved, and the limitations inherent in the art of compounding such an active compound for the treatment of individuals.

As previously noted, the agent may be administered continuously by pump or frequently during the day for extended periods of time. In certain embodiments, the agent may be administered at a rate of from about 0.3-100 ng/hour, preferably about 1-75 ng/hour, more preferably about 5-50 ng/hour, and even more preferably about 10-30 ng/hour. The agent may be administered at a rate of from about 0.1-100 µg/hr, preferably about 1-75 µg/hr, more preferably about 5-50 µg/hr, and even more preferably about 10-30 µg/hr It will also be appreciated that the effective dosage of antibody, protein, or polypeptide used for treatment may increase or decrease over the course of a particular treatment. Changes in dosage may result and become apparent from monitoring the level of undercarboxylated/uncarboxylated osteocalcin and/or adiponectin and/or insulin and/or monitoring glycemia control in a biological sample, preferably blood or serum.

In an embodiment of the invention, the agent can be delivered by subcutaneous, long-term, automated drug delivery using an osmotic pump to infuse a desired dose of the agent for a desired time. Insulin pumps are widely available and are used by diabetics to automatically deliver insulin over extended periods of time. Such insulin pumps can be adapted to deliver the agent. The delivery rate of the agent to control glucose intolerance, diabetes types 1 or 2 can be readily adjusted through a large range to accommodate changing insulin requirements of an individual (e.g., basal rates and bolus doses). New pumps permit a periodic dosing manner, i.e., liquid is delivered in periodic discrete doses of a small fixed volume rather than in a continuous flow manner. The overall liquid delivery rate for the device is controlled and adjusted by controlling and adjusting the dosing period. The pump can be coupled with a continuous blood glucose monitoring device and remote unit, such as a system described in U.S. Pat. No. 6,560,471, entitled "Analyte Monitoring Device and Methods of Use." In such an arrangement, the hand-held remote unit that controls the continuous blood glucose monitoring device could wirelessly communicate with and control both the blood glucose monitoring unit and the fluid delivery device delivering therapeutic agents of the present invention.

A "therapeutically effective amount" of a protein or polypeptide, small moleclue or nucleic acid is an amount that achieves the desired therapeutic result. For example, if a therapeutic agent is administered to treat or prevent atherosclerosis, a therapeutically effective amount is an amount that ameliorates one or more symptoms of the disease, or produces at least one effect selected from the group consisting of a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, a decrease in the thickness of arterial plaque, a reduction in clinical events such as heart attack, angina, or stroke, a decrease in hypertension, and the like. If a therapeutic agent is used for treating or preventing metabolic syndrome in an animal (including mammals, including humans and laboratory animals) a therapeutically effective amount is an amount that produces at least one effect selected from the group consisting of increasing pancreatic beta-cell proliferation, increasing insulin secretion, increasing insulin sensitivity, increasing glucose tolerance, decreasing weight gain, weight loss, decreasing fat mass, increasing serum adiponectin, and an a decrease in or improved control of atherosclerosis.

A therapeutically effective amount of protein or polypeptide, small molecule or nucleic acid for use in the present invention typically varies and can be an amount sufficient to achieve serum therapeutic agent levels typically of between about 1 nanogram per milliliter and about 10 micrograms per milliliter in the subject, or an amount sufficient to achieve serum therapeutic agent levels of between about 1 nanogram per milliliter and about 7 micrograms per milliliter in the subject. Other preferred serum therapeutic agent levels include about 0.1 nanogram per milliliter to about 3 micrograms per milliliter, about 0.5 nanograms per milliliter to about 1 microgram per milliliter, about 1 nanogram per milliliter to about 750 nanograms per milliliter, about 5 nanograms per milliliter to about 500 nanograms per milliliter, and about 5 nanograms per milliliter to about 100 nanograms per milliliter.

Expressed as a daily dose, this amount can be between about 0.1 nanograms per kilogram body weight per day and about 20 milligrams per kilogram body weight per day, and between about 1 nanogram per kilogram body weight per day and about 10 milligrams per kilogram body weight per day. Other preferred daily dosages include about 1 nanogram per kilogram body weight per day to about 20 milligrams per kilogram body weight per day, about 5 nanograms per kilogram body weight per day to about 5 milligrams per kilogram body weight per day, about 20 nanograms per kilogram body weight per day to about 500 micrograms per kilogram body weight per day, and about 500 nanograms per kilogram body weight per day to about 100 micrograms per kilogram body weight per day. However, the skilled artisan will appreciate that certain factors may influence the dosage required to effectively treat a subject, including but not limited to the severity of the condition, previous treatments, the general health and/or age of the subject, and other disorders or diseases present.

In certain embodiments, the pharmaceutical compositions of the present invention comprise about 0.1 mg to 5 g, about 0.5 mg to about 1 g, about 1 mg to about 750 mg, about 5 mg to about 500 mg, or about 10 mg to about 100 mg of therapeutic agent.

Moreover, treatment of a subject with a therapeutically effective amount of a protein, polypeptide, nucleotide or antibody can include a single treatment or, preferably, can include a series of treatments.

In certain embodiments, treatment of a subject with undercarboxylated/uncarboxylated osteocalcin leads to undercarboxylated/uncarboxylated osteocalcin being about 10%, about 15%, about 20%, about 25%, about 30%, about 35%, about 40%, about 45%, or about 50% of the total osteocalcin in the blood of the patient.

It is understood that the appropriate dose of a small molecule agent depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, and the effect which the practitioner desires the small molecule to have. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of OST-PTP or gamma-carboxylase, a relatively low dose may be prescribed at first, with the dose subsequently increased until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

For atherosclerosis prevention or treatment, a suitable subject can be an individual who is suspected of having, has been diagnosed as having, or is at risk of developing atherosclerosis, coronary artery disease, stroke, restenosis, vascular fibromuscular dysplasia, polyarteritis nodosa, Takayasu's arteritis, and like conditions as can be determined by one knowledgeable in the art. Another example of a suitable subject is an individual who is to undergo vascular surgery, including but not limited to vascular bypass surgery, atherectomy, endatherectomy, laser ablation, angioplasty, balloon angioplasty, cardiac allograft (cardiac transplant), insertion of a prosthesis, insertion of a graft, insertion of a stent, catheterization, or arterial blockage evaluation. Suitable routes of administration can include oral, intestinal, parenteral, transmucosal, transdermal, intramuscular, subcutaneous, transdermal, rectal, intramedullary, intrathecal, intravenous, intraventricular, intraatrial, intraaortal, intraarterial, or intraperitoneal administration. The pharmaceutical compositions of the present invention can be administered to the subject by a medical device, such as, but not limited to, catheters, balloons, implantable devices, biodegradable implants, prostheses, grafts, sutures, patches, shunts, or stents. For atherosclerosis, pharmaceutical compositions of the present invention can contain a therapeutic agent in an amount sufficient to prevent/slow down the development of atherosclerotic lesions. In one preferred embodiment, the therapeutic agent (e.g., undercarboxylated/uncarboxylated osteocalcin) can be coated on a stent for localized administration to the target area. In this situation a slow release preparation of undercarboxylated/uncarboxylated osteocalcin, for example, is preferred.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

In yet another aspect of the invention, undercarboxylated/uncarboxylated osteocalcin is administered as a pharmaceutical composition with a pharmaceutically acceptable excipient. Exemplary pharmaceutical compositions for undercarboxylated/uncarboxylated osteocalcin include injections as solutions or injections as injectable self-setting or self-gelling mineral polymer hybrids. Undercarboxylated/uncarboxylated osteocalcin may be administered using a porous crystalline biomimetic bioactive composition of calcium phosphate. See U.S. Pat. Nos. 5,830,682; 6,514,514; 6,511,958 and U.S. Pat. Pub. Nos.: 2006/0063699; 2006/0052327; 2003/199615; 2003/0158302; 2004/0157864; 2006/0292670; 2007/0099831 and 2006/0257492, all of which are incorporated herein in their entirety by reference.

Methods of Treatment

The present invention provides methods for modulating energy metabolism through the OST-PTP signaling pathway for treating or preventing a variety of different disorders relating to the OST-PTP signaling pathway involving gamma-carboxylase, osteocalcin, insulin and adiponectin. In particular, the methods are used to inhibit OST-PTP phosphorylase activity, reduce gamma-carboxylase activity, and/or increase undercarboxylated/uncarboxylated osteocalcin. According to the invention, the methods provide an amount of an agent effective to treat or prevent a disorder associated with the OST-PTP signaling pathway. The agent may be selected from the group consisting of small molecules, antibodies and nucleic acids. Such disorders include, but are not limited to, metabolic syndrome, glucose intolerance, diabetes type 1, diabetes type 2, atherosclerosis, and/or obesity.

In certain embodiments, the methods comprise identifying a patient in need of treatment or prevention of metabolic syndrome, glucose intolerance, diabetes type 1, diabetes type 2, vascular disorders (such as atherosclerosis), and/or obesity and then applying the methods disclosed herein to the patient.

Vascular disorders include atherosclerosis, arteriosclerosis and arteriolosclerosis. Arteriosclerosis, which means hardening (sclerosis) of the arteries (arterio-), is a general term for several diseases in which the wall of an artery becomes thicker and less elastic. There are three types: atherosclerosis, arteriolosclerosis, and Monckeberg's arteriosclerosis. Atherosclerosis, the most common type, means hardening related to atheromas, which are deposits of fatty materials. It affects medium-sized and large arteries of the brain, heart, kidneys, other vital organs, and legs. It is the most important and most common type of arteriosclerosis, a general term for several diseases in which the wall of an artery becomes thicker and less elastic.

Type 1 diabetes is usually diagnosed in children and young adults, and was previously known as juvenile diabetes. In type 1 diabetes, the body does not produce insulin. Insulin is a hormone that is needed to convert sugar (glucose), starches and other food into energy needed for daily life. Conditions associated with type 1 diabetes include hyperglycemia, hypoglycemia, ketoacidosis and celiac disease.

Type 2 diabetes is the most common form of diabetes. In type 2 diabetes, either the body does not produce enough insulin or the cells ignore the insulin. Conditions associated with type 2 diabetes include hyperglycemia and hypoglycemia.

Disorders associated with energy metabolism include diabetes, glucose intolerance, decreased insulin sensitivity, decreased pancreatic beta-cell proliferation, decreased insulin secretion, weight gain, increased fat mass and decreased serum adiponectin The methods of the invention increase serum osteocalcin levels (preferably undercarboxylated/uncarboxylated osteocalcin), serum adiponectin levels and/or serum insulin levels. The pharmaceutical compositions may also increase glucose tolerance, increase insulin sensitivity, and/or increase pancreatic beta-cell proliferation.

As used herein, the terms "animal," "patient," or "subject" include mammals, e.g., humans, dogs, cows, horses, kangaroos, pigs, sheep, goats, cats, mice, rabbits, rats, and transgenic non-human animals. The preferred animal, patient, or subject is a human.

In certain embodiments, the methods comprise administering undercarboxylated/uncarboxylated osteocalcin to a patient, preferably a human. In a specific embodiment of the invention, the daily dose of undercarboxylated/uncarboxylated osteocalcin is between about 0.1 nanograms per kilogram body weight per day and about 20 milligrams per kilogram body weight per day, or between about 1 nanogram per kilogram body weight per day and about 10 milligrams per kilogram body weight per day. Other preferred daily dosages include about 1 nanogram per kilogram body weight per day to about 20 milligrams per kilogram body weight per day, about 5 nanograms per kilogram body weight per day to about 5 milligrams per kilogram body weight per day, about 20 nanograms per kilogram body weight per day to about 500 micrograms per kilogram body weight per day, and about 500 nanograms per kilogram body weight per day to about 100 micrograms per kilogram body weight per day.

In some embodiments, the daily dosage is about 0.1 milligrams per kilogram body weight per day, about 0.25 milligrams per kilogram body weight per day, about 0.5 milligrams per kilogram body weight per day, about 0.75 milligrams per kilogram body weight per day, about 1 milligram per kilogram body weight per day, about 2 milligrams per kilogram body weight per day, about 5 milligrams per kilogram body weight per day, about 10 milligrams per kilogram body weight per day, or about 20 milligrams per kilogram body weight per day.

In one embodiment of the invention, the method of treatment comprises administering to a patient in need thereof a therapeutically effective amount of undercarboxylated/uncarboxylated osteocalcin sufficient to raise the patient's blood level of undercarboxylated/uncarboxylated osteocalcin compared to the pretreatment patient level. Preferably, the patient is a human. In another embodiment, the method of treatment comprises administering to a patient in need thereof a therapeutically effective amount of undercarboxylated/uncarboxylated osteocalcin sufficient to raise the ratio of undercarboxylated/uncarboxylated osteocalcin to total osteocalcin in the patient's blood compared to the pretreatment patient ratio.

In another aspect of the invention, a method is provided for treating or preventing metabolic syndrome in an animal comprising administering to an animal in need thereof undercarboxylated/uncarboxylated osteocalcin in a therapeutically effective amount that produces at least one effect selected from the group consisting of increasing pancreatic beta-cell proliferation, increasing insulin secretion, increasing insulin sensitivity, increasing glucose tolerance, decreasing weight gain, decreasing fat mass, weight loss and increasing serum adiponectin compared to pretreatment levels. Alternatively, the undercarboxylated/uncarboxylated osteocalcin is administered in an amount that produces at least one effect selected from the group consisting of a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, a decrease in the thickness of arterial plaque, a reduction in clinical events such as heart attack, angina, or stroke, and a decrease in hypertension as compared to pretreatment levels. Preferably, the patient is a human.

Insulin sensitivity can be measured by the insulin tolerance test or euglycemic hyperinsulinemic clamp. Glucose tolerance can be measured by glucose tolerance tests. Insulin secretion can be measured by the glucose stimulated insulin secretion test. The most common test for glycemic control in diabetic patients is a blood glucose test done typically by using test strips and one drop of blood. To better monitor the level of glycemic control over time, one can measure hemoglobin A1c (glycosylated hemoglobin).

In a specific embodiment of the invention, a method is provided for treating or preventing type 1 or type 2 diabetes or glucose intolerance in an animal comprising administering to an animal in need thereof undercarboxylated/uncarboxylated osteocalcin in a therapeutically effective amount that produces at least one effect selected from the group comprising increasing pancreatic beta-cell proliferation, increasing insulin secretion, increasing insulin sensitivity, increasing glucose tolerance, decreasing weight gain, decreasing fat mass, weight loss, and increasing serum adiponectin compared to pretreatment levels. Preferably, the patient is a human. In an embodiment of the invention, said method further comprises co-administration of anti-diabetic drugs such as insulin (preferably recombinant human insulin), incretins, sulfonylureas, meglitinides, D-Phenylalanine Derivatives (nateglinides), biguanides, thiazolidinediones, alpha-glucose inhibitors, GLP-1, GLP-1 analogues such as liraglutide, exendin-4 LY5448806 and CJC-1131, as well as dipeptidyl peptidase IV inhibitors.

Sulfonylureas are exemplified by glimepiride, glyburide, chlorpropamide, acetohexamide, glipizide, tolbutamide, and tolazamide. Meglitinides are exemplified by Repaglinide. Biguanides are exemplified by metformin and metformin hydrochloride. Thiazolidinediones are exemplified by pioglitazone and rosiglitazone. Alpha-glucose inhibitors are exemplified by miglitol and acarbose. Dipeptidyl peptidase 4 (DPP4) inhibitors are exemplified by vildagliptin, sitagliptin and saxagliptin.

Generally, there are six categories of insulins: rapid-acting, short-acting, intermediate acting, long acting, very long acting, and premixed. Incretins are a type of gastrointestinal hormone that cause an increase in the amount of insulin released from the beta-cells of the islets of Langerhans after eating, even before blood glucose levels become elevated. Incretins are exemplified by glucagon-like peptide-1 (GLP-1) and Gastric inhibitory peptide (aka glucose-dependent Insulinotropic peptide or GIP).

The present invention further provides (i) methods for treating or preventing obesity in an animal comprising administering to an animal in need thereof undercarboxylated/uncarboxylated osteocalcin in a therapeutically effective amount that decreases weight gain, decreases fat mass or results in loss of weight; (ii) methods for increasing insulin sensitivity in an animal comprising administering to an animal in need thereof undercarboxylated/uncarboxylated osteocalcin in a therapeutically effective amount that increases insulin sensitivity; (iii) methods for increasing glucose tolerance in an animal comprising administering to an animal in need thereof undercarboxylated/uncarboxylated osteocalcin in a therapeutically effective amount that increases glucose tolerance; (iv) methods for increasing insulin secretion in an animal comprising administering to an animal in need thereof undercarboxylated/uncarboxylated osteocalcin in a therapeutically effective amount that increases insulin secretion; and (v) methods for increasing beta-cell proliferation in an animal comprising administering to an animal in need thereof undercarboxylated/uncarboxylated osteocalcin in a therapeutically effective amount that increases beta-cell proliferation. Preferably, the animal is a human.

In another aspect of the invention, a method is provided for treating or preventing atherosclerosis in an animal comprising administering to an animal in need thereof undercarboxylated/uncarboxylated osteocalcin in a therapeutically effective amount that produces at least one effect selected from the group consisting of a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, a decrease in the thickness of arterial plaque, a reduction in clinical events such as heart attack, angina, or stroke, and a decrease in hypertension. Preferably, the animal is a human. In an embodiment of the invention, said method further comprises co-administration of compounds used to treat atherosclerosis such as low density lipoprotein peroxidation inhibitors, antihyperlipidemic agents, anticoagulants, vasodilators, and other drugs useful in the treatment of atherosclerosis.

Anticoagulants are exemplified by vitamin K antagonists, heparin and derivatives of heparin, and direct thrombin inhibitors. Vitamin K antagonists are exemplified by warfarin (also known under the brand names COUMADIN® (warfarin), JANTOVEN® (warfarin), MAREVAN® (warfarin), and WARAN® (warfarin)), acenocoumarol, phenprocoumon as well as phenindione. Heparin and derivatives of heparin are exemplified by low molecular weight heparin and fondaparinux. Direct thrombin inhibitors are exemplified by argatroban, lepirudin, bivalirudin and ximelagatran.

Vasodilators are exemplified by adenosine, amyl nitrite and other nitrites, 1-arginine, atrial natriuretic peptide (ANP), bradykinin, ethanol, endothelium-derived hyperpolarizing factor (EDHF), histamine, complement proteins C3a, C4a and C5a, niacin (nicotinic acid), nitric oxide, glyceryl trinitrate (commonly known as nitroglycerin), isosorbide mononitrate & isosorbide dinitrate, pentaerythritol tetranitrate (PETN), sodium_nitroprusside, PDE5 inhibitors, sildenafil, tadalafil, vardenafil, platelet activating factor (PAF), prostacyclin ($PGI_2$) as well as other prostaglandins, tetrahydrocannabinol (THC), theobromine, and papaverine.

Other drugs useful in the treatment of atherosclerosis are exemplified by statins, scilostazol, benzothiazepines, phenylalkylamines, dihydropyridines, epoprostenol, vitamin B3, and aspirin. Statins are further exemplified by atorvastatin, cerivastatin, fluvastatin, lovastatin, mevastatin, pitavastatin, pravastatin, rosuvastatin, and simvastatin. Benzothiazepines are exemplified by diltiazem. Phenylalkylamines are exemplified by verapamil. Dihydropyridines are exemplified by amlodipine, felodipine, isradipine, lacidipine, lercanidipine, nicardipine, nifedipine, nimodipine, nisoldipine, and nitrendipine.

In yet another embodiment of the invention, when administering undercarboxylated/uncarboxylated osteocalcin, it may be desirable to co-administered drugs normally administered to treat osteoporosis. Such drugs include, for example, raloxifene, calcitonin and alendronate.

In methods wherein adiponectin is co-administered with undercarboxylated/uncarboxylated osteocalcin, the adiponectin and undercarboxylated/uncarboxylated osteocalcin may be administered in a single pharmaceutical composition. Alternatively, the undercarboxylated/uncarboxylated osteocalcin and adiponectin may be administered in separate pharmaceutical compositions. In another embodiment of the invention, adiponectin and undercarboxylated/uncarboxylated osteocalcin are administered on the same day. In yet another embodiment, the adiponectin and undercarboxylated/uncarboxylated osteocalcin are administered on different days.

In an embodiment of the invention, a method is provided for treating or preventing a disease associated with low levels of serum osteocalcin in a patient comprising administering to a patient in need thereof an amount of a beta blocker or a vitamin K blocker or a combination thereof that causes an increase in the level of serum osteocalcin compared to pretreatment levels. Preferably, the patient is a human and the serum level of undercarboxylated/uncarboxylated osteocalcin is increased.

The present invention further provides a method of treating or preventing a disease including, but not limited to, metabolic syndrome, glucose intolerance, diabetes types 1 and 2, atherosclerosis and obesity in a patient comprising administering to a patient in need thereof a therapeutically effective amount of an agent that reduces OST-PTP expression or activity in osteoblasts sufficient to raise the patient's level of undercarboxylated/uncarboxylated osteocalcin. Preferably, the patient is a human.

The invention further provides a method of treating or preventing a disease selected from the group consisting of metabolic syndrome, glucose intolerance, diabetes types 1 and 2, atherosclerosis and obesity comprising administering to a patient in need thereof a therapeutically effective amount of an agent that reduces gamma-carboxylase expression or activity in osteoblasts sufficient to raise the patient level of undercarboxylated/uncarboxylated osteocalcin. Preferably, the patient is a human. Preferably, the patient is a human.

In an embodiment of the invention, a method is provided for treating or preventing metabolic syndrome in a patient comprising administering to a patient in need thereof a therapeutically effective amount of an agent that reduces OST-PTP expression or activity in osteoblasts sufficient to produce at least one effect selected from the group consisting of increasing pancreatic beta-cell proliferation, increasing insulin secretion, increasing insulin sensitivity, increasing glucose tolerance, decreasing weight gain, decreasing fat mass, weight loss, and increasing serum adiponectin, or which decreases or controls atherosclerosis compared to pretreatment levels. Preferably, the patient is a human.

In another aspect of the invention, a method is provided for treating or preventing type 1 or type 2 diabetes or glucose intolerance, in an animal comprising administering to an animal in need thereof adiponectin in a therapeutically effective amount so as to reduce OST-PTP expression or activity in osteoblasts sufficient to produce at least one effect selected from the group consisting of increasing pancreatic beta-cell proliferation, increasing insulin secretion, increasing insulin sensitivity, increasing glucose tolerance, decreasing weight gain, and increasing serum adiponectin compared to pretreatment levels. Preferably, the animal is a human.

A method is provided for treating or preventing atherosclerosis in an animal comprising administering to an animal in need thereof in a therapeutically effective amount an agent that reduces OST-PTP expression or activity in osteoblasts sufficient to produce at least one effect selected from the group consisting of a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, a decrease in the thickness of arterial plaque, a reduction in clinical events such as heart attack, angina, or stroke, and a decrease in hypertension compared to pretreatment levels. Preferably, the animal is a human.

In different embodiments of the invention, methods are provided (i) for treating or preventing obesity in an animal comprising administering to an animal in need thereof in a therapeutically effective amount an agent that reduces OST-PTP expression or activity in osteoblasts sufficient to decrease weight gain, decrease fat mass or result in weight loss compared to pretreatment levels; (ii) for treating or preventing glucose intolerance in an animal comprising administering to an animal in need thereof in a therapeutically effective amount an agent that reduces OST-PTP expression or activity in osteoblasts sufficient to increase glucose tolerance compared to pretreatment levels; (iii) for increasing insulin sensitivity in an animal comprising administering to an animal in need thereof in a therapeutically effective amount an agent that reduces OST-PTP expression or activity in osteoblasts sufficient to increase insulin sensitivity compared to pretreatment levels. Preferably, the animal is a human.

In another aspect of the invention, a method is provided for treating or preventing metabolic syndrome in an animal comprising administering to an animal in need thereof in a therapeutically effective amount an agent that reduces gamma-carboxylase expression or activity in osteoblasts sufficient to (1) produce at least one effect selected from the group consisting of increasing pancreatic beta-cell proliferation, increasing insulin secretion, increasing insulin sensitivity, increasing glucose tolerance, decreasing weight gain, decreasing fat mass, weight loss and increasing serum adiponectin compared to pretreatment levels, or (2) to produce at least one effect selected from the group consisting of a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, a decrease in the thickness of arterial plaque, a reduction in clinical events such as heart attack, angina, or stroke, and a decrease in hypertension compared to pretreatment levels. Preferably, the animal is a human.

In yet another embodiment of the invention, method for is provided for treating or preventing type 1 or type 2 diabetes or glucose intolerance in an animal comprising administering to an animal in need thereof in a therapeutically effective amount an agent that reduces gamma-carboxylase expression or activity in osteoblasts sufficient to produce at least one effect selected from the group consisting of increasing pancreatic beta-cell proliferation, increasing insulin secretion, increasing insulin sensitivity, increasing glucose tolerance, decreasing weight gain, decreasing fat mass, weight loss and increasing serum adiponectin compared to pretreatment levels. Preferably, the animal is a human.

A method is also provided for treating or preventing atherosclerosis in an animal comprising administering to an animal in need thereof in a therapeutically effective amount an agent that reduces gamma-carboxylase expression or activity in osteoblasts sufficient to produce at least one effect selected from the group consisting of a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, a decrease in the thickness of arterial plaque, a reduction in clinical events such as heart attack, angina, or stroke, and a decrease in hypertension compared to pretreatment levels. Preferably, the animal is a human.

The present invention is directed to methods (i) for treating or preventing obesity in an animal comprising administering to an animal in need thereof in a therapeutically effective amount an agent that reduces gamma-carboxylase expression or activity in osteoblasts sufficient to cause a decrease in weight gain, a decrease in fat mass, or weight loss compared to pretreatment levels (ii) for treating or preventing glucose intolerance in an animal comprising administering to an animal in need thereof in a therapeutically effective amount an agent that reduces gamma-carboxylase expression or activity in osteoblasts sufficient to increase glucose tolerance compared to pretreatment levels or (iii) for increasing insulin sensitivity in an animal comprising administering to an animal in need thereof in a therapeutically effective amount an agent that reduces gamma-carboxylase expression or activity in osteoblasts sufficient to increase insulin sensitivity compared to pretreatment levels. Preferably, the animal is a human. In an embodiment of the invention, the agent is an isolated nucleic acid that is selected from the group consisting of cDNA, antisense DNA, antisense RNA, and small interfering RNA, which nucleic acid is sufficiently complementary to the gene or mRNA encoding gamma-carboxylase to permit specific hybridization to the gene or mRNA, and wherein the hybridization prevents or reduces expression of gamma-carboxylase in osteoblasts. In another embodiment of the invention, the nucleic acid is conjugated to a phosphate group or other targeting ligand to facilitate uptake by osteoblasts.

In the methods described herein, it will be understood that "treating" a disease encompasses not only improving the disease or its symptoms but also retarding the progression of the disease or ameliorating the disease.

The present invention also encompasses the use of gene therapy for treatment of metabolic syndrome, including obesity, type 2 diabetes, glucose intolerance atherosclerosis, and type 1 diabetes. This can be accomplished by introducing a gene encoding osteocalcin or a biologically active fragment or variant thereof into a vector, and transfecting or infecting cells from a patient afflicted with the disease or at a high risk of developing the disease with the vector, according to various methods known in the art. The cells may be transfected or infected by ex vivo or by in vivo methods.

Adeno-associated virus (AAV) is one of the most promising vectors for gene therapy and may be used in the methods of the present invention. Conventional methods of gene transfer and gene therapy are described in, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996. AAV is an attractive vector system for human gene therapy because it is non-pathogenic for humans, it has a high frequency of integration, and it can infect non-dividing cells, thus making it useful for delivery of genes into mammalian cells both in tissue culture and in whole animals. Muzyczka, Curr. Top. Microbiol. Immunol., 158:97-129, 1992. Recent studies have demonstrated AAV to be a potentially useful vector for gene delivery. LaFace et al., Viology, 162:483-486, 1998; Zhou et al., Exp. Hematol. (NY), 21:928-933, 1993; Flotte et al., PNAS 90:10613-10617, 1993; and Walsh et al., Blood 84:1492-1500, 1994. Recombinant AAV vectors have been used successfully for in vitro and in vivo transduction of marker genes (Kaplitt et al., Nature Genetics, 8:148-154, 1994; Lebkowski et al., Mol. Cell. Biol. 8:3988-3996, 1988; Samulski et al., J. Virol., 63:3822-3828, 1989; Shelling, A. N., and Smith, M. G., Gene Therapy, 1:165-169, 1994; Yoder et al., Blood, 82:suppl. 1:347A, 1994; Zhou et al., J. Exp. Med., 179: 1867-1875, 1994; Hermonat, P. L. and Muzyczka, N., Proc. Natl. Acad. Sci. USA., 81:6466-6470, 1984; Tratschin et al., Mol. Cell. Biol., 4:2072-2081, 1984; McLaughlin et al., J. Virol., 62:1963-1973, 1988) as well as genes involved in human diseases (Flotte et al., Am. J. Respir. Cell Mol. Biol., 7:349-356, 1992; Luo et al., Blood, 82:suppl. 1,303A, 1994; Ohi et al., Gene, 89L:27914 282, 1990; Walsh et al., PNAS 89:7257-7261, 1992; Wei et al., Gene Therapy, 1:261-268, 1994).

In certain other embodiments, the gene of interest (e.g., osteocalcin) can be transferred into a target cell using a retroviral vector. Retroviruses refer to viruses that belong to the Retroviridae family, and include oncoviruses, foamy viruses (Russell, D. W. and Miller, A. D., J. Virol. 1996, 70:217-222; Wu, M. et al., J. Virol. 1999, 73:4498-4501), and lentiviruses (for example, HIV-1 (Naldini, L. et al., Science 1996, 272:263-267; Poeschla, E. et al., Proc. Natl. Acad. Sci. USA 1996, 93:11395-11399; Srinivasakumar, N. et al., J. Virol. 1997, 71:5841-5848; Zufferey, R., et al. Nat. Biotechnol. 1997, 15:871-875; Kim, V. N., et al., J. Virol. 1998, 72:811-816) and feline immunodeficiency virus (Johnston, J. C. et al., J. Virol. 1999, 73:4991-5000; Johnston, J. and Power, C., J. Virol. 1999, 73:2491-2498; Poeschla, E. M. et al., Nat. Med. 1998, 4:354-357)). Numerous gene therapy methods that take advantage of retroviral vectors for treating a wide variety of diseases are well-known in the art (see, e.g., U.S. Pat. Nos. 4,405,712 and 4,650,764; Friedmann, 1989, Science, 244:1275-1281; Mulligan, 1993, Science, 260:926-932, R. Crystal, 1995, Science 270:404-410, and U.S. Pat. No. 6,899,871, Kasahara, et al. each of which are incorporated herein by reference in their entirety). An increasing number of these methods are currently being applied in human clinical trials (Morgan, R., 1993, BioPharm, 6(1):32-35; see also The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety).

Efficacy of the methods of treatment described herein can be monitored by determining whether the methods ameliorate any of the symptoms of the disease being treated. Alternatively, one can monitor the level of serum undercarboxylated/uncarboxylated osteocalcin (either in absolute terms or as a ratio of undercarboxylated/uncarboxylated osteocalcin/total osteocalcin), and/or serum adiponectin, and/or serum insulin, which levels should increase in response to therapy. Alternatively efficacy can be measured by monitoring glycemia in the subject being treated.

Diagnostics

The present invention provides methods and compositions for diagnosing disorders such as those associated with decreased levels of undercarboxylated/uncarboxylated osteocalcin. Such disorders include, but are not limited to, metabolic syndrome, glucose intolerance, diabetes types 1 and 2, atherosclerosis and obesity.

In a specific embodiment of the invention, a method is provided for diagnosing a patient at risk of developing glucose intolerance or diabetes comprising: (i) determining a patient level of undercarboxylated/uncarboxylated osteocalcin in a biological sample taken from the patient and a control level of undercarboxylated/uncarboxylated osteocalcin in a biological sample taken from a subject that does not have glucose intolerance or diabetes, (ii) comparing the patient and control levels, and (iii) concluding that the patient is at risk of developing glucose intolerance or diabetes if the patient level is lower than the test level. In an embodiment of the invention, the diabetes is Type 1 or Type 2.

"Biological samples" include solid and body fluid samples. The biological samples of the present invention may include tissue, organs, cells, protein or membrane extracts of cells, blood or biological fluids such as blood, serum, ascites fluid or brain fluid (e.g., cerebrospinal fluid).

In another embodiment of the invention, a method is provided for diagnosing a patient at risk of developing glucose intolerance or diabetes comprising: (i) determining a patient level of undercarboxylated/uncarboxylated osteocalcin in a biological sample taken from the patient; and (ii) comparing the patient level to a standard level; where, if the patient level is lower than the standard level, the patient is at risk of developing diabetes. In instances where the method is practiced on humans, the standard level can be a level of undercarboxylated/uncarboxylated osteocalcin that has been previously determined to be the normal range for people who are not at risk of developing diabetes. In preferred embodiments, the biological sample is blood, serum, plasma, cerebrospinal fluid, urine, a cell sample, or a tissue sample. In an embodiment of the invention, the diabetes is Type 1 or Type 2.

A "standard level" of undercarboxylated/uncarboxylated osteocalcin in humans can include values of 0.1 ng/ml to 10 ng/ml, preferably 0.2 ng/ml to 7.5 ng/ml, more preferably 0.5 ng/ml to 5 ng/ml, and even more preferably 1 ng/ml to 5 ng/ml. A standard level of undercarboxylated/uncarboxylated osteocalcin in humans can also include about 0.1 ng/ml, about 0.5 ng/ml, about 1 ng/ml, about 2 ng/ml, about 3 ng/ml, about 4 ng/ml, about 5 ng/ml, about 6 ng/ml, about 7 ng/ml, or about 10 ng/ml.

In another embodiment of the invention, a method is provided for diagnosing a patient at risk of developing glucose intolerance or diabetes comprising: (i) determining the ratio of undercarboxylated/uncarboxylated osteocalcin to total osteocalcin in a biological sample taken from the patient; and (ii) comparing the ratio to a standard ratio; where, if the patient ratio is lower than the standard ratio, the patient is at risk of developing glucose intolerance or diabetes. In certain embodiments, the standard ratio is 5%-10%, 10%-15%, 15%-20%, 20%-25%, 25%-30%, or 30%-35%. In certain embodiments, the standard ratio is about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35%. Preferably, the patient is a human. In preferred embodiments, the biological sample is blood, serum, plasma, cerebrospinal fluid, urine, a cell sample, or a tissue sample. In an embodiment of the invention, the diabetes is Type 1 or Type 2.

The present invention further provides a method for diagnosing a patient at risk of developing atherosclerosis comprising: (i) determining a patient level of undercarboxylated/uncarboxylated osteocalcin in a biological sample taken from the patient and a control level of undercarboxylated/uncarboxylated osteocalcin in a biological sample taken from a subject that does not have atherosclerosis, (ii) comparing the patient and control levels, and (iii) concluding that the patient is at risk of developing atherosclerosis if the patient level is lower than the test level.

In another embodiment of the invention, a method is provided for diagnosing a patient at risk of developing atherosclerosis comprising: (i) determining a patient level of undercarboxylated/uncarboxylated osteocalcin in a biological sample taken from the patient; and (ii) comparing the patient level to a standard level; where, if the patient level is lower than the standard level, the patient is at risk of developing atherosclerosis. In instances where the method is practiced on humans, the standard level can be a level of undercarboxylated/uncarboxylated osteocalcin that has been previously determined to be the normal range for people who are not at risk of developing atherosclerosis. In preferred embodiments, the biological sample is blood, serum, plasma, cerebrospinal fluid, urine, a cell sample, or a tissue sample. Preferably, the patient is a human.

In another embodiment of the invention, a method is provided for diagnosing a patient at risk of developing atherosclerosis comprising: (i) determining the ratio of undercarboxylated/uncarboxylated osteocalcin to total osteocalcin in a biological sample taken from the patient; and (ii) comparing the ratio to a standard ratio; where, if the patient ratio is lower than the standard ratio, the patient is at risk of developing atherosclerosis. In certain embodiments, the standard ratio is 5%-10%, 10%-15%, 15%-20%, 20%-25%, 25%-30%, or 30%-35%. In certain embodiments, the standard ratio is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35%. Preferably, the patient is a human. In preferred embodiments, the biological sample is blood, serum, plasma, cerebrospinal fluid, urine, a cell sample or a tissue sample.

In yet another embodiment of the invention, a method is provided for diagnosing a patient at risk of developing metabolic syndrome comprising: (i) determining a patient level of undercarboxylated/uncarboxylated osteocalcin in a biological sample taken from the patient and a control level of undercarboxylated/uncarboxylated osteocalcin in a biological sample taken from a subject that does not have metabolic syndrome, (ii) comparing the patient and control levels, and (iii) concluding that the patient is at risk of developing metabolic syndrome if the patient level is lower than the test level.

In another embodiment of the invention, a method is provided for diagnosing a patient at risk of developing metabolic syndrome comprising: (i) determining a patient level of undercarboxylated/uncarboxylated osteocalcin in a biological sample taken from the patient; and (ii) comparing the patient level to a standard level; where, if the patient level is lower than the standard level, the patient is at risk of developing metabolic syndrome. In instances where the method is practiced on humans, the standard level can be a level of undercarboxylated/uncarboxylated osteocalcin that has been previously determined to be the normal range for people who are not at risk of developing metabolic syndrome. In preferred embodiments, the biological sample is blood, serum, plasma, cerebrospinal fluid, urine, a cell sample or a tissue sample. Preferably, the patient is a human.

In another embodiment of the invention, a method is provided for diagnosing a patient at risk of developing metabolic syndrome comprising: (i) determining the ratio of undercarboxylated/uncarboxylated osteocalcin to total osteocalcin in a biological sample taken from the patient; and (ii) comparing the ratio to a standard ratio; where, if the patient ratio is lower than the standard ratio, the patient is at risk of developing metabolic syndrome. In certain embodiments, the standard ratio is 5%-10%, 10%-15%, 15%-20%, 20%-25%, 25%-30%, or 30%-35%. In certain embodiments, the standard ratio is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35%. Preferably, the patient is a human. In preferred embodiments, the biological sample is blood, serum, plasma, cerebrospinal fluid, urine, a cell sample or a tissue sample.

In another aspect of the invention a method for diagnosing a patient at risk of developing obesity is provided comprising: (i) determining a patient level of undercarboxylated/uncarboxylated osteocalcin in a biological sample taken from the patient and a control level of undercarboxylated/uncarboxylated osteocalcin in a biological sample taken from a subject that does not have obesity, (ii) comparing the patient and control levels, and (iii) concluding that the patient is at risk of developing obesity if the patient level is lower than the test level.

In another embodiment of the invention, a method is provided for diagnosing a patient at risk of developing obesity comprising: (i) determining a patient level of undercarboxylated/uncarboxylated osteocalcin in a biological sample taken from the patient; and (ii) comparing the patient level to a standard level; where, if the patient level is lower than the standard level, the patient is at risk of developing obesity. In instances where the method is practiced on humans, the standard level can be a level of undercarboxylated/uncarboxylated osteocalcin that has been previously determined to be the normal range for people who are not at risk of developing obesity. In preferred embodiments, the biological sample is blood, serum, plasma, cerebrospinal fluid, urine, a cell sample or a tissue sample. Preferably, the patient is a human.

In another embodiment of the invention, a method is provided for diagnosing a patient at risk of developing obesity comprising: (i) determining the ratio of undercarboxylated/uncarboxylated osteocalcin to total osteocalcin in a biological sample taken from the patient; and (ii) comparing the ratio to a standard ratio; where, if the patient ratio is lower than the standard ratio, the patient is at risk of developing obesity. In certain embodiments, the standard ratio is 5%-10%, 10%-15%, 15%-20%, 20%-25%, 25%-30%, or 30%-35%. In certain embodiments, the standard ratio is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35%. Preferably, the patient is a human. In preferred embodiments, the biological sample is blood, serum, plasma, cerebrospinal fluid, urine, a cell sample or a tissue sample.

In yet another embodiment of the invention, a method is provided for diagnosing a patient at risk of developing a disease selected from the group consisting of glucose intolerance, impaired pancreatic beta-cell proliferation, impaired insulin secretion, and impaired insulin sensitivity comprising: (i) determining a patient level of undercarboxylated/uncarboxylated osteocalcin in a biological sample taken from the patient and a control level of undercarboxylated/uncarboxylated osteocalcin in a biological sample taken from a subject that does not have the disease, (ii) comparing the patient and control levels, and (iii) concluding that the patient is at risk of developing the disease if the patient level is lower than the test level.

In another embodiment of the invention, a method is provided for diagnosing a patient at risk of developing a disease selected from the group consisting of glucose intolerance, impaired pancreatic beta-cell proliferation, impaired insulin secretion, and impaired insulin sensitivity comprising: (i) determining a patient level of undercarboxylated/uncarboxylated osteocalcin in a biological sample taken from the patient; and (ii) comparing the patient level to a standard level; where, if the patient level is lower than the standard level, the patient is at risk of developing a disease selected from the group consisting of glucose intolerance, impaired pancreatic beta-cell proliferation, impaired insulin secretion, and impaired insulin sensitivity. In instances where the method is practiced on humans, the standard level can be a level of undercarboxylated/uncarboxylated osteocalcin that has been previously determined to be the normal range for people who are not at risk of developing a disease selected from the group consisting of glucose intolerance, impaired pancreatic beta-cell proliferation, impaired insulin secretion, and impaired insulin sensitivity. In preferred embodiments, the biological sample is blood, serum, plasma, cerebrospinal fluid, urine, a cell sample or a tissue sample. Preferably, the patient is a human.

In another embodiment of the invention, a method is provided for diagnosing a patient at risk of developing a disease selected from the group consisting of glucose intolerance, impaired pancreatic beta-cell proliferation, impaired insulin secretion, and impaired insulin sensitivity comprising: (i) determining the ratio of undercarboxylated/uncarboxylated osteocalcin to total osteocalcin in a biological sample taken from the patient; and (ii) comparing the ratio to a standard ratio; where, if the patient ratio is lower than the standard ratio, the patient is at risk of developing a disease selected from the group consisting of glucose intolerance, impaired pancreatic beta-cell proliferation, impaired insulin secretion, and impaired insulin sensitivity. In certain embodiments, the standard ratio is 5%-10%, 10%-15%, 15%-20%, 20%-25%, 25%-30%, or 30%-35%. In certain embodiments, the standard ratio is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35%. Preferably, the patient is a human. In preferred embodiments, the biological sample is blood, serum, plasma, cerebrospinal fluid, urine, a cell sample or a tissue sample.

In addition to assaying for levels of undercarboxylated/uncarboxylated osteocalcin, the present invention also provides methods and compositions for diagnosing disorders associated with decreased levels of adiponectin. Such disorders include, but are not limited to, metabolic syndrome, glucose intolerance, diabetes types 1 and 2, atherosclerosis and obesity. In a specific embodiment of the invention, a method is provided for diagnosing a patient at risk of developing diabetes comprising: (i) determining a patient level of adiponectin in a biological sample taken from the patient and a control level of adiponectin in a biological sample taken from a subject that does not have diabetes, (ii) comparing the patient and control levels, and (iii) concluding that the patient is at risk of developing diabetes if the patient level is lower than the test level.

In certain embodiments, the serum level of adiponectin and insulin are both measured and, if the serum levels of adiponectin and insulin in the patient are both lower than the levels in a subject without the disease, then the patient is at risk of developing the disease. In another embodiment, serum adiponectin and the glycemic index for the patient are measured and, if the serum level of adiponectin in the patient is lower than the level in a subject without the disease and the patient also has high glycemia, then the patient is at risk of developing the disease. Alternatively, serum adiponectin and uncarboxylated osteocalcin can be measured, or serum adiponectin, uncarboxylated osteocalcin and insulin can be measured and compared to controls for diagnosis of metabolic syndrome, its components, or type 1 diabetes.

In practicing the diagnostic methods of the invention, as set forth above, the biological sample is selected from the group consisting of blood, serum, plasma, cerebral spinal fluid, a cell sample or a tissue sample. In another embodiment, the sample is derived from a human.

Assays for detecting the levels of protein expression are well known to those of skill in the art. Such assays include, for example, antibody-based immunoassays. Methods for using antibodies as disclosed herein are particularly applicable to the cells, tissues and disorders that differentially express osteocalcin, OST-PTP, or gamma-carboxylase or that are involved in conditions as otherwise discussed herein. The methods use antibodies that selectively bind to the protein of interest and its fragments or variants. For therapeutic applications, antibodies that recognize OST-PTP and reduce its ability to bind to or dephosphorylate gamma-carboxylase are preferred. For diagnostic use, antibodies against undercarboxylated/uncarboxylated osteocalcin, gamma-carboxylase, adiponectin and vitamin K are preferred. An antibody is considered to selectively bind even if it also binds to other proteins that are not substantially homologous with the protein of interest. These other proteins share homology with a fragment or domain of the protein of interest. This conservation in specific regions gives rise to antibodies that bind to both proteins by virtue of the homologous sequence. In this case, it would be understood that antibody binding to the protein of interest is still selective. In certain embodiments, however, the antibodies do not substantially bind to proteins other than the protein of interest.

The amount of an antigen (e.g., osteocalcin or other protein of interest) in a biological sample may be determined by an assay such as a radioimmunoassay, an immunoradiometric assay, and/or an enzyme immunoassay. A "radioimmunoassay" is a technique for detecting and measuring the concentration of an antigen using a labeled (e.g., radioactively labeled) form of the antigen. Examples of radioactive labels for antigens include $^3$H, $^{14}$C, and $^{125}$I. The concentration of antigen (e.g., osteocalcin) in a sample (e.g., biological sample) is measured by having the antigen in the sample compete with a labeled (e.g., radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "Immunoradiometric Assay" (IRMA) is an immunoassay in which the antibody reagent is radioactively labeled. An IRMA requires the production of a multivalent antigen conjugate, by techniques such as conjugation to a protein, e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." The "Enzyme-Linked Immunosorbent Assay (ELISA)" is a technique for detecting and measuring the concentration of an antigen using a labeled (e.g., enzyme linked) form of the antibody. In a "sandwich ELISA", an antibody (e.g., to osteocalcin) is linked to a solid phase (e.g., a microtiter plate) and exposed to a biological sample containing antigen (e.g., osteocalcin). The solid phase is then washed to remove unbound antigen. A labeled (e.g., enzyme linked) antibody is then bound to the bound-antigen (if present) forming an antibody-antigen-antibody sandwich. Examples of enzymes that can be linked to the antibody are alkaline phosphatase, horseradish peroxidase, luciferase, urease, and β-galactosidase. The enzyme linked antibody reacts with a substrate to generate a colored reaction product that can be assayed.

In a "competitive ELISA," antibody is incubated with a sample containing antigen (e.g., osteocalcin). The antigen-antibody mixture is then contacted with an antigen-coated solid phase (e.g., a microtiter plate). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay," a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or β-galactosidase), or chemical methods (e.g., DAB/Substrate chromagen).

In addition to detecting levels of protein expression, the diagnostic assays of the invention may employ methods designed to detect the level of RNA expression. Levels of RNA expression may be determined using methods well known to those of skill in the art, including, for example, the use of northern blots, RT-PCR or in situ hybridizations.

Carboxylation of osteocalcin confers a greater affinity for hydroxyapatite. Typically, total osteocalcin is measured by immunoassay followed by incubation with hydroxyapatite and centrifugation. The supernatant, which contains osteocalcin that has not adsorbed to hyudroxyapatite is then measured using the same immunoassay. The results of this procedure can be expressed either as absolute concentrations or as a ratio of undercarbocylated to carboxylated osteocalcin.

Another procedure uses monoclonal antibodies that distinguish the carboxylation state of all or some of the Glu/Gla residues of osteocalcin. For example, GluOC4-5 (TaKaRa catalog no. M171) reacts with human osteocalcin with glutamic acid residues (decarboxylated) at positions 21 and 24, and does not react with react with Gla-type osteocalcin.

For a review of osteocalcin measurement methods, see Lee et al., 2000, Ann. Clin. Biochem. 37, 432-446.

Drug Screening and Assays

Cell-based and non-cell based methods of drug screening are provided to identify candidate agents that reduce OST-PTP or gamma-carboxylase activity or expression, or increase the level of undercarboxylated/uncarboxylated osteocalcin activity or expression. Such agents find use in treating or preventing a disorder related to energy metabolism and the OST-PTP signaling pathway. Such disorders include, metabolic syndrome, glucose intolerance, type 1 or type 2 diabetes, atherosclerosis, or obesity. Such agent may be used to treat disorders characterized by decreased insulin production, deceased insulin sensitivity, and decreased glucose tolerance or increased fat mass. Such assays may also be used to assay for the effectiveness of an agent in treating or preventing a disorder related to the OST-PTP pathway.

A non-cell based screening method is provided to identify compounds that bind to OST-PTP, gamma-carboxylase or osteocalcin and thereby modulate the activity of said proteins.

A screening method is provided to identify, or assay for, an agent that binds to OST-PTP, the method comprising the steps of: (i) providing a mixture comprising OST-PTP or a fragment or variant thereof, (ii) contacting the mixture with an agent, (iii) determining whether the agent binds to the OST-PTP, and (iv) identifying the agent if it binds to the OST-PTP or a fragment or variant thereof. The method may further comprise the step of determining whether the agent reduces the ability of OST-PTP to dephosphorylate gamma-carboxylase.

A screening method is provided to identify, or assay for, an agent that binds to the phosphatase 1 domain of OST-PTP, the method comprising the steps of: (i) providing a mixture comprising the phosphatase 1 domain of OST-PTP or a fragment or variant thereof, (ii) contacting the mixture with an agent, (iii) determining whether the agent binds to the phosphatase 1 domain of OST-PTP, and (iv) identifying the agent if it binds to the phosphatase 1 domain of OST-PTP or a fragment or variant thereof. The method may further comprise the step of determining whether the agent reduces the ability of OST-PTP to dephosphorylate gamma-carboxylase.

A screening method is provided to identify, or assay for, an agent that binds to gamma-carboxylase, the method comprising the steps of: (i) providing a mixture comprising the gamma-carboxylase or a fragment or variant thereof, (ii) contacting the mixture with an agent, (iii) determining whether the agent binds to the gamma-carboxylase, and (iv) identifying the agent if it binds to the gamma-carboxylase or a fragment or variant thereof. The method may further comprise the step of determining whether the agent reduces gamma-carboxylase activity.

A screening method is provided to identify, or assay for, an agent that binds to osteocalcin, the method comprising the steps of: (i) providing a mixture comprising osteocalcin or a fragment or variant thereof, (ii) contacting the mixture with an agent, (iii) determining whether the agent binds to the osteocalcin, and (iv) identifying the agent if it binds to the osteocalcin or a fragment or variant thereof. The method may further comprise the step of determining whether the agent increases osteocalcin activity.

The binding of the agent may be determined through the use of competitive binding assays. The competitor is a binding moiety known to bind to the target molecule (i.e. one of the various proteins), such as an antibody, peptide, binding partner, ligand, etc. Under certain circumstances, there may be competitive binding as between the agent and the binding moiety, with the binding moiety displacing the agent.

The agent may be labeled. Either the agent, or the competitor, or both, is added first to the protein for a time sufficient to allow binding, if present. Incubations may be performed at any temperature which facilitates optimal activity, typically between 4 degrees Centigrade. and 40 degrees Centigrade. Incubation periods are selected for optimum activity, but may also optimized to facilitate rapid high through put screening. Typically between 0.1 and 1 hour will be sufficient. Excess reagent is generally removed or washed away. The second component is then added, and the presence or absence of the labeled component is followed, to indicate binding.

Using such assays, the competitor may be added first, followed by the agent. Displacement of the competitor is an indication that the agent is binding to one of the various proteins and thus is capable of binding to, and potentially modulating, its activity. In this embodiment, either component can be labeled. Thus, for example, if the competitor is labeled, the presence of label in the wash solution indicates displacement by the agent. Alternatively, if the agent is labeled, the presence of the label on the support indicates displacement.

In another example, the agent is added first, with incubation and washing, followed by the competitor. The absence of binding by the competitor may indicate that the agent is bound to one of the various proteins with a higher affinity. Thus, if the agent is labeled, the presence of the label on the support, coupled with a lack of competitor binding, may indicate that the agent is capable of binding to one of the various proteins.

The method may comprise differential screening to identify agents that are capable of modulating the activity of one of the various proteins. In such an instance, the methods comprise combining a protein and a competitor in a first sample. A second sample comprises an agent, a protein and a competitor. Addition of the agent is performed under conditions which allow the modulation of one of the various proteins. The binding of the competitor is determined for both samples, and a change, or difference in binding between the two samples indicates the presence of an agent capable of binding to one of the various proteins and potentially modulating its activity. That is, if the binding of the competitor is different in the second sample relative to the first sample, the agent is capable of binding to one of the various proteins.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Non-cell based screening for agents that modulate the activity of one of the various proteins may also be done. Methods for screening for an agent capable of modulating the activity of one of the various proteins comprise the steps of adding an agent to a sample of one of the various proteins, as above, and determining an alteration in the biological activity of one of the various proteins. "Modulating the activity of one of the various proteins" includes an increase in activity, a decrease in activity, or a change in the type or kind of activity present. Thus, the agent should both bind to the protein (although this may not be necessary), and alter its biological or biochemical activity as defined herein.

Thus, in one example, the methods comprise combining a protein sample and an agent, and evaluating the effect on OST-PTP, gamma-carboxylase or osteocalcin. By enzyme activity, specifically OST-PTP or gamma-carboxylase activity or grammatical equivalents herein is meant one or more of the biological activities associated with the enzyme. For OST-PTP this activity is preferably the dephosphorylation of gamma-carboxylase or of the insulin receptor; for gamma-carboxylase it is the carboxylation of osteocalcin. The screening assay are designed to find agents that reduce OST-PTP or gamma-carboxylase activity, or increase levels of undercarboxylated/uncarboxylated osteocalcin and adiponectin in a biological sample taken from the transformed animal or cell.

Specifically, a screening method is provided to identify, or assay for, an agent that reduces OST-PTP activity, the method comprising the steps of: (a) providing a control and a test mixture comprising OST-PTP or a fragment or variant thereof, (b) contacting the mixture with an agent, (c) determining the level of activity of OST-PTP in the test mixture and in the control, and (d) selecting the bioactive agent if the level of OST-PTP activity in the test mixture is lower than the level in the control.

A screening method is provided to identify, or assay for, an agent that reduces gamma-carboxylase activity, the method comprising the steps of: (a) providing a control and a test mixture comprising or a fragment or variant thereof, (b) adding to the test mixture a bioactive agent under conditions that permit the bioactive agent to bind to the gamma-carboxylase or a fragment or variant thereof, (c) determining the level of activity of gamma-carboxylase in the test mixture and in the control, and (d) selecting the bioactive agent if the level of gamma-carboxylase activity in the test mixture is lower than the level in the control.

Cell-based screening methods are provided for identifying, or assaying for, agents which decrease the level of expression of the Esp gene encoding OST-PTP or the gene encoding gamma-carboxylase. Alternatively, the drug screening assays may be used to identify, or assay for, agents which increase the level of osteocalcin gene expression.

The present invention also provides a screening method to identify an agent that decarboxylates osteocalcin, the method comprising the steps of: (a) providing a control and a test mixture comprising carboxylated osteocalcin, (b) adding to the test mixture an agent, (c) determining the level of carboxylated osteocalcin in the test mixture and in the control, and (d) selecting an agent if the level of carboxylated osteocalcin in the test mixture is lower than the activity in the control.

A cell-based method is provided for identifying, or assaying for, an agent that reduces OST-PTP gene expression, the method comprising steps: (a) determining a first expression level of OST-PTP in a cell, (b) determining a second expression level of OST-PTP after contact with a test agent; and (c) comparing the first expression level with the second expression level, wherein an agent that is capable of reducing OST-PTP expression is identified if the level of expression in the first is higher than the second expression level. The level of OST-PTP gene expression may be determined by measuring the amount of the OST-PTP mRNA made or the amount of the OST-PTP protein made.

A cell-based method is provided for identifying, or assaying for, an agent that reduces gamma-carboxylase gene expression, the method comprising steps: (a) determining a first expression level of gamma-carboxylase in a cell, (b) determining a second expression level of gamma-carboxylase after contact with a test agent; and (c) comparing the first expression level with the second expression level, wherein an agent that is capable of reducing gamma-carboxylase expression is identified if the level of expression in the first is higher than the second expression level. The level of gamma-carboxylase gene expression may be determined by measuring the amount of the gamma-carboxylase mRNA made or the amount of gamma-carboxylase protein made.

A cell-based method is provided for identifying, or assaying for, an agent that increases osteocalcin gene expression, the method comprising steps: (a) determining a first expression level of osteocalcin in a cell, (b) determining a second expression level of osteocalcin expression after contact with a test agent; and (c) comparing the first expression level with the second expression level, wherein an agent that is capable of increasing osteocalcin expression is identified if the level of expression in the first is lower than the second expression level. The level osteocalcin gene expression may be determined by measuring the amount of the osteocalcin mRNA made or the amount of osteocalcin protein made.

A reporter gene may be utilized to screen for agent capable of modulating gene expression. In such assays, cells are generated that contain a gene construct wherein expression of a reporter gene is placed under the control of native gene expression regulatory elements of the native gene of interest, i.e., the OST-PTP, gamma-carboxylase or osteocalcin gene. Reporter genes include, but are not limited to CAT, LacZ, lucierase or GFP.

A cell-based method is provided for screening, or assaying, for an agent that reduces OST-PTP gene expression, the method comprising steps: (a) determining a first expression level of a reporter gene in a cell wherein expression of the reporter gene is under the control of native OST-PTP gene expression regulatory elements, (b) determining a second expression level of reporter gene exprssion after contact with a test agent; and (c) comparing the first expression level with the second expression level, wherein an agent that is capable of reducing reporter gene expression is identified if the level of expression in the first is higher than the second expression level.

A cell-based method is provided for screening, or assaying, for an agent that reduces gamma-carboxylase gene expression, the method comprising steps: (a) determining a first expression level of a reporter gene in a cell wherein expression of the reporter gene is under the control of native gamma-carboxylase gene expression regulatory elements, (b) determining a second expression level of reporter gene expression after contact with a test agent; and (c) comparing the first expression level with the second expression level, wherein an agent that is capable of reducing gamma-carboxylase gene expression is identified if the level of expression in the first is higher than the second expression level.

A cell-based method is provided for screening, or assaying, for an agent that increases osteocalcin gene expression, the method comprising steps: (a) determining a first expression level of a reporter gene in a cell wherein expression of the reporter gene is under the control of native osteocalcin gene expression regulatory elements, (b) determining a second expression level of reporter gene expression after contact with a test agent; and (c) comparing the first expression level with the second expression level, wherein an agent that is capable of increasing osteocalcin gene expression is identified if the level of expression in the first is lower than the second expression level.

Cell-based screening assays are provided for identifying agents that reduce OST-PTP or gamma-carboxylase activity.

Specifically, a cell-based method for screening for an agent that reduces OST-PTP activity is provided, the method comprising steps: (a) determining a first activity level in a first cell that expresses the phosphatase 1 domain of OST-PTP, (b) contacting a second cell that expresses the phosphatase 1 domain of OST-PTP with an agent, (c) determining a second activity level in the second cell that expresses the phosphatase 1 domain of OST-PTP; and (d) comparing the first activity level with the second activity level, wherein the agent reduces OST-PTP activity if the first activity level is higher than the second activity level. The level of OST-PTP activity may be determined by measuring the level of gamma-carboxylase activity. The level of OST-PTP activity may be determined by measuring the level of osteocalcin carboxylation.

A cell-based method for screening, or assaying, for an agent that reduces gamma-carboxylase activity is provided, the method comprising the steps: (a) determining a first activity level in a first cell that expresses gamma-carboxylase, (b) contacting a second cell that expresses gamma-carboxylase with an agent (c) determining a second activity level in the second cell that expresses gamma-carboxylase; and (d) comparing the first activity level with the second activity level, wherein the agent reduces gamma-carboxylase activity if the first activity level is higher than the second activity level. Assays for measuring gamma carboxylase activity are know to those of skill in the art (See, for example, Hubbard et al., (1989) Proc. Natl. Acad. Sci. USA 86:6893-6897; Rehemtulla et al., (1993) Proc. Natl. acad. Sci USA 90:4611-4615).

Gamma carboxylase catalyzes the posttranslational modification of specific glutamic acid residues within osteocalcin to form γ-carboxyglutamic acid residues. In an embodiment of the invention, the level of gamma carboxylase activity or decarboxylase activity is determined by measuring the level of osteocalcin carboxylation.

A cell based method is provided for screening for an agent that decarboxylates osteocalcin, the method comprising the steps of: (a) determining a first level of carboxylated osteocalcin in a first cell that expresses osteocalcin, (b) contacting a second cell that expresses carboxylated osteocalcin with an agent, (c) determining a second level of carboxylated osteocalcin, and (d) comparing the first level of carboxylated osteocalcin with the second level of carboxylated osteocalcin, wherein the agent decarboxylates osteocalcin if the first level of carboxylated osteocalcin is higher than the second level.

Cells to be used in the screening, or assaying, methods include cells that naturally express OST-PTP, gamma-carboxylase, or osteocalcin, cells that have been genetically engineered to express (or overexpress) OST-PTP, the phosphatase 1 domain of OST-PTP, gamma-carboxylase, or osteocalcin, as well as cells derived from the transgenic animals of the present invention. Such cells include transformed osteoblast that overexpresses OST-PTP or gamma-carboxylase.

A method is provided for testing an agent's effectiveness in increasing adiponectin expression in adipocytes, comprising: (a) co-culturing osteoblasts and adipocytes, (b) contacting the osteoblasts with a candidate agent, (c) determining whether the candidate agent increases the level of expression or secretion of adiponectin or a fragment or variant thereof above a control level measured in a control co-culture in which osteoblasts are not contacted with the candidate agent, and (d) if the candidate agent increases the level of adiponectin expression or secretion above the control level, then selecting the candidate agent as an agent that increases adiponectin expression or secretion in adipocytes.

A method is provided for testing an agent's effectiveness in increasing insulin expression or secretion in pancreatic beta cells, comprising: (a) co-culturing the osteoblasts and pancreatic beta cells, (b) contacting the osteoblasts with a candidate agent, (c) determining whether the candidate agent increases the level of insulin expression or secretion above a control level of insulin expression measured in a control co-culture in which osteoblasts are not contacted with the candidate agent, and (d) if the candidate agent increases the level of insulin expression or secretion above the control level, then selecting the candidate agent as an agent that increases insulin expression or secretion in pancreatic beta cells.

A method is provided for determining the ability of a candidate agent to treat or prevent in an animal metabolic syndrome or a phenotype associated with metabolic syndrome is provided that is selected from the group comprising predisposition to type 1 or 2 diabetes, glucose intolerance, decreased insulin production, decreased insulin sensitivity, decreased glucose tolerance, atherosclerosis and increased fat mass, comprising: (a) providing a test animal and a control animal, (b) administering the candidate agent to the test animal, (c) comparing the level of undercarboxylated/uncarboxylated osteocalcin in the test animal to the level of undercarboxylated/uncarboxylated osteocalcin in the control animal, and (d) selecting the candidate agent if the level of undercarboxylated/uncarboxylated osteocalcin is higher in the test animal than in the control animal. In a specific embodiment of the invention the level of undercarboxylated/uncarboxylated osteocalcin is measured in osteoblasts.

In one example, the level of undercarboxylated/uncarboxylated osteocalcin is measured in osteoblasts. The candidate agent may be bound to a phosphate group that facilitates its uptake by osteoblasts.

A method is provided for screening a candidate agent for the ability to treat or prevent metabolic syndrome in an animal or a phenotype associated with metabolic syndrome including predisposition to type 2 diabetes, glucose intolerance, decreased insulin production, decreased insulin sensitivity, decreased glucose tolerance, atherosclerosis and increased fat mass, comprising: (a) providing a first and a second animal, (b) administering to said first animal a candidate agent, and (c) comparing the level of OST-PTP expression or activity in the first animal of step (b) that was given the candidate agent to the level of OST-PTP in the second animal of step (a) that was not administered said candidate agent; wherein a candidate agent that reduces the level of OST-PTP expression or activity is selected as an agent that has effectiveness in treating metabolic syndrome or a phenotype associated therewith.

The level of OST-PTP expression or activity may be measured in osteoblasts. Further, the candidate agent may be bound to a phosphate group that facilitates its uptake by osteoblasts.

A method is provided for screening a candidate agent for the ability to treat or prevent metabolic syndrome in an animal, or a phenotype associated with metabolic syndrome including predisposition to type 1 and 2 diabetes, glucose intolerance, decreased insulin production, decreased insulin sensitivity, atherosclerosis, decreased glucose tolerance and increased fat mass, comprising: (a) providing a first and a second animal, (b) administering to said first animal a candidate agent, and (c) comparing the level of expression or activity or secretion of osteocalcin in the first animal of step (b) that was given the candidate agent to the level of expression or activity of osteocalcin in the second animal of step (a) that was not administered said candidate agent; wherein a candidate agent that in increases expression or activity or secretion of osteocalcin or a fragment or variant thereof is selected as an agent that has effectiveness in treating metabolic syndrome or a phenotype associated therewith.

A method is provided for screening a candidate agent for the ability to treat or prevent metabolic syndrome in an animal or a phenotype associated with metabolic syndrome including predisposition to type 1 or 2 diabetes, glucose intolerance, decreased insulin production, decreased insulin sensitivity, atherosclerosis, decreased glucose tolerance and increased fat mass, comprising: (a) providing a first and a second animal, (b) administering to said first animal a candidate agent, and (c) comparing the level of expression or secretion of adiponectin or a fragment or variant thereof in the first animal of step (b) that was given the candidate agent to the level of adiponectin expression or secretion in the second animal of step (a) that was not administered said candidate agent; wherein a candidate agent that increases the level of expression or secretion of adiponectin or a fragment or variant thereof is selected as an agent that has effectiveness in treating metabolic syndrome or a phenotype associated therewith. In such a method, the level of adiponectin expression or secretion is measured in adipocytes or in serum.

A method is provided for screening a candidate agent for the ability to treat or prevent metabolic syndrome in a osteocalcin-deficient mouse, wherein the osteocalcin-deficient mouse exhibits a phenotype relative to a wild type mice, which phenotype is selected from the group comprising reduced osteocalcin expression, type 1 or 2 diabetes predisposition, decreased insulin secretion, atherosclerosis, decreased insulin sensitivity, decreased expression or secretion of adiponectin or a fragment or variant thereof, decreased glucose tolerance, and increased fat mass, comprising: (a) providing a first and a second osteocalcin-deficient mouse that are both from the same strain as the osteocalcin-deficient mouse; (b) administering to said first osteocalcin-deficient mouse a candidate agent, and (c) comparing the phenotype of the first osteocalcin-deficient mouse of step (b) that was given the candidate agent to the phenotype of said second osteocalcin-deficient mouse of step (a) that was not administered said candidate agent; wherein a candidate agent that reduces or ameliorates the phenotype is selected as an agent that has effectiveness in treating metabolic syndrome.

A method is also provided for screening a candidate agent for the ability to treat metabolic syndrome in an adiponectin-deficient mouse, wherein the adiponectin-deficient mouse exhibits a phenotype selected from the group comprising type 1 or 2 diabetes predisposition; decreased insulin secretion; decreased insulin sensitivity; atherosclerosis, decreased glucose tolerance, and increased fat mass, comprising: (a) providing a first and a second adiponectin-deficient mouse that are both from the same strain, (b) administering to said first adiponectin-deficient mouse a candidate agent, and c) comparing the phenotype of the first adiponectin-deficient mouse of step (b) that was given the candidate agent to the phenotype of said second adiponectin-deficient mouse of step (a) not administered said candidate agent; wherein a candidate agent that reduces or ameliorates the phenotype is selected as an agent that has effectiveness in treating metabolic syndrome.

A method is provided for screening for an agent suspected to reduce OST-PTP activity or expression in osteoblasts for use as a therapeutic agent for treating or preventing a disease that is a member of the group comprising metabolic syndrome, type I or II diabetes, decreased insulin secretion, decreased insulin sensitivity, decreased glucose tolerance, increased fat mass and atherosclerosis, comprising: a) obtaining a control transgenic mouse overexpressing OST-PTP selectively in osteoblasts, and a second transgenic mouse from the same strain as the control, b) subjecting the first mouse to a placebo and the second mouse to a therapeutic agent, c) assaying for the level of OST-PTP activity in a sample of osteoblasts from the first and second mice, d) comparing the level of OST-PTP activity assayed in the first mouse to that in the second mouse, and e) concluding that the agent is useful as a therapeutic compound to treat or prevent the disease if the level in the first mouse is higher than the level in the second mouse.

A method is provided for screening a agent suspected to reduce gamma-carboxylase activity or expression in osteoblasts for use as a therapeutic compound for treating or preventing a disease that is a member of the group comprising metabolic syndrome, type I or II diabetes, decreased insulin secretion, decreased insulin sensitivity, decreased glucose tolerance, increased fat mass and atherosclerosis, comprising: a) obtaining a control transgenic mouse overexpressing gamma-carboxylase selectively in osteoblasts, and a second transgenic mouse from the same strain as the control, b) subjecting the first mouse to a placebo and the second mouse to the therapeutic compound under the same conditions that allow the therapeutic compound to have an effect, c) assaying for the level of gamma-carboxylase activity in a sample of osteoblasts from the first and second mice, d) comparing the level of gamma-carboxylase activity assayed in the first mouse to that in the second mouse, e) concluding that bioactive agent is useful as a therapeutic compound for use in reducing gamma-carboxylase activity or expression in osteoblasts if the level in the first mouse is higher than the level in the second mouse. The bioactive agent may be an enzyme inhibitor.

A method is provided for screening a agent suspected of having a therapeutic use to treat or prevent a disease that is a member of the group comprising metabolic syndrome, type I or II diabetes, decreased insulin secretion, decreased insulin sensitivity, decreased glucose tolerance, increased fat mass and atherosclerosis, comprising: (a) providing an animal that has the disease, (b) determining the amount of undercarboxylated/uncarboxylated osteocalcin in a pretreatment biological sample taken from the animal, (c) administering the bioactive agent to the test animal under conditions that permit the agent to have an effect, (d) determining the amount of undercarboxylated/uncarboxylated osteocalcin in a post-treatment biological sample taken from the animal, and (e) if the bioactive agent increases the amount of undercarboxylated/uncarboxylated osteocalcin in the post-treatment biological sample compared to the pre-treatment sample, concluding that the agent has the therapeutic use.

A method is provided for screening a bioactive agent suspected of having a therapeutic use to treat or prevent a disease that is a member of the group comprising metabolic syndrome, type I or II diabetes, decreased insulin secretion, decreased insulin sensitivity, decreased glucose tolerance, increased fat mass and atherosclerosis, comprising: (a) providing an animal that has the disease, (b) determining the amount of adiponectin in a pretreatment biological sample taken from the animal, (c) administering the bioactive agent to the test animal under conditions that permit the agent to have an effect, (d) determining the amount of adiponectin in a post-treatment biological sample taken from the animal, and (e) if the bioactive agent increases the amount of adiponectin in the post-treatment biological sample compared to the pre-treatment sample, concluding that the agent has the therapeutic use.

The term "agent" or "exogeneous compound" as used herein includes any molecule, e.g., protein, oligopeptide, small organic molecule, polysaccharide, polynucleotide, lipid, etc., or mixtures thereof, with the capability of directly or indirectly altering the bioactivity of one of the various proteins (OST-PTP, gamma-carboxylase, osteocalcin). Some of the agents can be used therapeutically. Generally a plurality of assay mixtures is run in parallel with different agent concentrations to obtain a differential response to the various concentrations. Typically, one of these concentrations serves as a negative control, i.e., at zero concentration or below the level of detection.

Agents for use in screening encompass numerous chemical classes, though typically they are organic molecules, preferably small organic compounds having a molecular weight of more than 100 and less than about 2,500 daltons, preferably less than about 500 daltons. Agents comprise functional groups necessary for structural interaction with proteins, particularly hydrogen bonding, and typically include at least an amine, carbonyl, hydroxyl or carboxyl group, preferably at least two of the functional chemical groups. The agent often comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof. Particularly preferred are peptides.

Libraries of high-purity small organic ligands and peptide agonists that have well-documented pharmacological activities are available from numerous sources. One example is an NCI diversity set which contains 1,866 drug-like compounds (small, intermediate hydrophobicity). Another is an Institute of Chemistry and Cell Biology (ICCB; maintained by Harvard Medical School) set of known bioactives (467 compounds) which includes many extended, flexible compounds. Some other examples of the ICCB libraries are: Chem Bridge DiverSet E (16,320 compounds); Bionet 1 (4,800 compounds); CEREP (4,800 compounds); Maybridge 1 (8,800 compounds); Maybridge 2 (704 compounds); Maybridge HitFinder (14,379 compounds); Peakdale 1 (2,816 compounds); Peakdale 2 (352 compounds); ChemDiv Combilab and International (28,864 compounds); Mixed Commercial Plate 1 (352 compounds); Mixed Commercial Plate 2 (320 compounds); Mixed Commercial Plate 3 (251 compounds); Mixed Commercial Plate 4 (331 compounds); ChemBridge Microformat (50,000 compounds); Commercial Diversity Setl (5,056 compounds). Other NCl Collections are: Structural Diversity Set, version 2 (1,900 compounds); Mechanistic Diversity Set (879 compounds); Open Collection 1 (90,000 compounds); Open Collection 2 (10,240 compounds); Known Bioactives Collections: NINDS Custom Collection (1,040 compounds); ICCB Bioactives 1 (489 compounds); SpecPlus Collection (960 compounds); ICCB Discretes Collections. The following ICCB compounds were collected individually from chemists at the ICCB, Harvard, and other collaborating institutions: ICCB1 (190 compounds); ICCB2 (352 compounds); ICCB3 (352 compounds); ICCB4 (352 compounds). Natural Product Extracts: NCl Marine Extracts (352 wells); Organic fractions—NCl Plant and Fungal Extracts (1,408 wells); Philippines Plant Extracts 1 (200 wells); ICCB-ICG Diversity Oriented Synthesis (DOS) Collections; DDS1 (DOS Diversity Set) (9600 wells). Compound libraries are also available from a commercial suppliers, such as ActiMol, Albany Molecular, Bachem, Sigma-Aldrich, TimTec, and others.

Known and novel pharmacological agents identified in screens may be further subjected to directed or random chemical modifications, such as acylation, alkylation, esterification, amidification to produce structural analogs.

When screening, designing or modifying compounds, other factors to consider include the Lipinski rule-of-five (not more than 5 hydrogen bond donors (OH and NH groups); not more than 10 hydrogen bond acceptors (notably N and O); molecular weight under 500 g/mol; partition coefficient log P less than 5), and Veber criteria, which are recognized in the pharmaceutical art and relate to properties and structural features that make molecules more or less drug-like.

The agent may be a protein. By "protein" in this context is meant at least two covalently attached amino acids, which includes proteins, polypeptides, oligopeptides and peptides. The protein may be made up of naturally occurring amino acids and peptide bounds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acids" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

The agent may be a naturally occurring protein or fragment or variant of a naturally occurring protein. Thus, for example, cellular extracts containing proteins, or random or directed digests of proteinaceous cellular extracts, may be used. In this way, libraries of prokaryotic and eukaryotic proteins may be made for screening against one of the various proteins. Libraries of bacterial, fungal, viral, and mammalian proteins, with the latter being preferred, and human proteins being especially preferred may be used.

Agents may be peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized agent bioactive proteinaceous agents.

The library may be fully randomized, with no sequence preferences or constants at any position. The library may be biased. That is, some positions within the sequence are either held constant, or are selected from a limited number of possibilities. For example, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

The agent may be an isolated nucleic acid, preferably antisense, siRNA, or cDNA that binds to either the gene encoding the protein of interest, or its mRNA to block gene expression or mRNA translation, respectively. By "nucleic acid" or "oligonucleotide" or grammatical equivalents herein means at least two nucleotides covalently linked together. Such nucleic acids will generally contain phosphodiester bonds, although in some cases, as outlined below, nucleic acid analogs are included that may have alternate backbones, comprising, for example, phosphoramide (Beaucage et al., Tetrahedron 49)10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), pohsphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114: 1895 (1992); Meier et al., Chem. Int. Ed. Engl. 31:1008 (1992); Nielsen, Nature, 365:566 (1993); Carlsson et al., Nature 380:207 (1996), all of which are incorporated by reference).

Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleoside 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in antisense Research", Ed. Y. S. Sanghui and P. Can Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxathine, isocytosine, isoguanine, etc.

As described above generally for proteins, nucleic acid agents may be naturally occurring nucleic acids, random nucleic acids, or "biased" random nucleic acids. For example, digests of prokaryotic or eukaryotic genomes may be used as is outlined above for proteins.

The agents may be obtained from combinatorial chemical libraries, a wide variety of which are available in the literature. By "combinatorial chemical library" herein is meant a collection of diverse chemical compounds generated in a defined or random manner, generally by chemical synthesis. Millions of chemical compounds can be synthesized through combinatorial mixing.

The determination of the binding of the agent to one of the various proteins may be done in a number of ways. In a preferred embodiment, the agent is labeled, and binding determined directly. For example, this may be done by attaching all or a portion of one of the various proteins to a solid support, adding a labeled agent (for example an agent comprising a fluorescent label), washing off excess reagent, and determining whether the label is present on the solid support. Various blocking and washing steps may be utilized as is known in the art.

By "labeled" herein is meant that the agent is either directly or indirectly labeled with a label which provides a detectable signal, e.g. a radioisotope (such as $^{3}H$, $^{14}C$, $^{32}P$, $^{33}P$, $^{35}S$, or $^{125}I$), a fluorescent or chemiluminescent compound (such as fluorescein isothiocyanate, rhodamine, or luciferin), an enzyme (such as alkaline phosphatase, beta-galactosidase or horseradish peroxidase), antibodies, particles such as magnetic particles, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal. Only one of the components may be labeled. Alternatively, more than one component may be labeled with different labels.

Sequence Listings

Full nucleic acid and amino acid sequence listings relevant to this application are listed below. Transgenic mice and isolated cells from them (especially osteoblasts and adipocytes) that over or under express any of the listed nucleic acids (cDNA for Esp, osteocalcin, adiponectin, gamma-carboxylase, apolipoprotein E) can be made using routine methods known in the art and described herein, including knock in and knock out mice. In certain instances, nucleic acids are inserted into the genome of the host organism operably connected to and under the control of a promoter and regulatory elements (endogenous or heterogeneous) that will cause the organism to over express the nucleic acid gene or mRNA. One example of an exogenous/heterogeneous promoter included in the transfecting vector carrying the gene to be amplified is alpha 1(I) collagen. Many such promoters are known in the art. Human osteoblasts can be transfected with vectors carrying the cDNA for human Esp or human osteocalcin (or fragments or variants thereof) operably linked to known promoters and regulatory elements that cause the transfected human osteoblast to overexpress osteocalcin (or fragments or variants thereof). Disclosed herein are transgenic mice and mouse cells, and transfected human cells over expressing osteocalcin (or fragments or variants thereof), OST-PTP or gamma-carboxylase. Also disclosed herein are double mutant mice that have deletions of one or both alleles for osteocalcin, Esp, gamma-carboxylase and adiponectin, and various combinations of double mutants. Also disclosed herein are vectors carrying the cDNA or mRNA encoding the proteins for insertion into the genome of a target animal or cell. Such vectors can optionally include promoters and regulatory elements operably linked to the cDNA or mRNA. By "operably linked" is meant that promoters and regulatory elements are connected to the cDNA or mRNA in such a way as to permit expression of the cDNA or mRNA under the control of the promoters and regulatory elements.

Antisense and small interfering RNAs for use in reducing expression of OST-PTP and gamma-carboxylase thereby treating or preventing metabolic syndrome or a component thereof in an animal or type 1 diabetes, can be made that specifically hybridize to the gene and mRNA encoding OST-PTP or gamma-carboxylase, respectively. The sequence for mouse (OST-PTP, Ptprv) cDNA is set forth in SEQ ID NO:18. The amino acid sequence for OST-PTP, Ptprv) protein is set forth in SEQ ID NO:19. This cDNA will hybridize with mRNA for OST-PTP and thereby interfere with its translation. Reducing OST-PTP expression will increase undercarboxylated/uncarboxylated osteocalcin. The cDNA for mouse gamma-carboxylase is identified by SEQ ID NO:12, and its amino acid sequence is SEQ ID NO:13. This cDNA will hybridize with mRNA for gamma-carboxylase and thereby interfere with its translation and is a preferred embodiment. The cDNA for human gamma-carboxylase is identified by SEQ ID NO:10, and the amino acid sequence is SEQ ID NO:11. Human gamma-carboxylase cDNA can be used therapeutically to reduce gamma-carboxylase expression to treat or prevent metabolic syndrome and its components and type 1 or type 2 diabetes.

EXAMPLES

The invention is illustrated herein by the experiments described above and by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Materials and Methods

Esp-nLacZ mice refers to an Esp-deficient mouse model in which one (+/−) or both alleles (−/−) for OST-PTP have been inactivated in all of the cells in the animal. The nLacZ (or LacZ) mouse is made by homologous recombination of a targeted OST-PTP allele with a transgene having a sequence encoding a nuclear-localized LacZ cassette, which is homologously recombined into exon 6 of the OST-PTP allele, such that the transgene is in frame with the OST-PTP gene, and expression of the transgene is operably linked to the native gene expression regulatory sequences of the OST-PTP allele. Esp KI (Knock In)=Esp nLacZ (−/−) mice.

Esp-nLacZ mice were generated using a targeting vector designed to insert a nuclear-localized LacZ (nLacZ) cassette into exon 6 such that LacZ was in frame with OST-PTP sequence (Dacquin et al., 2004; Ducy et al., 1996). Genomic clones spanning the entire mouse Ptprv gene were isolated from a mouse genomic library (129ola strain) by using fragments of the mouse cDNA (Lee et al., [1996]). A targeting vector was constructed that contains an HPRT hypoxanthine guanine phosphoribosyl transferase minigene selection cassette, an internal ribosomal entry site (Mountford et al., 1994), and a reporter containing SV40 nuclear localization sequences fused to the LacZ gene (nLacZ). Into this were cloned 4.4 kb of homology from the 5' end of the gene and 1.9 kb of homology from the 3' end of the gene. Gene targeting was conducted by using standard techniques (Joyner, 1999) in E14Tg2A feeder-independent embryonic stem (ES) cells (Hooper et al., 1987). Targeted ES cells were selected in HAT (10 microM hypoxanthine, 9 microM aminopterin, 20 microM thymidine) selection medium as previously described (Thompson et al., 1989). Tissue culture medium was GMEM (Glasgow Modified Eagles Media; Gibco) supplemented with 10% fetal calf serum (FCS), 0.1 mM 2 mercaptoethanol, 1 mM sodium pyruvate, and approximately $10^3$ U/ml of leukemia inhibitory factor. A total of $5 \times 10^6$ cells were electroporated in 800 microliters of phosphate buffered saline (PBS) with 20 micrograms of NotI linearized vector DNA at 800 V and 3 microFD by using a Gene Pulser (Bio-Rad) and plated onto gelatin coated 10-cm tissue culture plates. After 48 hr, the cells were transferred to HAT selection medium. Targeted ES cell clones were identified by Southern hybridization using radiolabeled cDNA fragments complementary to regions outside the homology of the targeting vector both 5' and 3' of the integration site and by using a LacZ probe to check for single copy integration. Targeted ES cells were injected in C57BL/6 blastocysts, which were subsequently transferred into foster mothers. Chimeric males were mated with MF1 strain females, and Southern blot analysis or polymerase chain reaction (PCR) of tail tip DNA from grey offspring was used to identify heterozygous animals. The mutation was crossed to the MF1 strain for five generations to provide heterozygous mice for subsequent analysis. This mutation resulted in deletion of most of OST-PTP extracellular domain, its transmembrane and intracellular domains (1). This type of mutant allele is referred to as the Esp nLacZ mutant allele or as the Esp KI (Knock In) mutant allele. In the Esp nLacZ mutant mice, one (+/−) or both alleles (−/−) for OST-PTP have been inactivated in all of the cells in the animal thereby interfering with OST-PTP expression.

"Esp osb mutant mice" are Esp-deficient mouse models in which one (+/−) or both alleles (−/−) for OST-PTP have been deleted or knocked out from osteoblasts only in the animal, thereby blocking synthesis of OST-PTP selectively in osteoblasts. This is not to be confused with the ob mutant which is lacking one or both alleles of leptin. An Esp osb mouse carries a disruption in one or both endogenous OST-PTP alleles in which exons 24 to 35 encoding the phosphatase domain of the OST-PTP allele have been deleted and replaced by a neomycin resistance gene floxed by loxP sites in one (+/−) or both alleles (−/−) for OST-PTP.

A targeting vector harboring LoxP sites within introns 23 and 35 as well as a floxed neomycin resistance cassette was electroporated into ES cells. Targeted ES cells were injected in 129Sv/EV blastocysts to generate chimeric mice harboring the floxed allele ($Esp_{flox}$). $Esp_{flox/+}$ mice were crossed with α1(I)collagen-Cre mice to generate $Esp_{ob-/+}$ mice and their progeny was intercrossed to obtain $Esp_{ob-/-}$ mice. The mice harboring floxed Esp alleles can be crossed with transgenic mice expressing the recombinase under the control of any promoter of interest to specifically inactivate the Esp gene in the cells where this promoter is active. In the $Esp_{ob}$, one (+/−) or both alleles (−/−) for OST-PTP have been inactivated in osteoblasts only thereby interfering with OST-PTP expression only in these cells. Molecular analysis showed that recombination occurred at high frequency at the Esp locus in osteoblasts but not in any other tissues or cell types including testis, adipocytes or pancreas beta-cells (FIGS. 1C and 1D). Northern blot analysis verified that it was a null allele while Souther blot hybridization was used to demonstrate the efficiency of Esp excision in osteoblasts (FIG. 1C). Quantitative RT-PCR and Western analysis failed to detect Esp mRNA or OST-PTP protein, respectively, in bone of $Esp_{ob}-/-$ mice while both Esp mRNA and OST-PTP protein were present in the testis of $Esp_{osb}-/-$ mice (FIG. 1D). These data indicate that an osteoblast-specific inactivation of Esp was achieved.

As used herein, "Esp-deficient mice" means either of two strains of transgenic mice in which both alleles for osteotesticular protein tyrosine phosphatase OST-PTP (encoded by the Esp gene) have been deleted (knocked out) as in the Esp osb-/- mouse, or have been disrupted or (knocked in) as in the Esp-nLacz-/- mouse.

FIG. 22 shows certain details of the method for generating $Esp_{osb}-/-$ mice and normal bone formation in Esp-/- animals. FIG. 23 compares 1 month-old WT and Esp-/- mice with respect to various metabolic and physiologic parameters: serum levels of C-peptide (A), serum Glucagon level (left) and glucagons content in pancreas (right) (B) and serum levels of IGF-1 (C), PYY (D), and amylin (E) in Esp-/- mice; (F) Ratio of muscle mass over body mass calculated by proton magnetic resonance spectroscopy ($^1$H-MRS) in 10 week-old WT and Esp-/- mice; (G) Representative images of proton $^1$H-MRS of 10 week-old WT and Esp-/- mice; (H) Food intake per day in 1 month- and 3 month-old Esp-/- and WT mice; (I and J) Comparison of expression level by real time PCR (I) and of serum levels (J) of TNF-α (left) and IL-6 (right) in 1 month-old Esp-/- and WT mice; and (K) Serum leptin (left) and resistin (right) levels in 1 month-old Esp-/- and WT mice. In all panels data represent the means±SD of experiments. *, $P<0.01$ (t-test).

Figure 24:
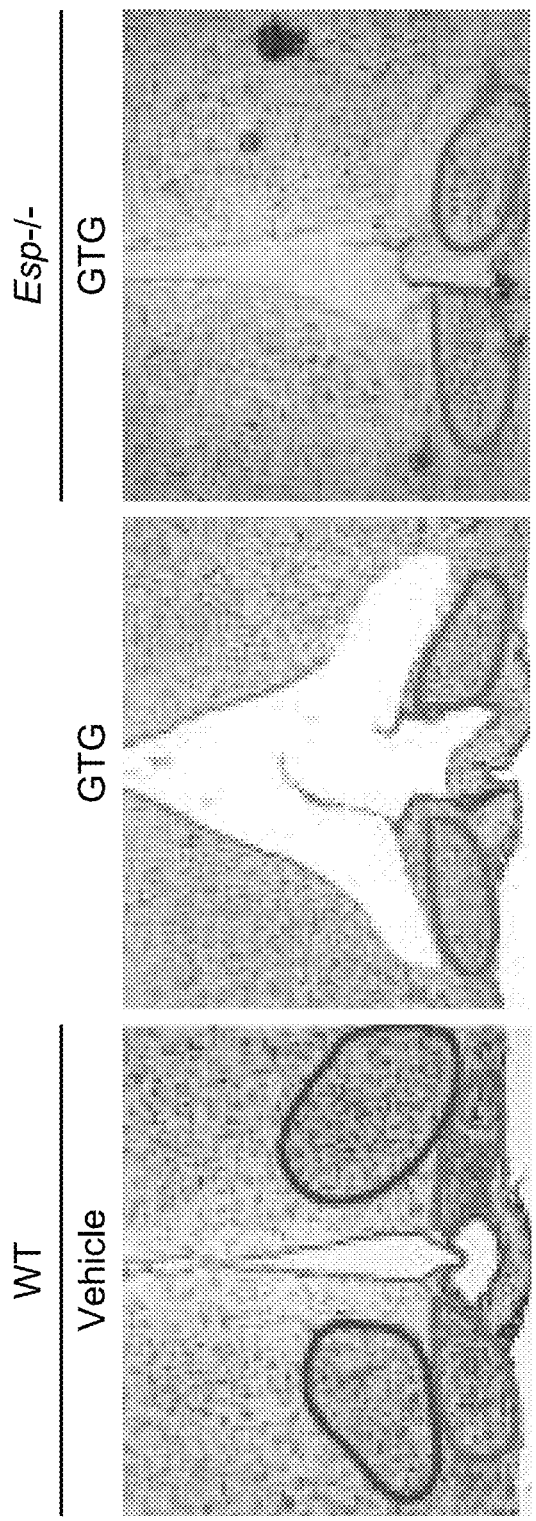
FIG. 24. Destruction of VMH nuclei by GTG. Cresyl violet staining of section from hypothalamus of WT and Esp−/− mice injected with GTG or vehicle. Arcuate nuclei are circled in blue, VMH in red.
Figure 25A:
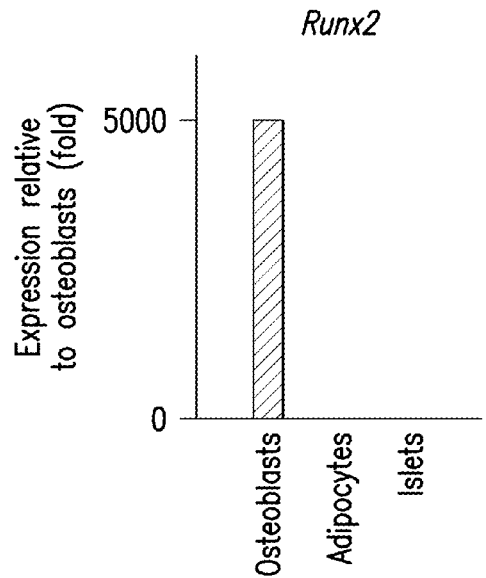
FIG. 25A-D. Absence of cell transdifferentiation during the co-culture assays.
Figure 25B:
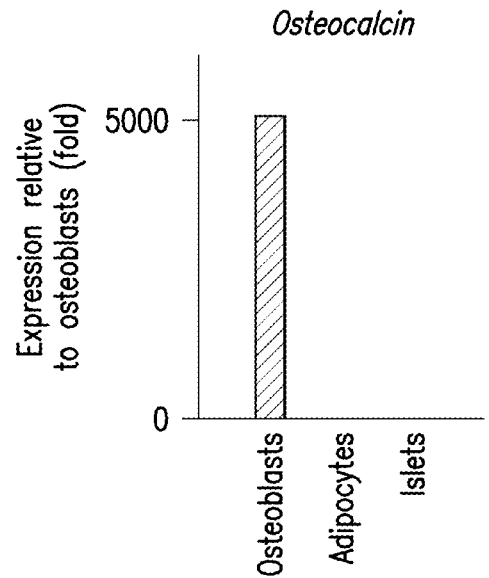
Figure 25C:
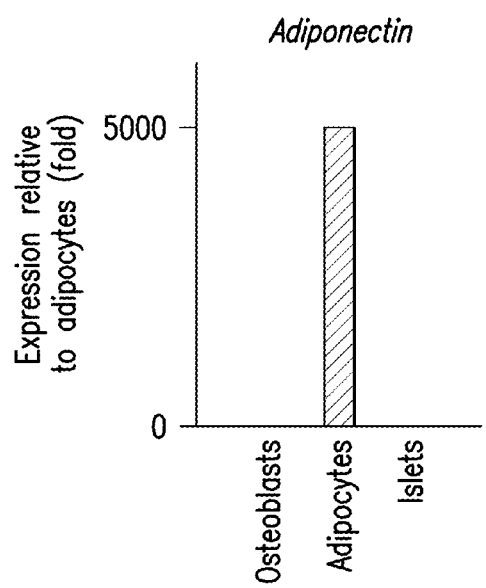
Figure 25D:
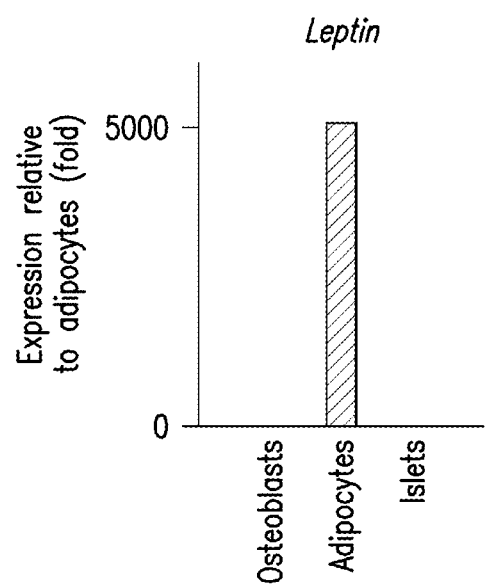
Figure 26A:
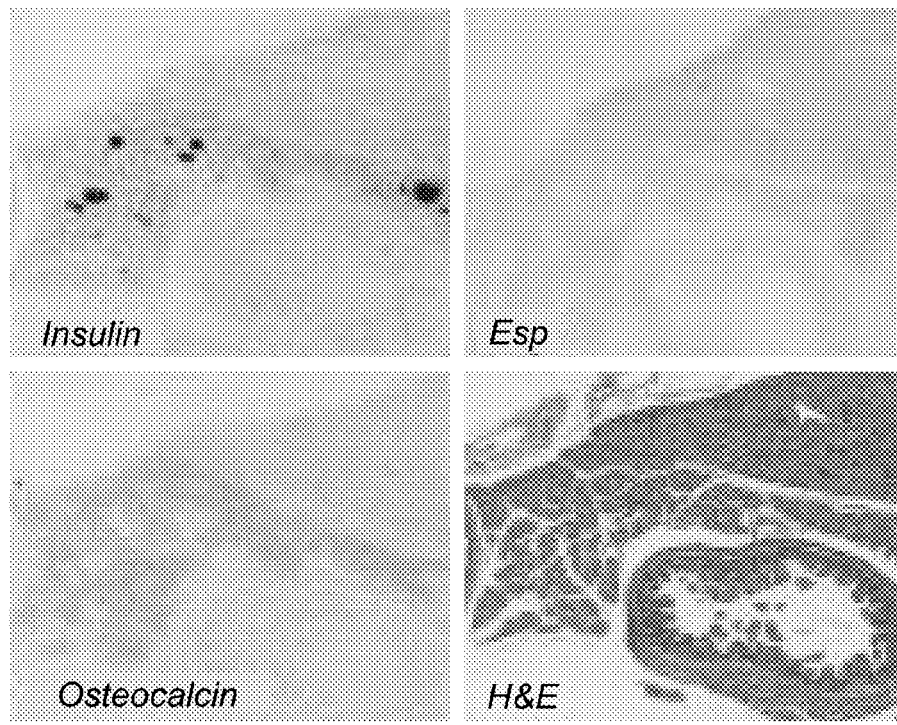
FIG. 26A-B. Bone-specific expression of osteocalcin.
Figure 26B:
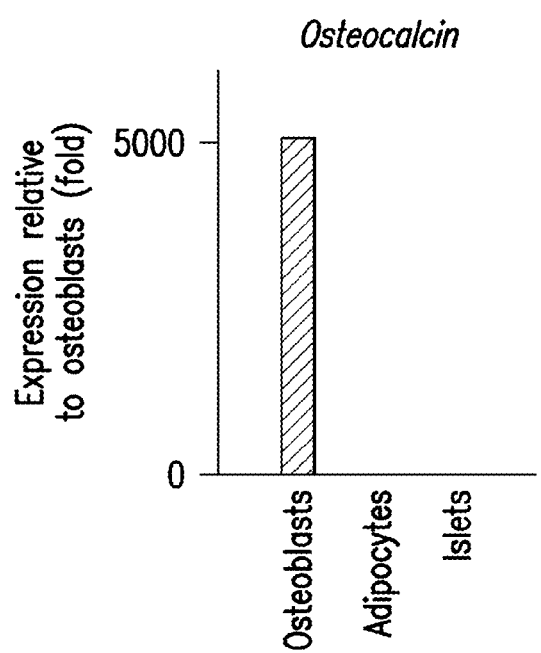
Figure 27A:
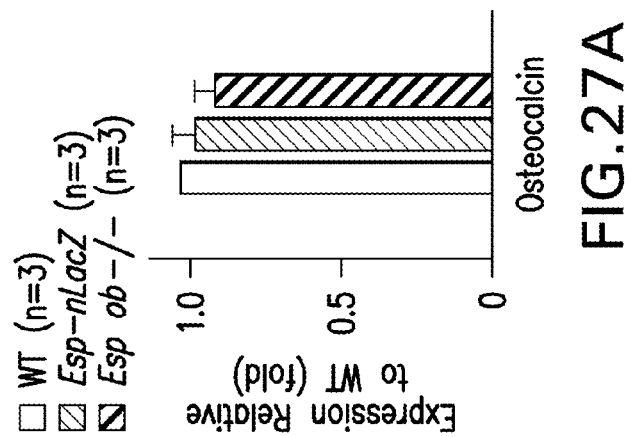
FIG. 27A-C. Normal osteocalcin expression and serum level in Esp−/− and alpha1(I) Esp mice.
Figure 27B:
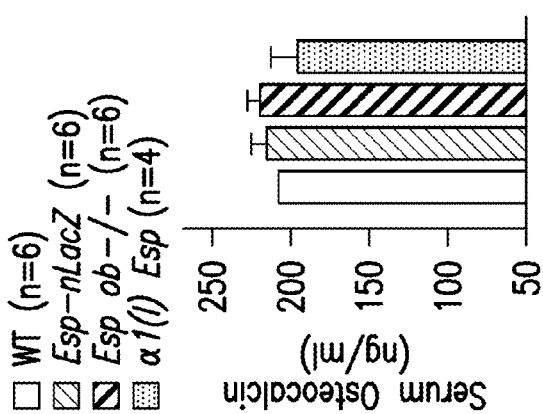
Figure 27C:
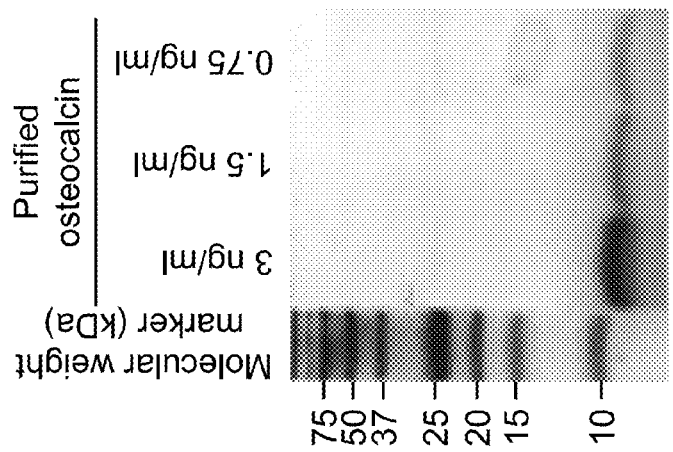
Figure 28A:
FIG. 28A-F. Overexpression of adiponectin in transgenic mice decreases fat mass and increases insulin sensitivity.
Figure 28B:
Figure 28C:
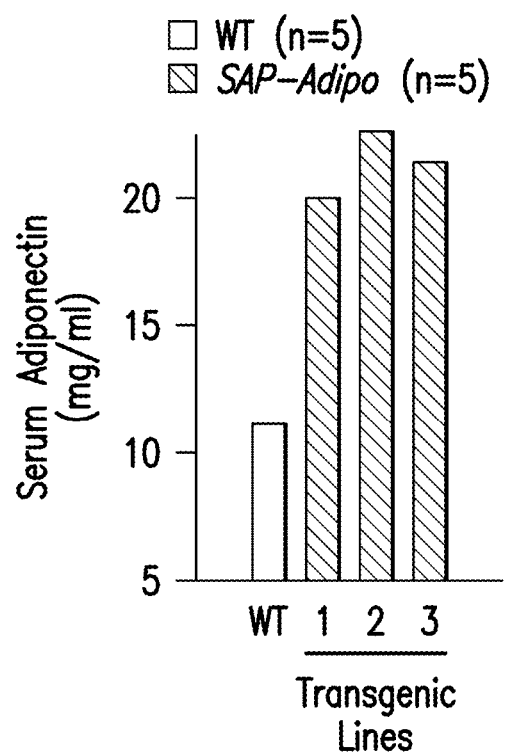
Figure 28D:
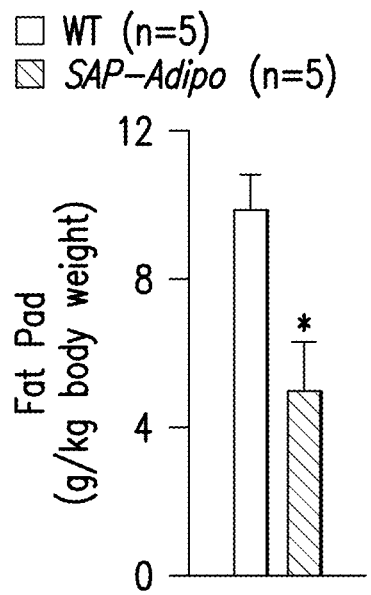
Figure 28E:
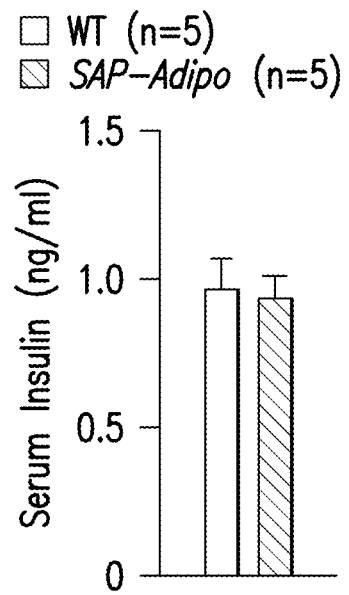
Figure 28F:
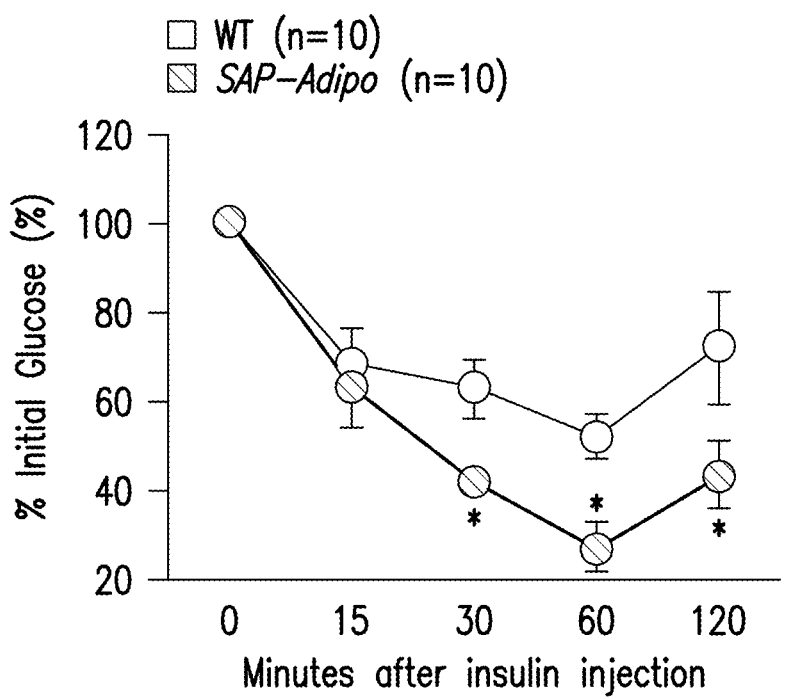
Figure 29A:
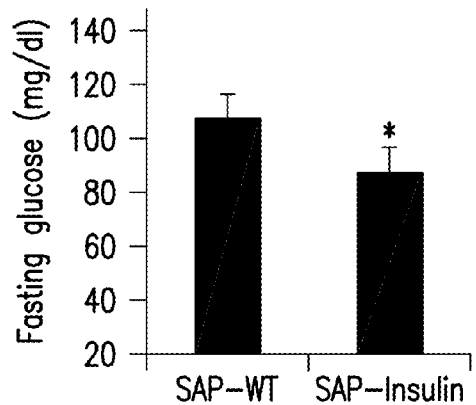
FIG. 29A-G: Overexpression of insulin in transgenic mice decreases fat mass and increases glucose tolerance.
Figure 29B:
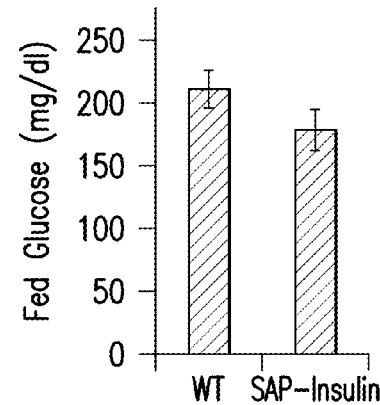
Figure 29C:
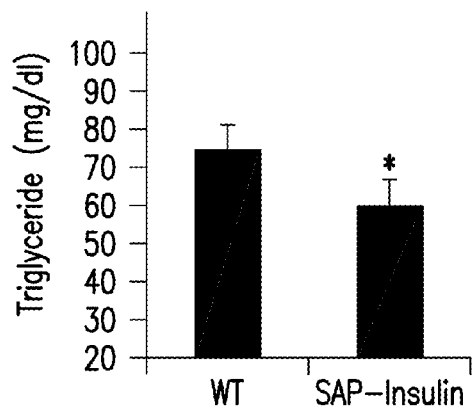
Figure 29D:
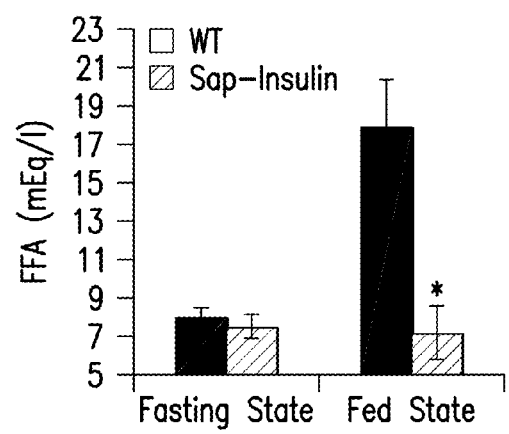
Figure 29F:
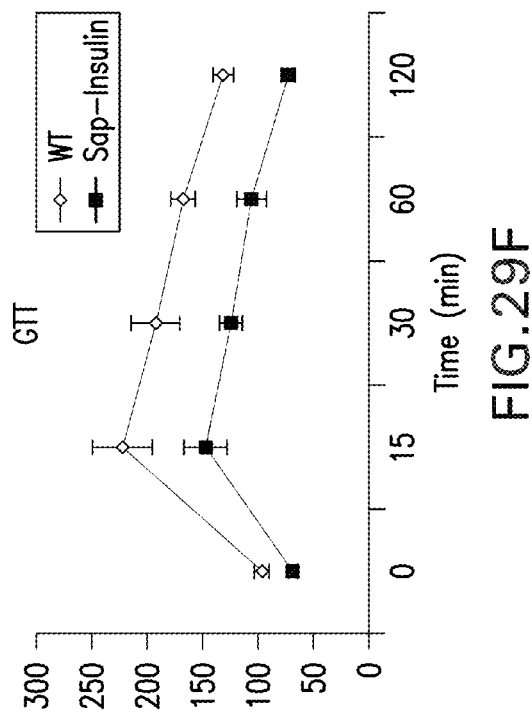
Figure 29G:
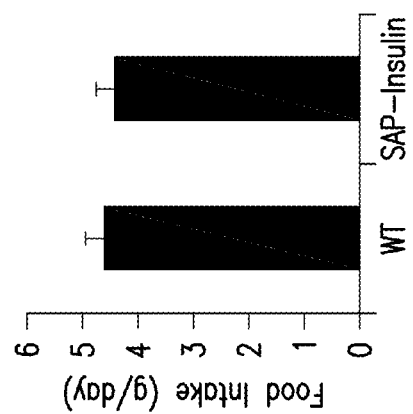
Figure 29E:
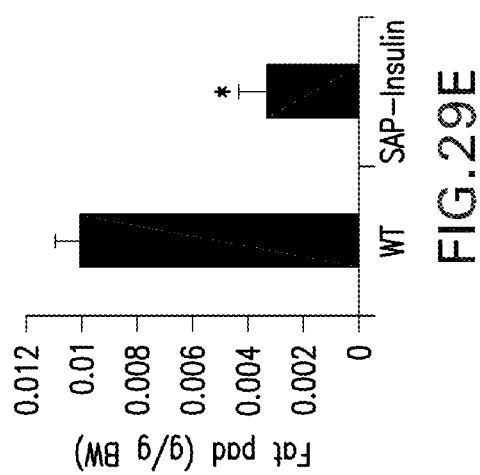

FIG. 24 shows the anatomy of the destruction of VMH nuclei by GTG. FIG. 25 shows that there is no cell transdifferentiation during the co-culture assays. FIG. 26 shows that Osteocalcin expression is bone specific. In situ hybridization analysis of osteocalcin and Esp expression in pancreas of 18.5 dpc embryos show that neither gene is expressed in pancreas. Insulin expression was used as a positive control. Hematoxylin-eosin staining of adjacent sections was used to assess tissues integrity. Real time PCR analysis of osteocalcin expression in osteoblasts, adipocytes, and pancreatic islets collected from 1 month-old WT mice showed that osteocalcin is not expressed in adipocytes or islets.

Generation of Collagen alpha 1(I)-PTP and Collagen alpha 1(I)-PTP$_{ED}$ transgenic mice. Transgenic mice over expressing either the full length Esp cDNA (alpha1(I) collagen-OST-PTP) or a truncated version of this cDNA encoding only the OST-PTP extracellular (also herein referred to as the soluble domain) domain (alpha 1(I) collagen-OST-PTP$_{Ec}$ mice) were generated. The extracellular domain is also herein referred to as the soluble domain (SD). These cDNA genes were under the control of the osteoblast-specific regulatory elements of the alpha 1(I) collagen to make mice that over express ESP (OST-PTP) or the OST-PTP extracellular domain in osteoblast in vivo.

At 1 month of age, the alpha 1(I) collagen-Esp transgenic mice displayed an increase in serum glucose both after fasting and after feeding, a decrease in insulin serum level after feeding, and a decrease in energy expenditure. Accordingly, glucose tolerance tests (GTT) showed that alpha1(I) collagen-Esp mice were glucose-intolerant while insulin tolerance tests (ITT) established that they were insulin-resistant (FIG. 4). Altogether the phenotype of the transgenic mice is the mirror image (the opposite) of the one observed in Esp-deficient mice. Moreover, this Esp cDNA full transcript transgene corrected all the metabolic abnormalities in Esp-deficient, diabetes-resistant mice. Transgenic mice over-expressing either the full-length Esp cDNA (alpha1(I) collagen-Esp) or a truncated version of this cDNA encoding only the OST-PTP extracellular domain are herein referred to as the soluble domain) domain (alpha 1(I) collagen-Esp$_{EC}$ mice.

Generation of ApoE-PTP, ApoE-PTP$_{SD}$ (also named ApoE-PTP$_{ED}$) transgenic mice. The full-length mouse Esp cDNA or fragment of the Esp mouse cDNA encoding amino acids 1 to 1111 of the extracellular domain (ED) was cloned into a vector directing liver-specific expression using the promoter of the ApoE gene. In contrast to expression of the full cDNA transcript for OST-PTP, Apolipoprotein E-OST-PTP$_{EC}$ transgenic mice that express a truncated version of this cDNA encoding only OST-PTP extracellular domain were indistinguishable from wild type mice. These experiments further prove that OST-PTP regulates energy metabolism through its intracellular phosphatase domain.

Generation of Osteocalcin-deficient (also named Ocn-/- or Bgp-/-) mice. "Osteocalcin-deficient mice" means a strain of mice in which both osteocalcin alleles were deleted. In the osteocalcin deficient transgenic mice described herein, Exon 4 of osteocalcin gene 1 (OG1) coding for the mature protein, and the entire osteocalcin gene 2 (OG2) sequence were deleted, while osteocalcin-related gene (ORG) was left in place. Correct targeting resulted in the replacement of the entire mature osteocalcin protein-coding sequences by the pGKNeo selection cassette.

Generation of Osteocalcin-/- mice was previously reported (Ducy et al., 1996). Exon 4 of osteocalcin gene 1 (OG1) coding for the mature protein, and the entire osteocalcin gene 2 (OG2) sequence were deleted, while osteocalcin-related gene (ORG) was left in place. Correct targeting resulted in the replacement of the entire mature osteocalcin protein-coding sequences by the pGKNeo selection cassette. Analysis of these mice is reported FIGS. 5-7 and Table 1.

Generation of Adiponectin-deficient Mice and Ocn+/-; Adiponectin+/- mice. Adiponectin-deficient mice were generated according to a previously described strategy (Maeda et al., 2002) where Exons 2 and 3 of either one (+/-) or both (-/-) alleles of the adiponectin gene were deleted. Adiponectin+/- or -/- were then crossed with Ocn-/- or +/- mice to generate Adiponectin+/-; Ocn+/- mice. Analysis of these mice is reported FIG. 6.

Generation of SAP-Adiponectin transgenic mice. Transgenic mice may be generated which overexpress adiponectin. Such a transgenic mouse's genome carries heterogeneous cDNA encoding adiponectin under the control of the regulatory elements of the mouse serum amyloid protein (SAP) gene, that produces an effect, relative to a wild-type effect, that is selected from the group consisting of an increase in adiponectin production, secretion and activity. In some cases, the cDNA is defined by SEQ ID NO:8. Constructs for use in generating such a mouse include one comprising the cDNA for adiponectin under the control of the serum amyloid protein promoter, which construct is designated pSAP-Adipo. Cells, including adipocytes, may be isolated from such transgenic animals.

To generate mice that over express adiponectin, the mouse cDNA for adiponectin was subcloned upstream of a cassette containing the human SAP promoter and rabbit β-globin non-coding exon/intron (FIG. 28). Fat pad weight was measured in WT and adiponectin transgenic pups and mice of each sex at 3 months of age (FIG. 28D). Food intake and energy expenditure were assessed in WT and Sap-Adiponectin transgenic mice to ascertain if the increase in energy expenditure observed in Esp-deficient mice is due solely to their increase in adiponectin serum levels. It was also verified that increasing serum adiponectin level will not affect appetite. To that end, metabolic cages and equipment were used. Serum glucose level was measured at birth, 2, 4, 8, and 16 weeks of age in WT and Sap-Adiponectin transgenic mice. In adult mice, this was done both after fasting and after feeding. In the same samples, serum insulin and adiponectin levels were measured (FIGS. 28C and 28E). Serum leptin levels were measured in serum of adult mice. Insulin sensitivity was assessed by insulin tolerance test (FIG. 28F): mice were fasted for six hours, injected IP with insulin (0.2 U/kg BW) and glucose levels were measured at indicated times as described (Mauvais-Jarvis et al., 2002). ITT data are presented as percentage of initial blood glucose concentration. Insulin secretion was assayed both by a glucose tolerance test performed following glucose intraperitoneal injection and by a glucose stimulated insulin secretion. Blood samples were obtained at 0, 2, 5, 15, and 30 minutes for GSIS or at 0, 15, 30, 60, and 120 minutes for GTT after intraperitoneal injection of 2 g/kg dextrose. Whole blood glucose values were determined using an automatic glucose monitor. Histological analysis. We have observed that in Esp-deficient mice there are fewer adipocytes than in WT mice yet they are larger, suggesting that they cannot release fat. The same analysis may be performed in 1 and 2 month old WT and Sap-Adiponectin transgenic mice. To ascertain that the large size of the adipocytes betrays their inability to release fat, WT, Esp-deficient and Sap-Adiponectin 1 month-old mice may be fasted for 16 or 24 hours and measured for free fatty acid (FFA) serum levels. It is expected that FFA serum levels will not increase in Esp-deficient and Sap-Adiponectin as it will in WT mice.

Generation of Sap-Insulin transgenic mice. A transgenic mouse is disclosed herein whose genome carries cDNA encoding full length mouse insulin under the control of the promoter and regulatory elements of the mouse serum amyloid protein (SAP) gene, that produces an effect, relative to a wild-type, comprising increased insulin expression and secretion.

To generate mice that over express insulin, the mouse cDNA for insulin was subcloned upstream of a cassette containing the human SAP promoter and rabbit β-globin non-coding exon/intron. These transgenic mice were analyzed using the same batteries of metabolic/molecular tests, including than the ones used for studying the Sap-Adiponectin transgenic mice. These studies are presented in FIG. 29.

Substrate Trapping. Plasmids for substrate trapping experiments were made as follows: Rat OST-PTP sequences encoding the first phosphatase domain (a.a 1116-a.a 1412) were cloned into the BamHI site of pGEX 4T3 (Amersham) encoding GST (Glutathione S-Transferase). This construct (GST-PTP) was used to generate Asp1316Ala GST-PTP DA, which is a catalytic mutant form which leads to the stabilization of the enzyme-substrate interaction, by site directed mutagenesis. The mutation was made in the phosphatase 1 domain that is known to mediate the dephosphorylation function of this class of phosphatases. The GST-PTP$^{D1316A}$ mutant has reduced phosphatase activity but increased substrate binding ability compared to wild type OST-PTP. It can thus retain, i.e. "Trap," the substrate better than the wild type protein. Cells expressing the mutant OST-PTP$^{D1316A}$ will trap any substrate that is the usual target of OST-PTP, but the mutant enzyme cannot dephosphorylate the substrate. It therefore holds onto the substrate without releasing it. Protein complexes for each experimental condition were then pulled down by centrifugation, washed 4 times and analyzed by western blot.

For the substrate-trapping experiments, cells were lysed in lysis buffer (50 mM Tris-HCl, pH 7.5, 5 mM EDTA, 150 mM NaCl, 1% Triton, 0.1% CHAPS, 5 mM iodoacetic acid, 10 mM sodium phosphate, 10 mM NaF). Cell lysates were incubated with either GST, GST-PTP$^{WT}$ (a fusion of GST with the phosphatase domain I of OST-PTP), or with GST-PTP$^{D1316A}$ (a trapping mutant of the Asp of the phosphatase domain I). Recombinant proteins bound to Sepharose beads for 1 hour at 4° C. (insulin receptor trapping) or for 2 h at 4° C. (gamma-carboxylase substrate trapping). Precipitates were collected, washed four times with lysis buffer and resolved on SDS-PAGE, followed by western blotting. Insulin receptor (InsR) was detected using rabbit anti-insulin receptor antibodies (Santa-Cruz, C-19) and GST was detected by mouse anti-GST antibodies (Santa-Cruz). Gamma-carboxylase was detected using rabbit anti-gamma-carboxylase antibody.

OST-PTP substrates are insulin receptor and gamma-carboxylase. To determine if OST-PTP acts through gamma-carboxylase, we conducted substrate-trapping experiments in primary osteoblasts. Differentiated primary osteoblasts (d10) were cultured for 10 days in alpha MEM/10% fetal bovine serum (FBS) supplemented with ascorbic acid (100 μg/ml) and Beta-glycerophosphate (5 mM). They were then starved for 24 hours in the same medium supplemented with 1% FBS only and treated with pervanadate (100 μM), an irreversible protein-tyrosine phosphatase inhibitor, and 20% FBS for 30 minutes. Cell lysates were incubated for 2 h at 4° C. with either GST, GST-PTP$^{WT}$ or GST-PTP$^{D1316A}$. Different amounts of the total cell extract were also loaded as control.

Transformed cells that over express full-length or truncated OST-PTP. Eukaryotic expression vectors that express flag-tagged full-length OST-PTP or flag-tagged truncated OST-PTP containing only its extracellular domain (OST-PTP$_{EC}$) were used to perform DNA permanent transfection experiments in ROS (rat osteoblast cells) 17/2.8 osteoblastic cells transfected with these flag-tagged vectors, and as a negative control in COS 7 cells. Following selection, and isolation of clones of cells that have incorporated each of the two genes in chromosomes (flag-tagged full-length OST-PTP or flag-tagged truncated OST-PTP containing only its extracellular domain) it was verified that the genes were transcribed and that the proteins were made using RT-PCR and Western blot analysis of cell lysates respectively. The cells were then cultured in a serum-free medium overnight. The supernatant of cells transfected with the empty vector, or vector encoding the full length or the truncated Esp cDNA was isolated and a Western analysis was performed using a commercially available anti-Flag antibody.

Bacterial expression vectors for osteocalcin production. We have generated prokaryotic expression vectors for GST-tagged mouse osteocalcin, GST-tagged human osteocalcin, GST-tagged mutants of mouse and human osteocalcin and GST-tagged truncation mutants of mouse and human osteocalcin.

Diet and GTG induced obesity and type 2 diabetes. For diet-induced obesity, male and female six-week old WT and osteocalcin-deficient mice (n=10 per group) were fed for 4, 6, 8, or 12 weeks with either a normal or a "western" diet" of 45% fat, 35% carbohydrate, and 20% protein. For GTG-induced obesity, male and female 4 week-old WT and osteocalcin-deficient mice (n=10 per group) were injected with 0.5 mg/kg of GTG and sacrificed at 12 weeks of age.

In both type of experiments, WT and mutant mice were analyzed as follows. Physical inspection: Whole body weight of each mouse at the start of the experiment and every week thereafter until sacrifice was measured. Food intake: This parameter was assessed to ascertain in particular that GTG lesions induce an increase in food intake. To that end, metabolic cages and equipment were used. Metabolic studies: Serum glucose and insulin levels were measured after fasting overnight and after feeding. Serum adiponectin and leptin levels were also measured in each mouse. Insulin secretion was assayed both by a glucose tolerance test (GTT) performed following glucose intraperitoneal injection and or glucose stimulated insulin secretion test (GSIS). Blood samples were obtained at 0, 2, 5, 15 and 30 minutes or at 0, 15, 30, 60 and 120 minutes following intraperitoneal injection of 2 g/kg dextrose for GTT. Whole blood glucose values were determined using an automatic glucose monitor. Molecular analysis: Expression of multiple markers of insulin sensitivity in hepatocytes, adipocytes and myoblasts at the end of each experiment was measured.

Co-culture of osteoblasts and adipocytes to study regulation of adiponectin expression/secretion by osteocalcin. A co-culture assay was developed between osteoblasts and adipocytes to analyze modifications in adiponectin expression. We used in this assay osteoblast from WT, Esp-deficient or osteocalcin-deficient mice along with primary adipocytes taken from any of these same mice. As a negative control, we co-cultured mouse embryonic fibroblasts of each genotype with adipocytes. Osteoblasts and fibroblasts were prepared according standard protocols that have been routinely used in the laboratory for the last twelve years (Ducy and Karsenty 1995), incorporated by reference as if set forth fully herein. Osteoblasts or fibroblasts were plated at 70% confluence in alpha MEM, 10% fetal bovine serum (FBS) 36 h prior to the beginning of the experiment. Prior to adding adipocytes, culture medium was changed to decrease the FBS concentration to 1%. Adipocytes were added for 0, 2, 4, 8, or 12 hours the following morning. At the end of the experiment, adipocytes that were present as non adherent cells were collected by centrifuging the culture medium. Adipocytes were used to extract RNA and to measure by real time the PCR expression of adiponectin and possibly other adipocyte-derived hormones including leptin. Culture medium was used to measure osteocalcin, adiponectin, leptin and other adipokine levels.

Co-culture of osteoblasts and beta-cells to study regulation of insulin expression/secretion by osteocalcin. A co-culture assay between osteoblasts and pancreatic beta-cells was developed to analyze modifications in insulin expression. Osteoblasts from WT, Esp-deficient or osteocalcin-deficient mice were used along with pancreatic beta-cells taken from any of these same mice. As a negative control, mouse embryonic fibroblasts of each genotype were co-cultured with adipocytes. Osteoblasts and fibroblasts were prepared according standard protocols that have been routinely used in the laboratory for the last twelve years. (Ducy and Karsenty 1995, incorporated by reference as if set forth fully herein). Osteoblasts or fibroblasts were plated at 70% confluence in alpha MEM 10% fetal bovine serum (FBS) 36 h prior to the beginning of the experiment. Prior to adding beta-cells, culture medium was changed to decrease the FBS concentration to 1%. Beta-cells were added for 0, 2, 4, 8, or 12 hours the following morning. At the end of the experiment, beta-cells that were present as non adherent cells were collected by centrifuging the culture medium. Beta-cells were used to extract RNA and to measure by real time the PCR expression of insulin and other beta-cell-derived hormones as well as the expression of molecules known to regulate insulin expression and cell proliferation. Culture medium was used to measure osteocalcin, adiponectin, insulin and other cytokine levels.

Metabolic studies. For glucose tolerance test (GTT), glucose (2 g/kg body weight (BW)) was injected intraperitoneally (IP) after an overnight fast and blood glucose was monitored using blood glucose strips and the Accu-Check glucometer (Roche) at indicated times. For glucose stimulated insulin secretion test (GSIS), glucose (3 g/kg BW) was injected IP after an overnight fast; sera were collected from tails and insulin measured as described (Mauvais-Jarvis et al., 2000). For insulin tolerance test (ITT), mice were fasted for six hours, injected IP with insulin (0.2 U/kg BW) and blood glucose levels were measured at indicated times as described (Mauvais-Jarvis et al., 2002). ITT data are presented as percentage of initial blood glucose concentration. Gold thioglucose (600 mg/kg BW, USP) was injected IP after an overnight fast, mice were sacrificed 3 months later for analysis. Streptozotocin (150 mg/ml single injection, Sigma) was injected IP and blood glucose measured as described above every 2 days thereafter. After 8 days, pancreases were isolated to measure insulin content as previously described (Mauvais-Jarvis et al., 2000). Food intake was measured using metabolic cages as the daily change of food weight. Energy expenditure was measured using metabolic cages connected to a calorimeter (Columbus Instrument). Heat values (Kcal/Hr) were recorded over 2 days and reported to each mouse BW.

Laboratory measurements. Blood was collected by heart puncture of isoflurane anesthetized mice in the fed and fasted states. Colorimetric assays were used to measure serum levels of free fatty acids (Wako Chemicals) and of triglycerides (Sigma). Serum levels of insulin (Crystal Chem Inc. kit), adiponectin (Linco kit), leptin (Crystal Chem Inc. kit) and resistin (Linco kit) were quantified by ELISA, osteocalcin levels by IRMA (Immunotopics kit). There is no IRA, IRMA, or ELISA designed to differentiate carboxylated from undercarboxylated osteocalcin in mice. The existing kits measure total osteocalcin, but cannot specifically recognize undercarboxylated osteocalcin. Therefore, hydroxyapatite (HA) resin was used to separate the two forms. The carboxylated form is the only one that binds to the HA.

Mouse islets and adipocytes isolation. Islets were isolated using a Histopaque gradient (1077, Sigma). In brief, after clamping the common bile duct at its entrance to the duodenum, 1 mg/ml collagenase P (Sigma) in M199 medium (GIBCO) was injected into the duct. The swollen pancreas was surgically removed and incubated at 37° C. for 17 min. Digested pancreata were dispersed by pipetting and rinsed twice with the same medium. After filtering the tissue suspension through a Spectra-mesh (400 μm), the digested tissue was resuspended in Histopaque and overlaid with M199 medium. The sample was then centrifuged at 1,700 g for 20 min, and the islets were collected from the interface. The recovered material was washed twice with cold M199 medium, resuspended in M199/1% NCS or αMEM/1% FBS (GIBCO) medium and cultured at 37° C. in 5% $CO_2$.

Primary adipocytes were isolated from epididymal fat pads by collagenase digestion. Briefly, minced adipose tissue was digested by 1 mg/ml collagenase P in KRP Buffer (20 mM HEPES, 120 mM NaCl, 6 mM KCl, 1.2 mM $MgSO_4$, 1 mM $CaCl_2$, 0.6 mM $Na_2HPO_4$, 0.4 mM $NaH_2PO_4$, 2.5 mM D-glucose, 2% BSA, pH 7.4) for 1 h at 37° C. The isolated cells were washed twice with KRP Buffer before being cultured in αMEM/1% FBS at 37° C. in 5% $CO_2$.

Cell culture experiments. Primary osteoblasts were prepared from calvaria of 5 day-old pups as previously described (Ducy et al., 2000a) and were cultured in αMEM/10% FBS in the presence of 100 μg/ml ascorbic acid and 5 mM β-glycerophosphate for 5 days. Skin fibroblasts were isolated by collagenase digestion (0.5 mg/ml) and were cultured in αMEM/10% FBS. Twenty-four hours before addition of primary islets (or adipocytes), osteoblasts (or fibroblasts) were placed in αMEM/1% FBS. For warfarin treatment, ROS17/2.8 osteoblastic cells were maintained in DMEM/F12/10% FBS until being supplemented with 50 μM warfarin or vehicle in DMEM/F12/1% FBS for 48 h prior to co-culture with adipocytes. After 4 h of co-culture, either in the presence or absence of (1 μm) culture inserts (Falcon) islets (or adipocytes) were collected for RNA isolation using TRIZOL (Invitrogen).

Gene expression analyses. All gene expression analyses were performed using real time PCR. DNAse I-treated total RNA was converted to cDNA with the SuperScript III kit (Invitrogen). Real-time PCR were performed using the Taq SYBR Green Supermix with ROX (Biorad) on an MX3000 instrument (Stratagene); beta-actin amplification was used as an internal reference for each sample. All primers were from SuperArray.

Osteocalcin/hydroxyapatite (HA) binding assay. Sera from 1 month-old mice, obese patients or supernatant from warfarin-treated osteoblast cultures were added to HA slurry to achieve a final concentration of 25 mg slurry/ml. After 15 min (mouse sera, supernatant) or 30 min (human sera), HA beads were pelleted by centrifugation and HA-bound osteocalcin was eluted with 0.5M sodium phosphate buffer, pH 8.0. Osteocalcin present in eluates and initial samples was measured by IRMA. Values represent percentage of HA-bound osteocalcin over initial osteocalcin content. Hauschka, P. V., et al., Physiol Review 69, 990-1047 (1989).

Figure 2C:
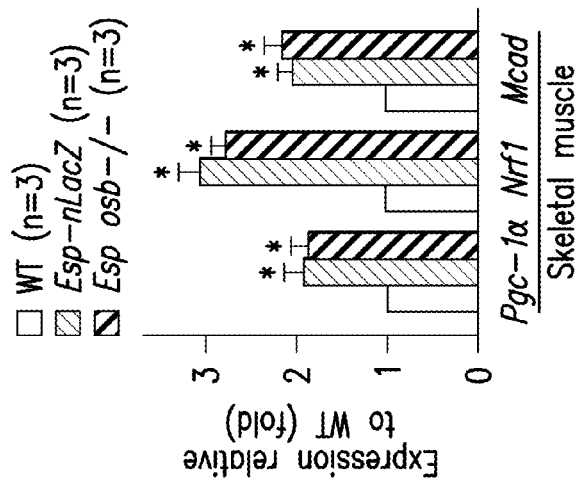
(FIG. 2C) Expression of markers of insulin sensitivity in skeletal muscle measured by real-time PCR.
Figure 2B:
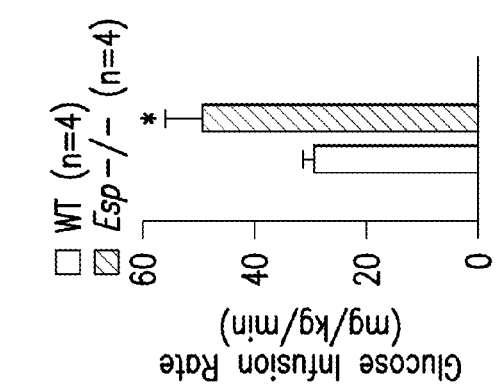
(FIG. 2B) Glucose infusion rate during hyperinsulinemic-euglycemic clamp.

Statistical analyses. Results are given as means±standard deviations except in FIGS. 2B and 5F where means±standard errors of the mean are shown. Statistical analyses were performed using unpaired, two-tailed Student's t or ANOVA tests followed by post hoc tests. A p value<0.05 was considered significant and is indicated by a star in all figures unless otherwise indicated.

Recombinant Osteocalcin. Recombinant osteocalcin was bacterially produced and purified on glutathione beads according to standard procedures. Osteocalcin was then cleaved from the GST subunit using thrombin digestion. Thrombin contamination was removed using an affinity column. The purity of the product was qualitatively assessed by SDS-PAGE. Bacteria do not have a gamma-carboxylase gene. Therefore, recombinant osteocalcin produced in bacteria is always completely undercarboxylated at all three sites. Osteocalcin can be made in many ways known in the art, including being chemically synthesized, since it can be made without gamma-carboxylation when chemically synthesized.

Human studies. This study enrolled a group of obese and non-obese Caucasian women participating in a Clinical investigation performed at the Center of Research on Human Nutrition, Hôtel-Dieu Hospital, Paris, France (PHRC protocol No A0R076). This study was approved by the Ethics Committees of Hôtel-Dieu (Paris). All subjects gave their informed consent. Subjects were weight stable for at least 3 months before the investigation day. Clinical and biochemical parameters were assessed in the morning (8:00 am) at the fasting state.

Histology. Frozen sections of livers were cryoembedded, sectioned at 5 μm and stained with Oil red 0. Fat and pancreatic tissues were fixed overnight in 10% neutral formalin, embedded in paraffin, and sectioned at 5 μm. Histology sections were stained with hematoxylin and eosin (H&E). Immunohistochemistry was performed using rabbit anti-insulin (SantaCruz, 1:100) and mouse anti-Ki67 (Vector, 1:100) antibodies and ABC Elite kits (Vector). Hypothalamic histology was performed as described (Takeda et al., 2002). To evaluate cell sizes or numbers, 5 to 10 sections (each 50 micrometers apart) were analyzed using a 40× objective on a Leica microscope outfitted with a CCD camera (SONY). Images were processed using the Osteomeasure software. Beta-cell area represents the surface positive for insulin immunostaining divided by the total pancreatic surface. Beta-cell mass was calculated as beta-cell area multiplied by pancreatic weight. At least 3 mice were analyzed per condition. Tibia anterior muscles were fixed in 4% PFA/2% glutaraldehyde/0.1 M sodium cacodylate ph 7.3, post-fixed in 1% osmium tetraoxide and embedded in epoxy resin (Epon). Ultrathin sections were stained in 4% aqueous Uranyl Acetate and 2 min in Reynolds' Lead Citrate and examined with a JEOL 2000FX. Ten electron micrographs per mouse were digitized and the area of each clearly distinguishable mitochondrion was analyzed using ImageJ software. Fifteen to 25 individual mitochondria were measured in 4 mice of each genotype.

Results

Figure 22A:
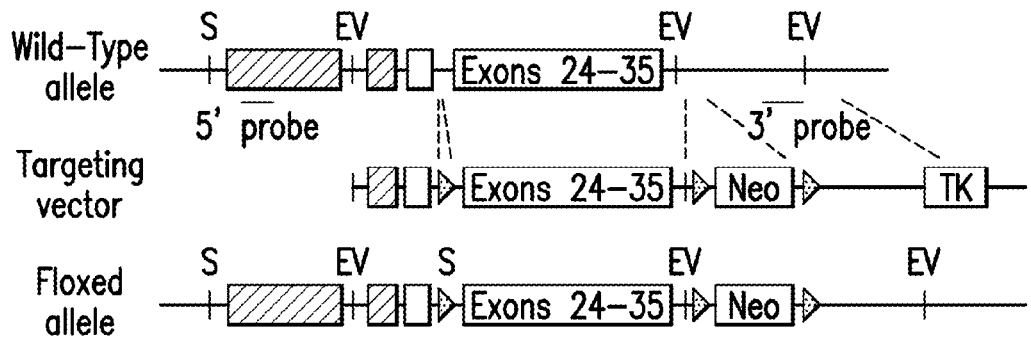
FIG. 22A-F. Generation of Esposb–/– mice and normal bone formation in Esp–/– animals.
Figure 22B:
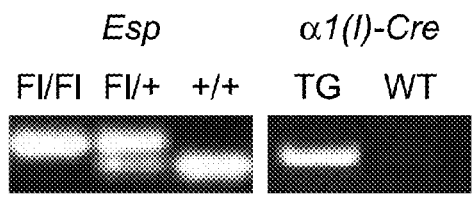
Figure 22C:
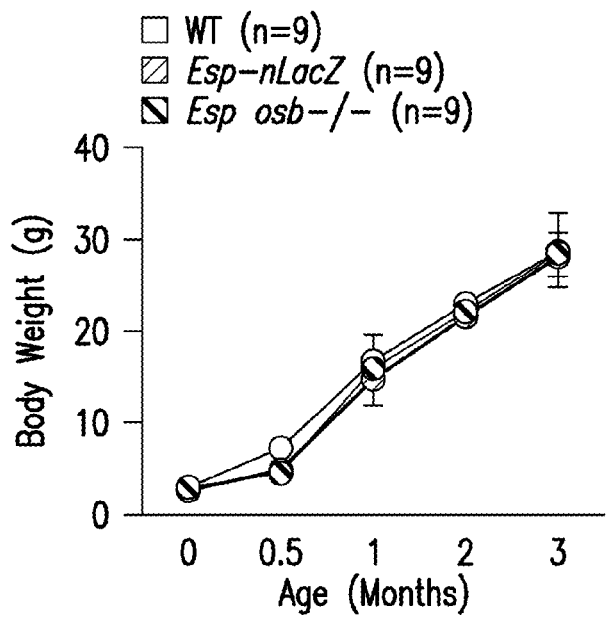

Generation and perinatal lethality of Esp−/− mouse models. To study OST-PTP, Esp was disrupted in a classical way (Esp-nLacZ) (Dacquin et al., 2004) and in an osteoblast-specific manner ($Esp_{ob}$−/−) by deleting exons 24 to 35 that encode the phosphatase domain using the LoxP/Cre recombinase technology (FIG. 22A). Mice harboring Esp floxed alleles were crossed with α1(1) collagen-Cre mice (Dacquin et al., 2002) to generate osteoblast-specific Esp-deficient mice ($Esp_{ob}$−/−) (FIG. 22B). Southern blot analysis showed that recombination occurred at high frequency at the Esp locus in osteoblasts (FIG. 1C). Accordingly, Esp expression was reduced nearly 90% in $Esp_{ob}$−/− osteoblasts and was unaffected in testis, the other site of Esp expression (FIG. 1D). Esp expression could not be detected in adipocytes or pancreatic beta-cells (data not shown). These data established that an osteoblast-specific inactivation of Esp was achieved. For the sake of clarity, reference to Esp−/− mice will be made when both Esp-nLacZ and $Esp_{ob}$−/− mice were studied.

Figures 22D, 22E, 22F:
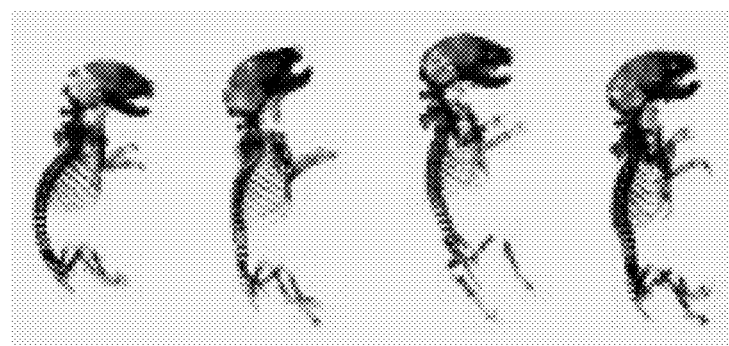

When analyzed at weaning, intercrosses of Esp−/− mice in either a 129Sv/EV or a C57BL/6 genetic background yielded only about 25% of Esp−/− mice (FIG. 1F). To determine if this early post-natal lethality was due to a delay in skeletal development, skeletal preparations of newborn wild-type (WT) and Esp−/− pups were stained. No abnormality of bone formation was detected that could explain this lethality (FIGS. 22D-22F). Experiments were conducted to determine whether Esp−/− pup lethality could be due to a maternal effect, possibly a humoral abnormality. If it were the case, mutant pups born from homozygous mutant mothers should die at a higher frequency than those born from heterozygous mothers. That is precisely what was observed. While lethality of Esp−/− pups born from Esp+/− mothers never reached 15%, up to 35% of Esp−/− pups born from Esp−/− mothers died before weaning (FIG. 1F). These data indicate that the lethality of Esp−/− pups was caused in part by a maternal effect.

Increased beta-cell proliferation and insulin secretion in Esp−/− mice. To determine if the maternal effect responsible of Esp−/− mice perinatal lethality was caused by a humoral abnormality, metabolic parameters were measured in newborn pups prior to milk ingestion. Esp−/− pups, regardless of genetic background, sex, and type of deletion performed, showed only one abnormality: a 3-fold reduction of blood glucose levels (FIG. 1G). In some mutant pups blood glucose levels were even too low to be detected. Albeit less severe, a significant decrease in blood glucose level was also observed in 1 and 3 month-old Esp−/− mice after feeding (FIG. 1G). This hypoglycemia was explained by a significant hyperinsulinemia in newborn, 1 and 3 month-old fed Esp−/− mice (FIG. 1H). On the other hand, expression of Glucagon, a hormone secreted by pancreatic beta-cells, was normal (FIG. 23B), thus indicating that Esp mutation affects beta-cells specifically.

Figure 1J:
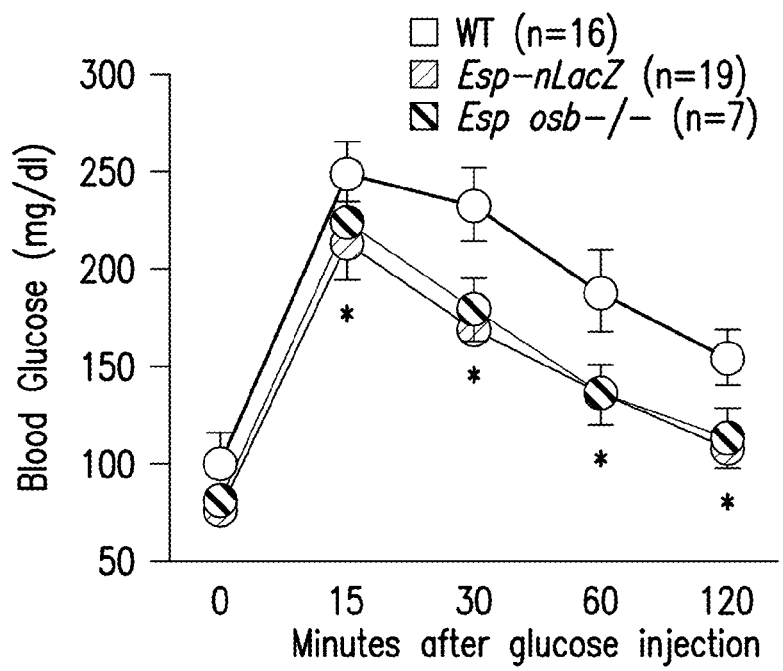

To establish more firmly that there was an increase in insulin secretion in the Esp−/− mice, intraperitonel (IP) glucose stimulated insulin secretion tests (GSIS) were performed at 1 and 3 months of age. These assays showed that insulin secretion was enhanced by the absence of OST-PTP (FIGS. 1H and 1L). To assess how this increase in insulin secretion affects the ability to dispose of a glucose load, glucose tolerance tests were performed following IP injection of glucose (2 g/kg of body weight) after an overnight fast (GTT). These tests revealed that 1 and 3 month-old Esp−/− mice had a significantly higher tolerance to glucose than WT mice (FIG. 1J).

Figure 1K:
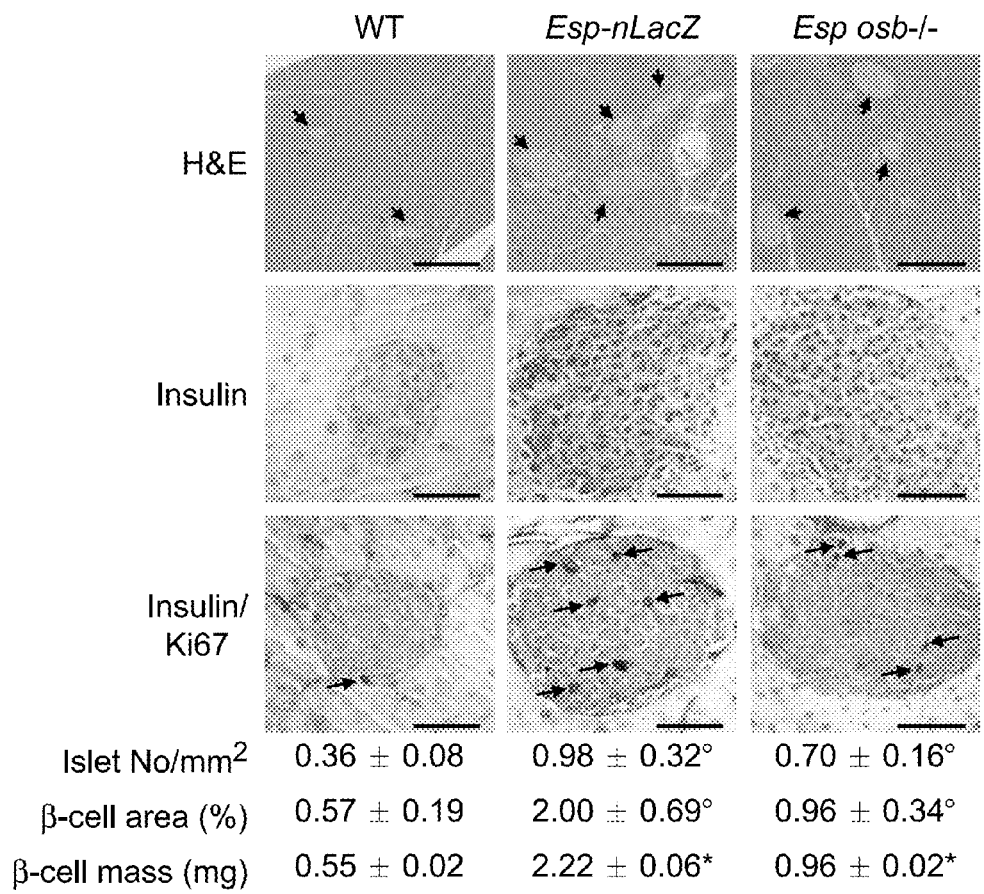
Figure 1L:
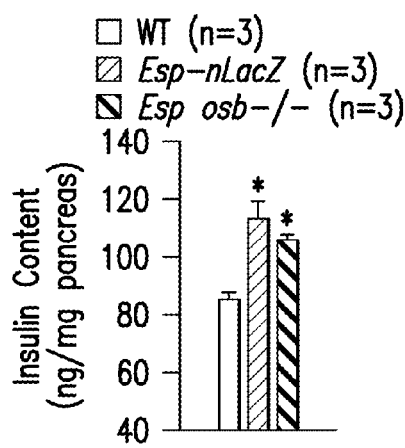
Figure 1M:
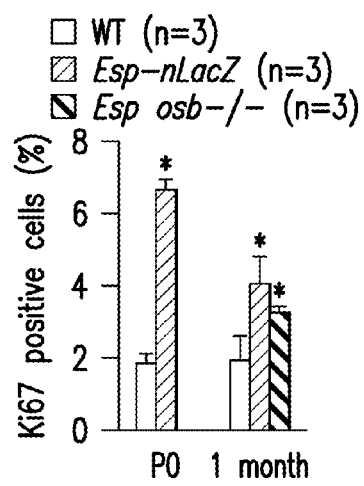

Histological and immunochemical analyses showed an increase in pancreas insulin content, the number of islets, islet size and overall of beta-cell mass in the Esp−/− pancreas (FIGS. 1K and 1L). A TUNEL assay failed to detect any abnormal apoptosis, and Ki67 immunostaining performed in 5 day-old pups (P5) and 1 month-old mice showed that beta-cell proliferation was increased 60 to 300% in Esp−/− mice (FIG. 1M). These data demonstrate that OST-PTP expressed in osteoblasts influences a pathway regulating beta-cell proliferation.

Figure 2A:
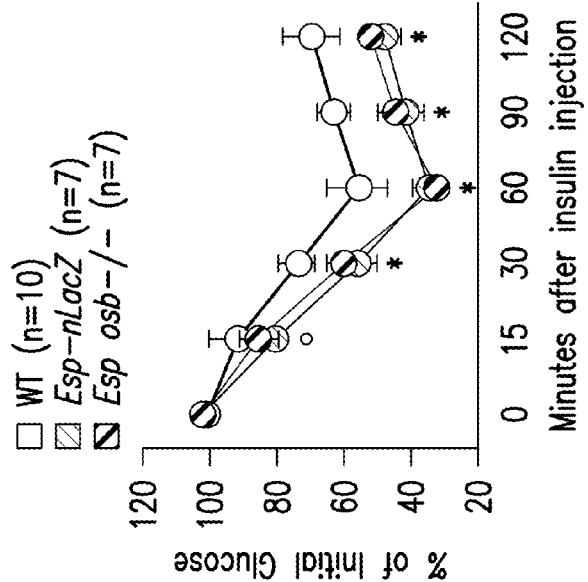
FIG. 2A-N. Increased Insulin Sensitivity and Adiponectin Expression in Esp−/− Mice. All experiments compare 1-month-old mice WT and Esp−/− unless otherwise indicated.
Figure 2D:
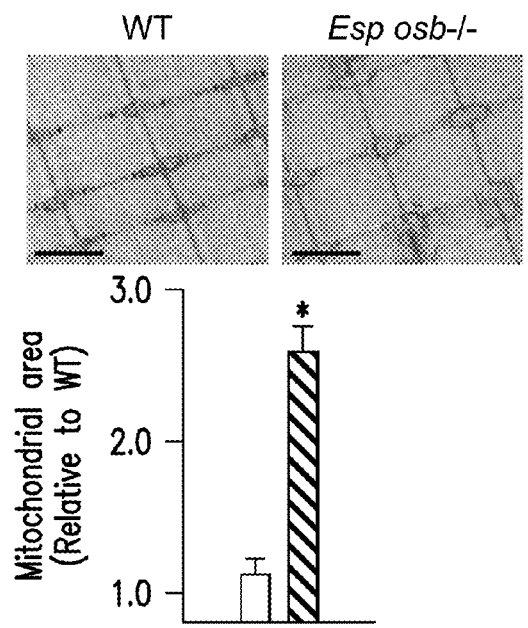
(FIG. 2D) Electron microscopy images (upper panel, 20,0003) and corresponding quantification (lower panel) of mitochondrial area in gastrocnemius muscle. Scale bars are 1 mm.
Figure 2E:
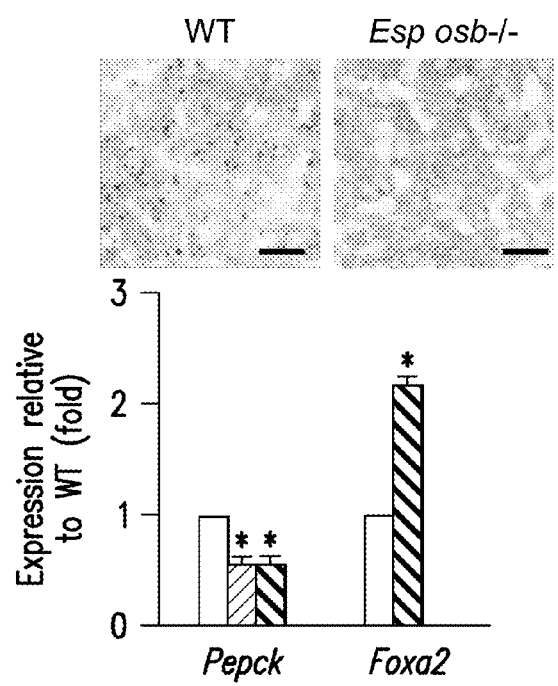
(FIG. 2E) Decreased number of lipid droplets on Oil red O stained liver sections (upper panel) and modified expression of insulin target genes by real-time PCR (lower panel) in Esposb−/− mice. Scale bars are 50 mm.
Figure 2H:
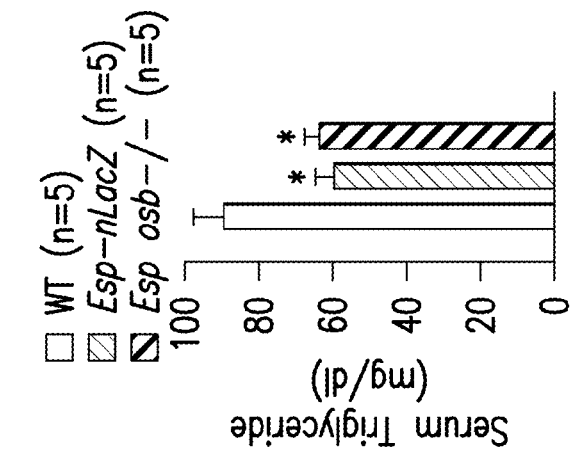
(FIG. 2H) Serum triglyceride levels after an overnight fast.
Figure 2G:
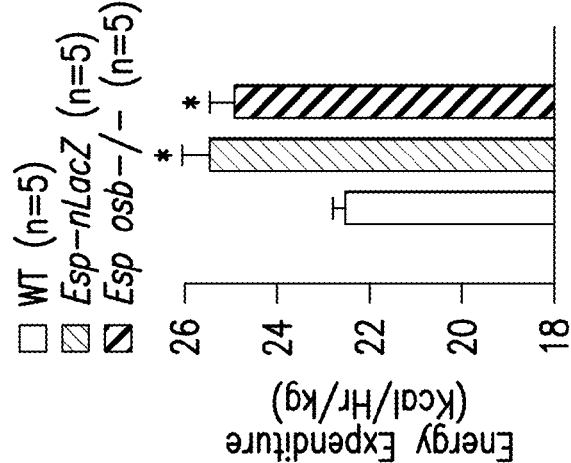
(FIG. 2G) Energy expenditure.

Increased insulin sensitivity in Esp−/− mice. To determine whether the enhanced ability of Esp−/− mice to dispose of a glucose load was secondary to an increase in insulin sensitivity, insulin tolerance tests (ITT) were performed. Insulin sensitivity, defined by the drop in blood glucose level following IP insulin injection, was significantly increased in 1 and 3 month-old Esp−/− compared to WT mice (FIG. 2A). Accordingly, expression of molecular markers of insulin sensitivity in fat (PPARα, PPARγ), liver (Foxa2, PPARα) and skeletal muscle (Pgc-1α, Nrf-1, Mcad) were also markedly increased in Esp−/− compared to WT mice. Pepck expression was decreased in Esp−/− liver indicating that gluconeogenesis was inhibited in this organ (FIG. 2E). It was speculated that as a result of these molecular events energy expenditure was increased in Esp−/− mice (FIG. 2G). In all analyses, heterozygous Esp+/− mice behaved as their WT littermates.

The experimental data show that Esp (OST-PTP) inactivation causes hypoglycemia, potentially lethal in newborn pups, that is associated with an increase in insulin secretion and sensitivity. That these abnormalities were observed to the same extent in both Esp-nLacZ−/− and in $Esp_{ob}$−/− mice established that it is the Esp gene expressed in osteoblasts, and not in any other cells or tissues, that is responsible for the metabolic phenotype.

Figure 2F:
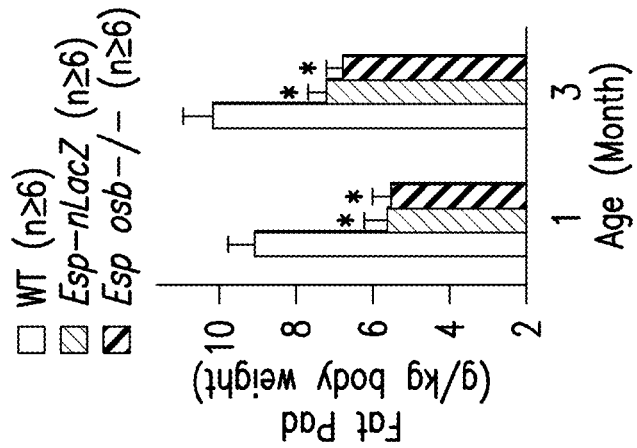
(FIG. 2F) Fat pad mass (fat pad weight over body weight).
Figure 2I:
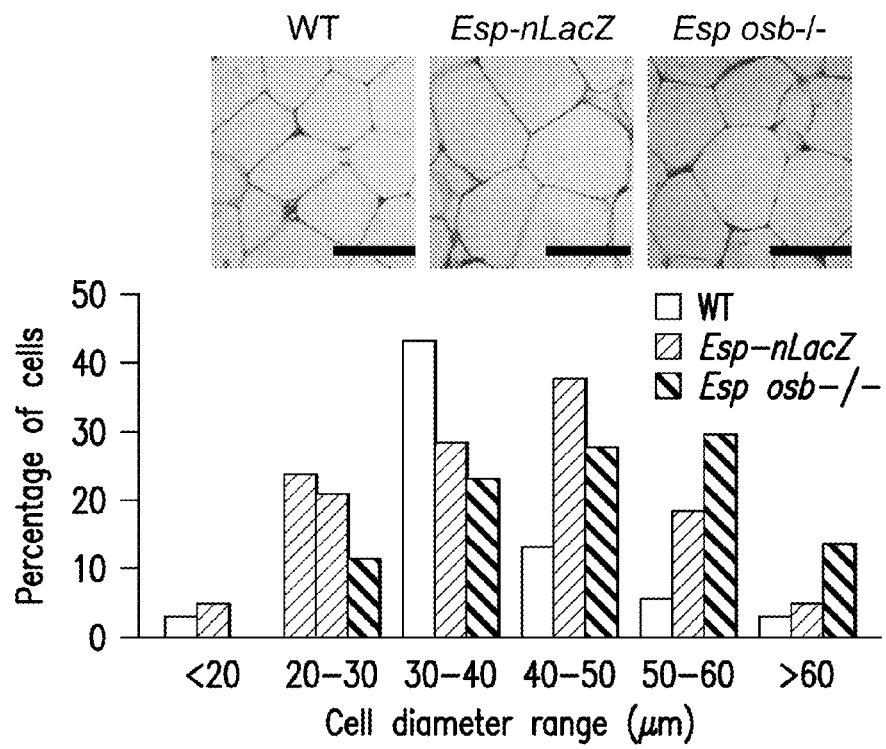
(FIG. 2I) H&E staining of adipose tissues of WT and Esp−/− mice (upper panel) and respective distribution of diameters for 100 measured adipocytes per slide (lower panel). Scale bars are 50 mm.
Figure 2J:
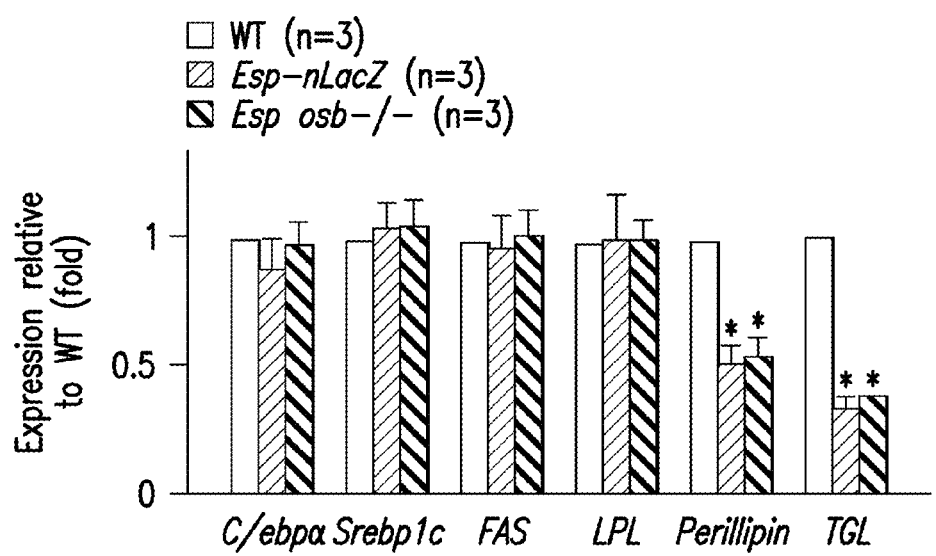
(FIG. 2J) Expression of markers of adipogenesis, lipogenesis, fat uptake, and lipolysis in fat.
Figure 2K:
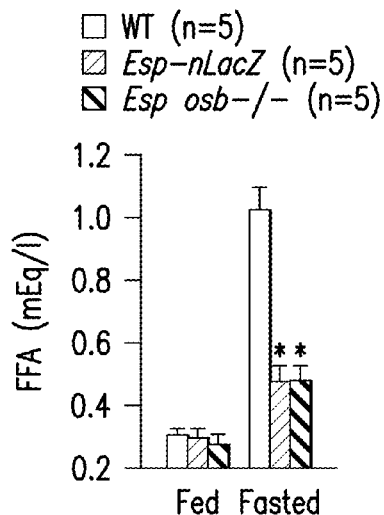
(FIG. 2K) Serum free fatty acid (FFA) in fed and overnight-fasted mice.

One and 3 month-old Esp−/− mice displayed another phenotypic abnormality; their fat pads were significantly lighter than those of their WT littermates (FIG. 2F). Serum triglyceride levels were also lower in Esp−/− than in WT mice (FIG. 2H). Since Esp is not expressed in fat and food intake is normal in Esp−/− mice (FIG. 23H), this decrease in fat mass is secondary to the increase in insulin sensitivity. Although there were fewer adipocytes in Esp−/− than in WT mice (WT, 93.2±10.7×10$^3$ adipocytes/fat pad (n=5); Esp−/−, 37±5.1×10$^3$ adipocytes/fat pad (n=3)) they were larger (FIG. 2I). To understand this phenotype the expression of multiple molecular markers was studied. C/EBPα, Srebp1c, Fatty acid synthase (FAS) and Lipoprotein lipase (LPL) were similarly expressed in Esp−/− and WT adipocytes, showing that adipogenesis, lipogenesis and fat uptake were not overtly affected by the mutation (FIG. 2J). In contrast, expression of molecular markers of insulin sensitivity (PPARγ and the regulator of fat oxidation PPARα) was increased, thus explaining enhanced insulin sensitivity without fat accumulation. Furthermore, expression of Perilipin and Triglyceride lipase (TGL), two anti-lipolytic proteins, was markedly decreased in Esp−/− compared to WT adipocytes (FIG. 2J) indicating that lipolysis is inhibited in Esp−/− mice. Accordingly, the serum level of free fatty acid did not increase following an overnight fast in Esp−/− mice as it did in WT littermates (FIG. 2K). The combination of increased insulin sensitivity and fat oxidation with inhibition of fat release from adipocytes synergized to produce the observed phenotype of low adiposity with large adipocytes in Esp−/− mice. These results are consistent with the increase in insulin secretion in Esp-deficient mice because insulin is a potent inhibitor of lipolysis.

Figure 2L:
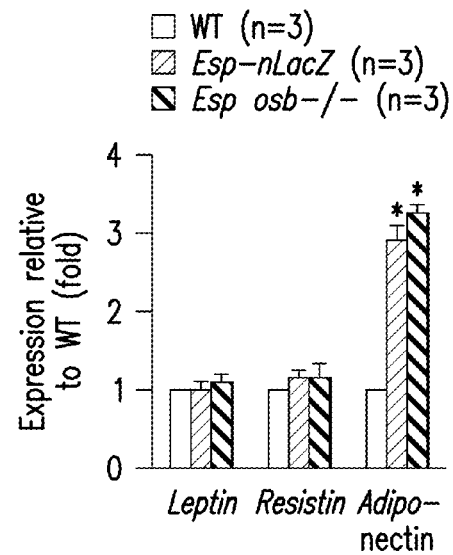
(FIG. 2L) Expression of Leptin, Resistin, and Adiponectin in fat.
Figure 2M:
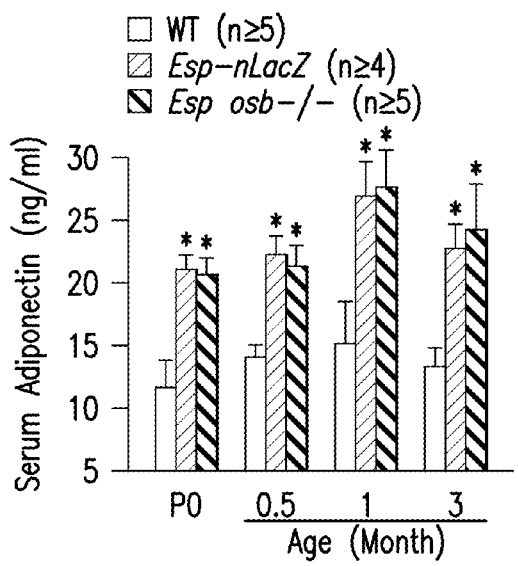
(FIG. 2M) Serum levels of adiponectin in newborn mice before feeding (P0) and after random feeding at other indicated ages.
Figure 2N:
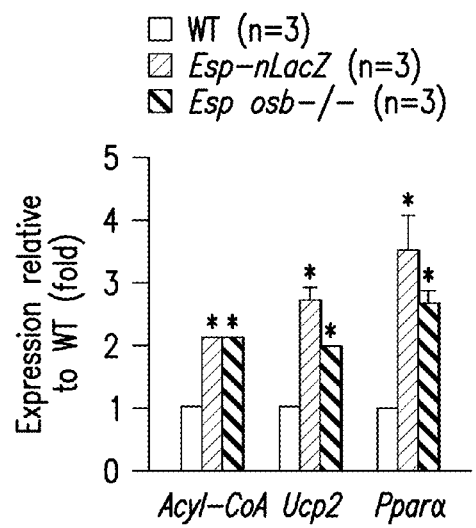
Figure 23F:
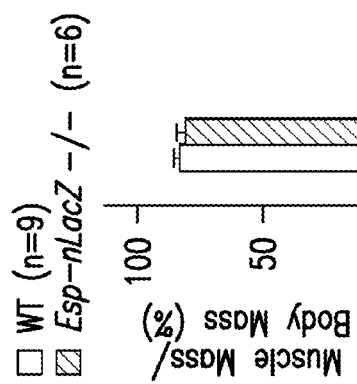
Figure 23G:
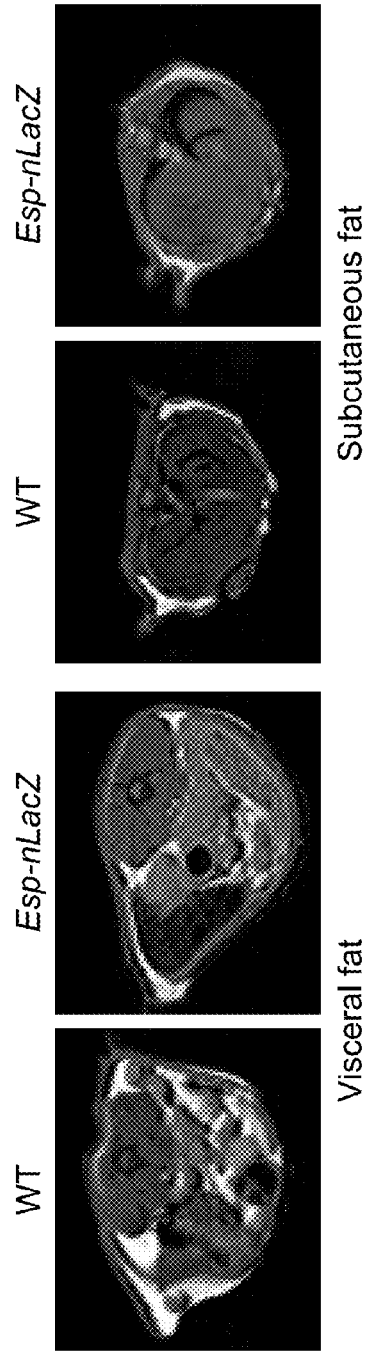
Figure 23H:
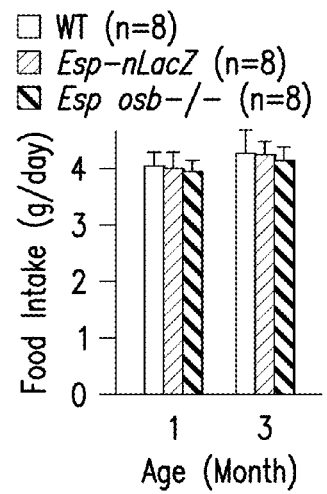
Figure 23I:
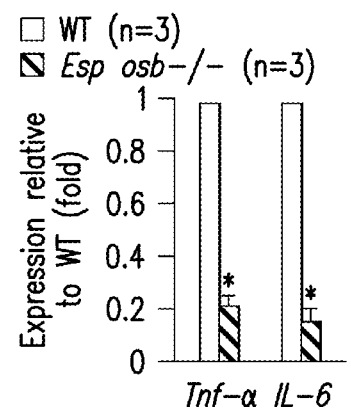
Figure 23J:
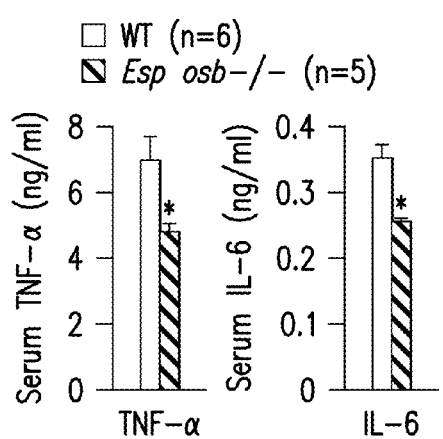
Figure 23K:
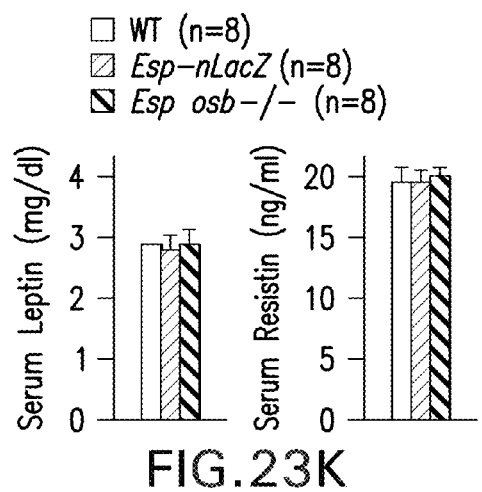

Increased adiponectin expression in Esp−/− mice. Experiments were conducted to determine whether there was a humoral basis for the increase in insulin sensitivity observed in Esp−/− mice. Expression and serum levels of Resistin, an adipokine mediating insulin resistance, were virtually unaffected by Esp deletion. The same was true for leptin, an insulin-sensitizing hormone (Friedman and Halaas, 1998; Steppan et al., 2001) (FIGS. 2L and 23K). This latter observation is in agreement with the fact that food intake was normal in Esp−/− mice (FIG. 23H). By contrast, expression and serum levels of adiponectin, an adipokine able to enhance sensitivity to insulin (Yamauchi et al., 2001), were respectively increased three and two-fold in Esp−/− mice at birth, 1 and 3 months of age regardless of their sex and genetic background (FIGS. 2L and 23M). Accordingly, it was observed that expression of adiponectin target genes such as Acyl-CoA Oxidase, PPARα and Ucp2 was increased in Esp−/− mice (FIG. 2N) (Kadowaki and Yamauchi, 2005). This increase in adiponectin expression and serum levels provides one mechanism to explain the increase in insulin sensitivity observed in Esp−/− mice.

In summary, Esp inactivation caused hypoglycemia as a result of increased pancreatic beta-cell proliferation, enhanced insulin secretion and improved insulin sensitivity in peripheral tissues with decreased adiposity. That these abnormalities were observed in both Esp-nLacZ−/− and $Esp_{ob}$−/− mice demonstrated that the skeleton via osteoblasts is involved in regulating glucose homeostasis.

Esp−/− mice are protected from obesity and glucose intolerance. The increase in insulin secretion and sensitivity characterizing Esp−/− mice raised the prospect that these mutant mice could be protected from obesity and diabetes. Esp-nLacZ−/− and $Esp_{ob}$−/− showed identical metabolic and molecular abnormalities. In some experiments only one or the other model were tested so for the sake of clarity we will refer to Esp−/− in this case.

Figure 3A:
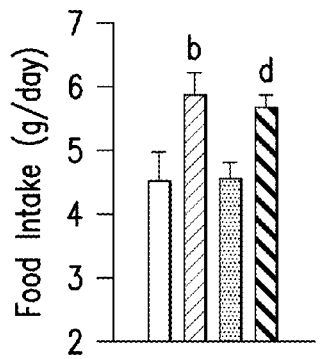
FIG. 3A-N. Esp−/− Mice Are Protected from Obesity and Glucose Intolerance.
Figure 3B:
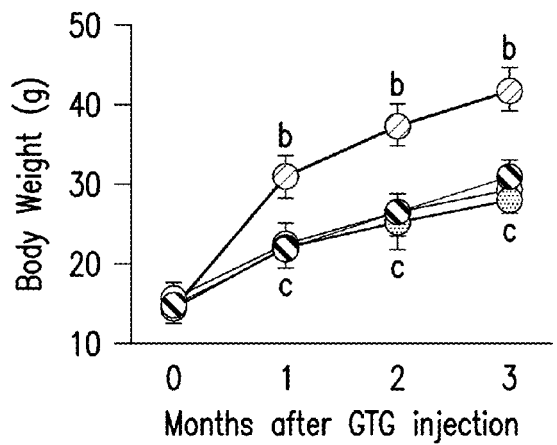
Figure 3C:
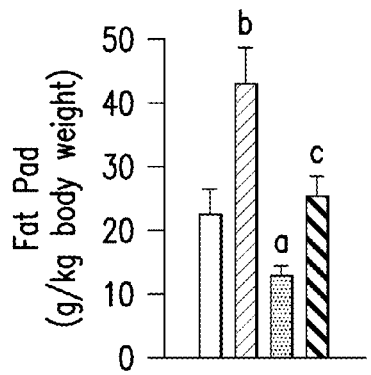
Figure 3D:
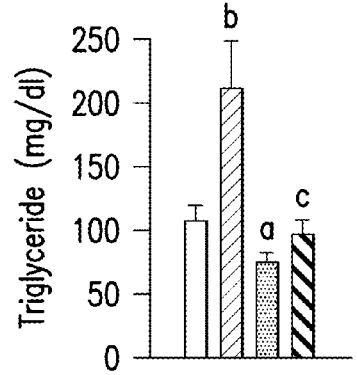
Figure 3E:
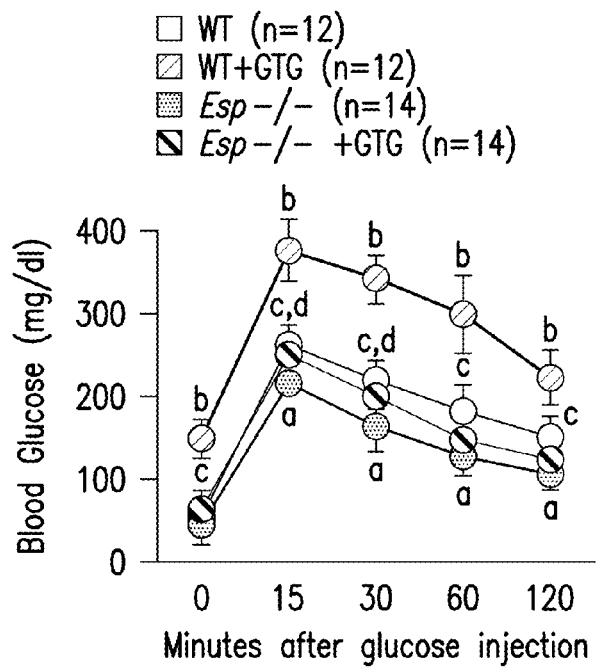
Figure 3F:
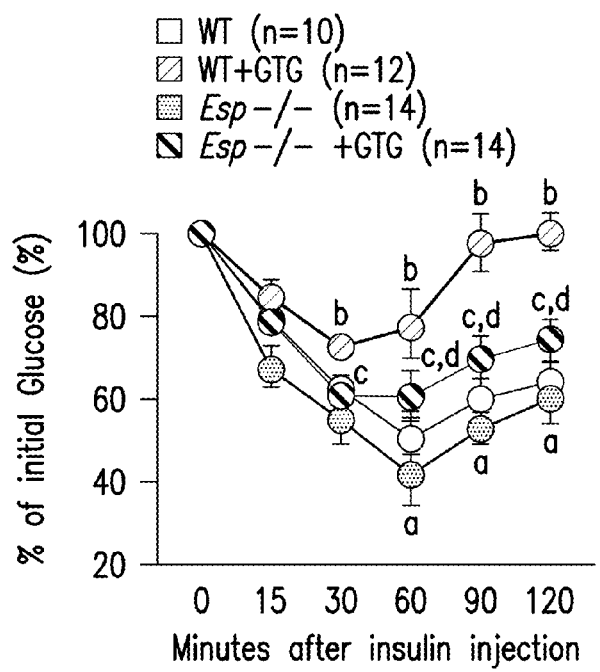

First, gold thioglucose (GTG) was injected in 1 month-old mice to induce specific lesions in the ventromedial hypothalamus (Brecher et al., 1965). As expected, GTG induced ventromedial hypothalamic lesions (FIG. 24) and hyperphagia (FIG. 3A) in both WT and Esp−/− mice. When analyzed 3 months after injection, GTG-treated WT mice were obese and their fat pad mass and serum triglyceride levels were significantly increased. GTT and ITT analyses showed that glucose intolerance and insulin resistance also increased (FIGS. 3E-3F). By contrast, GTG-treated Esp−/− mice were not obese, had fat pad mass and serum triglyceride levels similar to those of PBS-treated WT mice, and they displayed no evidence of glucose intolerance or of insulin insensitivity (FIGS. 3E-3F).

Figure 3H:
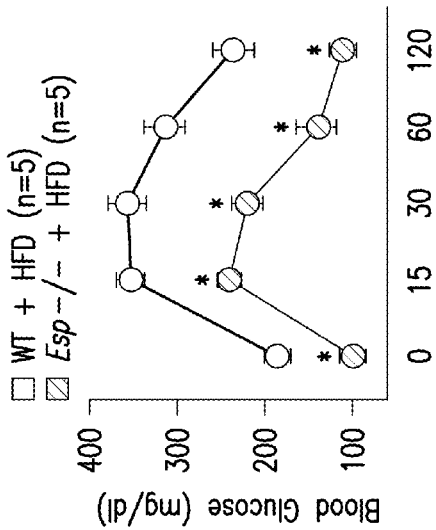
(FIG. 3G-I) Body weight curve (FIG. 3G), GTT (FIG.3H), and ITT (FIG. 3I) in 3 month-old WT and Esp−/− mice fed a high fat diet for 6 weeks.
Figure 3I:
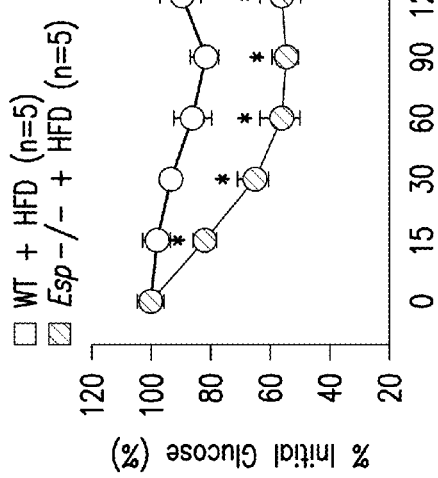
Figure 3G:
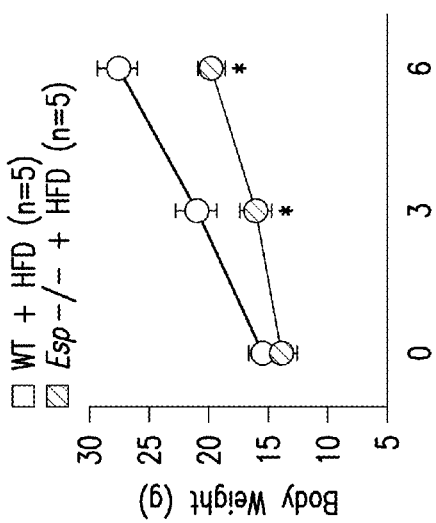

Next, 1 month-old WT and Esp-deficient mice were fed with a high fat diet (HFD) (58% fat kcal) for six weeks. It was discovered that body weights were significantly lower in Esp-nLacZ−/− mice than in WT mice at the end of this six week period (FIGS. 3G-3I). Glucose tolerance testing (GTT) demonstrated that after being fed a HFD for six weeks Esp-nLacZ−/− mice kept a normal tolerance to glucose, and insulin sensitivity determined by ITT remained normal. By contrast these parameters were altered in WT mice fed a high fat diet (HFD).

Figure 3J:
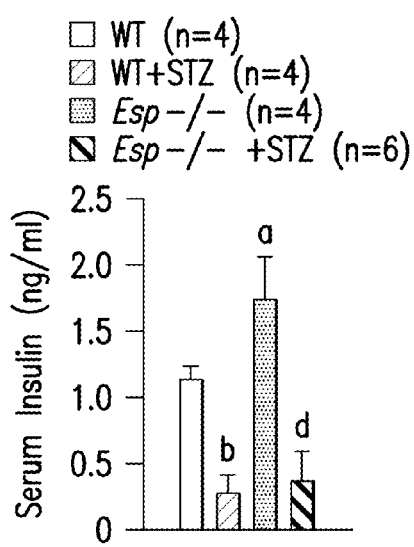
(FIG. 3J and K) Serum insulin levels (FIG. 3J) and pancreatic insulin content (FIG. 3K) in 1-month-old WT and Esp−/− mice 8 days after STZ or vehicle injection.
Figure 3K:
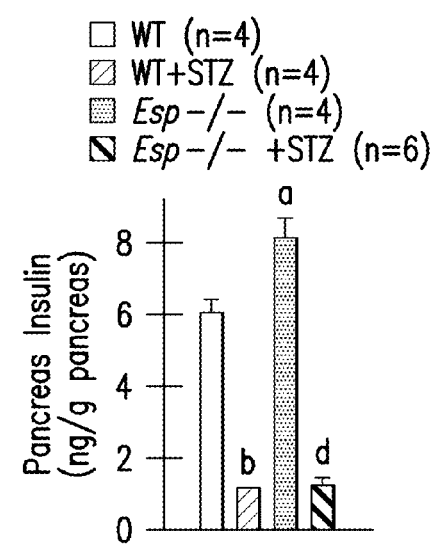
Figure 3N:
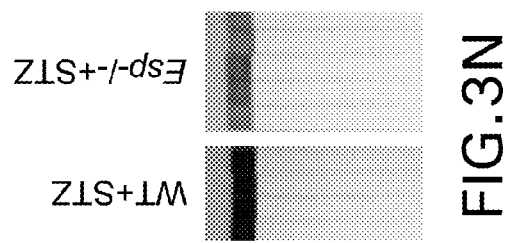
Figure 3M:
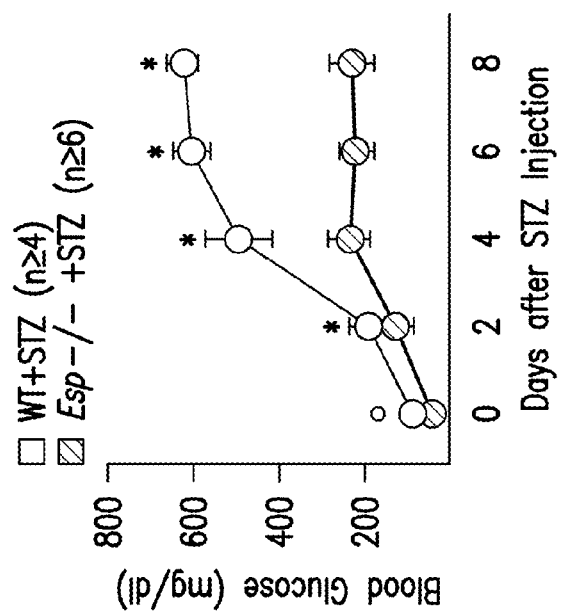
Figure 3L:
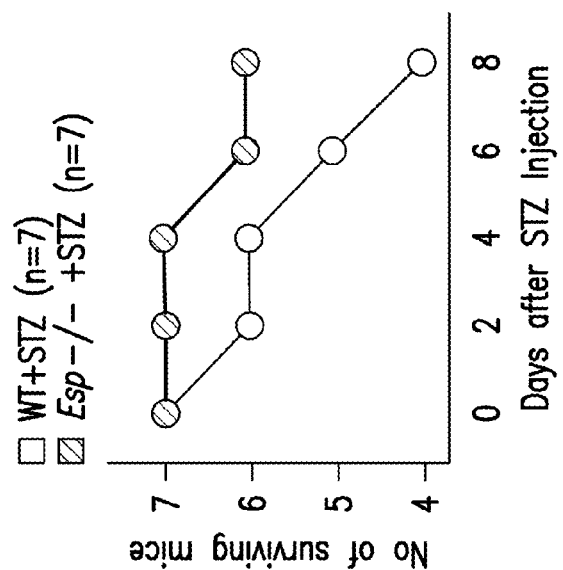
(FIG. 3L and M) Survival of mice (FIG. 3L) and change of blood glucose levels (FIG. 3M) in 1-month-old WT and Esp−/− mice during the 8 days following STZ injection.

Whether the increase in insulin sensitivity could protect Esp−/− mice from pancreatic beta-cell failure was determined. To that end, mice were injected with streptozotocin (STZ) to provoke oxidative stress in beta-cells and cell death as are seen in type 2 diabetes (Le May et al., 2006). STZ treatment markedly decreased pancreas insulin content and insulin serum level in both genotypes (FIGS. 3J and 3K). Eight days after STZ injection, 3 of the 7 STZ-treated WT mice had died and all the surviving ones had serum glucose levels above 500 mg/dl (FIGS. 3L and 3M). On the other hand, only one STZ-treated Esp−/− mouse died during this period and the blood glucose level of the surviving ones did not exceed 250 mg/dl. Unlike STZ-treated WT mice, glucose could not be detected in urine of STZ-injected Esp−/− mice (FIG. 3N). Since both STZ-treated WT and Esp−/− mice had a major decrease in islet insulin content, the absence of an overt diabetic phenotype in STZ-treated Esp−/− mice showed that their increase in insulin sensitivity occurred independently of their increase in insulin secretion. These results establish that Esp function (OST-PTP) is required for the development of obesity and glucose intolerance in mice.

Esp influences the biological activity of an osteoblast-secreted molecule. The next question was how Esp, through its expression in osteoblasts could regulate insulin secretion and sensitivity. Cell-based assays failed to provide evidence that the OST-PTP extracellular domain could be either cleaved and secreted or expressed independently of the phosphatase domain. Therefore, COS cells that do not normally express Esp, were transfected with vectors expressing either a full-length flag tagged OST-PTP or its flag-tagged extracellular domain only. The cells were transfected using the standard calcium phosphate method well known in the art. At the end of the experiment, supernatant was collected, cells were lysed and both supernatant and cell lysate assayed for the presence of OST-PTP. Western blot analysis using either cell lysates or cell supernatants was then performed. Recombinant full-length or truncated proteins were detected in cell lysates but never in the supernatants, showing that OST-PTP extracellular domain is not normally secreted by cells. An antibody was made against the OST-PTP extracellular domain to be able to perform these experiments; certain embodiments of this invention are directed to this antibody and to other antibodies that bind to the OST-PTP extracellular domain. The OST-PTP extracellular domain is accessible to antibodies because it is not sequestered inside the cell membrane. An antibody against the transmembrane domain of OST also exists. Both of these antibodies are polyclonal and could be administered to an animal to inhibit OST-PTP, thereby increasing osteocalcin activity, which in turn increases adiponectin production and secretion from adipocytes, which in turn increases insulin production and sensitivity. Of course, monoclonal antibodies can be used as well.

Figures 4A, 4B:
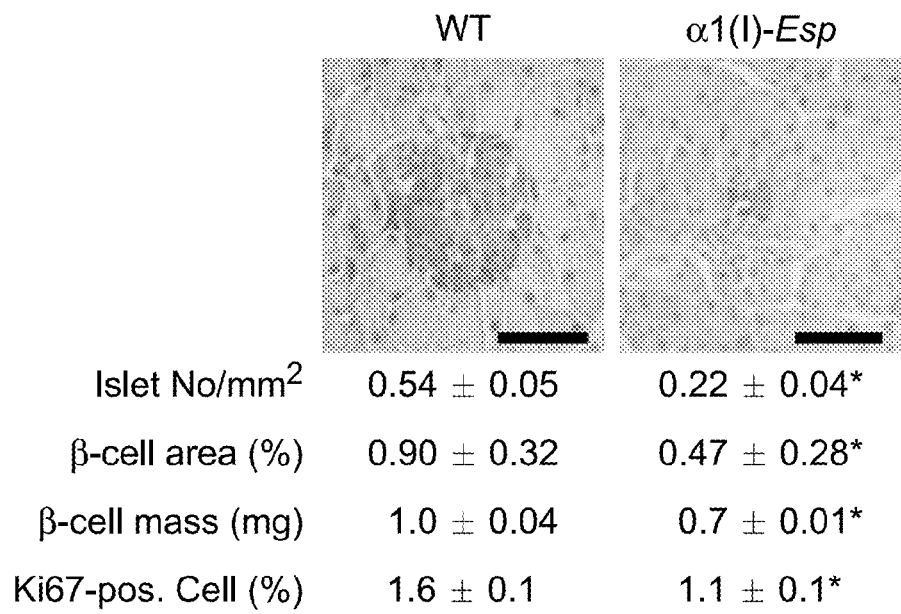

To further study OST-PTP function, transgenic mice expressing either full-length OST-PTP or its extracellular domain only in osteoblasts were generated and analysed. Transgenic mice overexpressing full-length Esp cDNA selectively in osteoblasts (alpha1(I)-OST-PTP mice) were made that displayed decreased beta-cell proliferation, lower beta-cell mass, hypoinsulinemia in the fed state and impaired insulin secretion in response to glucose (FIGS. 4A-C). They also showed lower adiponectin serum concentrations (FIG. 4B). As a result, alpha1(I)-OST-PTP mice developed hyperglycemia on regular chow, glucose intolerance and insulin resistance (FIGS. 4B, 4D and 4E). The fact that this phenotype, which is the mirror image of the one observed in Esp−/− mice, is only observed in transgenic mice over expressing full-length OST-PTP shows that the phosphatase activity of OST-PTP is required to affect glucose homeostasis. Furthermore, the fact that these mice over expressed Esp in osteoblasts further supports the conclusion that OST-PTP regulates the bioactivity of an osteoblast-derived secreted molecule that in turn regulates glucose homeostasis. By contrast, alpha$_1$(I) collagen-Esp$_{sd}$ mice, which express only OST-PTP extracellular domain, had no energy metabolism abnormalities of any kind. These results taken with the well-described fact that OST-PTP phosphatase domain is an active one, show that it is through its phosphatase domain and not through its extracellular domain that OST-PTP regulates insulin secretion and adiponectin expression and further confirm that OST-PTP act on the regulation of energy metabolism via its expression in osteoblasts.

Apolipoprotein E-OST-PTP$_{EC}$ transgenic mice were also generated that express the OST-PTP extracellular domain and release it into the general circulation. The apolipoprotein E promoter was used to direct Esp expression in liver cells thereby causing release of the OST-PTP extracellular domain into the general circulation. These transgenic mice were indistinguishable from wild type mice, further proving that OST-PTP regulates energy metabolism through its intracellular phosphatase domain and its expression in osteoblasts.

Figure 4F:
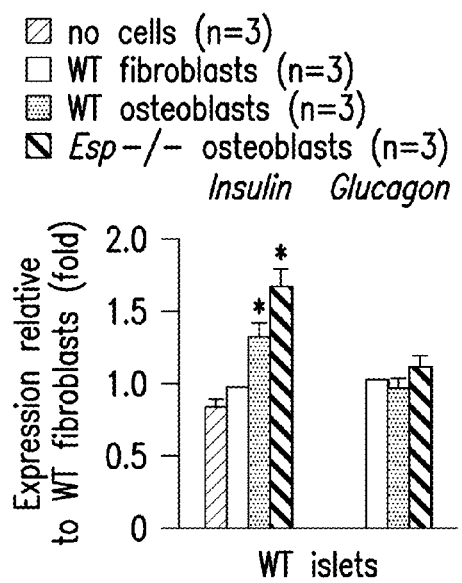

To further prove that osteoblasts secrete a factor that acts on pancreatic beta-cells and adipocytes, osteoblasts, which are adherent cells, were co-cultured with either pancreatic islets or adipocytes, which are non-adherent cells. Co-culture of differentiated WT osteoblasts with islets isolated from WT mice increased insulin expression in islets 40% (FIG. 4F). In full agreement with the increase in insulin secretion observed in Esp−/− mice, Esp−/− osteoblasts further enhanced insulin expression (FIG. 4F). Osteoblasts or fibroblasts were also co-cultured with adipocytes. WT osteoblasts, but not fibroblasts, increased expression of adiponectin and Esp−/− osteoblasts were twice as potent as WT osteoblasts in enhancing adiponectin expression (FIG. 4G).

Figure 4G:
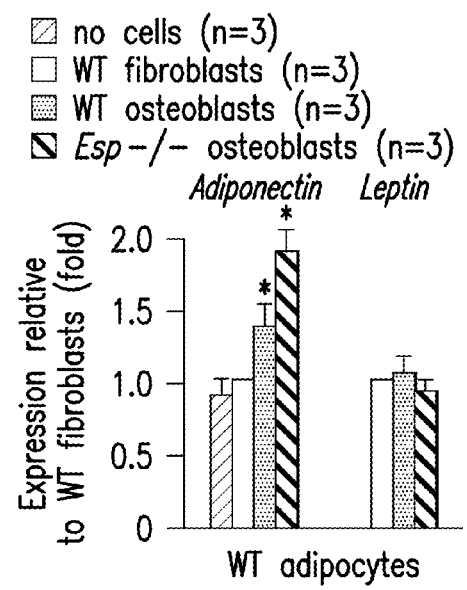
Figure 4J:
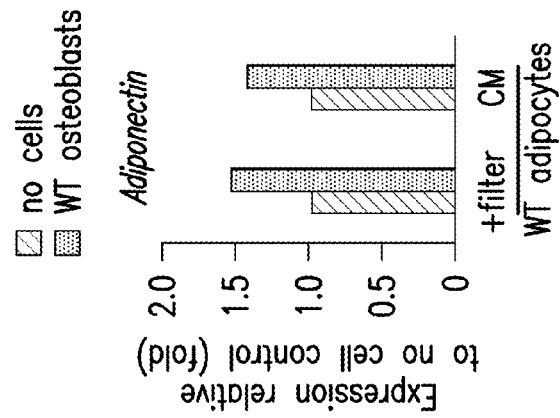
Figure 4I:
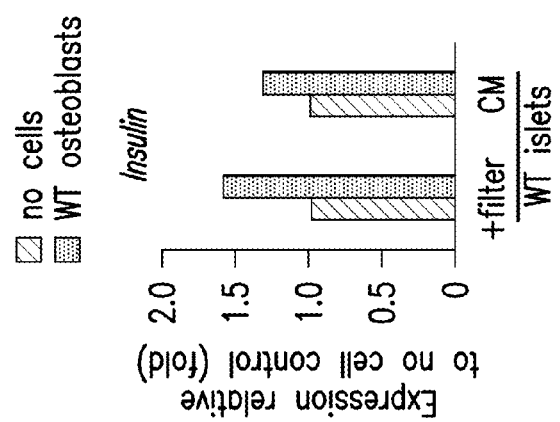
Figure 4H:
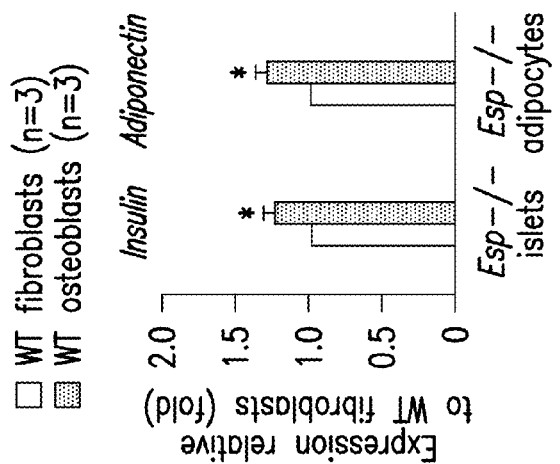

In this assay, adiponectin was the only adipokine whose expression was affected (FIG. 4G). Control experiments using WT osteoblasts co-cultured with Esp−/− islets or adipocytes showed the same increase in insulin and adiponectin expression as seen when using WT islets or adipocytes (FIG. 4H).

To establish that osteoblasts influence insulin and adiponectin expression via the release of secreted molecule(s), additional experiments were performed. First, osteoblasts were co-cultured with either islets or adipocytes using a filter preventing cell-cell contact. Second, islets and adipocytes were co-cultured in the presence of supernatant of primary osteoblast cultures. In both cases, a significant increase in insulin and adiponectin expression was observed (FIGS. 4I and 4J). Taken together, these data indicate that Esp expressed in osteoblasts regulates the expression or activity of a secreted molecule that affects insulin and adiponectin expression in beta-cells and adipocytes.

Osteocalcin is the osteoblast-derived secreted molecule that increases proliferation, insulin secretion and insulin sensitivity. To identify the molecule(s) secreted by osteoblasts that regulate glucose homeostasis, energy metabolism parameters were analysed in mutant mouse strains lacking osteocalcin, an osteoblast-specific secreted molecule present in serum. In earlier studies, it was observed that, upon their generation, oc−/− mice were abnormally fat. Ducy et al Nature 1996, herein incorporated by reference. At the time there was no explanation for why these animals were so fat and therefore the obesity aspect of these mice was observed but not published. Both homozygous (Oc−/−) and heterozygous strains (Oc+/−) were made.

Osteocalcin is one of the major non-collagenous proteins made by osteoblasts and is also an osteoblast-specific molecule. Like many secreted proteins, including peptide hormones, osteocalcin is generated as pre-pro-osteocalcin and undergoes cleavage and post-translational modifications in the cytoplasm before being secreted. In addition, osteocalcin belongs to the family of gla proteins in which some glutamic acid residues are carboxylated by a gamma-carboxylase to form gla residues. Hence the other name of osteocalcin: bone gla protein (BGP). Gla residues confer on gla proteins a high affinity for mineral ions.

Figure 5A:
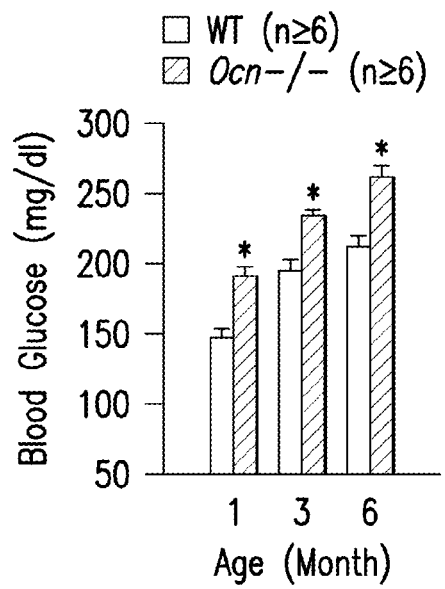
FIG. 5A-T. Osteocalcin Regulates Beta-Cell Proliferation, Insulin Secretion, and Insulin sensitivity. All experiments compare 3-month-old WT and Oc−/− mice unless otherwise indicated.
Figure 5B:
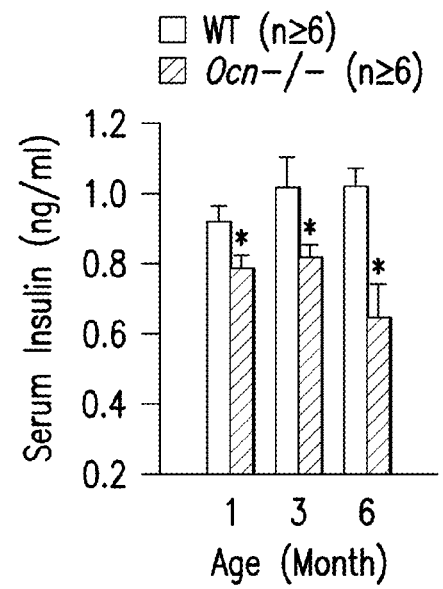
(FIG. 5B) Insulin levels.
Figure 5C:
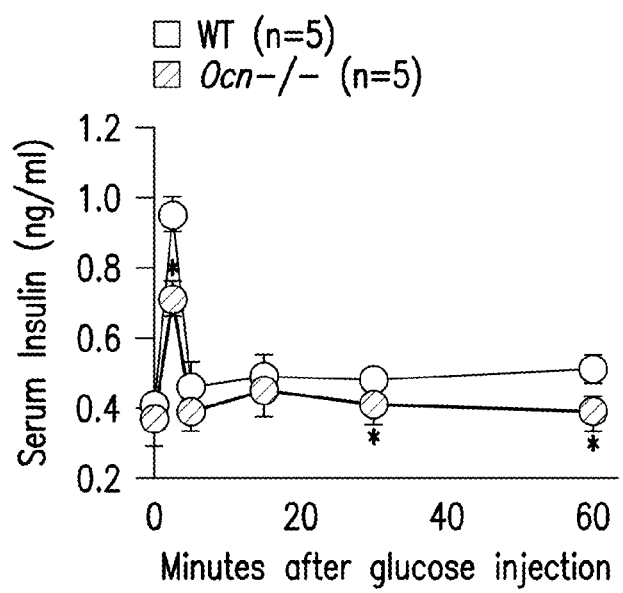
(FIG. 5C) GSIS test.
Figure 5N:
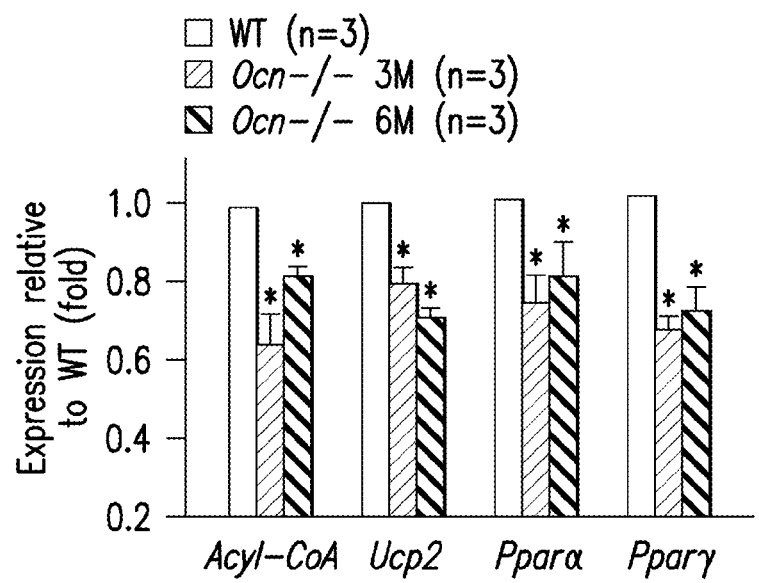
(FIG. 5N) Expression of adiponectin target genes by real time PCR.

Osteocalcin−/− mice had higher blood glucose and lower insulin serum levels than WT mice (FIGS. 5A and 5B). Insulin secretion and sensitivity as well as glucose tolerance analyzed by GSIS, GTT and ITT were all decreased in Osteocalcin−/− mice, as was energy expenditure (FIGS. 5C-5E and 5G). Accordingly, the expression of genes involved in insulin action was decreased in skeletal muscle and liver while Pepck expression was increased (FIG. 5H). Islet size and number, beta-cell mass, pancreas insulin content and insulin immunoreactivity were all markedly decreased in Osteocalcin−/− mice (FIG. 5I). Beta-cell proliferation measured by Ki67 immunostaining was decreased two fold in Osteocalcin−/− pancreas in P5 pups and at 3 months of age (FIG. 5I). Accompanying this marked decrease in beta-cell proliferation, insulin secretion and sensitivity, was an increase in fat pad mass, adipocyte number (WT, 93.2±10.7×10$^3$ adipocytes/fat pad (n=5); Osteocalcin−/−, 125.6±10.6×10$^3$ adipocytes/fat pad (n=3)) and serum triglyceride levels (FIGS. 5J and 5K). Adiponectin expression and serum levels were significantly lower in Osteocalcin−/− than in WT mice, especially considering their increased fat pad mass, while expression of other adipokines was not affected (FIGS. 5L and 5M). Expression of molecular targets of adiponectin action was decreased in Osteocalcin−/− mice (FIG. 5N). However, Osteocalcin+/− mice were undistinguishable from WT littermates (data not shown). The cDNA sequence for mouse adiponectin is SEQ ID NO:8; and it identified also by amino acid SEQ ID NO:9. The cDNA sequence for human adiponectin is SEQ ID NO:6; and it identified also by amino acid SEQ ID NO:7.

Figure 5O:
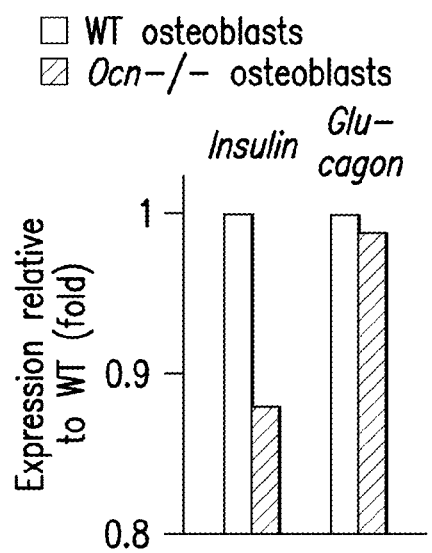
(FIG. 5O) Expression of Insulin and Glucagon in WT pancreatic islets co-cultured with osteoblasts of indicated genotypes.
Figure 5P:
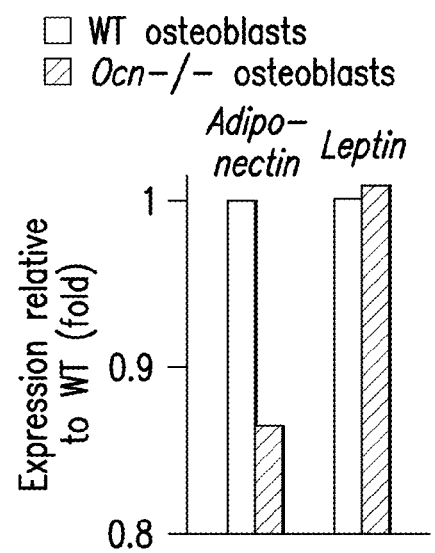
(FIG. 5P) Expression of Adiponectin and Leptin in WT adipocytes co-cultured with osteoblasts of indicated genotypes.
Figure 5Q:
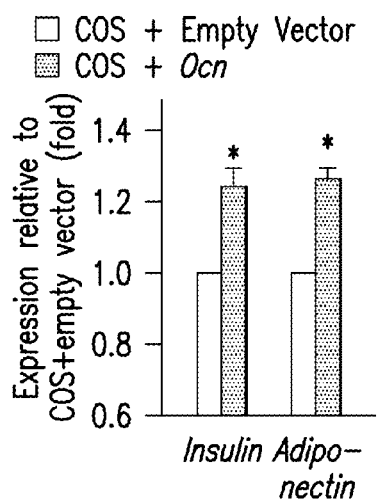
(FIG. 5Q) Expression of Insulin and Adiponectin in WT indicated cells cultured in presence of conditioned media from COS cells transfected with an Osteocalcin expression vector or its empty counterpart.
Figure 5R:
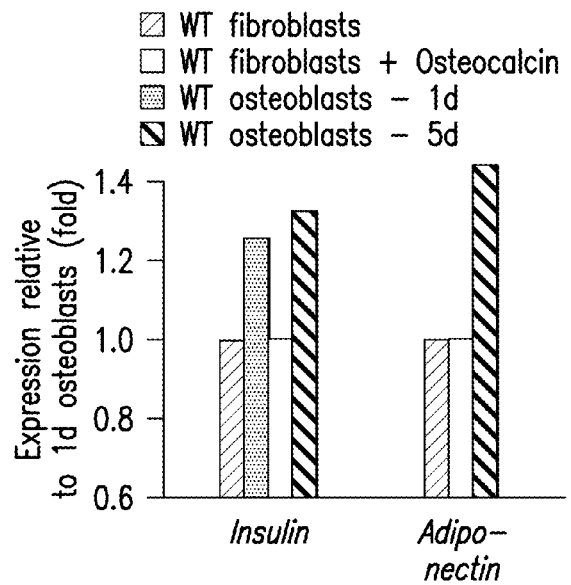
(FIG. 5R) Expression of Insulin and Adiponectin in WT islets and adipocytes co-cultured with fibroblasts in presence of recombinant osteocalcin (3 ng/ml) or vehicle, or with osteoblasts expressing (5 d) or not (1 d) Osteocalcin.
Figure 5S:
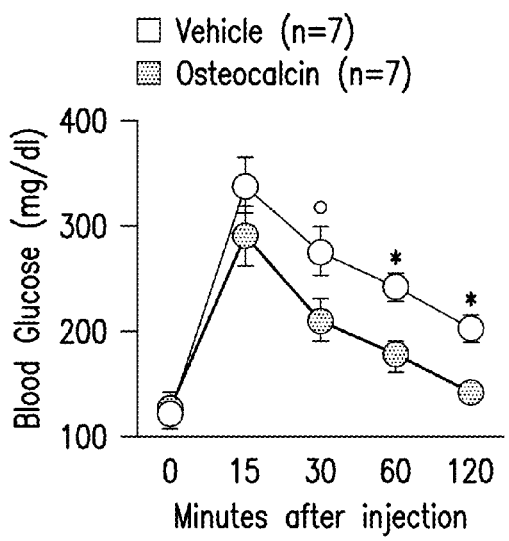
(FIG. 5S and T) Dynamic of glucose (FIG. 5S) and insulin levels (FIG. 5T) in Ocn−/− mice injected simultaneously with glucose and 20 ng of recombinant osteocalcin or vehicle.
Figure 5T:
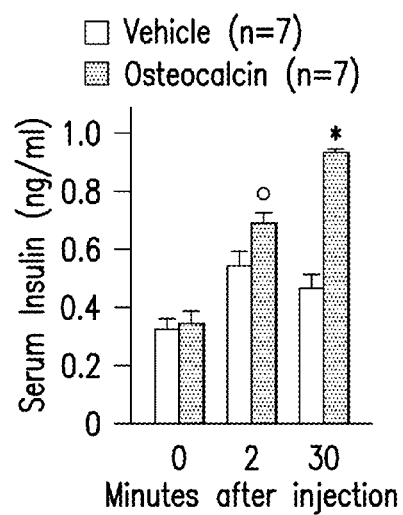

To demonstrate that osteocalcin is the molecule secreted by osteoblasts that affects insulin and adiponectin expression, further co-culture experiments were performed. Unlike WT osteoblasts, Osteocalcin−/− osteoblasts failed to enhance expression of insulin and adiponectin in islets and adipocytes, respectively (FIGS. 5O and 5P). In a converse experiment, forced expression of osteocalcin in COS cells allowed these cells to increase insulin expression in islets and adiponectin expression in adipocytes (FIG. 5Q). WT immature osteoblasts, that do not express osteocalcin (Ducy et al., 2000b) were co-cultured with either islets or adipocytes. These cells failed to induce either insulin or adiponectin expression (FIG. 5R). Taken together, these data provide genetic and cellular evidence indicating that osteocalcin is the molecule secreted by differentiated osteoblasts that regulates insulin and adiponectin expression.

Osteocalcin regulates insulin sensitivity through adiponectin. To determine whether insulin and adiponectin both contribute, independently of each other, to the metabolic phenotype of the Osteocalcin−/− mice, two related questions were asked. First, does osteocalcin regulate adiponectin expression independently of its action on insulin secretion, and if so, does the decrease in adiponectin expression noted in the Osteocalcin−/− mice explain the decrease in insulin sensitivity? If both hypotheses are correct, then compound heterozygote Osteocalcin+/−; Adiponectin+/− mice should have lower expression of adiponectin than WT littermates and should show a decrease in insulin sensitivity similar to the one observed in the Osteocalcin−/− or in the Adiponectin−/− mice (Maeda et al., 2002). Certain embodiments are directed to these heterozygous transgenic strains.

As shown in FIGS. 6A-D, insulin sensitivity was markedly decreased in Osteocalcin+/−; Adiponectin+/− mice while blood glucose levels, insulin serum levels and insulin secretion as determined by GSIS test remained within the normal range. Adiponectin serum levels were also significantly decreased in Osteocalcin+/−; Adiponectin+/− compared to WT or single heterozygote mice (FIG. 6E). These observations are consistent with the notion that osteocalcin regulates insulin sensitivity at least in part through its regulation of adiponectin expression and secretion.

To show that the increase in insulin sensitivity and decrease in fat weight observed in the Esp-deficient mice was secondary to the increase in adiponectin expression, Sap-Adiponectin transgenic mice harboring a two-fold increase in serum adiponectin level similar to the one observed in Esp-deficient mice were generated. The Sap-Adiponectin transgenic mice also showed the phenotype of low fat pad weight, high energy expenditure and metabolic and molecular evidence of increased insulin sensitivity similar to those observed in Esp-deficient mice (FIG. 22). This result shows that the increase in adiponectin expression was the main identifiable cause of the increase in insulin production and sensitivity in Esp-deficient mice. Certain embodiments of the invention are thus directed to human cells transfected with the gene for adiponectin under the control of a promoter that causes the cell to over express adiponectin.

OST-PTP regulates osteocalcin bioactivity by influencing indirectly its carboxylation. The metabolic phenotype of Osteocalcin−/− mice is the mirror image of the one observed in Esp−/− mice suggesting that in the latter there is a gain of osteocalcin activity. To further prove that Esp-deficient mice (OST-PTP−/−) are a model of a gain of activity of osteocalcin, double mutants were made by introducing additional mutations into Esp-deficient transgenic mice, specifically by making them osteocalcin+/−.

Figure 7A:
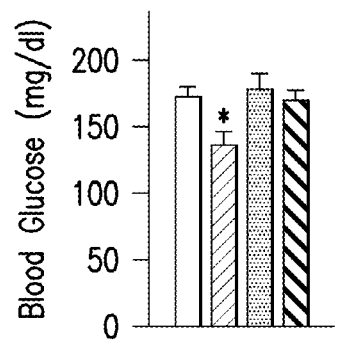
Figure 7B:
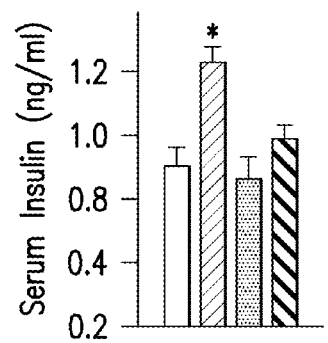
Figure 7C:
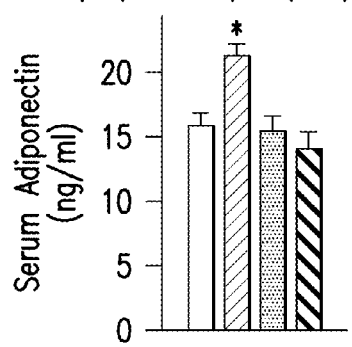
Figure 7D:
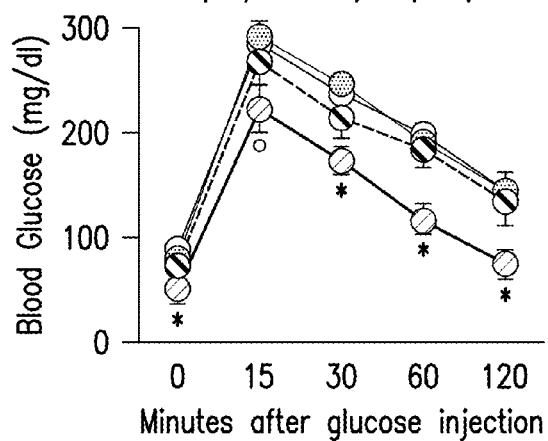

It was hypothesized that the metabolic abnormalities of Esp−/− mice would be reversible by reducing osteocalcin expression. This is exactly what was observed: Esp−/− mice lacking one allele of osteocalcin showed a remarkable reversal of all their metabolic abnormalities such as blood glucose, insulin and adiponectin serum levels, glucose tolerance, insulin secretion and sensitivity (FIGS. 7A-F). Ki67 staining showed that beta-cell proliferation was also reduced in these mutant mice (FIG. 7G).

Indeed, Esp−/−; Ocn+/− mice display a decrease in insulin synthesis and sensitivity compared to Esp−/− without any osteocalcin deletion, showing a fully corrected/normalization of all metabolic abnormalities of the Esp−/− mice compared to wt mice. This experiment established genetically that OST-PTP and osteocalcin are in the same signaling cascade, and that the $Esp_{ob}$−/− mouse phenotype is a model of a gain of activity of osteocalcin. In other words, the metabolic phenotype seen in $Esp_{ob}$−/− mice is due to an increase in osteocalcin activity.

Figure 7H:
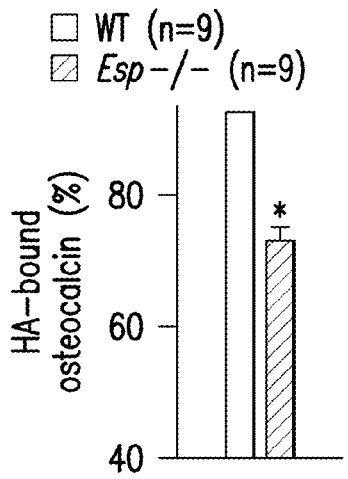
(FIG. 7H and I) Quantification of the percentage of osteocalcin bound to hydroxyapatite (HA) resin after a 15 min incubation of serum of 1-month-old mice of indicated genotypes (FIG. 7H) or of conditioned medium from osteoblast cultures treated with warfarin or vehicle (FIG. 7I).
Figure 20:
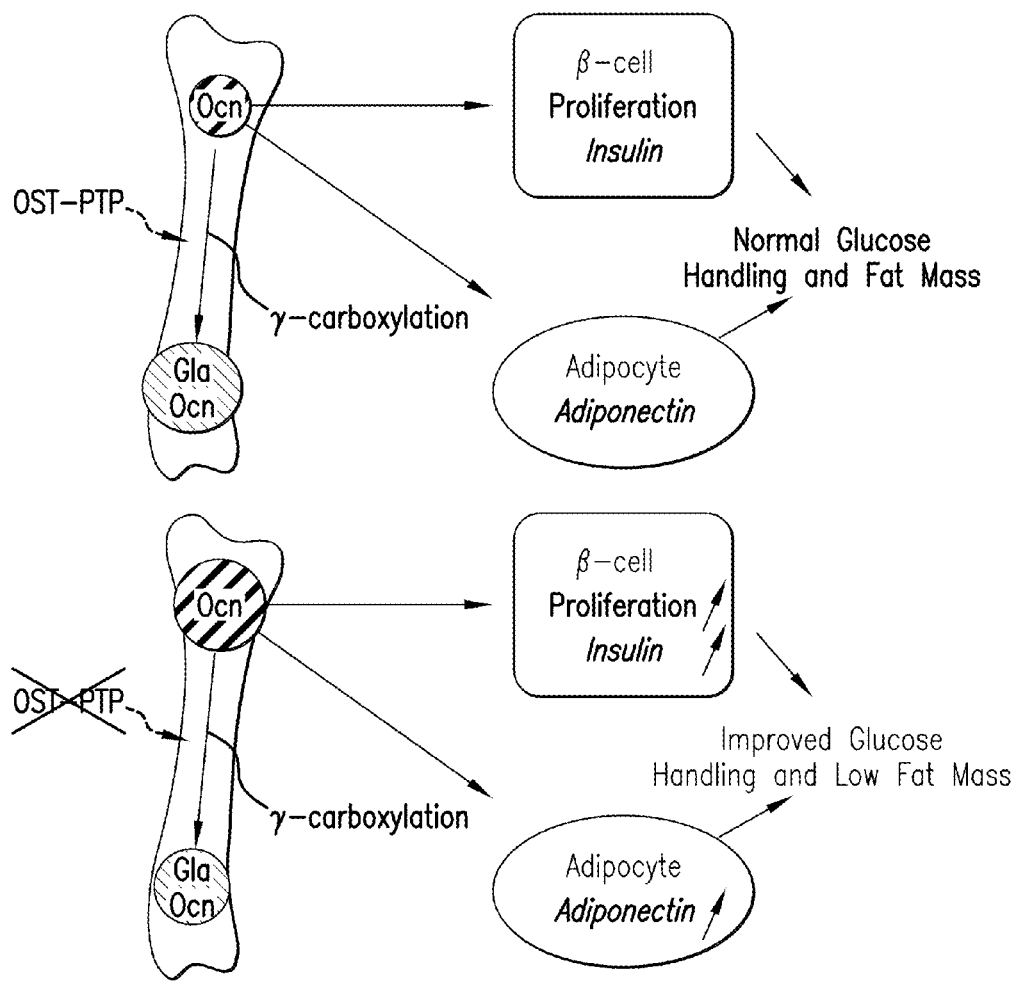
FIG. 20. The pathway for regulation of osteocalcin production by bone. (Upper panel) OST-PTP, the protein encoded by Esp favors the γ-carboxylation of osteocalcin thus lowering the pool of uncarboxylated osteocalcin, which is the active form of this hormone. As a result β-cell proliferation, Insulin expression and Adiponectin expression are normally stimulated. (Lower panel) In absence of OST-PTP γ-carboxylation of osteocalcin is hampered, there is more uncarboxylated osteocalcin and, as a result, β-cell proliferation, Insulin expression and Adiponectin expression are increased. This results in improved glucose handling and decreased fat mass.

Because osteocalcin expression and serum levels were normal in Esp−/− mice, OST-PTP regulation of osteocalcin expression was ruled out (FIG. 20) In contrast, Esp−/− mice showed a decreased ratio of serum carboxylated osteocalcin to total osteocalcin (FIG. 7H). Carboxylated osteocalcin has a higher affinity for hydroxyapatite (HA) than undercarboxylated osteocalcin (Hauschka et al., 1989; Price, 1989). An assay was used where carboxylated osteocalcin is measured as the % of total osteocalcin able to bind to hydroxyapatite (HA). This assay showed that this value is decreased by 20% in Esp−/− mice compared to wt mice. In the presence of an equal amount of total osteocalcin, this means that undercarboxylated osteocalcin is increased 20% in Esp−/− mice compared to WT.

Figure 7I:
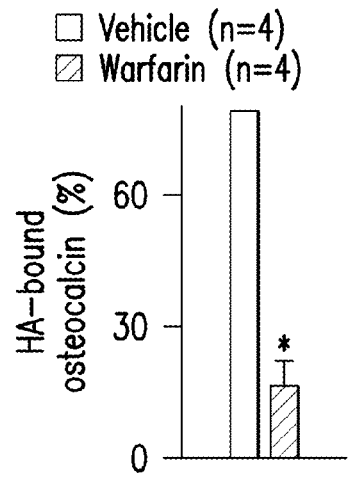
Figure 7J:
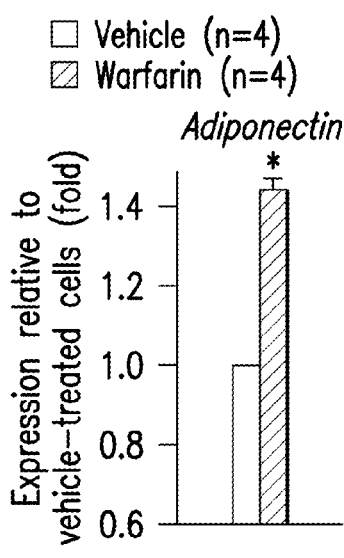
(FIG. 7J) Expression of Adiponectin in WT adipocytes cocultured with osteoblasts treated with warfarin or vehicle.
Figure 7K:
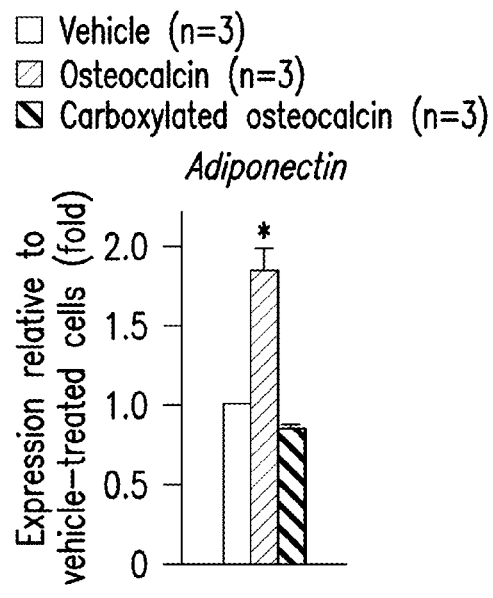
(FIG. 7K) Expression of Adiponectin in WT adipocytes cultured in presence of vehicle or of 1 ng/ml of commercially available carboxylated osteocalcin (Immunotopics) or bacterially produced uncarboxylated osteocalcin.
Figure 70:
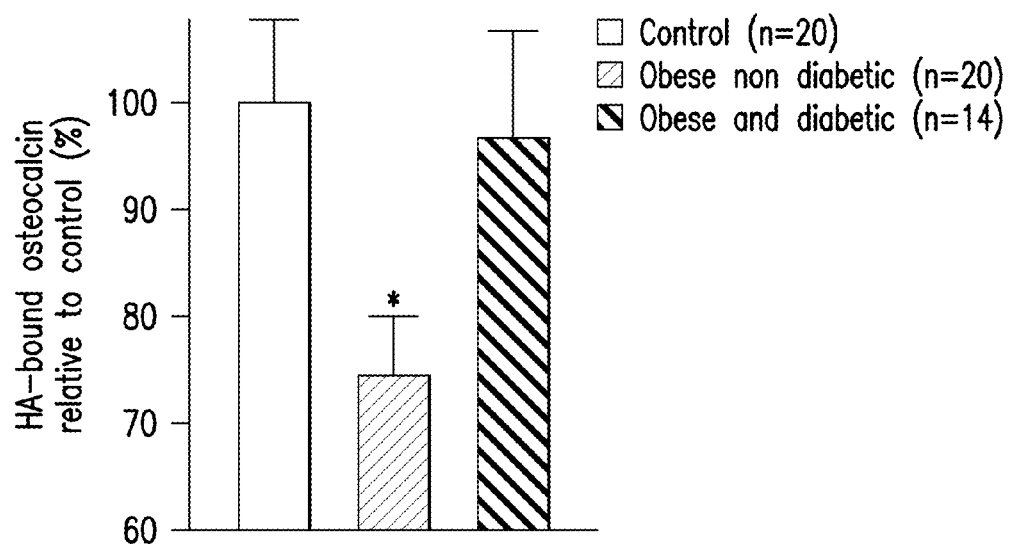

This experiment suggested that OST-PTP influences osteocalcin function by regulating its degree of gamma-carboxylation and that it was the undercarboxylated form of osteocalcin that regulated glucose homeostasis. To determine whether the was the case, two additional experiments were performed. WT primary osteoblasts were treated with warfarin, an inhibitor of gamma-carboxylation (Bergner, 2005) prior to and during co-culture assays. This treatment resulted in a marked decrease in the percentage of osteocalcin bound to HA, indicating that, as expected, these osteoblasts secrete less carboxylated osteocalcin (FIG. 7I). Nevertheless, and despite secreting less osteocalcin than WT osteoblasts (+vehicle, 10 ng/ml; +warfarin, 2 ng/ml) (Hauschka et al., 1989), warfarin-treated osteoblasts induced adiponectin expression to a significantly higher extent than vehicle-treated osteoblasts (FIG. 7J). Second, carboxylated osteocalcin and bacterially produced mouse osteocalcin, which is not carboxylated, were used in cell-based assays. While carboxylated osteocalcin failed to induce adiponectin expression, bacterially produced osteocalcin did (FIG. 7K). Likewise, undercarboxylated osteocalcin induced insulin expression as well as expression of Cyclin D1, a molecular marker of beta-cell proliferation (Kushner et al., 2005) (FIG. 7L). Lastly, we studied human obese patients that are hyperinsulinemic but not diabetic (FIG. 7M). The amount of uncarboxylated osteocalcin was significantly increased in these patients while osteocalcin serum levels were not affected (FIGS. 7M-O). Taken together these data indicate that OST-PTP influences osteocalcin bioactivity by enhancing its degree of carboxylation.

OST-PTP affects enzymes involved in the carboxylation process. A mandatory event in every function of any cell type is the ability of intracellular proteins to be phosphorylated by protein kinases and/or dephosphorylated by protein phosphatase. In particular phosphorylation of tyrosine residues accounts for 0.1% of the total cellular phosphoamino acid content; as a result protein tyrosine phosphatases (PTPs) are critically important intracellular proteins (23).

Protein tyrosine phosphatases can be schematically grouped into four classes: the classical receptor-like PTPs that have an extracellular domain that sometimes is cleaved (RPTPs); OST-PTP is a receptor-like PTP. Other classes include the classical non-receptor PTPs, the dual specificity PTPs and the low molecular weight PTPs (24). There are approximately 20 RPTPs in the human genome. RPTPs that are predominantly localized in the plasma membrane can be involved in cell to cell functions, cell-cell adhesion and in hormone signaling. However, two questions remain often unanswered regarding their biology. One is to determine the identity of substrate(s) for their phosphatase activity and the second one is to identify their ligands.

Results suggested that OST-PTP could dephosphorylate a specific substrate present in osteoblasts, thereby increasing the substrate's expression and/or activity. This substrate would then be released by osteoblasts and signal to pancreatic beta-cells and adipocytes, thereby affecting insulin secretion and sensitivity. While osteocalcin was a logical target candidate for OST-PTP physiologically speaking, osteocalcin is not phosphorylated. It was thus eliminated as a direct target.

To decipher how OST-PTP might influence osteocalcin activity we asked whether it was regulating gamma-carboxylation of osteocalcin, which is the main post-translational modification known for this molecule (Hauschka et al., 1989). This post-translational modification occurs both in rodent and in human; Poser et al analyzed the primary structure of human osteocalcin, and reported that human osteocalcin is a mixture of $Glu^7$ osteocalcin (herein "Ocglu") with the 17-position being glutamic acid, and $Gla^7$ osteocalcin with the 17-position being gamma-carboxyglutamic acid (herein "BGP", also bone Gla-protein) [Poser, J. W. et al., Proc. Natl. Acad. Sci. U.S., 255, 8685-8691 (1980)]. Gla residues usually confer on proteins a high affinity for mineral ions. However, loss and gain of function experiments failed to identify a function for osteocalcin in extracellular matrix mineralization in vivo (Ducy et al., 1996; Murshed et al., 2004).

OST-PTP Substrates Include Insulin Receptor and Gamma-Carboxylase. A computer search revealed that gamma-carboxylase, also known as vitamin K-dependent gamma-glutamyl carboxylase, has PTP consensus sites. This enzyme catalyzes the conversion of glutamic acid to gamma-carboxyglutamic acid in substrate proteins like osteocalcin. To determine if OST-PTP acts on gamma-carboxylase, substrate-trapping experiments were conducted in COS cells, Ros17/2.8 osteoblast cells and differentiated primary osteoblasts. d10 bone-derived cells were cultured for 10 days in alpha MEM/10% fetal bovine serum (FBS) supplemented with ascorbic acid (100 μg/ml) and beta-glycerophosphate (5 mM)). These cells were then starved for 24 hours in alpha MEM culture medium supplemented with 1% FBS only and treated with pervanadate (100 mM), an irreversible protein-tyrosine phosphatase inhibitor, and 20% FBS for 30 minutes. Cell lysates were incubated for 2 h at 4° C. with either GST, GST-PTP$^{WT}$ or GST-PTP$^{D1316A}$. Different amounts of the total cell extract were also loaded as control.

Figure 9:
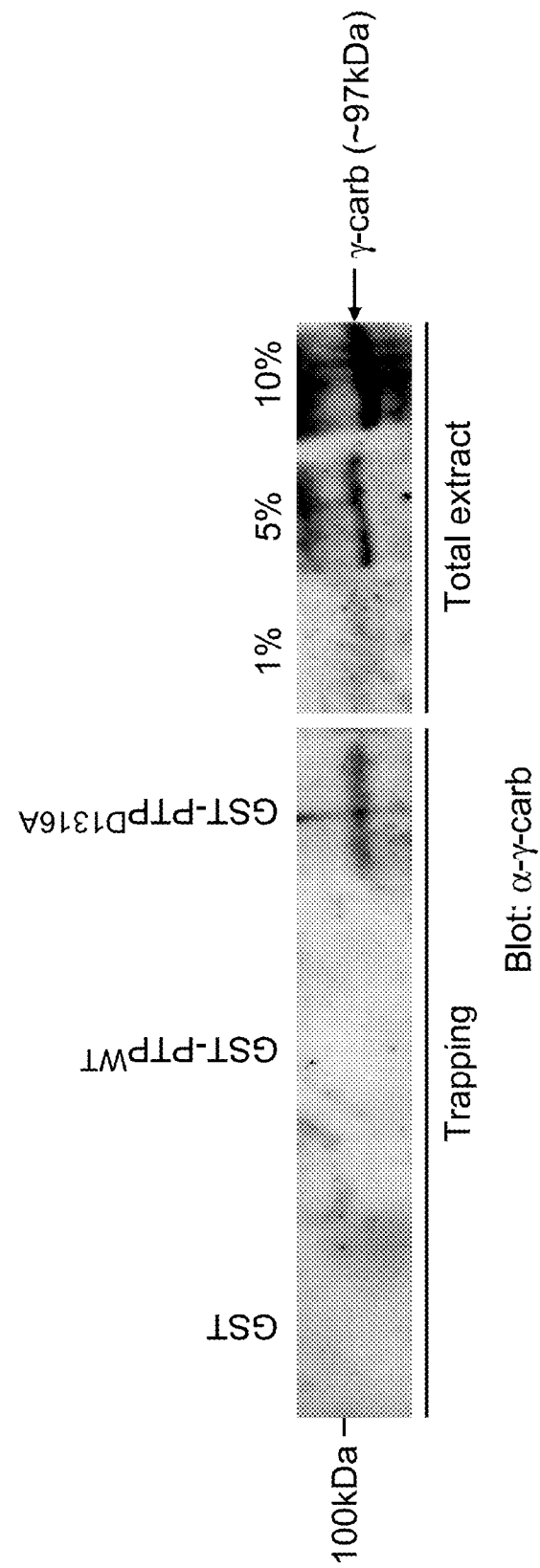
FIG. 9. Mutant enzyme OST-PTP$^{D1316A}$ traps gamma-carboxylase, thereby demonstrating that gamma-carboxylase is a substrate of OST-PTP. This, however, does not mean that gamma-carboxylase is the only substrate of OST-PTP. There was no binding in the GST lane because there is no PTP transfected. It is a control to show that if there is trapping, it is not due to the GST part of any GST fusion protein. There was also no trapping with GST-PTP$^{WT}$ because this form dephosphorylated the substrate gamma-carboxylase, which is then released. A band is clearly seen in the lane having the mutant OST-PTP (GST-PTP$^{D1316A}$) because the mutation engineered a defect in OST-PTP phosphatase activity that allowed the substrate to irreversibly bind to and be retained by the enzyme.

The results in FIG. 9 showed that the mutant enzyme GST-PTP$^{D1316A}$ trapped gamma-carboxylase, thereby demonstrating that gamma-carboxylase is a substrate of OST-PTP. This, however, does not mean that gamma-carboxylase is the only substrate of OST-PTP. There was no binding in the GST lane because there is no PTP transfected. It is a control to show that if there is trapping, it is not due to the GST part of any GST fusion protein. There was also no trapping with GST-PTP$^{WT}$ because this form dephosphorylated the substrate gamma-carboxylase, which is then released. A band is clearly seen in the lane having the mutant GST-PTP$^{D1316A}$ because the mutation engineered a defect in OST-PTP phosphatase activity that allowed the substrate to irreversibly bind to and be retained by the enzyme.

These results show that gamma-carboxylase is a substrate for OST-PTP in osteoblasts. This enabled elucidation of part of the biochemical pathway through which OST-PTP regulates osteocalcin bioactivity: OST-PTP dephosphorylates gamma-carboxylase, thereby activating it. Activated gamma-carboxylase in turn causes an increase in carboxylated osteocalcin. There is less dephosphorylated active gamma-carboxylase in OST-PTP-deficient mice, which leads to secretion of more undercarboxylated osteocalcin. This explains why the OST-PTP-deficient mice have elevated levels of undercarboxylated osteocalcin, which itself causes resistance to metabolic syndrome and diabetes.

Figure 8:
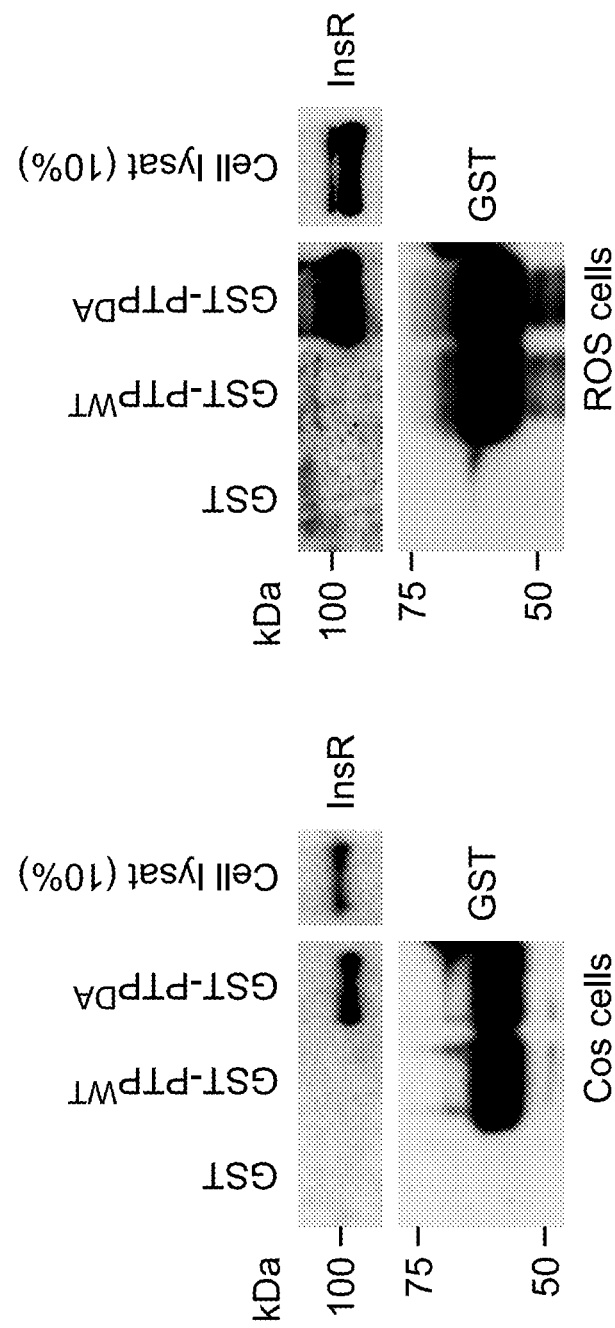
FIG. 8. OST-PTP was mutated in COS cells using site directed mutagenesis using a PCR method and a commercially available kit. Mutated OST-PTP (GST-PTP CA) interacts with insulin receptor (InsR) in COS cells (left upper panel) and ROS cells (right upper panel) and third lane) whereas WT OST-PTP (GST-PTP WT) does not interact (second lane). The same amount of GST fusion proteins were used for substrate trapping (lower panels). GST=Recombinant bacterially produced glutathione S-Transferase protein.

Using the same substrate trapping assay, it was also discovered that the insulin receptor which is expressed in osteoblasts is a substrate for OST-PTP (FIG. 8). The results of the substrate-trapping experiments show that mutated OST-PTP (GST-PTP$^{DA}$) interacts with the insulin receptor (InsR) expressed in COS cells (left upper panel) and ROS17/2.8 osteoblasts cells (right upper panel) (third lane). By contrast, WT OST-PTP (GST-PTP$^{WT}$) did not interact with the insulin receptor (second lane). The same amount of GST fusion proteins were used for substrate trapping.

Human Patient Data. FIG. 7O shows that human obese patients that are hyperinsulinemic but not diabetic, have significantly elevated levels of undercarboxylated osteocalcin (about 30% higher) compared to normal patients, even though osteocalcin serum levels (7M) are about the same. This shows that in mice and in humans the level of carboxylation of osteocalcin influences its bioactivity. FIG. 7O further shows that obese non-diabetic patients have an increase in undercarboxylated osteocalcin compared to patients who are obese and diabetic. The ratio of carboxylated osteocalcin compared to total osteocalcin was measured in serum from non-medicated normal, obese non-diabetic and obese-diabetic patients.

Figure 10:
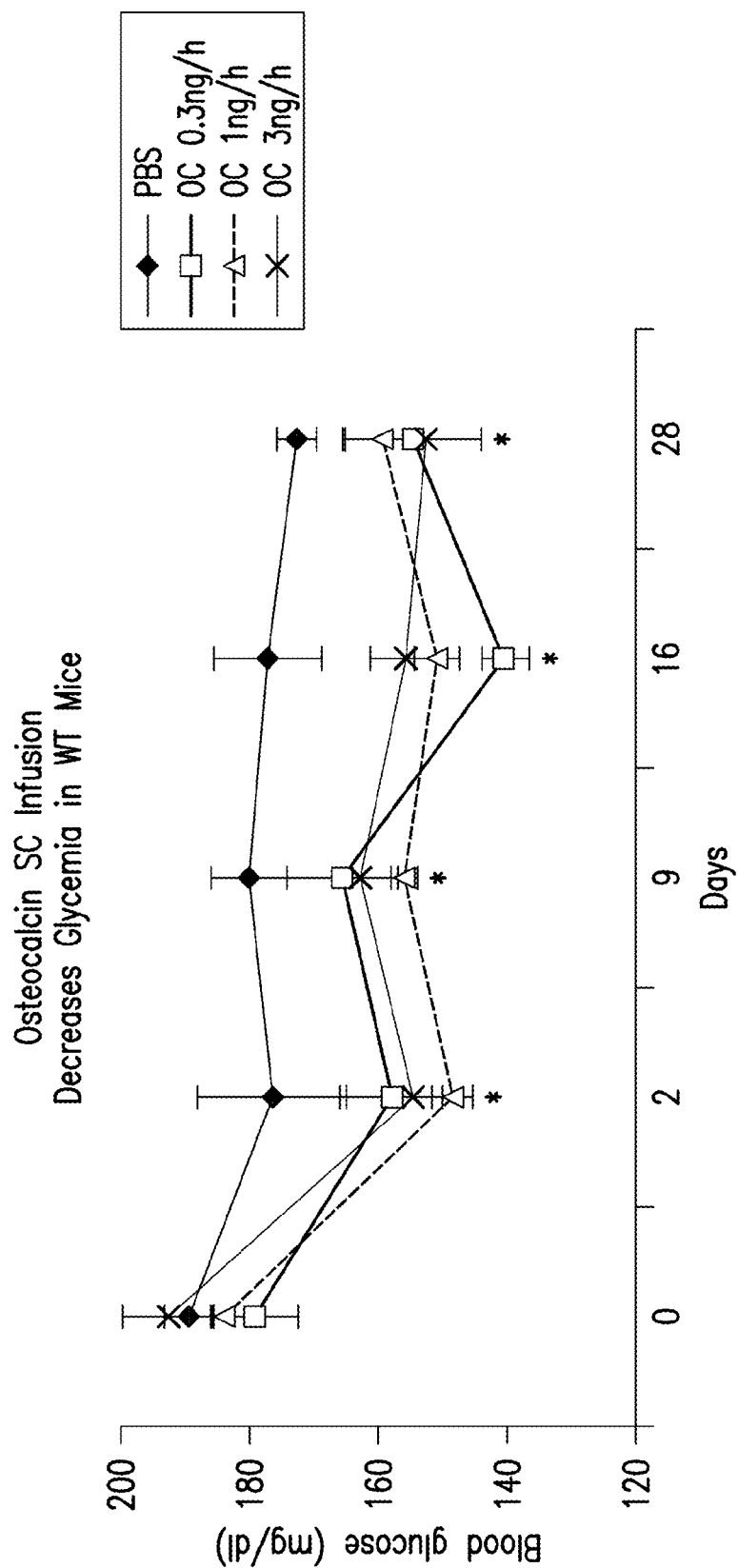
FIG. 10. Osteocalcin subcutaneous infusion decreases glycemia in wt mice. Indicated doses of recombinant osteocalcin or PBS were infused subcutaneously for 28 days in wt mice. Blood glucose was measured at indicated days.

An in vivo experiment was conducted in which the effect of undercarboxylated osteocalcin on glycemia was monitored. Wild type mice were infused with 3 different amounts of mouse recombinant undercarboxylated osteocalcin or placebo (PBS) subcutaneously for 28 days (0.3, 1 and 3 ng/hour). Compared to the control animal infused with placebo, all three doses of undercarboxylated osteocalcin decreased glycemia in vivo over the 28 day period (FIG. 10).

Figure 11:
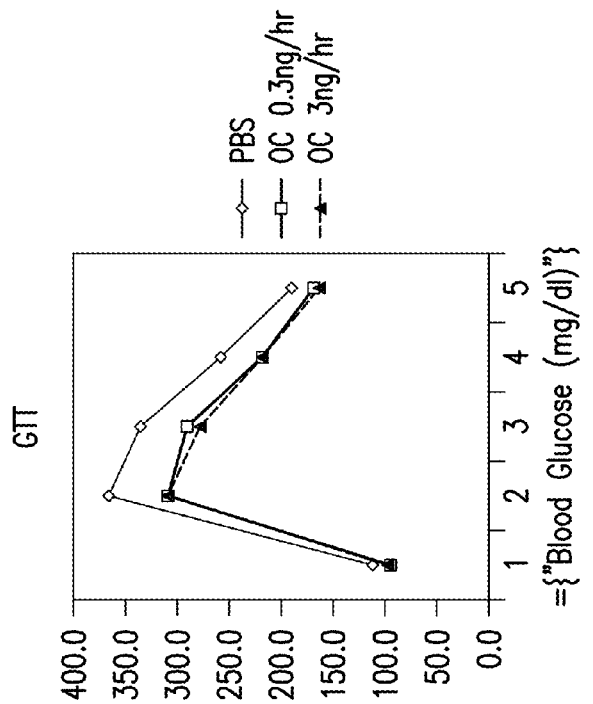
FIG. 11. Osteocalcin subcutaneous infusion increases glucose tolerance in wt mice. Wt mice were infused subcutaneously with indicated doses of recombinant osteocalcin or PBS for 14 days before receiving a single injection of glucose. Blood glucose was measured thereafter at indicated times.

In another in vivo experiment, the effect of uncarboxylated osteocalcin on glucose tolerance was investigated. Wild type mice were infused subcutaneously with either 0.3 or 3 ng/hour doses of recombinant uncarboxylated osteocalcin or PBS for 14 days before receiving a single injection of glucose. Blood glucose was measured thereafter at the indicated times. The results show that both doses of uncarboxylated osteocalcin increased glucose tolerance above control levels over the 120 minute time period following the glucose injection (FIG. 11).

Figure 12:
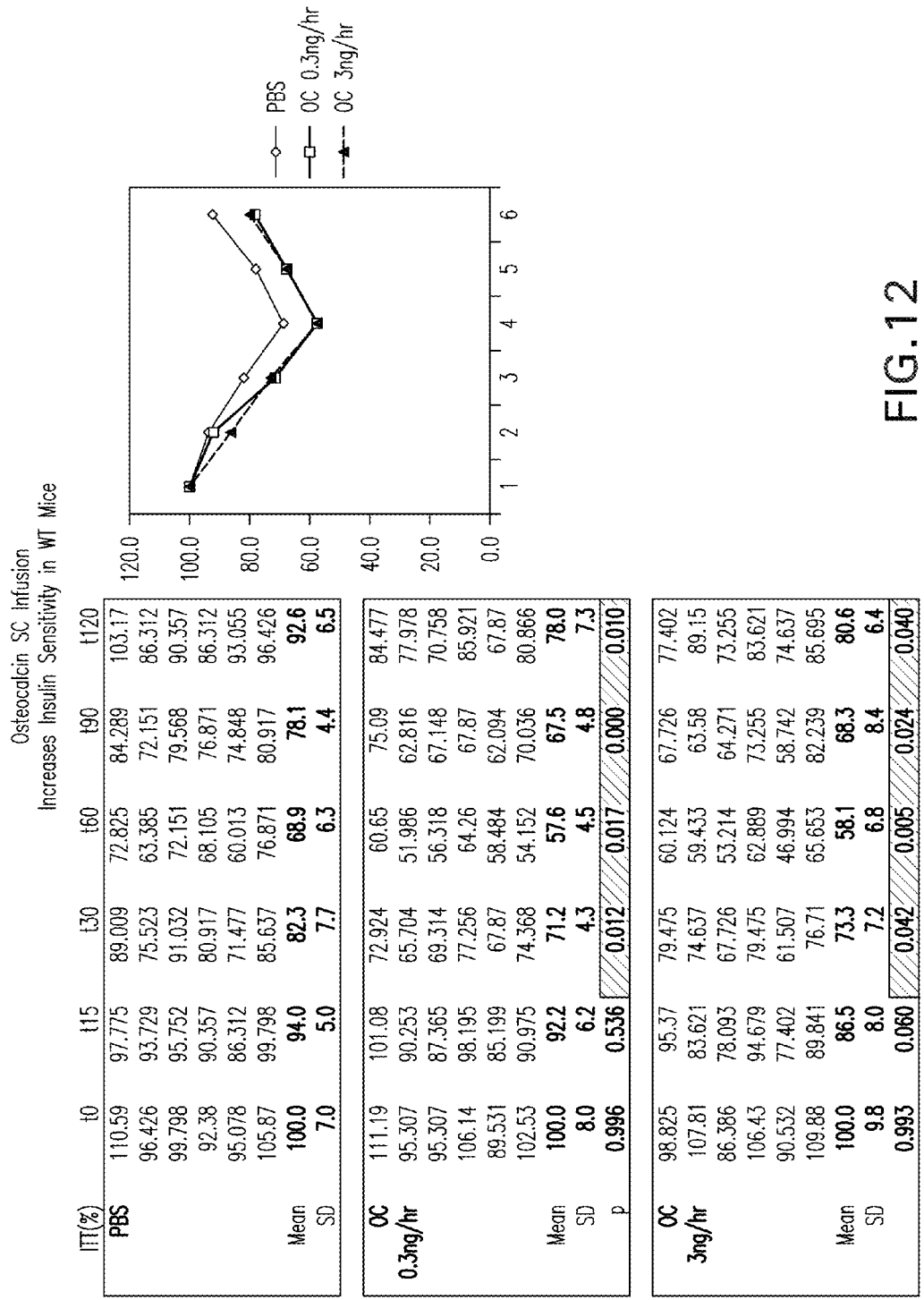
FIG. 12. Osteocalcin subcutaneous infusion increases insulin sensitivity in wt mice. Wt mice were infused subcutaneously with indicated doses of recombinant osteocalcin or PBS for 18 days before receiving a single injection of insulin. Blood glucose was measured thereafter at indicated times.

The effect of uncarboxylated osteocalcin on insulin sensitivity was also examined. Wild type mice were infused subcutaneously with 0.3 or 3 ng/hour doses of recombinant osteocalcin or PBS for 18 days before receiving a single injection of insulin. Blood glucose was measured thereafter at the indicated times from 0-120 minutes after injection. The results show that insulin sensitivity was increased by both doses of uncarboxylated osteocalcin (FIG. 12).

In another in vivo experiment, the effect of uncarboxylated osteocalcin on body weight and fat pad mass was monitored (FIG. 13). Wild type mice were infused subcutaneously for 28 days with PBS or uncarboxylated osteocalcin at 0.3, 1 or 3 ng/hour. The results show that body weight was slightly reduced by uncarboxylated osteocalcin with the highest dose being the most effective. (FIG. 13) Gonadal fat pad mass, measured after 28 days, decreased by about %18 with 3 ng/hour uncarboxylated osteocalcin treatment. The other doses did not significantly decrease fat pad mass in that period.

Figure 14:
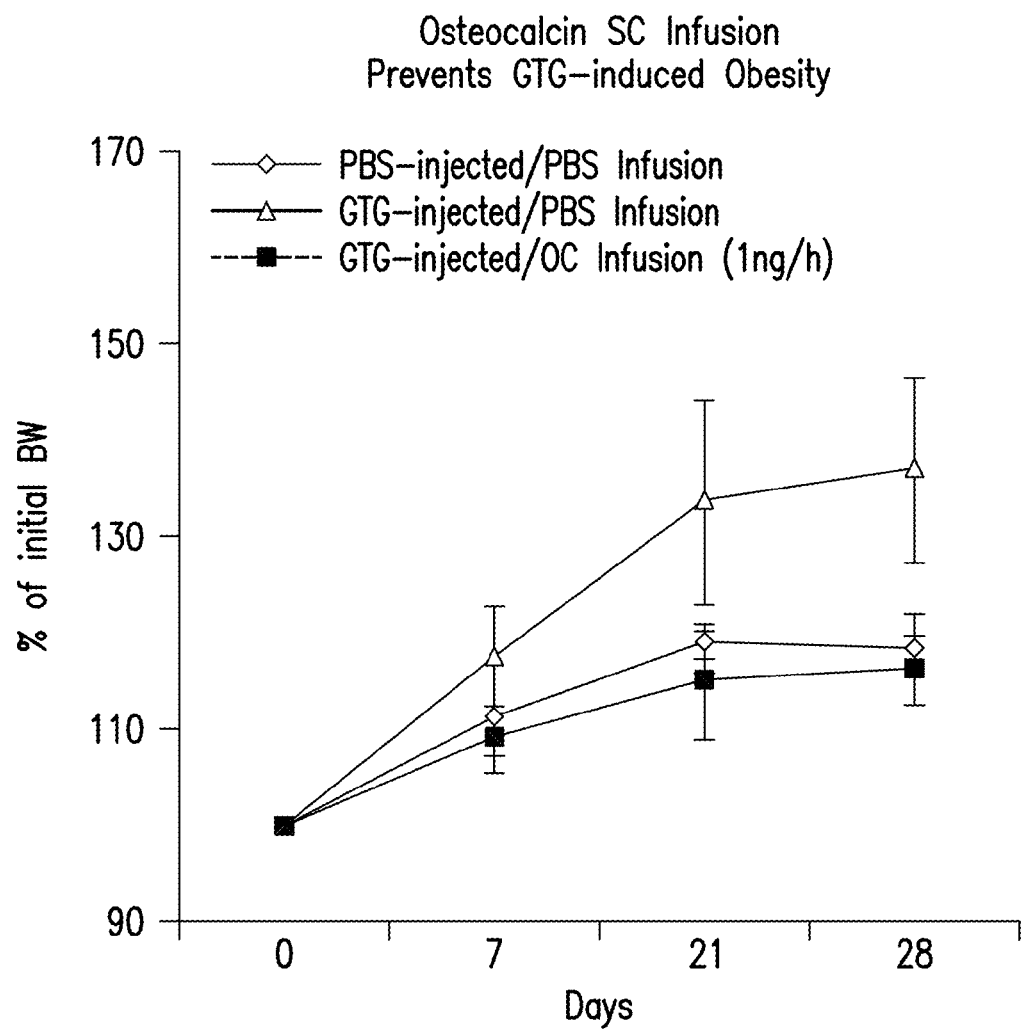
FIG. 14. Osteocalcin subcutaneous infusion prevents GTG-induced obesity in wt mice. Wt mice were injected with gold thioglucose (GTG) or vehicle to induce hyperphagia and obesity. Two weeks later they were implanted with subcutaneous osmotic pumps infusing ln/hr of recombinant osteocalcin or PBS for 28 days before. Body weight gain was recorded thereafter at indicated days.

The effect of uncarboxylated osteocalcin on GTG-induced obesity was investigated (FIG. 14). Wild type mice were injected with gold thioglucose (GTG) to induce hyperphagia and obesity or vehicle. Two weeks later they were implanted with subcutaneous osmotic pumps infusing 1 ng/hr of recombinant uncarboxylated osteocalcin or PBS for 28 days. Body weight gain was significantly reduced with both doses of uncarboxylated osteocalcin by the first time point checked, 7 days, and remained lower than controls for the entire 28 day period. At 28 days, body weight was reduced by about 15% with uncarboxylated osteocalcin treatment.

Figure 15:
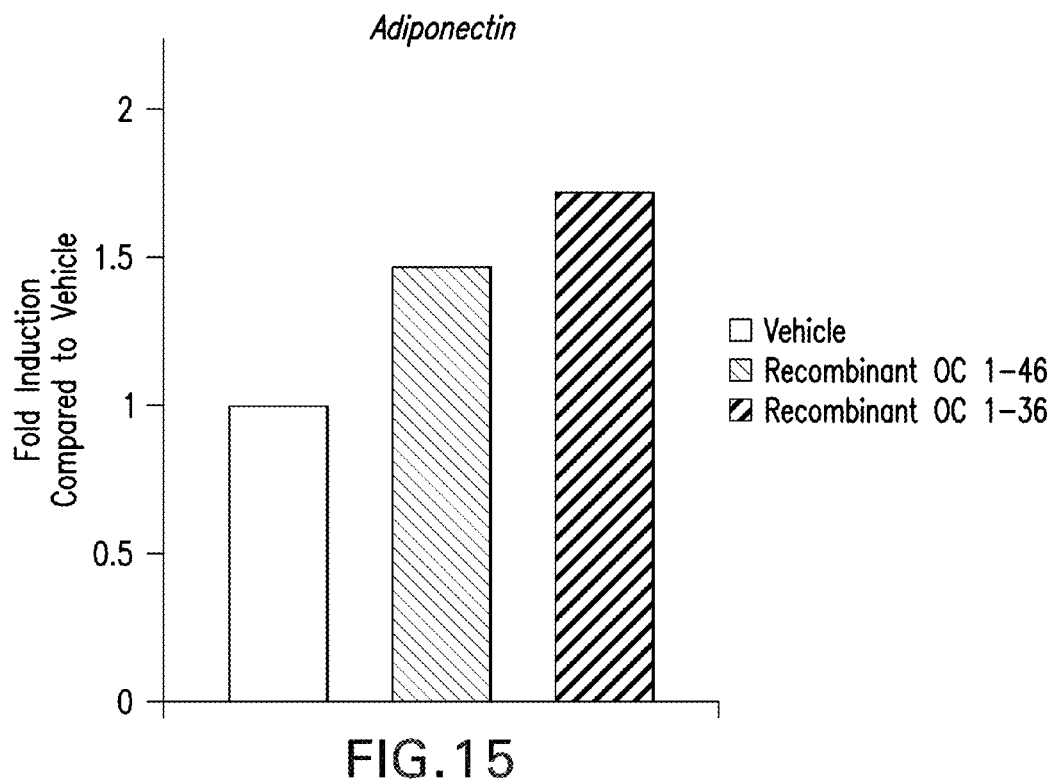
FIG. 15. A fragment of osteocalcin (1-36) is as potent as native osteocalcin in inducing adiponectin expression in vitro. Wt adipocytes were treated for 4 hours with recombinant full-length osteocalcin (1-46) or a truncated form (1-36) or vehicle. Adiponectin expression was then quantified by real time PCR.

A fragment of uncarboxylated osteocalcin is biologically active. Experiments were performed to test whether truncated osteocalcin was as effective as full-length uncarboxylated osteocalcin in stimulating adiponectin secretion from mouse adipocytes in vitro. Wild type adipocytes were treated for 4 hours with recombinant full-length osteocalcin (1-46) or a truncated form (1-36) (having a deletion of the first ten amino acids from the C-terminal end) or vehicle. Adiponectin expression was then quantified by real time PCR. The results show that full-length uncarboxylated osteocalcin produced about a 1.5 fold increase, and the 1-36 fragment of uncarboxylated osteocalcin produced about a 1.8 fold increase (FIG. 15). Thus, the full length molecule is not needed for biological activity; at least up to 10 amino acids can be deleted from the C-terminal end of the mouse osteocalcin molecule to achieve the same biological effects on adipocytes and beta-cells. Certain embodiments of the invention are directed to osteocalcin from which the first ten amino acids from the C-terminal end have been deleted, preferably human osteocalcin, preferably undercarboxylated osteocalcin.

Figure 21:
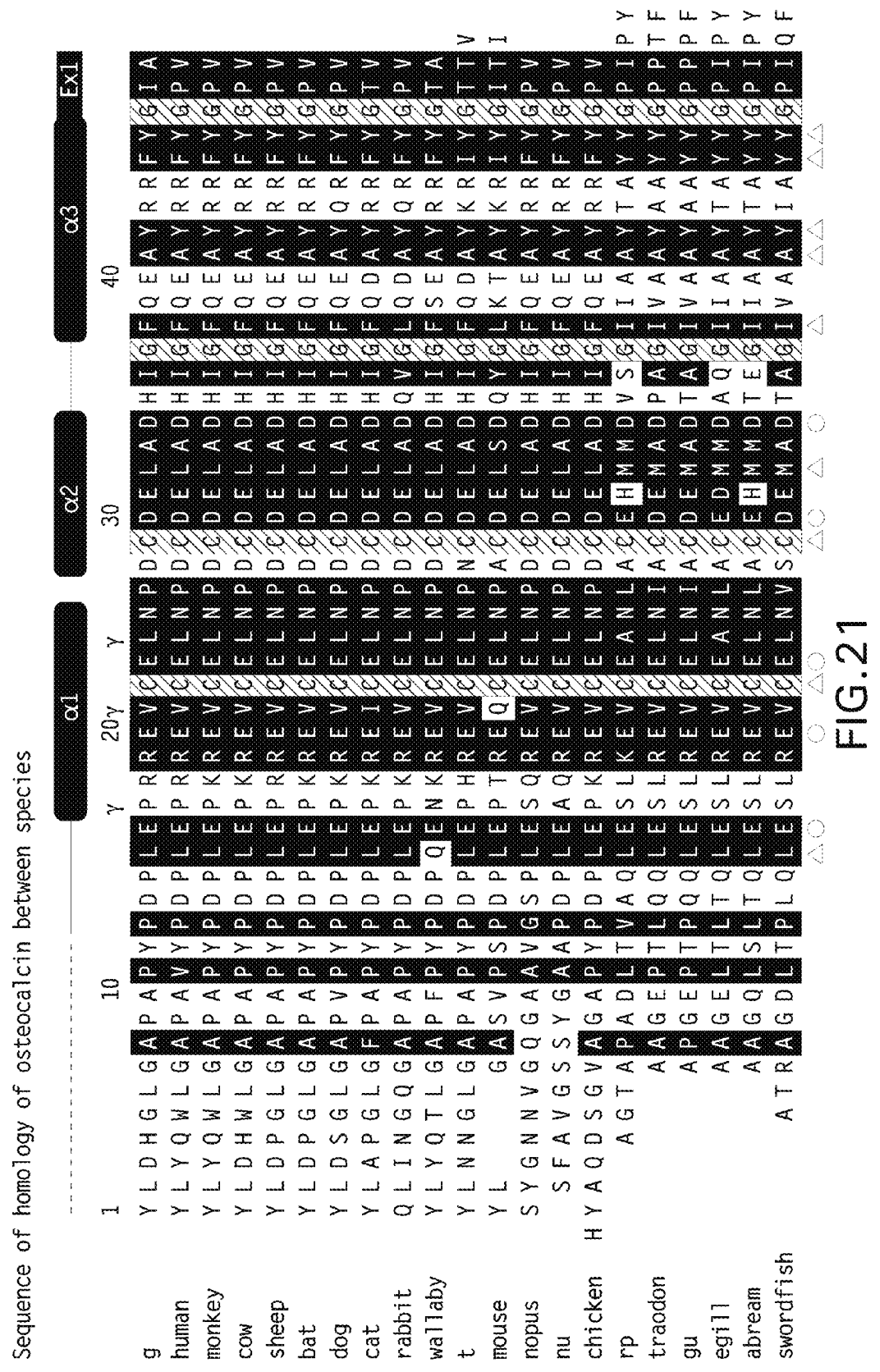

The primary sequence of osteocalcin is highly conserved among species and it is one of the ten most abundant proteins in the human body (FIG. 21), suggesting that its function is preserved throughout evolution. Conserved features importantly include 3 Gla residues at positions 17, 21, and 24, a disulfide bridge between Cys23 and Cys29, and most species contain a hydroxyproline at position 9. The N-terminus of osteocalcin shows highest sequence variation in comparison to other parts of the molecule. The high degree of conservation of human and mouse osteocalcin underscores the relevance of the mouse as an animal model for the human, in both healthy and diseased states, and validates our claims to the therapeutic and diagnostic use of osteocalcin to treat or prevent metabolic syndrome or any of its components and type 1 diabetes.

Vitamin K and Statins Increase Osteocalcin. Vitamin K is required for gamma-carboxylation. Warfarin and other COUMADIN® (warfarin) derivatives block vitamin K-dependent gamma-carboxylation, thus increasing the level of active, undercarboxylated osteocalcin. This is in agreement with data showing that warfarin-treated osteoblasts produce elevated levels of undercarboxylated osteocalcin compared to vehicle-treated osteoblasts (FIG. 7I). Others have shown that four weeks of treatment of osteoporotic patients with Vitamin K caused a dramatic percentage mean decrease in undercarboxylated osteocalcin of 85% compared to controls without Vitamin K treatment. Vitamin D had no significant effect alone or when administered together with Vitamin K. Takahashi, et al, Clinical Endocrinology (2001) 54, 291-224. See also Sugiyama, T., J Bone Miner Metabolism (2001) 19, 146-159. This observation suggests that warfarin or another COUMADIN® (warfarin) derivative could be used to block vitamin K-dependent gamma-carboxylation and increase the level of undercarboxylated osteocalcin in patients with the goal to prevent/treat metabolic disorders.

Warfarin, sold as the brand name COUMADIN® (warfarin), is used as an oral anticoagulant that inhibits the synthesis of clotting factors, thus preventing blood clot formation. However, COUMADIN® (warfarin) can cause bleeding and necrosis (gangrene) of the skin. Many drugs, both prescription and nonprescription (OTC), can affect the anticoagulant action of COUMADIN® (warfarin). Some medications can enhance the action of COUMADIN® (warfarin) and cause excessive blood thinning and life-threatening bleeding. A few examples of such medications include Aspirin, TYLENOL® (ibuprofen), alcohol, ibuprofen (MOTRIN® (ibuprofen)), cimetidine (TAGAMET® (cimetidine)), oxandrolone (OXANDRIN® (oxandrolone)), certain vitamins, and antibiotics.

Others have shown that the statin ZOCOR® (simvastatin at 20 mg/day in humans) significantly increased serum levels of osteocalcin (p value less than 0.05) after four weeks of treatment, although undercarboxylated osteocalcin could not be distinguished from intact osteocalcin. Chan, M. H., et al., J Clin Endocrinology and Metabolism (2001) Vol 86(9), 4556-59. Even though there is no experimental proof that the level of undercarboxylated osteocalcin was increased by statins, a significant increase in the overall expression of osteocalcin, could cause a saturation of the gamma-carboxylase activity and an inability to carboxylate all of the osteocalcin produced. As a result statins could indirectly increase the amount of undercarboxylated osteocalcin released in the blood. Moreover, administering statins together with drugs that block gamma-carboxylation, such as warfarin, which blocks vitamin K, or inhibitors of OST-PTP and gamma-carboxylase, could work together to elevate serum undercarboxylated osteocalcin and have therapeutic use. Statins and vitamin K inhibitors could be administered in a single preparation or in separate preparations.

Therefore certain aspects of the present invention are directed to the use of vitamin K inhibitors and statins to increase undercarboxylated osteocalcin levels in serum, and to their therapeutic use in treating metabolic syndrome and its various components.

Figure 16:
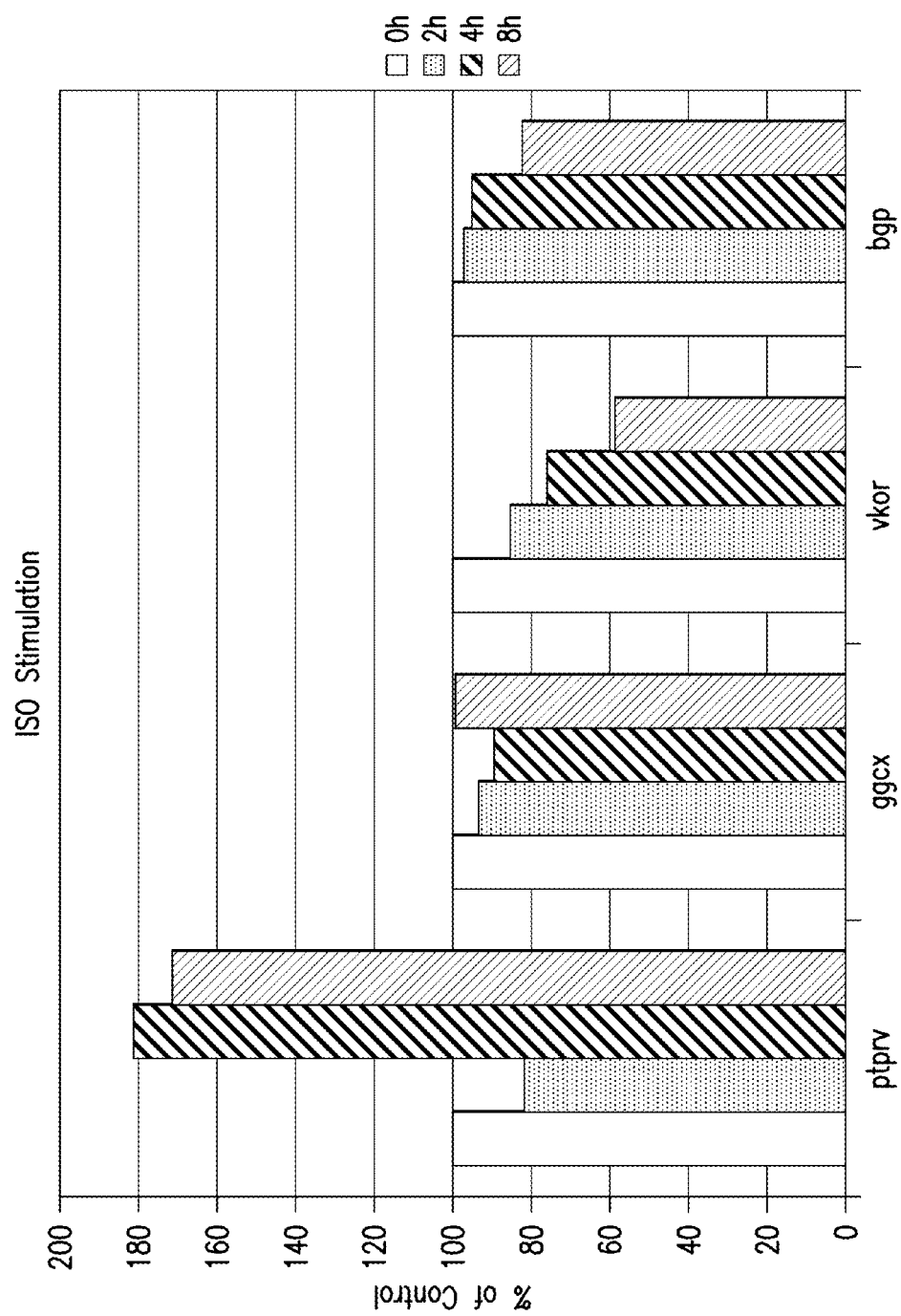
FIG. 16. Shows the effect of applying isoproterenol (enhancing SNS activity) to wild type osteoblasts on the expression of ptpry=Esp/OST-PTP, Ggcx=gamma-carboxylase, Vkor=recycling of vitamin K/necessary for ggcx activity, and Bgp=osteocalcin. mRNA levels in wt osteoblasts were measured using quantitative PCR.

The sympathetic nervous system positively regulates OST-PTP expression. It was discovered that sympathetic nervous system (SNS) activity positively regulates Esp expression in osteoblasts. Indeed, FIG. 16 shows that stimulation of SNS signaling with isoproterenol, a beta adrenergic receptor agonist, increased Esp expression by about 80% by 4 hours, and that this increase remains steady even at 8 hours. However, increased SNS activity did not increase expression of gamma-carboxylase (ggcx), vkor (an enzyme involved in recycling of vitamin K that is necessary for ggcx activity) or osteocalcin. This experiment shows that SNS signaling positively regulates Esp expression in osteoblasts. Thus, decreasing sympathetic activity should lead to a decrease in Esp expression and thereby to an increase in the undercarboxylated, active form of osteocalcin.

Figure 17:
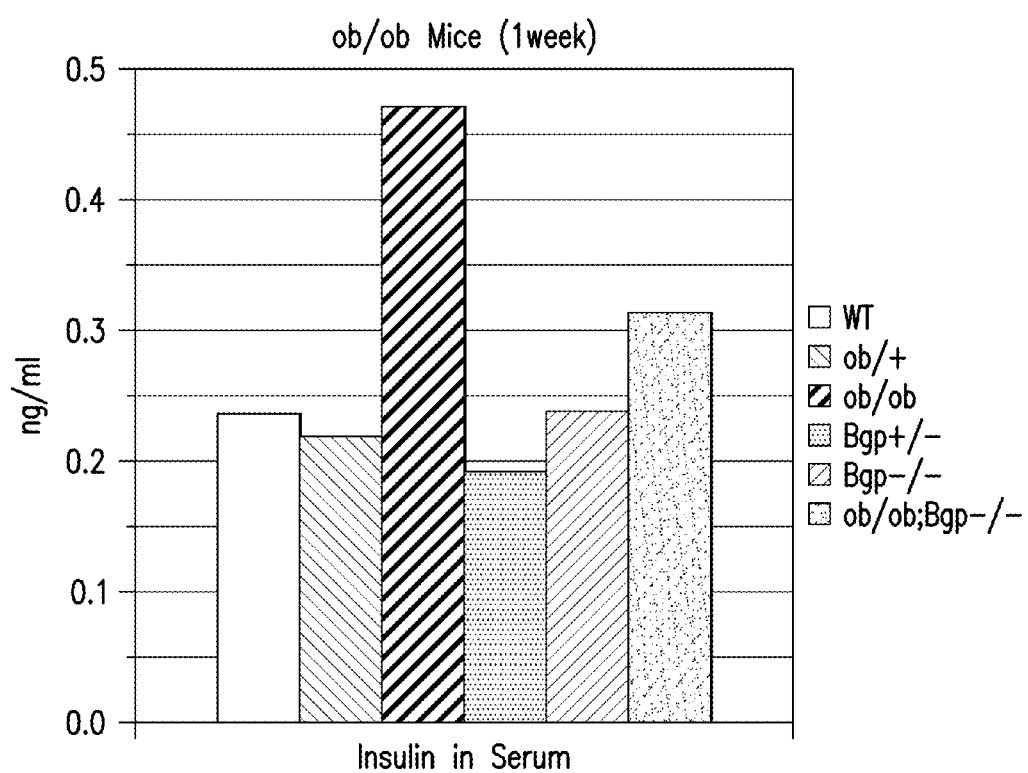
FIG. 17. The level of serum insulin in one week old mice having various genotypes: WT mice, ob–/+ mice (heterozygous for obesity), ob/ob mice, Bgp–/+ (heterozygous for osteocalcin), BGP–/– mice, and ob/ob/mice that are also Bgp–/– (Oc deficient).
Figure 18:
FIG. 18. Osteocalcin-deficient mice develop atherogenic lesions after 6 weeks on the western diet. Histological analysis of the entrance aorta at the level of the aortic valves clearly shows that atherogenic lesions are present.
Figure 19:
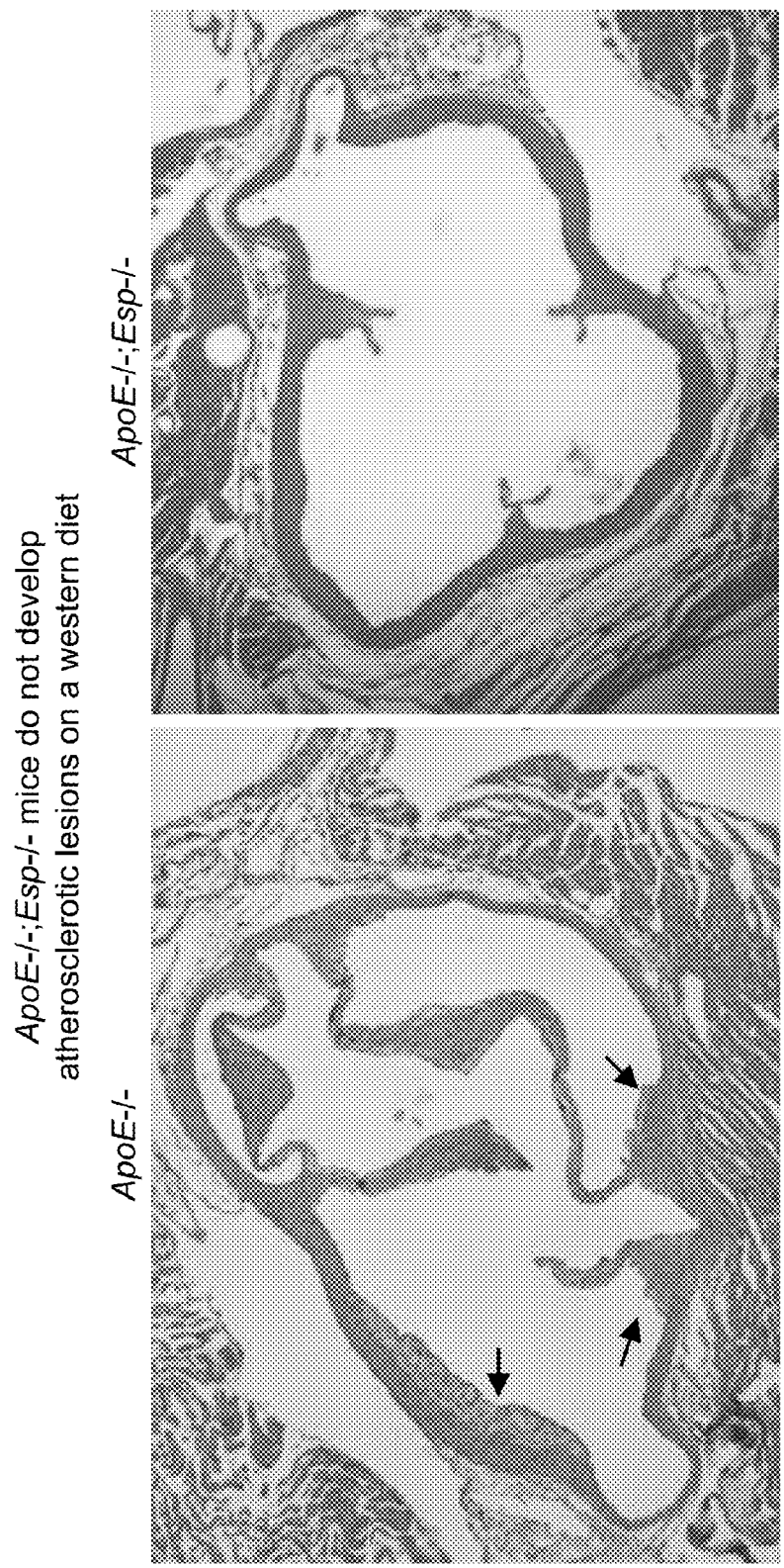
FIG. 19. Absence of the Esp gene that encodes OST-PTP protects ApoE–/– mice from developing atherosclerotic lesions. ApoE–/– mice develop atherosclerotic lesions after being fed a western diet for 6 weeks, while double mutant ApoE–/–; Esp–/– mice on the same diet do not.

In vivo experiments using ob/ob mice, which have low sympathetic activity, confirmed this hypothesis, and showed that there is a genetic link between leptin (the product of the ob gene) and osteocalcin. It has been shown that leptin signals to osteoblasts via the SNS. Thus, ob/ob mice are a model of decreased SNS signaling on osteoblasts. It has been shown that ob/ob mice display an increase in insulin before they develop any other metabolic abnormalities. This increase could be due to decreased SNS activity on osteoblasts, which as a result would express less OST-PTP and secrete more bioactive undercarboxylated osteocalcin, leading to increased insulin expression. The level of serum insulin was measured in one week old mice having various genotypes: WT mice, ob−/+ mice (hemizygous for obesity), ob/ob mice, Bgp−/+ (hemizygous for osteocalcin), BGP−/− mice, and ob/ob mice that are also Bgp−/− (Ocn deficient). One week old mice were chosen because ob/ob mice at one week are not yet obese and they are relatively normal metabolically, except for having high serum insulin levels. The results show that ob/ob mice indeed have increased serum insulin levels but if both alleles of the Bgp gene (encoding osteocalcin) are deleted in ob/ob mice their serum insulin levels returns to normal. FIG. 17. This experiment demonstrates that the increase in insulin observed in ob/ob mice is dependent on osteocalcin.

Taken together the results presented above mean that administering beta blockers, which decrease SNS activity, will likewise decrease Esp expression and thereby increase the level of undercarboxylated osteocalcin. As such they could be used to prevent/treat metabolic disorders via an increase in osteocalcin activity. Beta blockers have been used clinically for a long time, therefore the amounts that are safe for human use are established. Routine experimentation will determine the optimum amount of a particular beta blocker to administer to achieve increased levels of serum undercarboxylated osteocalcin. New beta-blockers, targeting more preferentially the cells of the skeleton could also be developed to more specifically increase osteocalcin activity and reduce the risk of side effects.

TABLE 2

| | Wild-type (n = 4) | Esp−/− (n = 3) | Ocn−/− (n = 4) |
|---|---|---|---|
| Basal hepatic glucose production (mg/kg/min) | 13.2 ± 1.9 | 16.6 ± 1.3 | 15.5 ± 1.8 |
| Clamp hepatic glucose production (mg/kg/min) | 10.3 ± 1.9 | −5.5 ± 1.8* | 16.1 ± 1.9* |
| Glucose turnover (mg/kg/min) | 41.8 ± 1.3 | 50.6 ± 2.6* | 38.2 ± 3.7 |
| Glycogen synthesis (mg/kg/min) | 19.2 ± 2.7 | 19.4 ± 3.2 | 11.5 ± 1.3* |
| Muscle glucose uptake (nmol/g/min) | 229 ± 29 | 358 ± 65* | 188 ± 15 |

TABLE 2-continued

|  | Wild-type (n = 4) | Esp-/- (n = 3) | Ocn-/- (n = 4) |
|---|---|---|---|
| White adipose glucose uptake (nmol/g/min) | 16.7 ± 2.7 | 31.7 ± 8.2* | 7.5 ± 0.9* |
| Brown adipose glucose uptake (nmol/g/min) | 2022 ± 205 | 3330 ± 263* | ND |

*$p \leq 0.05$, Student t-test,
ND, not done
Analysis of 3 month-old Esp-/- and Ocn-/- mice by hyperinsulinemic-euglycemic clamps.

TABLE 3

| | SEQ ID NO: | | |
|---|---|---|---|
| | cDNA | Amino Acid | GenBank Accession No: |
| Human Osteocalcin cDNA | 1 | 2 | NM_199173 |
| Mouse osteocalcin gene 1 | 3 | 5 | NM_007541 |
| Mouse osteocalcin gene 2 | 4 | 5 | NM_001032298 |
| Human Adiponectin | 6 | 7 | NM_004797 |
| Mouse Adiponectin | 8 | 9 | NM_009605 |
| Human Gamma-glutamyl carboxylase | 10 | 11 | NM_000821 |
| Mouse Gamma-glutamyl carboxylase | 12 | 13 | NM_019802 |
| Human ApoE | 14 | 15 | NM_000041 |
| Mouse ApoE | 16 | 17 | NM_009696 |
| Mouse Esp (OST-PTP, Ptprv) | 18 | 19 | NM_007955 |
| E. coli β-galactosidase | 20 | 21 | |
| Rat (OST-PTP, Ptprv) | 24 | 25 | NM_033099 |

REFERENCES

Berkner, K. L. (2005). The vitamin K-dependent carboxylase. Annu Rev Nutr 25, 127-149.

Brecher, G., Laqueur, G. L., Cronkite, E. P., Edelman, P. M., and Schwartz, I. L. (1965). The Brain Lesion of Goldthioglucose Obesity. J Exp Med 121, 395-401.

Cousin, W., Courseaux, A., Ladoux, A., Dani, C., and Peraldi, P. (2004). Cloning of hOST-PTP: the only example of a protein-tyrosine-phosphatase the function of which has been lost between rodent and human. Biochem Biophys Res Commun 321, 259-265.

Dacquin, R., Mee, P. J., Kawaguchi, J., Olmsted-Davis, E. A., Gallagher, J. A., Nichols, J., Lee, K., Karsenty, G., and Smith, A. (2004). Knock-in of nuclear localised beta-galactosidase reveals that the tyrosine phosphatase Ptpry is specifically expressed in cells of the bone collar. Dev Dyn 229, 826-834.

Dacquin, R., Starbuck, M., Schinke, T., and Karsenty, G. (2002). Mouse alpha1(I)-collagen promoter is the best known promoter to drive efficient Cre recombinase expression in osteoblast. Dev Dyn 224, 245-251.

Ducy, P., Amling, M., Takeda, S., Priemel, M., Schilling, A. F., Beil, F. T., Shen, J., Vinson, C., Rueger, J. M., and Karsenty, G. (2000a). Leptin inhibits bone formation through a hypothalamic relay: a central control of bone mass. Cell 100, 197-207.

Ducy, P., Desbois, C., Boyce, B., Pinero, G., Story, B., Dunstan, C., Smith, E., Bonadio, J., Goldstein, S., Gundberg, C., et al. (1996). Increased bone formation in osteocalcin-deficient mice. Nature 382, 448-452.

Ducy, P., Schinke, T., and karsenty, G. (2000b). The osteoblast: A sophisticated fibroblast under central surveillance. Science 289, 1501-1504.

Flint, A. J., Tiganis, T., Barford, D., and Tonks, N. K. (1997). Development of "substrate-trapping" mutants to identify physiological substrates of protein tyrosine phosphatases. Proc Natl Acad Sci USA 94, 1680-1685.

Friedman, J. M., and Halaas, J. L. (1998). Leptin and the regulation of body weight in mammals. Nature 395, 763-770.

Harada, S., and Rodan, G. A. (2003). Control of osteoblast function and regulation of bone mass. Nature 423, 349-355.

Hauschka, P. V., Lian, J. B., Cole, D. E., and Gundberg, C. M. (1989). Osteocalcin and matrix Gla protein: vitamin K-dependent proteins in bone. Physiol Rev 69, 990-1047.

Herman, M. A., and Kahn, B. B. (2006). Glucose transport and sensing in the maintenance of glucose homeostasis and metabolic harmony. J Clin Invest 116, 1767-1775.

Kadowaki, T., and Yamauchi, T. (2005). Adiponectin and adiponectin receptors. Endocr Rev 26, 439-451.

Karsenty, G. (2006). Convergence between bone and energy homeostases: Leptin regulation of bone mass. Cell Metab 4, 341-348.

Kasuga, M. (2006). Insulin resistance and pancreatic beta-cell failure. J Clin Invest 116, 1756-1760.

Kushner, J. A., Ciemerych, M. A., Sicinska, E., Wartschow, L. M., Teta, M., Long, S. Y., Sicinski, P., and White, M. F. (2005). Cyclins D2 and D1 are essential for postnatal pancreatic beta-cell growth. Mol Cell Biol 25, 3752-3762.

Le May, C., Chu, K., Hu, M., Ortega, C. S., Simpson, E. R., Korach, K. S., Tsai, M. J., and Mauvais-Jarvis, F. (2006). Estrogens protect pancreatic beta-cells from apoptosis and prevent insulin-deficient diabetes mellitus in mice. Proc Natl Acad Sci USA 103, 9232-9237.

Maeda, N., Shimomura, I., Kishida, K., Nishizawa, H., Matsuda, M., Nagaretani, H., Furuyama, N., Kondo, H., Takahashi, M., Arita, Y., et al. (2002). Diet-induced insulin resistance in mice lacking adiponectin/ACRP30. Nat Med 8, 731-737.

Mauro, L. J., Olmsted, E. A., Skrobacz, B. M., Mourey, R. J., Davis, A. R., and Dixon, J. E. (1994). Identification of a hormonally regulated protein tyrosine phosphatase associated with bone and testicular differentiation. J Biol Chem 269, 30659-30667.

Mauvais-Jarvis, F., Ueki, K., Fruman, D. A., Hirshman, M. F., Sakamoto, K., Goodyear, L. J., Iannacone, M., Accili, D., Cantley, L. C., and Kahn, C. R. (2002). Reduced expression of the murine p85alpha subunit of phosphoinositide 3-kinase improves insulin signaling and ameliorates diabetes. J Clin Invest 109, 141-149.

Mauvais-Jarvis, F., Virkamaki, A., Michael, M. D., Winnay, J. N., Zisman, A., Kulkarni, R. N., and Kahn, C. R. (2000). A model to explore the interaction between muscle insulin resistance and beta-cell dysfunction in the development of type 2 diabetes. Diabetes 49, 2126-2134.

Murshed, M., Schinke, T., McKee, M. D., and Karsenty, G. (2004). Extracellular matrix mineralization is regulated locally; different roles of two gla-containing proteins. J Cell Biol 165, 625-630.

Price, P. A. (1989). Gla-containing proteins of bone. Connect Tissue Res 21, 51-57; discussion 57-60.

Rosato, M. T., Schneider, S. H., and Shapses, S. A. (1998). Bone turnover and insulin-like growth factor I levels increase after improved glycemic control in noninsulin-dependent diabetes mellitus. Calcif Tissue Int 63, 107-111.

Spiegelman, B. M., and Flier, J. S. (2001). Obesity and the regulation of energy balance. Cell 104, 531-543.

Steppan, C. M., Bailey, S. T., Bhat, S., Brown, E. J., Banerjee, R. R., Wright, C. M., Patel, H. R., Ahima, R. S., and Lazar, M. A. (2001). The hormone resistin links obesity to diabetes. Nature 409, 307-312.

Takayanagi, H. (2006). Osteoimmunology: the integrated understanding of the bone and immune systems. Nat Rev Genet In press.

Takeda, S., Elefteriou, F., Levasseur, R., Liu, X., Zhao, L., Parker, K. L., Armstrong, D., Ducy, P., and Karsenty, G. (2002). Leptin regulates bone formation via the sympathetic nervous system. Cell 111, 305-317.

Teitelbaum, S. L., and Ross, F. P. (2003). Genetic regulation of osteoclast development and function. Nat Rev Genet. 4, 638-649.

Urakawa, I., Yamazaki, Y., Shimada, T., Iijima, K., Hasegawa, H., Okawa, K., Fujita, T., Fukumoto, S., and Yamashita, T. (2006). Klotho converts canonical FGF receptor into a specific receptor for FGF23. Nature.

Watanabe, M., Houten, S. M., Mataki, C., Christoffolete, M. A., Kim, B. W., Sato, H., Messaddeq, N., Harney, J. W., Ezaki, O., Kodama, T., et al. (2006). Bile acids induce energy expenditure by promoting intracellular thyroid hormone activation. Nature 439, 484-489.

Yamauchi, T., Kamon, J., Waki, H., Terauchi, Y., Kubota, N., Hara, K., Mori, Y., Ide, T., Murakami, K., Tsuboyama-Kasaoka, N., et al. (2001). The fat-derived hormone adiponectin reverses insulin resistance associated with both lipoatrophy and obesity. Nat Med 7, 941-946.

Zacchigna, L., Vecchione, C., Notte, A., Cordenonsi, M., Dupont, S., Maretto, S., Cifelli, G., Ferrari, A., Maffei, A., Fabbro, C., et al. (2006). Emilin1 links TGF-beta maturation to blood pressure homeostasis. Cell 124, 929-942.

What is claimed is:

1. A method of determining the level of complexes between an antibody that selectively binds undercarboxylated/uncarboxylated osteocalcin and undercarboxylated/uncarboxylated osteocalcin in a biological sample comprising:

(a) obtaining the biological sample from blood of a human patient suspected of being at risk for at least one condition comprising at least one of glucose intolerance, type 1 diabetes, type 2 diabetes, metabolic syndrome, atherosclerosis, or obesity;

(b) contacting the biological sample with the antibody under conditions such that the antibody forms complexes with undercarboxylated/uncarboxylated osteocalcin if osteocalcin GLU17 is uncarboxylated in the sample;

(c) determining the level of complex formed in step (b) to determine if the patient is at risk for the at least one condition; and (d) administering a pharmaceutical composition comprising undercarboxylated/uncarboxylated osteocalcin to the patient based on the determined risk in step (c).

* * * * *

UNITED STATES PATENT AND TRADEMARK OFFICE
CERTIFICATE OF CORRECTION

PATENT NO. : 9,746,463 B2
APPLICATION NO. : 14/032008
DATED : August 29, 2017
INVENTOR(S) : Gerard Karsenty and Patricia F. Ducy It is certified that error appears in the above-identified patent and that said Letters Patent is hereby corrected as shown below:

In the Specification

Please amend the second paragraph under Column 1, Line 13 with the following paragraph:

STATEMENT AS TO FEDERALLY SPONSORED RESEARCH
This invention was made with government support under Grant No. DK067936 awarded by the National Institutes of Health. The Government has certain rights in this invention.

Signed and Sealed this
Twenty-fourth Day of October, 2017

Joseph Matal
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 48

<210> SEQ ID NO 1
<211> LENGTH: 498
<212> TYPE: DNA
<213> ORGANISM: Homo sapiens
<220> FEATURE:
<221> NAME/KEY: CDS
<222> LOCATION: (19)..(318)

<400> SEQUENCE: 1
cgcagccacc gagacacc atg aga gcc ctc aca ctc ctc gcc cta ttg gcc        51
                    Met Arg Ala Leu Thr Leu Leu Ala Leu Leu Ala
                    1               5                   10 ctg gcc gca ctt tgc atc gct ggc cag gca ggt gcg aag ccc agc ggt        99
Leu Ala Ala Leu Cys Ile Ala Gly Gln Ala Gly Ala Lys Pro Ser Gly
            15                  20                  25 gca gag tcc agc aaa ggt gca gcc ttt gtg tcc aag cag gag ggc agc       147
Ala Glu Ser Ser Lys Gly Ala Ala Phe Val Ser Lys Gln Glu Gly Ser
        30                  35                  40 gag gta gtg aag aga ccc agg cgc tac ctg tat caa tgg ctg gga gcc       195
Glu Val Val Lys Arg Pro Arg Arg Tyr Leu Tyr Gln Trp Leu Gly Ala
    45                  50                  55 cca gtc ccc tac ccg gat ccc ctg gag ccc agg agg gag gtg tgt gag       243
Pro Val Pro Tyr Pro Asp Pro Leu Glu Pro Arg Arg Glu Val Cys Glu
60                  65                  70                  75 ctc aat ccg gac tgt gac gag ttg gct gac cac atc ggc ttt cag gag       291
Leu Asn Pro Asp Cys Asp Glu Leu Ala Asp His Ile Gly Phe Gln Glu
                80                  85                  90 gcc tat cgg cgc ttc tac ggc ccg gtc tagggtgtcg ctctgctggc              338
Ala Tyr Arg Arg Phe Tyr Gly Pro Val
                95                  100 ctggccggca accccagttc tgctcctctc caggcaccct tctttcctct tcccttgcc      398 cttgccctga cctccagcc ctatggatgt ggggtcccca tcatcccagc tgctcccaaa      458
taaactccag aagaggaatc tgaaaaaaaa aaaaaaaaaa                           498

<210> SEQ ID NO 2
<211> LENGTH: 100
<212> TYPE: PRT
<213> ORGANISM: Homo sapiens

<400> SEQUENCE: 2

Met Arg Ala Leu Thr Leu Leu Ala Leu Leu Ala Leu Ala Ala Leu Cys
1               5                   10                  15
```

```
Ile Ala Gly Gln Ala Gly Ala Lys Pro Ser Gly Ala Glu Ser Ser Lys
            20                  25                  30

Gly Ala Ala Phe Val Ser Lys Gln Glu Gly Ser Glu Val Val Lys Arg
                35                  40                  45

Pro Arg Arg Tyr Leu Tyr Gln Trp Leu Gly Ala Pro Val Pro Tyr Pro
        50                  55                  60

Asp Pro Leu Glu Pro Arg Arg Glu Val Cys Glu Leu Asn Pro Asp Cys
65                  70                  75                  80

Asp Glu Leu Ala Asp His Ile Gly Phe Gln Ala Tyr Arg Arg Phe
                85                  90                  95

Tyr Gly Pro Val
            100

<210> SEQ ID NO 3
<211> LENGTH: 494
<212> TYPE: DNA
<213> ORGANISM: mus musculus

<400> SEQUENCE: 3
agaacagaca agtcccacac agcagcttgg cccagaccta gcagacacca tgaggaccat      60
ctttctgctc actctgctga ccctggctgc gctctgtctc tctgacctca cagatgccaa     120
gcccagcggc cctgagtctg acaaagcctt catgtccaag caggagggca ataaggtagt     180
gaacagactc cggcgctacc ttggagcctc agtcccagc ccagatcccc tggagcccac      240
ccgggagcag tgtgagctta accctgcttg tgacgagcta tcagaccagt atggcttgaa     300
gaccgcctac aaacgcatct atggtatcac tatttaggac ctgtgctgcc ctaaagccaa     360
actctggcag ctcggctttg gctgctctcc gggacttgat cctccctgtc ctctctctct     420
gccctgcaag tatggatgtc acagcagctc caaaataaag ttcagatgag gaagtgcaaa     480
aaaaaaaaaa aaaa                                                       494

<210> SEQ ID NO 4
<211> LENGTH: 470
<212> TYPE: DNA
<213> ORGANISM: mus musculus
<220> FEATURE:
<221> NAME/KEY: CDS
<222> LOCATION: (49)..(333)

<400> SEQUENCE: 4
gaacagacaa gtcccacaca gcagcttggt gcacacctag cagacacc atg agg acc        57
                                                    Met Arg Thr
                                                     1 ctc tct ctg ctc act ctg ctg gcc ctg gct gcg ctc tgt ctc tct gac       105
Leu Ser Leu Leu Thr Leu Leu Ala Leu Ala Ala Leu Cys Leu Ser Asp
  5                  10                  15 ctc aca gat ccc aag ccc agc ggc cct gag tct gac aaa gcc ttc atg       153
Leu Thr Asp Pro Lys Pro Ser Gly Pro Glu Ser Asp Lys Ala Phe Met
 20                  25                  30                  35 tcc aag cag gag ggc aat aag gta gtg aac aga ctc cgg cgc tac ctt       201
Ser Lys Gln Glu Gly Asn Lys Val Val Asn Arg Leu Arg Arg Tyr Leu
                 40                  45                  50 gga gcc tca gtc ccc agc cca gat ccc ctg gag ccc acc cgg gag cag       249
Gly Ala Ser Val Pro Ser Pro Asp Pro Leu Glu Pro Thr Arg Glu Gln
             55                  60                  65 tgt gag ctt aac cct gct tgt gac gag cta tca gac cag tat ggc ttg       297
Cys Glu Leu Asn Pro Ala Cys Asp Glu Leu Ser Asp Gln Tyr Gly Leu
         70                  75                  80
```

```
aag acc gcc tac aaa cgc atc tac ggt atc act att taggacctgt       343
Lys Thr Ala Tyr Lys Arg Ile Tyr Gly Ile Thr Ile
 85                  90                  95 gctgccctaa agccaaactc tggcagctcg gctttggctg ctctccggga cttgatcctc  403
cctgtcctct ctctctgccc tgcaagtatg gatgtcacag cagctccaaa ataaagttca  463
gatgagg                                                           470

<210> SEQ ID NO 5
<211> LENGTH: 95
<212> TYPE: PRT
<213> ORGANISM: mus musculus

<400> SEQUENCE: 5

Met Arg Thr Leu Ser Leu Leu Thr Leu Leu Ala Leu Ala Ala Leu Cys
 1               5                  10                  15

Leu Ser Asp Leu Thr Asp Pro Lys Pro Ser Gly Pro Glu Ser Asp Lys
                20                  25                  30

Ala Phe Met Ser Lys Gln Glu Gly Asn Lys Val Val Asn Arg Leu Arg
            35                  40                  45

Arg Tyr Leu Gly Ala Ser Val Pro Ser Pro Asp Pro Leu Glu Pro Thr
50                  55                  60

Arg Glu Gln Cys Glu Leu Asn Pro Ala Cys Asp Glu Leu Ser Asp Gln
65                  70                  75                  80

Tyr Gly Leu Lys Thr Ala Tyr Lys Arg Ile Tyr Gly Ile Thr Ile
                85                  90                  95

<210> SEQ ID NO 6
<211> LENGTH: 4592
<212> TYPE: DNA
<213> ORGANISM: homo sapiens
<220> FEATURE:
<221> NAME/KEY: CDS
<222> LOCATION: (85)..(816)

<400> SEQUENCE: 6
aggctgttga ggctgggcca tctcctcctc acttccattc tgactgcagt ctgtggttct   60
gattccatac cagagggct cagg atg ctg ttg ctg gga gct gtt cta ctg       111
                         Met Leu Leu Leu Gly Ala Val Leu Leu
                          1               5 cta tta gct ctg ccc ggt cat gac cag gaa acc acg caa ggg ccc         159
Leu Leu Ala Leu Pro Gly His Asp Gln Glu Thr Thr Thr Gln Gly Pro
 10                  15                  20                  25 gga gtc ctg ctt ccc ctg ccc aag ggg gcc tgc aca ggt tgg atg gcg     207
Gly Val Leu Leu Pro Leu Pro Lys Gly Ala Cys Thr Gly Trp Met Ala
                30                  35                  40 ggc atc cca ggg cat ccg ggc cat aat ggg gcc cca ggc cgt gat ggc     255
Gly Ile Pro Gly His Pro Gly His Asn Gly Ala Pro Gly Arg Asp Gly
            45                  50                  55 aga gat ggc acc cct ggt gag aag ggt gag aaa gga gat cca ggt ctt     303
Arg Asp Gly Thr Pro Gly Glu Lys Gly Glu Lys Gly Asp Pro Gly Leu
60                  65                  70 att ggt cct aag gga gac atc ggt gaa acc gga gta ccc ggg gct gaa     351
Ile Gly Pro Lys Gly Asp Ile Gly Glu Thr Gly Val Pro Gly Ala Glu
            75                  80                  85 ggt ccc cga ggc ttt ccg gga atc caa ggc agg aaa gga gaa cct gga     399
Gly Pro Arg Gly Phe Pro Gly Ile Gln Gly Arg Lys Gly Glu Pro Gly
 90                  95                 100                 105 gaa ggt gcc tat gta tac cgc tca gca ttc agt gtg gga ttg gag act     447
Glu Gly Ala Tyr Val Tyr Arg Ser Ala Phe Ser Val Gly Leu Glu Thr
```

-continued

```
                    110                 115                 120
tac gtt act atc ccc aac atg ccc att cgc ttt acc aag atc ttc tac      495
Tyr Val Thr Ile Pro Asn Met Pro Ile Arg Phe Thr Lys Ile Phe Tyr
                125                 130                 135 aat cag caa aac cac tat gat ggc tcc act ggt aaa ttc cac tgc aac      543
Asn Gln Gln Asn His Tyr Asp Gly Ser Thr Gly Lys Phe His Cys Asn
            140                 145                 150 att cct ggg ctg tac tac ttt gcc tac cac atc aca gtc tat atg aag      591
Ile Pro Gly Leu Tyr Tyr Phe Ala Tyr His Ile Thr Val Tyr Met Lys
        155                 160                 165 gat gtg aag gtc agc ctc ttc aag aag gac aag gct atg ctc ttc acc      639
Asp Val Lys Val Ser Leu Phe Lys Lys Asp Lys Ala Met Leu Phe Thr
170                 175                 180                 185 tat gat cag tac cag gaa aat aat gtg gac cag gcc tcc ggc tct gtg      687
Tyr Asp Gln Tyr Gln Glu Asn Asn Val Asp Gln Ala Ser Gly Ser Val
                190                 195                 200 ctc ctg cat ctg gag gtg ggc gac caa gtc tgg ctc cag gtg tat ggg      735
Leu Leu His Leu Glu Val Gly Asp Gln Val Trp Leu Gln Val Tyr Gly
            205                 210                 215 gaa gga gag cgt aat gga ctc tat gct gat aat gac aat gac tcc acc      783
Glu Gly Glu Arg Asn Gly Leu Tyr Ala Asp Asn Asp Asn Asp Ser Thr
        220                 225                 230 ttc aca ggc ttt ctt ctc tac cat gac acc aac tgatcaccac taactcagag    836
Phe Thr Gly Phe Leu Leu Tyr His Asp Thr Asn
        235                 240 cctcctccag gccaaacagc cccaaagtca attaaaggct ttcagtacgg ttaggaagtt    896
gattattatt tagttggagg cctttagata ttattcattc atttactcat tcatttattc    956
attcattcat caagtaactt taaaaaaatc atatgctatg ttcccagtcc tggggagctt   1016
cacaaacatg accagataac tgactagaaa gaagtagttg acagtgctat tttgtgccca   1076
ctgtctctcc tgatgctcat atcaatccta taaggcacag gaacaagca ttctcctgtt    1136 tttacagatt gtatcctgag gctgagagag ttaagtgaat gtctaaggtc acacagtatt   1196
aagtgacagt gctagaaatc aaacccagag ctgtggactt tgttcactag actgtgccct   1256
tttatagagg tacatgttct cttttggagtg ttggtaggtg tctgtttccc acctcacctg  1316
agagccattg aatttgcctt cctcatgaat taaaacctcc cccaagcaga gcttcctcag   1376
agaaagtggt tctatgatga agtcctgtct tggaaggact actactcaat ggcccctgca   1436
ctactctact tcctcttacc tatgtccctt ctcatgcctt tccctccaac ggggaaagcc   1496
aactccatct ctaagtgctg aactcatccc tgttcctcaa ggccacctgg ccaggagctt   1556
ctctgatgtg atatccactt tttttttttt tgagatggag tctcactctg tcacccaggc   1616
tggagtacag tgcacgacc tcggctcact gcagcctcct tctcctgggt ccaagcaatt    1676
attgtgcctc agcctcccga gtagctgaga cttcaggtgc attccaccac acatggctaa   1736
tttttgtatt tttagtagaa atggggtttc gtcatgttgg ccaggctggt ctcgaactcc   1796
tggcctaggt gatccacccg cctcgacctc ccaaagtgct gggattacag gcatgagcca   1856
ccatgcccag tcgatatctc acttttttatt ttgccatgga tgagagtcct gggtgtgagg   1916
aacacctccc accaggctag aggcaactgc ccaggaagga ctgtgcttcc gtcacctcta   1976
aatcccttgc agatccttga taaatgcctc atgaagacca atctcttgaa tcccatatct   2036
acccagaatt aactccattc cagtctctgc atgtaatcag ttttatccac agaaacattt   2096
tcattttagg aaatccctgg ttttaagtat caatccttgt tcagctggac aatatgaatc   2156
ttttccactg aagttaggga tgactgtgat tttcagaaca cgtccagaat ttttcatcaa   2216
```

```
gaaggtagct tgagcctgaa atgcaaaacc catggaggaa ttctgaagcc attgtctcct    2276
tgagtaccaa cagggtcagg gaagactggg cctcctgaat ttattattgt tctttaagaa    2336
ttacaggttg aggtagttga tggtggtaaa cattctctca ggagacaata actccagtga    2396
tgttcttcaa agattttagc aaaaacagag taaatagcat tctctatcaa tatataaatt    2456
taaaaaacta tcttttttgct tacagtttta aattctgaac aattctctct tatatgtgta   2516
ttgctaatca ttaaggtatt attttttcca catataaagc tttgtctttt tgttgttgtt    2576
gttgttttta agatggagtt tccctctgtt gccaggctag agtgcagtgg catgatctcg    2636
gcttactgca acctttgcct cccaggttca agcgattctt ctgcctcagc ctcccgagta    2696
gctgggacca caggtgccta ccaccatgcc aggctaattt ttgtattttt agtaaagaca    2756
gggtttcacc atattggcca ggctggtctc gaactcctga ccttgtgatc tgcccgcctc    2816
cattttttgtt gttattttt gagaaagata gatatgaggt ttagagaggg atgaagaggt    2876
gagagtaagc cttgtgttag tcagaactct gtgttgtgaa tgtcattcac aacagaaaac    2936
ccaaaatatt atgcaaacta ctgtaagcaa gaaaaataaa ggaaaaatgg aaacatttat    2996
tcctttgcat aatagaaatt accagagttg ttctgtctttt agataaggtt tgaaccaaag    3056
ctcaaaacaa tcaagaccct tttctgtatg tccttctgtt ctgccttccg cagtgtaggc    3116
tttaccctca ggtgctacac agtatagttc tagggtttcc ctcccgatat caaaaagact    3176
gtggcctgcc cagctctcgt atccccaagc cacaccatct ggctaaatgg acatcatgtt    3236
ttctggtgat gcccaaagag gagagaggaa gctctctttc ccagatgccc cagcaagtgt    3296
aaccttgcat ctcattgctc tggctgagtt gtgtgcctgt ttctgaccaa tcactgagtc    3356
aggaggatga aatattcata ttgacttaat tgcagcttaa gttaggggta tgtagaggta    3416
ttttccctaa agcaaaattg ggacactgtt atcagaaata ggagagtgga tgatagatgc    3476
aaaataatac ctgtccacaa caaactctta atgctgtgtt tgagcttta tgagtttccc    3536
agagagacat agctggaaaa ttcctattga ttttctctaa aatttcaaca agtagctaaa    3596
gtctggctat gctcacagtc tcacatctgg ttggggtggg ctccttacag aacacgcttt    3656
cacagttacc ctaaactctc tggggcaggg ttattccttt gtggaaccag aggcacagag    3716
agagtcaact gaggccaaaa gaggcctgag agaaactgag gtcaagattt caggattaat    3776
ggtcctgtga tgctttgaag tacaattgtg gatttgtcca attctcttta gttctgtcag    3836
cttttgcttc atatatttta gcgctctatt attagatata tacatgttta gtattatgtc    3896
ttattggtgc atttactctc ttatcattat gtaatgtcct tctttatctg tgataatttt    3956
ctgtgttctg aagtctactt tgtctaaaaa taacatacgc actcaacttc cttttcttc    4016
ttccttcctt tctttcttcc ttccttctt tctctctctc tctctttcct tccttccttc    4076
ctccttttct ttctctctct ctctctctct cttttttttga cagactctcg ttctgtggcc    4136
ctggctggag ttcagtggtg tgatcttggc tcactgctac ctctaccatg agcaattctc    4196
ctgcctcagc ctcccaagta gctggaacta caggctcatg ccactgcgcc cagctaattt    4256
ttgtattttt cgtagagacg gggtttcacc acattcgtca ggttggtttc aaactcctga    4316
ctttgtgatc cacccgcctc ggcctcccaa agtgctggga ttacaggcat gagccatcac    4376
acctggtcaa ctttctttg attagtgttt ttgtggtata tcttttcca tcatgttact    4436
ttaaatatat ctatattatt gtatttaaaa tgtgtttctt acagactgca tgtagttggg    4496
tataattttt atccagtcta aaaatatctg tcttttaatt ggtgtttaga caatttatat    4556
```

```
ttaataaaat tgttgaattt aaaaaaaaaa aaaaaa                                    4592
```

<210> SEQ ID NO 7
<211> LENGTH: 244
<212> TYPE: PRT
<213> ORGANISM: homo sapiens

<400> SEQUENCE: 7

```
Met Leu Leu Leu Gly Ala Val Leu Leu Leu Ala Leu Pro Gly His
1               5                   10                  15

Asp Gln Glu Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
    35                      40                  45

His Asn Gly Ala Pro Gly Arg Asp Gly Arg Asp Gly Thr Pro Gly Glu
    50                      55                      60

Lys Gly Glu Lys Gly Asp Pro Gly Leu Ile Gly Pro Lys Gly Asp Ile
65              70                      75                  80

Gly Glu Thr Gly Val Pro Gly Ala Glu Gly Pro Arg Gly Phe Pro Gly
                    85                  90                  95

Ile Gln Gly Arg Lys Gly Glu Pro Gly Glu Gly Ala Tyr Val Tyr Arg
                100                     105                     110

Ser Ala Phe Ser Val Gly Leu Glu Thr Tyr Val Thr Ile Pro Asn Met
            115                     120                     125

Pro Ile Arg Phe Thr Lys Ile Phe Tyr Asn Gln Gln Asn His Tyr Asp
    130                     135                     140

Gly Ser Thr Gly Lys Phe His Cys Asn Ile Pro Gly Leu Tyr Tyr Phe
145                 150                     155                     160

Ala Tyr His Ile Thr Val Tyr Met Lys Asp Val Lys Val Ser Leu Phe
                165                     170                     175

Lys Lys Asp Lys Ala Met Leu Phe Thr Tyr Asp Gln Tyr Gln Glu Asn
                180                     185                     190

Asn Val Asp Gln Ala Ser Gly Ser Val Leu Leu His Leu Glu Val Gly
            195                     200                     205

Asp Gln Val Trp Leu Gln Val Tyr Gly Glu Gly Glu Arg Asn Gly Leu
        210                     215                     220

Tyr Ala Asp Asn Asp Asn Asp Ser Thr Phe Thr Gly Phe Leu Leu Tyr
225                     230                     235                     240

His Asp Thr Asn
```

<210> SEQ ID NO 8
<211> LENGTH: 1233
<212> TYPE: DNA
<213> ORGANISM: mus musculus
<220> FEATURE:
<221> NAME/KEY: CDS
<222> LOCATION: (115)..(855)

<400> SEQUENCE: 8

```
taagctgggg tctgcctgtc cccatgagta ccagactaat gagacctggc cactttctcc      60
tcatttctgt ctgtacgatt gtcagtggat ctgacgacac caaagggct cagg atg         117
                                                            Met
                                                            1 cta ctg ttg caa gct ctc ctg ttc ctc tta atc ctg ccc agt cat gcc        165
Leu Leu Leu Gln Ala Leu Leu Phe Leu Leu Ile Leu Pro Ser His Ala
        5                   10                  15 gaa gat gac gtt act aca act gaa gag cta gct cct gct ttg gtc cct        213
```

```
                Glu Asp Asp Val Thr Thr Thr Glu Leu Ala Pro Ala Leu Val Pro
                    20                  25                  30 cca ccc aag gga act tgt gca ggt tgg atg gca ggc atc cca gga cat        261
Pro Pro Lys Gly Thr Cys Ala Gly Trp Met Ala Gly Ile Pro Gly His
 35                  40                  45 cct ggc cac aat ggc aca cca ggc cgt gat ggc aga gat ggc act cct        309
Pro Gly His Asn Gly Thr Pro Gly Arg Asp Gly Arg Asp Gly Thr Pro
 50                  55                  60                  65 gga gag aag gga gag aaa gga gat gca ggt ctt ctt ggt cct aag ggt        357
Gly Glu Lys Gly Glu Lys Gly Asp Ala Gly Leu Leu Gly Pro Lys Gly
                     70                  75                  80 gag aca gga gat gtt gga atg aca gga gct gaa ggg cca cgg ggc ttc        405
Glu Thr Gly Asp Val Gly Met Thr Gly Ala Glu Gly Pro Arg Gly Phe
                 85                  90                  95 ccc gga acc cct ggc agg aaa gga gag cct gga gaa gcc gct tat gtg        453
Pro Gly Thr Pro Gly Arg Lys Gly Glu Pro Gly Glu Ala Ala Tyr Val
            100                 105                 110 tat cgc tca gcg ttc agt gtg ggg ctg gag acc cgc gtc act gtt ccc        501
Tyr Arg Ser Ala Phe Ser Val Gly Leu Glu Thr Arg Val Thr Val Pro
115                 120                 125 aat gta ccc att cgc ttt act aag atc ttc tac aac caa cag aat cat        549
Asn Val Pro Ile Arg Phe Thr Lys Ile Phe Tyr Asn Gln Gln Asn His
130                 135                 140                 145 tat gac ggc agc act ggc aag ttc tac tgc aac att ccg gga ctc tac        597
Tyr Asp Gly Ser Thr Gly Lys Phe Tyr Cys Asn Ile Pro Gly Leu Tyr
                150                 155                 160 tac ttc tct tac cac atc acg gtg tac atg aaa gat gtg aag gtg agc        645
Tyr Phe Ser Tyr His Ile Thr Val Tyr Met Lys Asp Val Lys Val Ser
            165                 170                 175 ctc ttc aag aag gac aag gcc gtt ctc ttc acc tac gac cag tat cag        693
Leu Phe Lys Lys Asp Lys Ala Val Leu Phe Thr Tyr Asp Gln Tyr Gln
        180                 185                 190 gaa aag aat gtg gac cag gcc tct ggc tct gtg ctc ctc cat ctg gag        741
Glu Lys Asn Val Asp Gln Ala Ser Gly Ser Val Leu Leu His Leu Glu
    195                 200                 205 gtg gga gac caa gtc tgg ctc cag gtg tat ggg gat ggg gac cac aat        789
Val Gly Asp Gln Val Trp Leu Gln Val Tyr Gly Asp Gly Asp His Asn
210                 215                 220                 225 gga ctc tat gca gat aac gtc aac gac tct aca ttt act ggc ttt ctt        837
Gly Leu Tyr Ala Asp Asn Val Asn Asp Ser Thr Phe Thr Gly Phe Leu
                230                 235                 240 ctc tac cat gat acc aac tgactgcaac tacccatagc ccatacacca              885
Leu Tyr His Asp Thr Asn
            245 ggagaatcat ggaacagtcg acacactttc agcttagttt gagagattga ttttattgct     945 tagtttgaga gtcctgagta ttatccacac gtgtactcac ttgttcatta aacgactta      1005 taaaaaataa tttgtgttcc tagtccagaa aaaaggcac tccctggtct ccacgactct      1065 tacatggtag caataacaga atgaaaatca catttggtat gggggcttca caatattcgc     1125 atgactgtct ggaagtagac catgctatt ttctgctcac tgtacacaaa tattgttcac      1185 ataaacccta taatgtaaat atgaaataca gtgattactc ttctcact                  1233

<210> SEQ ID NO 9
<211> LENGTH: 247
<212> TYPE: PRT
<213> ORGANISM: mus musculus

<400> SEQUENCE: 9
```

```
Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
            20                  25                  30

Pro Pro Pro Lys Gly Thr Cys Ala Gly Trp Met Ala Gly Ile Pro Gly
        35                  40                  45

His Pro Gly His Asn Gly Thr Pro Gly Arg Asp Gly Arg Asp Gly Thr
50                  55                  60

Pro Gly Glu Lys Gly Glu Lys Gly Asp Ala Gly Leu Leu Gly Pro Lys
65                  70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Tyr
            100                 105                 110

Val Tyr Arg Ser Ala Phe Ser Val Gly Leu Glu Thr Arg Val Thr Val
        115                 120                 125

Pro Asn Val Pro Ile Arg Phe Thr Lys Ile Phe Tyr Asn Gln Gln Asn
130                 135                 140

His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
            165                 170                 175

Ser Leu Phe Lys Lys Asp Lys Ala Val Leu Phe Thr Tyr Asp Gln Tyr
        180                 185                 190

Gln Glu Lys Asn Val Asp Gln Ala Ser Gly Ser Val Leu Leu His Leu
    195                 200                 205

Glu Val Gly Asp Gln Val Trp Leu Gln Val Tyr Gly Asp Gly Asp His
210                 215                 220

Asn Gly Leu Tyr Ala Asp Asn Val Asn Asp Ser Thr Phe Thr Gly Phe
225                 230                 235                 240

Leu Leu Tyr His Asp Thr Asn
                245

<210> SEQ ID NO 10
<211> LENGTH: 3236
<212> TYPE: DNA
<213> ORGANISM: homo sapiens
<220> FEATURE:
<221> NAME/KEY: CDS
<222> LOCATION: (29)..(2302)

<400> SEQUENCE: 10
gtgacccacc tgcctcctcc gcagagca atg gcg gtg tct gcc ggg tcc gcg       52
                                Met Ala Val Ser Ala Gly Ser Ala
                                1               5 cgg acc tcg ccc agc tca gat aaa gta cag aaa gac aag gct gaa ctg      100
Arg Thr Ser Pro Ser Ser Asp Lys Val Gln Lys Asp Lys Ala Glu Leu
    10                  15                  20 atc tca ggg ccc agg cag gac agc cga ata ggg aaa ctc ttg ggt ttt      148
Ile Ser Gly Pro Arg Gln Asp Ser Arg Ile Gly Lys Leu Leu Gly Phe
25                  30                  35                  40 gag tgg aca gat ttg tcc agt tgg cgg agg ctg gtg acc ctg ctg aat      196
Glu Trp Thr Asp Leu Ser Ser Trp Arg Arg Leu Val Thr Leu Leu Asn
                45                  50                  55 cga cca acg gac cct gca agc tta gct gtc ttt cgt ttt ctt ttt ggg      244
Arg Pro Thr Asp Pro Ala Ser Leu Ala Val Phe Arg Phe Leu Phe Gly
            60                  65                  70
```

| | | |
|---|---|---|
| ttc ttg atg gtg cta gac att ccc cag gag cgg ggg ctc agc tct ctg<br>Phe Leu Met Val Leu Asp Ile Pro Gln Glu Arg Gly Leu Ser Ser Leu<br>       75                    80                      85 | 292 |
| gac cgg aaa tac ctt gat ggg ctg gat gtg tgc cgc ttc ccc ttg ctg<br>Asp Arg Lys Tyr Leu Asp Gly Leu Asp Val Cys Arg Phe Pro Leu Leu<br> 90                  95                    100 | 340 |
| gat gcc cta cgc cca ctg cca ctt gac tgg atg tat ctt gtc tac acc<br>Asp Ala Leu Arg Pro Leu Pro Leu Asp Trp Met Tyr Leu Val Tyr Thr<br>105               110               115              120 | 388 |
| atc atg ttt ctg ggg gca ctg ggc atg atg ctg ggc ctg tgc tac cgg<br>Ile Met Phe Leu Gly Ala Leu Gly Met Met Leu Gly Leu Cys Tyr Arg<br>                    125               130              135 | 436 |
| ata agc tgt gtg tta ttc ctg cta cca tac tgg tat gtg ttt ctc ctg<br>Ile Ser Cys Val Leu Phe Leu Leu Pro Tyr Trp Tyr Val Phe Leu Leu<br>                    140               145              150 | 484 |
| gac aag aca tca tgg aac aac cac tcc tat ctg tat ggg ttg ttg gcc<br>Asp Lys Thr Ser Trp Asn Asn His Ser Tyr Leu Tyr Gly Leu Leu Ala<br>155               160               165 | 532 |
| ttt cag cta aca ttc atg gat gca aac cac tac tgg tct gtg gac ggt<br>Phe Gln Leu Thr Phe Met Asp Ala Asn His Tyr Trp Ser Val Asp Gly<br> 170                 175               180 | 580 |
| ctg ctg aat gcc cat agg agg aat gcc cac gtg ccc ctt tgg aac tat<br>Leu Leu Asn Ala His Arg Arg Asn Ala His Val Pro Leu Trp Asn Tyr<br>185               190               195             200 | 628 |
| gca gtg ctc cgt ggc cag atc ttc att gtg tac ttc att gcg ggt gtg<br>Ala Val Leu Arg Gly Gln Ile Phe Ile Val Tyr Phe Ile Ala Gly Val<br>                    205               210              215 | 676 |
| aaa aag ctg gat gca gac tgg gtt gaa ggc tat tcc atg gaa tat ttg<br>Lys Lys Leu Asp Ala Asp Trp Val Glu Gly Tyr Ser Met Glu Tyr Leu<br>                    220               225              230 | 724 |
| tcc cgg cac tgg ctc ttc agt ccc ttc aaa ctg ctg ttg tct gag gag<br>Ser Arg His Trp Leu Phe Ser Pro Phe Lys Leu Leu Leu Ser Glu Glu<br>                    235               240              245 | 772 |
| ctg act agc ctg ctg gtc gtg cac tgg ggt ggg ctg ctg ctt gac ctc<br>Leu Thr Ser Leu Leu Val Val His Trp Gly Gly Leu Leu Leu Asp Leu<br> 250                 255               260 | 820 |
| tca gct ggt ttc ctg ctc ttt ttt gat gtc tca aga tcc att ggc ctg<br>Ser Ala Gly Phe Leu Leu Phe Phe Asp Val Ser Arg Ser Ile Gly Leu<br>265               270               275              280 | 868 |
| ttc ttt gtg tcc tac ttc cac tgc atg aat tcc cag ctt ttc agc att<br>Phe Phe Val Ser Tyr Phe His Cys Met Asn Ser Gln Leu Phe Ser Ile<br>                    285               290              295 | 916 |
| ggt atg ttc tcc tac gtc atg ctg gcc agc agc cct ctc ttc tgc tcc<br>Gly Met Phe Ser Tyr Val Met Leu Ala Ser Ser Pro Leu Phe Cys Ser<br>                    300               305              310 | 964 |
| cct gag tgg cct cgg aag ctg gtg tcc tac tgc ccc cga agg ttg caa<br>Pro Glu Trp Pro Arg Lys Leu Val Ser Tyr Cys Pro Arg Arg Leu Gln<br>                    315               320              325 | 1012 |
| caa ctg ttg ccc ctc aag gca gcc cct cag ccc agt gtt tcc tgt gtg<br>Gln Leu Leu Pro Leu Lys Ala Ala Pro Gln Pro Ser Val Ser Cys Val<br> 330                 335               340 | 1060 |
| tat aag agg agc cgg ggc aaa agt ggc cag aag cca ggg ctg cgc cat<br>Tyr Lys Arg Ser Arg Gly Lys Ser Gly Gln Lys Pro Gly Leu Arg His<br>345               350               355              360 | 1108 |
| cag ctg gga gct gcc ttc acc ctg ctc tac ctc ctg gag cag cta ttc<br>Gln Leu Gly Ala Ala Phe Thr Leu Leu Tyr Leu Leu Glu Gln Leu Phe<br>                    365               370              375 | 1156 |
| ctg ccc tat tct cat ttt ctc acc cag ggc tat aac aac tgg aca aat<br>Leu Pro Tyr Ser His Phe Leu Thr Gln Gly Tyr Asn Asn Trp Thr Asn<br> 380                 385               390 | 1204 |

```
                                                 -continued ggg ctg tat ggc tat tcc tgg gac atg atg gtg cac tcc cgc tcc cac    1252
Gly Leu Tyr Gly Tyr Ser Trp Asp Met Met Val His Ser Arg Ser His
        395                 400                 405 cag cac gtg aag atc acc tac cgt gat ggc cgc act ggc gaa ctg ggc    1300
Gln His Val Lys Ile Thr Tyr Arg Asp Gly Arg Thr Gly Glu Leu Gly
    410                 415                 420 tac ctt aac cct ggg gta ttt aca cag agt cgg cga tgg aag gat cat    1348
Tyr Leu Asn Pro Gly Val Phe Thr Gln Ser Arg Arg Trp Lys Asp His
425                 430                 435                 440 gca gac atg ctg aag caa tat gcc act tgc ctg agc cgc ctg ctt ccc    1396
Ala Asp Met Leu Lys Gln Tyr Ala Thr Cys Leu Ser Arg Leu Leu Pro
                445                 450                 455 aag tat aat gtc act gag ccc cag atc tac ttt gat att tgg gtc tcc    1444
Lys Tyr Asn Val Thr Glu Pro Gln Ile Tyr Phe Asp Ile Trp Val Ser
            460                 465                 470 atc aat gac cgc ttc cag cag agg att ttt gac cct cgt gtg gac atc    1492
Ile Asn Asp Arg Phe Gln Gln Arg Ile Phe Asp Pro Arg Val Asp Ile
        475                 480                 485 gtg cag gcc gct tgg tca ccc ttt cag cgc aca tcc tgg gtg caa cca    1540
Val Gln Ala Ala Trp Ser Pro Phe Gln Arg Thr Ser Trp Val Gln Pro
    490                 495                 500 ctc ttg atg gac ctg tct ccc tgg agg gcc aag tta cag gaa atc aag    1588
Leu Leu Met Asp Leu Ser Pro Trp Arg Ala Lys Leu Gln Glu Ile Lys
505                 510                 515                 520 agc agc cta gac aac cac act gag gtg gtc ttc att gca gat ttc cct    1636
Ser Ser Leu Asp Asn His Thr Glu Val Val Phe Ile Ala Asp Phe Pro
                525                 530                 535 gga ctg cac ttg gag aat ttt gtg agt gaa gac ctg ggc aac act agc    1684
Gly Leu His Leu Glu Asn Phe Val Ser Glu Asp Leu Gly Asn Thr Ser
            540                 545                 550 atc cag ctg ctg cag ggg gaa gtg act gtg gag ctt gtg gca gaa cag    1732
Ile Gln Leu Leu Gln Gly Glu Val Thr Val Glu Leu Val Ala Glu Gln
        555                 560                 565 aag aac cag act ctt cga gag gga gaa aaa atg cag ttg cct gct ggt    1780
Lys Asn Gln Thr Leu Arg Glu Gly Glu Lys Met Gln Leu Pro Ala Gly
    570                 575                 580 gag tac cat aag gtg tat acg aca tca cct agc cct tct tgc tac atg    1828
Glu Tyr His Lys Val Tyr Thr Thr Ser Pro Ser Pro Ser Cys Tyr Met
585                 590                 595                 600 tac gtc tat gtc aac act aca gag ctt gca ctg gag caa gac ctg gca    1876
Tyr Val Tyr Val Asn Thr Thr Glu Leu Ala Leu Glu Gln Asp Leu Ala
                605                 610                 615 tat ctg caa gaa tta aag gaa aag gtg gag aat gga agt gaa aca ggg    1924
Tyr Leu Gln Glu Leu Lys Glu Lys Val Glu Asn Gly Ser Glu Thr Gly
            620                 625                 630 cct cta ccc cca gag ctg cag cct ctg ttg gaa ggg gaa gta aaa ggg    1972
Pro Leu Pro Pro Glu Leu Gln Pro Leu Leu Glu Gly Glu Val Lys Gly
        635                 640                 645 ggc cct gag cca aca cct ctg gtt cag acc ttt ctt aga cgc caa caa    2020
Gly Pro Glu Pro Thr Pro Leu Val Gln Thr Phe Leu Arg Arg Gln Gln
    650                 655                 660 agg ctc cag gag att gaa cgc cgg cga aat act cct ttc cat gag cga    2068
Arg Leu Gln Glu Ile Glu Arg Arg Arg Asn Thr Pro Phe His Glu Arg
665                 670                 675                 680 ttc ttc cgc ttc ttg ttg cga aag ctc tat gtc ttt cgc cgc agc ttc    2116
Phe Phe Arg Phe Leu Leu Arg Lys Leu Tyr Val Phe Arg Arg Ser Phe
                685                 690                 695 ctg atg act tgt atc tca ctt cga aat ctg ata tta ggc cgt cct tcc    2164
Leu Met Thr Cys Ile Ser Leu Arg Asn Leu Ile Leu Gly Arg Pro Ser
```

-continued

```
              700                 705                 710
ctg gag cag ctg gcc cag gag gtg act tat gca aac ttg aga ccc ttt    2212
Leu Glu Gln Leu Ala Gln Glu Val Thr Tyr Ala Asn Leu Arg Pro Phe
            715                 720                 725 gag gca gtt gga gaa ctg aat ccc tca aac acg gat tct tca cat tct    2260
Glu Ala Val Gly Glu Leu Asn Pro Ser Asn Thr Asp Ser Ser His Ser
        730                 735                 740 aat cct cct gag tca aat cct gat cct gtc cac tca gag ttc            2302
Asn Pro Pro Glu Ser Asn Pro Asp Pro Val His Ser Glu Phe
745                 750                 755 tgaaggggc cagatgttgg gtgcagatgt agaagcagcc agtcacagac ccattctatg    2362
caatggacat ttatttgaaa aaaattctca aaagtttttt tttttttttt ggggggcgg    2422 ggttctaaag ctgtttttaa ctccgagatt acaacttaga ggaaccaagg aaataaagca    2482
aataagattt aacaacccaa gattaagagg ccaggaagag gttagacgca atgtgaaact    2542
gtcctcctag gataaggttt aaagtggctt tttgggggct gggtgccgtg gctcacgcct    2602
gtaatcccag cattttggga ggctgaggtg gcagatcac ttgaggccag gagttcgaga    2662
ccagcctggc caacatggca aaacccttc tctactaaaa atacaaaaat tagccagacg    2722
tggtggtggg tgcctgtaat ccaactaccc aggaggctga ggcatgagaa tcgcttgggc    2782
ccaggaggtg gaggttgcag tgagccgaga tcgagccact gcactcctgg caacagagc    2842 aagacttcgt ctcaaaataa ataaataaag tggctcttgg ggaaaagcaa tttaatgtac    2902
cacgatgaat agctaactgt tcccaagtgt ttgctatgtg caacacaccg cgtgagcagt    2962
gttacctgca ttattacatt aggctgagag gtaaataat ttgcccgaag acatacagct    3022
agtgacgaat ggactgatgg tttgaactta acgtctattt gacttaaggt cctgcaccct    3082
gccacttgta attttcagaa tcactgataa tctgaaataa tgcagcttaa aacatgtttt    3142
cttaattaaa agtataaaaa aaaaaaaaaa aaaaaaaaa aaaaaaaaaa aaaaaaaaaa    3202
aaaaaaaaaa aaaaaaaaaa aaaaaaaaaa aaaa                             3236
```

<210> SEQ ID NO 11
<211> LENGTH: 758
<212> TYPE: PRT
<213> ORGANISM: homo sapiens

<400> SEQUENCE: 11

```
Met Ala Val Ser Ala Gly Ser Ala Arg Thr Ser Pro Ser Ser Asp Lys
1               5                   10                  15

Val Gln Lys Asp Lys Ala Glu Leu Ile Ser Gly Pro Arg Gln Asp Ser
            20                  25                  30

Arg Ile Gly Lys Leu Leu Gly Phe Glu Trp Thr Asp Leu Ser Ser Trp
        35                  40                  45

Arg Arg Leu Val Thr Leu Leu Asn Arg Pro Thr Asp Pro Ala Ser Leu
    50                  55                  60

Ala Val Phe Arg Phe Leu Phe Gly Phe Leu Met Val Leu Asp Ile Pro
65                  70                  75                  80

Gln Glu Arg Gly Leu Ser Ser Leu Asp Arg Lys Tyr Leu Asp Gly Leu
                85                  90                  95

Asp Val Cys Arg Phe Pro Leu Leu Asp Ala Leu Arg Pro Leu Pro Leu
            100                 105                 110

Asp Trp Met Tyr Leu Val Tyr Thr Ile Met Phe Leu Gly Ala Leu Gly
        115                 120                 125

Met Met Leu Gly Leu Cys Tyr Arg Ile Ser Cys Val Leu Phe Leu Leu
```

```
            130                 135                 140
Pro Tyr Trp Tyr Val Phe Leu Leu Asp Lys Thr Ser Trp Asn Asn His
145                 150                 155                 160

Ser Tyr Leu Tyr Gly Leu Leu Ala Phe Gln Leu Thr Phe Met Asp Ala
                165                 170                 175

Asn His Tyr Trp Ser Val Asp Gly Leu Leu Asn Ala His Arg Arg Asn
                180                 185                 190

Ala His Val Pro Leu Trp Asn Tyr Ala Val Leu Arg Gly Gln Ile Phe
                195                 200                 205

Ile Val Tyr Phe Ile Ala Gly Val Lys Lys Leu Asp Ala Asp Trp Val
    210                 215                 220

Glu Gly Tyr Ser Met Glu Tyr Leu Ser Arg His Trp Leu Phe Ser Pro
225                 230                 235                 240

Phe Lys Leu Leu Leu Ser Glu Glu Leu Thr Ser Leu Leu Val Val His
                245                 250                 255

Trp Gly Gly Leu Leu Leu Asp Leu Ser Ala Gly Phe Leu Leu Phe Phe
                260                 265                 270

Asp Val Ser Arg Ser Ile Gly Leu Phe Phe Val Ser Tyr Phe His Cys
                275                 280                 285

Met Asn Ser Gln Leu Phe Ser Ile Gly Met Phe Ser Tyr Val Met Leu
    290                 295                 300

Ala Ser Ser Pro Leu Phe Cys Ser Pro Glu Trp Pro Arg Lys Leu Val
305                 310                 315                 320

Ser Tyr Cys Pro Arg Arg Leu Gln Gln Leu Leu Pro Leu Lys Ala Ala
                325                 330                 335

Pro Gln Pro Ser Val Ser Cys Val Tyr Lys Arg Ser Arg Gly Lys Ser
                340                 345                 350

Gly Gln Lys Pro Gly Leu Arg His Gln Leu Gly Ala Ala Phe Thr Leu
                355                 360                 365

Leu Tyr Leu Leu Glu Gln Leu Phe Leu Pro Tyr Ser His Phe Leu Thr
    370                 375                 380

Gln Gly Tyr Asn Asn Trp Thr Asn Gly Leu Tyr Gly Tyr Ser Trp Asp
385                 390                 395                 400

Met Met Val His Ser Arg Ser His Gln His Val Lys Ile Thr Tyr Arg
                405                 410                 415

Asp Gly Arg Thr Gly Glu Leu Gly Tyr Leu Asn Pro Gly Val Phe Thr
                420                 425                 430

Gln Ser Arg Arg Trp Lys Asp His Ala Asp Met Leu Lys Gln Tyr Ala
                435                 440                 445

Thr Cys Leu Ser Arg Leu Leu Pro Lys Tyr Asn Val Thr Glu Pro Gln
    450                 455                 460

Ile Tyr Phe Asp Ile Trp Val Ser Ile Asn Asp Arg Phe Gln Gln Arg
465                 470                 475                 480

Ile Phe Asp Pro Arg Val Asp Ile Val Gln Ala Ala Trp Ser Pro Phe
                485                 490                 495

Gln Arg Thr Ser Trp Val Gln Pro Leu Leu Met Asp Leu Ser Pro Trp
                500                 505                 510

Arg Ala Lys Leu Gln Glu Ile Lys Ser Ser Leu Asp Asn His Thr Glu
                515                 520                 525

Val Val Phe Ile Ala Asp Phe Pro Gly Leu His Leu Glu Asn Phe Val
    530                 535                 540

Ser Glu Asp Leu Gly Asn Thr Ser Ile Gln Leu Leu Gln Gly Glu Val
545                 550                 555                 560
```

```
Thr Val Glu Leu Val Ala Glu Gln Lys Asn Gln Thr Leu Arg Glu Gly
                565                 570                 575

Glu Lys Met Gln Leu Pro Ala Gly Glu Tyr His Lys Val Tyr Thr Thr
            580                 585                 590

Ser Pro Ser Pro Ser Cys Tyr Met Tyr Val Tyr Val Asn Thr Thr Glu
        595                 600                 605

Leu Ala Leu Glu Gln Asp Leu Ala Tyr Leu Gln Glu Leu Lys Glu Lys
    610                 615                 620

Val Glu Asn Gly Ser Glu Thr Gly Pro Leu Pro Glu Leu Gln Pro
625                 630                 635                 640

Leu Leu Glu Gly Glu Val Lys Gly Gly Pro Glu Pro Thr Pro Leu Val
                645                 650                 655

Gln Thr Phe Leu Arg Arg Gln Arg Leu Gln Glu Ile Glu Arg Arg
                660                 665                 670

Arg Asn Thr Pro Phe His Glu Arg Phe Phe Arg Phe Leu Leu Arg Lys
    675                 680                 685

Leu Tyr Val Phe Arg Arg Ser Phe Leu Met Thr Cys Ile Ser Leu Arg
    690                 695                 700

Asn Leu Ile Leu Gly Arg Pro Ser Leu Glu Gln Leu Ala Gln Glu Val
705                 710                 715                 720

Thr Tyr Ala Asn Leu Arg Pro Phe Glu Ala Val Gly Glu Leu Asn Pro
                725                 730                 735

Ser Asn Thr Asp Ser Ser His Ser Asn Pro Pro Glu Ser Asn Pro Asp
            740                 745                 750

Pro Val His Ser Glu Phe
        755

<210> SEQ ID NO 12
<211> LENGTH: 2905
<212> TYPE: DNA
<213> ORGANISM: mus musculus
<220> FEATURE:
<221> NAME/KEY: CDS
<222> LOCATION: (75)..(2345)

<400> SEQUENCE: 12
agacagcaag tctaagtctg gaggttccac tgggtccgac ctggctgcag agaggctcac      60
ctgtccctgc agtc atg gct gtg cac cgc ggc tcc gca ctg gtt gct ccc      110
                Met Ala Val His Arg Gly Ser Ala Leu Val Ala Pro
                 1               5                  10 gcc tca gat aaa gta cag aaa aac aag tct gca cag aca tca gga ctg      158
Ala Ser Asp Lys Val Gln Lys Asn Lys Ser Ala Gln Thr Ser Gly Leu
        15                  20                  25 aaa cag ggc agc cga atg gag aaa att tta ggg ttt gaa tgg aca gat      206
Lys Gln Gly Ser Arg Met Glu Lys Ile Leu Gly Phe Glu Trp Thr Asp
 30                  35                  40 tta tct agc tgg cag agt gtc gtg acc ctg ctt aac aaa cca acg gac      254
Leu Ser Ser Trp Gln Ser Val Val Thr Leu Leu Asn Lys Pro Thr Asp
45                  50                  55                  60 cct gca aac ctg gct gtc ttt cgt ttt ctc ttt gct ttc ttg atg ctg      302
Pro Ala Asn Leu Ala Val Phe Arg Phe Leu Phe Ala Phe Leu Met Leu
                 65                  70                  75 ctg gac att ccc cag gaa cgc ggc ctt agc tcc ctg gac cga aaa tac      350
Leu Asp Ile Pro Gln Glu Arg Gly Leu Ser Ser Leu Asp Arg Lys Tyr
             80                  85                  90 ttg gat ggg ctg gat gtg tgc cgt ttc ccc ttg ctg gat gcc ttg cgc      398
Leu Asp Gly Leu Asp Val Cys Arg Phe Pro Leu Leu Asp Ala Leu Arg
```

|   |   |
|---|---|
| cca ctg cca ctg gac tgg atg tat ctt gtc tac acc atc atg ttt ctg<br>Pro Leu Pro Leu Asp Trp Met Tyr Leu Val Tyr Thr Ile Met Phe Leu<br>110                    115                    120 | 446 |
| ggg gca ctg ggc atg atg ctg ggg cta tgc tac cgg cta agc tgt gtg<br>Gly Ala Leu Gly Met Met Leu Gly Leu Cys Tyr Arg Leu Ser Cys Val<br>125                    130                    135                    140 | 494 |
| tta ttc ctg cta ccg tac tgg tac gtg ttt ctc ctg gac aag act tcg<br>Leu Phe Leu Leu Pro Tyr Trp Tyr Val Phe Leu Leu Asp Lys Thr Ser<br>                    145                    150                    155 | 542 |
| tgg aac aat cac tcc tat ctg tat ggt ttg ttg gcc ttt cag ttg aca<br>Trp Asn Asn His Ser Tyr Leu Tyr Gly Leu Leu Ala Phe Gln Leu Thr<br>              160                    165                    170 | 590 |
| ttc atg gat gca aac cac tac tgg tct gtg gat ggc ttg ctg aat gcc<br>Phe Met Asp Ala Asn His Tyr Trp Ser Val Asp Gly Leu Leu Asn Ala<br>        175                    180                    185 | 638 |
| cga aag aag aat gct cac gtg ccc ctt tgg aac tac aca gtt ctg cgt<br>Arg Lys Lys Asn Ala His Val Pro Leu Trp Asn Tyr Thr Val Leu Arg<br>190                    195                    200 | 686 |
| ggc cag atc ttc atc gtg tac ttc atc gcg ggt gtg aag aag ctc gat<br>Gly Gln Ile Phe Ile Val Tyr Phe Ile Ala Gly Val Lys Lys Leu Asp<br>205                    210                    215                    220 | 734 |
| gct gac tgg gtt ggg ggc tac tcc atg gag cac ctg tcc cgg cac tgg<br>Ala Asp Trp Val Gly Gly Tyr Ser Met Glu His Leu Ser Arg His Trp<br>                    225                    230                    235 | 782 |
| ctc ttc agt ccc ttc aag ctg gtg ttg tcg gag gag ctg aca agc ctg<br>Leu Phe Ser Pro Phe Lys Leu Val Leu Ser Glu Glu Leu Thr Ser Leu<br>              240                    245                    250 | 830 |
| ctg gta gta cac tgg tgt ggg ctt ctc ctt gac ctc tcg gct ggc ttc<br>Leu Val Val His Trp Cys Gly Leu Leu Leu Asp Leu Ser Ala Gly Phe<br>        255                    260                    265 | 878 |
| ctc ctc ttc ttt gat gcc tcc aga ccc gtc ggc ctg ttc ttc gtg tcc<br>Leu Leu Phe Phe Asp Ala Ser Arg Pro Val Gly Leu Phe Phe Val Ser<br>270                    275                    280 | 926 |
| tac ttt cac tgc atg aac tcg cag ctc ttc agc atc ggg atg ttt ccc<br>Tyr Phe His Cys Met Asn Ser Gln Leu Phe Ser Ile Gly Met Phe Pro<br>285                    290                    295                    300 | 974 |
| tat gtc atg ctg gcc agc agc cct ctc ttc tgc tca gct gaa tgg cct<br>Tyr Val Met Leu Ala Ser Ser Pro Leu Phe Cys Ser Ala Glu Trp Pro<br>                    305                    310                    315 | 1022 |
| cgg aag ttg gta gcc cga tgc ccg aaa agg ctg caa gag ctg ctg ccc<br>Arg Lys Leu Val Ala Arg Cys Pro Lys Arg Leu Gln Glu Leu Leu Pro<br>              320                    325                    330 | 1070 |
| acc aaa gcc gct cct cgg cct agt gct tcc tgt gtg tat aag agg tcc<br>Thr Lys Ala Ala Pro Arg Pro Ser Ala Ser Cys Val Tyr Lys Arg Ser<br>        335                    340                    345 | 1118 |
| cgg ggc aaa gct ggc ccg aag ccc ggg ctg cgc cac cag ctg gga gcc<br>Arg Gly Lys Ala Gly Pro Lys Pro Gly Leu Arg His Gln Leu Gly Ala<br>350                    355                    360 | 1166 |
| atc ttc acc ctg ctc tac ctc cta gag cag ctc ttc ctg ccc tat tcc<br>Ile Phe Thr Leu Leu Tyr Leu Leu Glu Gln Leu Phe Leu Pro Tyr Ser<br>365                    370                    375                    380 | 1214 |
| cac ttc ctg acc cag ggt tac aat aac tgg aca aat ggg ctg tat ggc<br>His Phe Leu Thr Gln Gly Tyr Asn Asn Trp Thr Asn Gly Leu Tyr Gly<br>                    385                    390                    395 | 1262 |
| tat tcc tgg gac atg atg gtg cac tcc cgc tcc cac cag cac gta aag<br>Tyr Ser Trp Asp Met Met Val His Ser Arg Ser His Gln His Val Lys<br>        400                    405                    410 | 1310 |
| atc acc tac cgc gac ggc ctc acg ggc gag cta ggc tac ctt aac cct | 1358 |

```
                Ile Thr Tyr Arg Asp Gly Leu Thr Gly Glu Leu Gly Tyr Leu Asn Pro
                    415                 420                 425 ggg gta ttc aca cag agc cgg cga tgg aag gat cat gca gac atg ctg          1406
Gly Val Phe Thr Gln Ser Arg Arg Trp Lys Asp His Ala Asp Met Leu
        430                 435                 440 aag caa tat gcc act tgc ctg agc ctc ctg ctt ccc aag tac aat gtc          1454
Lys Gln Tyr Ala Thr Cys Leu Ser Leu Leu Leu Pro Lys Tyr Asn Val
445                 450                 455                 460 act gag ccc cag atc tac ttt gat att tgg gtc tcc atc aat gac cgc          1502
Thr Glu Pro Gln Ile Tyr Phe Asp Ile Trp Val Ser Ile Asn Asp Arg
                    465                 470                 475 ttc cag cag agg ctt ttt gac cct cgt gtg gac atc gtg cag gct gtc          1550
Phe Gln Gln Arg Leu Phe Asp Pro Arg Val Asp Ile Val Gln Ala Val
                480                 485                 490 tgg tcc ccc ttc cag cgc aca cct tgg gtg cag cca ctc ttg atg gat          1598
Trp Ser Pro Phe Gln Arg Thr Pro Trp Val Gln Pro Leu Leu Met Asp
            495                 500                 505 tta tct ccc tgg agg acc aag tta cag gat att aag agc agt ctg gac          1646
Leu Ser Pro Trp Arg Thr Lys Leu Gln Asp Ile Lys Ser Ser Leu Asp
        510                 515                 520 aac cac acc gag gtg gtc ttc att gca gat ttc cct ggg ctt cac ttg          1694
Asn His Thr Glu Val Val Phe Ile Ala Asp Phe Pro Gly Leu His Leu
525                 530                 535                 540 gag aat ttt gtg agt gaa gac ctg ggc aac act agc atc cag ctg ctg          1742
Glu Asn Phe Val Ser Glu Asp Leu Gly Asn Thr Ser Ile Gln Leu Leu
                    545                 550                 555 cag gga gaa gtc acc gtg gaa ttg gtg gca gaa cag aaa aat cag act          1790
Gln Gly Glu Val Thr Val Glu Leu Val Ala Glu Gln Lys Asn Gln Thr
                560                 565                 570 ctt caa gaa gga gag aaa atg cag ttg cct gct gga gag tac cat aaa          1838
Leu Gln Glu Gly Glu Lys Met Gln Leu Pro Ala Gly Glu Tyr His Lys
            575                 580                 585 gtc tat act gta tca tct agt cct tcc tgc tac atg tac gtc tat gtc          1886
Val Tyr Thr Val Ser Ser Ser Pro Ser Cys Tyr Met Tyr Val Tyr Val
        590                 595                 600 aac act aca gag gtc gca ctg gag caa gac ctg gca tat ctg caa gaa          1934
Asn Thr Thr Glu Val Ala Leu Glu Gln Asp Leu Ala Tyr Leu Gln Glu
605                 610                 615                 620 tta aag gag aag gtg gag aac gga agt gaa aca ggg ccc ctg cct cca          1982
Leu Lys Glu Lys Val Glu Asn Gly Ser Glu Thr Gly Pro Leu Pro Pro
                    625                 630                 635 gaa ctt cag cct ctt ttg gaa ggg gaa gta aaa ggg ggc cct gag cca          2030
Glu Leu Gln Pro Leu Leu Glu Gly Glu Val Lys Gly Gly Pro Glu Pro
                640                 645                 650 aca cct ctg gtc caa act ttt ctc aga cga cag agg aag ctc caa gaa          2078
Thr Pro Leu Val Gln Thr Phe Leu Arg Arg Gln Arg Lys Leu Gln Glu
            655                 660                 665 att gaa cgc agg cga aat agc cct ttc cat gag cga ttt ctc cgc ttc          2126
Ile Glu Arg Arg Arg Asn Ser Pro Phe His Glu Arg Phe Leu Arg Phe
        670                 675                 680 gtg ctg cga aag ctc tac gtc ttt cga cgc agc ttc ctg atg act cga          2174
Val Leu Arg Lys Leu Tyr Val Phe Arg Arg Ser Phe Leu Met Thr Arg
685                 690                 695                 700 att tca ctc cga aac ctg cta tta ggc cgc cct tcc cta gag caa cta          2222
Ile Ser Leu Arg Asn Leu Leu Leu Gly Arg Pro Ser Leu Glu Gln Leu
                    705                 710                 715 gcc caa gag gtg aca tat gca aac ttg cga cca ttt gaa cca gtt gat          2270
Ala Gln Glu Val Thr Tyr Ala Asn Leu Arg Pro Phe Glu Pro Val Asp
                720                 725                 730
```

-continued

```
gag tca agt gct tca aac aca gat tct tca aat cac ccg tca gag cca    2318
Glu Ser Ser Ala Ser Asn Thr Asp Ser Ser Asn His Pro Ser Glu Pro
        735                 740                 745 gat tct gag cat gtt cac tct gag ttc tgagggatgt acagatgctc          2365
Asp Ser Glu His Val His Ser Glu Phe
750                 755 tgtgcagatg tgggggcagc ctgttatagg cttattgtct acgcaaagaa catattttg   2425 gagaaaaatg atatgggaca ggctttcaca gtacagccca ggctggcctc aaactcatgg  2485
ttggtccctc tgcttcagcc tgttttgtaa ttacatagta tcaccaaacc tagttgcttt  2545 tcccttaca ttttttcccc ttataagttc tttaaaatta tagcttacat ttttctttt    2605 ttctttttt ttttttgta tttttcttt gtcaagacag gtctctctct gtgtagcact     2665
ggctgtcctg gaactcactc tgtagtccag gctggcctcc aactcagaaa ttctcctgcc  2725
tctgcctccc aagtgctggg attaaaggtg tgtgccacca cgccccactg gcttttagt   2785 ttttatagac aagatttctc catgtagacc agaccagctc tcctgagtgc tgaaattaaa  2845
ggcacgggac atcactacct ggctttctta ttaaacttgt tttagtggtc tcaacaaaaa  2905
```

<210> SEQ ID NO 13
<211> LENGTH: 757
<212> TYPE: PRT
<213> ORGANISM: mus musculus

<400> SEQUENCE: 13

```
Met Ala Val His Arg Gly Ser Ala Leu Val Ala Pro Ala Ser Asp Lys
1               5                   10                  15

Val Gln Lys Asn Lys Ser Ala Gln Thr Ser Gly Leu Lys Gln Gly Ser
            20                  25                  30

Arg Met Glu Lys Ile Leu Gly Phe Glu Trp Thr Asp Leu Ser Ser Trp
        35                  40                  45

Gln Ser Val Val Thr Leu Leu Asn Lys Pro Thr Asp Pro Ala Asn Leu
    50                  55                  60

Ala Val Phe Arg Phe Leu Phe Ala Phe Leu Met Leu Leu Asp Ile Pro
65                  70                  75                  80

Gln Glu Arg Gly Leu Ser Ser Leu Asp Arg Lys Tyr Leu Asp Gly Leu
                85                  90                  95

Asp Val Cys Arg Phe Pro Leu Leu Asp Ala Leu Arg Pro Leu Pro Leu
            100                 105                 110

Asp Trp Met Tyr Leu Val Tyr Thr Ile Met Phe Leu Gly Ala Leu Gly
        115                 120                 125

Met Met Leu Gly Leu Cys Tyr Arg Leu Ser Cys Val Leu Phe Leu Leu
    130                 135                 140

Pro Tyr Trp Tyr Val Phe Leu Leu Asp Lys Thr Ser Trp Asn Asn His
145                 150                 155                 160

Ser Tyr Leu Tyr Gly Leu Leu Ala Phe Gln Leu Thr Phe Met Asp Ala
                165                 170                 175

Asn His Tyr Trp Ser Val Asp Gly Leu Leu Asn Ala Arg Lys Lys Asn
            180                 185                 190

Ala His Val Pro Leu Trp Asn Tyr Thr Val Leu Arg Gly Gln Ile Phe
        195                 200                 205

Ile Val Tyr Phe Ile Ala Gly Val Lys Lys Leu Asp Ala Asp Trp Val
    210                 215                 220

Gly Gly Tyr Ser Met Glu His Leu Ser Arg His Trp Leu Phe Ser Pro
225                 230                 235                 240
```

```
Phe Lys Leu Val Leu Ser Glu Glu Leu Thr Ser Leu Leu Val Val His
                245                 250                 255

Trp Cys Gly Leu Leu Leu Asp Leu Ser Ala Gly Phe Leu Leu Phe Phe
            260                 265                 270

Asp Ala Ser Arg Pro Val Gly Leu Phe Phe Val Ser Tyr Phe His Cys
        275                 280                 285

Met Asn Ser Gln Leu Phe Ser Ile Gly Met Phe Pro Tyr Val Met Leu
    290                 295                 300

Ala Ser Ser Pro Leu Phe Cys Ser Ala Glu Trp Pro Arg Lys Leu Val
305                 310                 315                 320

Ala Arg Cys Pro Lys Arg Leu Gln Glu Leu Leu Pro Thr Lys Ala Ala
                325                 330                 335

Pro Arg Pro Ser Ala Ser Cys Val Tyr Lys Arg Ser Arg Gly Lys Ala
            340                 345                 350

Gly Pro Lys Pro Gly Leu Arg His Gln Leu Gly Ala Ile Phe Thr Leu
        355                 360                 365

Leu Tyr Leu Leu Glu Gln Leu Phe Leu Pro Tyr Ser His Phe Leu Thr
    370                 375                 380

Gln Gly Tyr Asn Asn Trp Thr Asn Gly Leu Tyr Gly Tyr Ser Trp Asp
385                 390                 395                 400

Met Met Val His Ser Arg Ser His Gln His Val Lys Ile Thr Tyr Arg
                405                 410                 415

Asp Gly Leu Thr Gly Glu Leu Gly Tyr Leu Asn Pro Gly Val Phe Thr
            420                 425                 430

Gln Ser Arg Arg Trp Lys Asp His Ala Asp Met Leu Lys Gln Tyr Ala
        435                 440                 445

Thr Cys Leu Ser Leu Leu Pro Lys Tyr Asn Val Thr Glu Pro Gln
    450                 455                 460

Ile Tyr Phe Asp Ile Trp Val Ser Ile Asn Asp Arg Phe Gln Gln Arg
465                 470                 475                 480

Leu Phe Asp Pro Arg Val Asp Ile Val Gln Ala Val Trp Ser Pro Phe
                485                 490                 495

Gln Arg Thr Pro Trp Val Gln Pro Leu Leu Met Asp Leu Ser Pro Trp
            500                 505                 510

Arg Thr Lys Leu Gln Asp Ile Lys Ser Ser Leu Asp Asn His Thr Glu
        515                 520                 525

Val Val Phe Ile Ala Asp Phe Pro Gly Leu His Leu Glu Asn Phe Val
530                 535                 540

Ser Glu Asp Leu Gly Asn Thr Ser Ile Gln Leu Leu Gln Gly Glu Val
545                 550                 555                 560

Thr Val Glu Leu Val Ala Glu Gln Lys Asn Gln Thr Leu Gln Glu Gly
                565                 570                 575

Glu Lys Met Gln Leu Pro Ala Gly Glu Tyr His Lys Val Tyr Thr Val
            580                 585                 590

Ser Ser Ser Pro Ser Cys Tyr Met Tyr Val Tyr Val Asn Thr Thr Glu
        595                 600                 605

Val Ala Leu Glu Gln Asp Leu Ala Tyr Leu Gln Glu Leu Lys Glu Lys
    610                 615                 620

Val Glu Asn Gly Ser Glu Thr Gly Pro Leu Pro Glu Leu Gln Pro
625                 630                 635                 640

Leu Leu Glu Gly Glu Val Lys Gly Gly Pro Glu Pro Thr Pro Leu Val
                645                 650                 655

Gln Thr Phe Leu Arg Arg Gln Arg Lys Leu Gln Glu Ile Glu Arg Arg
```

```
                  660                 665                 670
Arg Asn Ser Pro Phe His Glu Arg Phe Leu Arg Phe Val Leu Arg Lys
                675                 680                 685

Leu Tyr Val Phe Arg Arg Ser Phe Leu Met Thr Arg Ile Ser Leu Arg
            690                 695                 700

Asn Leu Leu Leu Gly Arg Pro Ser Leu Glu Gln Leu Ala Gln Glu Val
705                 710                 715                 720

Thr Tyr Ala Asn Leu Arg Pro Phe Glu Pro Val Asp Glu Ser Ser Ala
                725                 730                 735

Ser Asn Thr Asp Ser Ser Asn His Pro Ser Glu Pro Asp Ser Glu His
            740                 745                 750

Val His Ser Glu Phe
            755

<210> SEQ ID NO 14
<211> LENGTH: 1223
<212> TYPE: DNA
<213> ORGANISM: homo sapiens
<220> FEATURE:
<221> NAME/KEY: CDS
<222> LOCATION: (84)..(1034)

<400> SEQUENCE: 14
gggatccttg agtcctactc agccccagcg gaggtgaagg acgtccttcc ccaggagccg      60
actggccaat cacaggcagg aag atg aag gtt ctg tgg gct gcg ttg ctg gtc    113
                        Met Lys Val Leu Trp Ala Ala Leu Leu Val
                          1               5                  10 aca ttc ctg gca gga tgc cag gcc aag gtg gag caa gcg gtg gag aca      161
Thr Phe Leu Ala Gly Cys Gln Ala Lys Val Glu Gln Ala Val Glu Thr
                 15                  20                  25 gag ccg gag ccc gag ctg cgc cag cag acc gag tgg cag agc ggc cag      209
Glu Pro Glu Pro Glu Leu Arg Gln Gln Thr Glu Trp Gln Ser Gly Gln
             30                  35                  40 cgc tgg gaa ctg gca ctg ggt cgc ttt tgg gat tac ctg cgc tgg gtg      257
Arg Trp Glu Leu Ala Leu Gly Arg Phe Trp Asp Tyr Leu Arg Trp Val
         45                  50                  55 cag aca ctg tct gag cag gtg cag gag gag ctg ctc agc tcc cag gtc      305
Gln Thr Leu Ser Glu Gln Val Gln Glu Glu Leu Leu Ser Ser Gln Val
 60                  65                  70 acc cag gaa ctg agg gcg ctg atg gac gag acc atg aag gag ttg aag      353
Thr Gln Glu Leu Arg Ala Leu Met Asp Glu Thr Met Lys Glu Leu Lys
 75                  80                  85                  90 gcc tac aaa tcg gaa ctg gag gaa caa ctg acc ccg gtg gcg gag gag      401
Ala Tyr Lys Ser Glu Leu Glu Glu Gln Leu Thr Pro Val Ala Glu Glu
                 95                 100                 105 acg cgg gca cgg ctg tcc aag gag ctg cag gcg gcg cag gcc cgg ctg      449
Thr Arg Ala Arg Leu Ser Lys Glu Leu Gln Ala Ala Gln Ala Arg Leu
             110                 115                 120 ggc gcg gac atg gag gac gtg tgc ggc cgc ctg gtg cag tac cgc ggc      497
Gly Ala Asp Met Glu Asp Val Cys Gly Arg Leu Val Gln Tyr Arg Gly
         125                 130                 135 gag gtg cag gcc atg ctc ggc cag agc acc gag gag ctg cgg gtg cgc      545
Glu Val Gln Ala Met Leu Gly Gln Ser Thr Glu Glu Leu Arg Val Arg
 140                 145                 150 ctc gcc tcc cac ctg cgc aag ctg cgt aag cgg ctc ctc cgc gat gcc      593
Leu Ala Ser His Leu Arg Lys Leu Arg Lys Arg Leu Leu Arg Asp Ala
155                 160                 165                 170 gat gac ctg cag aag cgc ctg gca gtg tac cag gcc ggg gcc cgc gag      641
Asp Asp Leu Gln Lys Arg Leu Ala Val Tyr Gln Ala Gly Ala Arg Glu
```

```
                    175                 180                 185
ggc gcc gag cgc ggc ctc agc gcc atc cgc gag cgc ctg ggg ccc ctg         689
Gly Ala Glu Arg Gly Leu Ser Ala Ile Arg Glu Arg Leu Gly Pro Leu
            190                 195                 200 gtg gaa cag ggc cgc gtg cgg gcc gcc act gtg ggc tcc ctg gcc ggc         737
Val Glu Gln Gly Arg Val Arg Ala Ala Thr Val Gly Ser Leu Ala Gly
            205                 210                 215 cag ccg cta cag gag cgg gcc cag gcc tgg ggc gag cgg ctg cgc gcg         785
Gln Pro Leu Gln Glu Arg Ala Gln Ala Trp Gly Glu Arg Leu Arg Ala
    220                 225                 230 cgg atg gag gag atg ggc agc cgg acc cgc gac cgc ctg gac gag gtg         833
Arg Met Glu Glu Met Gly Ser Arg Thr Arg Asp Arg Leu Asp Glu Val
235                 240                 245                 250 aag gag cag gtg gcg gag gtg cgc gcc aag ctg gag gag cag gcc cag         881
Lys Glu Gln Val Ala Glu Val Arg Ala Lys Leu Glu Glu Gln Ala Gln
                255                 260                 265 cag ata cgc ctg cag gcc gag gcc ttc cag gcc cgc ctc aag agc tgg         929
Gln Ile Arg Leu Gln Ala Glu Ala Phe Gln Ala Arg Leu Lys Ser Trp
            270                 275                 280 ttc gag ccc ctg gtg gaa gac atg cag cgc cag tgg gcc ggg ctg gtg         977
Phe Glu Pro Leu Val Glu Asp Met Gln Arg Gln Trp Ala Gly Leu Val
            285                 290                 295 gag aag gtg cag gct gcc gtg ggc acc agc gcc gcc cct gtg ccc agc        1025
Glu Lys Val Gln Ala Ala Val Gly Thr Ser Ala Ala Pro Val Pro Ser
    300                 305                 310 gac aat cac tgaacgccga agcctgcagc catgcgaccc cacgccaccc               1074
Asp Asn His
315 cgtgcctcct gcctccgcgc agcctgcagc gggagaccct gtccccgccc cagccgtcct     1134 cctggggtgg accctagttt aataaagatt caccaagttt cacgcaaaaa aaaaaaaaaa     1194 aaaaaaaaaa aaaaaaaaaa aaaaaaaa                                        1223

<210> SEQ ID NO 15
<211> LENGTH: 317
<212> TYPE: PRT
<213> ORGANISM: homo sapiens

<400> SEQUENCE: 15

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140
```

```
Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Leu Gln Lys Arg
            165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
290                 295                 300

Val Gly Thr Ser Ala Ala Pro Val Pro Ser Asp Asn His
305                 310                 315

<210> SEQ ID NO 16
<211> LENGTH: 1104
<212> TYPE: DNA
<213> ORGANISM: mus musculus
<220> FEATURE:
<221> NAME/KEY: CDS
<222> LOCATION: (46)..(978)

<400> SEQUENCE: 16
ggacttgttt cggaaggagc tgactggcca atcacaattg cgaag atg aag gct ctg    57
                                               Met Lys Ala Leu
                                                 1 tgg gcc gtg ctg ttg gtc aca ttg ctg aca gga tgc cta gcc gag gga   105
Trp Ala Val Leu Leu Val Thr Leu Leu Thr Gly Cys Leu Ala Glu Gly
  5              10                  15                  20 gag ccg gag gtg aca gat cag ctc gag tgg caa agc aac caa ccc tgg   153
Glu Pro Glu Val Thr Asp Gln Leu Glu Trp Gln Ser Asn Gln Pro Trp
                25                  30                  35 gag cag gcc ctg aac cgc ttc tgg gat tac ctg cgc tgg gtg cag acg   201
Glu Gln Ala Leu Asn Arg Phe Trp Asp Tyr Leu Arg Trp Val Gln Thr
            40                  45                  50 ctg tct gac cag gtc cag gaa gag ctg cag agc tcc caa gtc aca caa   249
Leu Ser Asp Gln Val Gln Glu Glu Leu Gln Ser Ser Gln Val Thr Gln
        55                  60                  65 gaa ctg acg gca ctg atg gag gac act atg acg gaa gta aag gct tac   297
Glu Leu Thr Ala Leu Met Glu Asp Thr Met Thr Glu Val Lys Ala Tyr
    70                  75                  80 aaa aag gag ctg gag gaa cag ctg ggt cca gtg gcg gag gag aca cgg   345
Lys Lys Glu Leu Glu Glu Gln Leu Gly Pro Val Ala Glu Glu Thr Arg
85                  90                  95                 100 gcc agg ctg ggc aaa gag gtg cag gcg gca cag gcc cga ctc gga gcc   393
Ala Arg Leu Gly Lys Glu Val Gln Ala Ala Gln Ala Arg Leu Gly Ala
                105                 110                 115 gac atg gag gat cta cgc aac cga ctc ggg cag tac cgc aac gag gtg   441
Asp Met Glu Asp Leu Arg Asn Arg Leu Gly Gln Tyr Arg Asn Glu Val
            120                 125                 130
```

```
cac acc atg ctg ggc cag agc aca gag gag ata cgg gcg cgg ctc tcc       489
His Thr Met Leu Gly Gln Ser Thr Glu Glu Ile Arg Ala Arg Leu Ser
        135                 140                 145 aca cac ctg cgc aag atg cgc aag cgc ttg atg cgg gat gcc gat gat       537
Thr His Leu Arg Lys Met Arg Lys Arg Leu Met Arg Asp Ala Asp Asp
    150                 155                 160 ctg cag aag cgc cta gct gtg tac aag gca ggg gca cgc gag ggc gcc       585
Leu Gln Lys Arg Leu Ala Val Tyr Lys Ala Gly Ala Arg Glu Gly Ala
165                 170                 175                 180 gag cgc ggt gtg agt gcc atc cgt gag cgc ctg ggg cct ctg gtg gag       633
Glu Arg Gly Val Ser Ala Ile Arg Glu Arg Leu Gly Pro Leu Val Glu
                185                 190                 195 caa ggt cgc cag cgc act gcc aac cta ggc gct ggg gcc gcc cag cct       681
Gln Gly Arg Gln Arg Thr Ala Asn Leu Gly Ala Gly Ala Ala Gln Pro
            200                 205                 210 ctg cgc gat cgc gcc cag gct ttt ggt gac cgc atc cga ggg cgg ctg       729
Leu Arg Asp Arg Ala Gln Ala Phe Gly Asp Arg Ile Arg Gly Arg Leu
        215                 220                 225 gag gaa gtg ggc aac cag gcc cgt gac cgc cta gag gag gtg cgt gag       777
Glu Glu Val Gly Asn Gln Ala Arg Asp Arg Leu Glu Glu Val Arg Glu
    230                 235                 240 cac atg gag gag gtg cgc tcc aag atg gag gaa cag acc cag caa ata       825
His Met Glu Glu Val Arg Ser Lys Met Glu Glu Gln Thr Gln Gln Ile
245                 250                 255                 260 cgc ctg cag gcg gag atc ttc cag gcc cgc ctc aag ggc tgg ttc gag       873
Arg Leu Gln Ala Glu Ile Phe Gln Ala Arg Leu Lys Gly Trp Phe Glu
                265                 270                 275 cca ata gtg gaa gac atg cat cgc cag tgg gca aac ctg atg gag aag       921
Pro Ile Val Glu Asp Met His Arg Gln Trp Ala Asn Leu Met Glu Lys
            280                 285                 290 ata cag gcc tct gtg gct acc aac ccc atc atc acc cca gtg gcc cag       969
Ile Gln Ala Ser Val Ala Thr Asn Pro Ile Ile Thr Pro Val Ala Gln
        295                 300                 305 gag aat caa tgagtatcct tctcctgtcc tgcaacaaca tccatatcca              1018
Glu Asn Gln
    310 gccaggtggc cctgtctcaa gcacctctct ggccctctgg tggcccttgc ttaataaaga    1078 ttctccgagc aaaaaaaaaa aaaaaa                                         1104

<210> SEQ ID NO 17
<211> LENGTH: 311
<212> TYPE: PRT
<213> ORGANISM: mus musculus

<400> SEQUENCE: 17

Met Lys Ala Leu Trp Ala Val Leu Leu Val Thr Leu Leu Thr Gly Cys
1               5                   10                  15

Leu Ala Glu Gly Glu Pro Glu Val Thr Asp Gln Leu Glu Trp Gln Ser
            20                  25                  30

Asn Gln Pro Trp Glu Gln Ala Leu Asn Arg Phe Trp Asp Tyr Leu Arg
        35                  40                  45

Trp Val Gln Thr Leu Ser Asp Gln Val Gln Glu Glu Leu Gln Ser Ser
    50                  55                  60

Gln Val Thr Gln Glu Leu Thr Ala Leu Met Glu Asp Thr Met Thr Glu
65                  70                  75                  80

Val Lys Ala Tyr Lys Lys Glu Leu Glu Glu Gln Leu Gly Pro Val Ala
                85                  90                  95
```

```
Glu Glu Thr Arg Ala Arg Leu Gly Lys Val Gln Ala Ala Gln Ala
            100                 105                 110

Arg Leu Gly Ala Asp Met Glu Asp Leu Arg Asn Arg Leu Gly Gln Tyr
        115                 120                 125

Arg Asn Glu Val His Thr Met Leu Gly Gln Ser Thr Glu Glu Ile Arg
130                 135                 140

Ala Arg Leu Ser Thr His Leu Arg Lys Met Arg Lys Arg Leu Met Arg
145                 150                 155                 160

Asp Ala Asp Asp Leu Gln Lys Arg Leu Ala Val Tyr Lys Ala Gly Ala
                165                 170                 175

Arg Glu Gly Ala Glu Arg Gly Val Ser Ala Ile Arg Glu Arg Leu Gly
            180                 185                 190

Pro Leu Val Glu Gln Gly Arg Gln Arg Thr Ala Asn Leu Gly Ala Gly
        195                 200                 205

Ala Ala Gln Pro Leu Arg Asp Arg Ala Gln Ala Phe Gly Asp Arg Ile
    210                 215                 220

Arg Gly Arg Leu Glu Glu Val Gly Asn Gln Ala Arg Asp Arg Leu Glu
225                 230                 235                 240

Glu Val Arg Glu His Met Glu Glu Val Arg Ser Lys Met Glu Glu Gln
                245                 250                 255

Thr Gln Gln Ile Arg Leu Gln Ala Glu Ile Phe Gln Ala Arg Leu Lys
            260                 265                 270

Gly Trp Phe Glu Pro Ile Val Glu Asp Met His Arg Gln Trp Ala Asn
        275                 280                 285

Leu Met Glu Lys Ile Gln Ala Ser Val Ala Thr Asn Pro Ile Ile Thr
    290                 295                 300

Pro Val Ala Gln Glu Asn Gln
305                 310

<210> SEQ ID NO 18
<211> LENGTH: 5555
<212> TYPE: DNA
<213> ORGANISM: mus musculus
<220> FEATURE:
<221> NAME/KEY: CDS
<222> LOCATION: (316)..(5430)

<400> SEQUENCE: 18
ggctgtggga gagcagaaga ggagctggaa gagcagccta caacagctgt cgggagggac      60
cagggctagt tcacacttgg aagctgggat gccaggaccg gccctcctgc ctctctcggt     120
ctccatcggc ctcctggtca gctcactcca cactgagacg attctgaagt aagatgctcc     180
tggctcctca cagactctgc tacaagagac agagtgaagt gtccccaggg ctcagagcct     240
ttgactctgc tccttccctt cccacggctg agttggcaca ggagcacctg ggtgagctgc     300
accagactta agaag atg agg ccc ctg att ctg tta gct gcc ctc ctc tgg     351
                Met Arg Pro Leu Ile Leu Leu Ala Ala Leu Leu Trp
                1               5                   10 ctc cag gac tct ttg gcc cag gaa gat gta tgc tca tcc ttg gat ggg     399
Leu Gln Asp Ser Leu Ala Gln Glu Asp Val Cys Ser Ser Leu Asp Gly
        15                  20                  25 agc cca gac agg cag ggt gga ggt cca cct ctg agt gtg aac gtc agc     447
Ser Pro Asp Arg Gln Gly Gly Gly Pro Pro Leu Ser Val Asn Val Ser
    30                  35                  40 agc cgc gga aag cct acc agc ctg ttt ctg agc tgg gta gct gca gag     495
Ser Arg Gly Lys Pro Thr Ser Leu Phe Leu Ser Trp Val Ala Ala Glu
45                  50                  55                  60
```

-continued

| | | |
|---|---|---|
| cca ggt gga ttt gac tat gcc ctc tgc ctc agg gct atg aac ttg tcg<br>Pro Gly Gly Phe Asp Tyr Ala Leu Cys Leu Arg Ala Met Asn Leu Ser<br>65 70 75 | | 543 |
| ggt ttt cca gaa ggg caa cag ctc caa gct cat acc aac gag tcc agc<br>Gly Phe Pro Glu Gly Gln Gln Leu Gln Ala His Thr Asn Glu Ser Ser<br>80 85 90 | | 591 |
| ttt gag ttc cat ggc ctg gtg cca ggg agt cgc tac cag ctg gaa ctg<br>Phe Glu Phe His Gly Leu Val Pro Gly Ser Arg Tyr Gln Leu Glu Leu<br>95 100 105 | | 639 |
| act gtc cta aga ccc tgt tgg cag aat gtc aca att acc ctc act gct<br>Thr Val Leu Arg Pro Cys Trp Gln Asn Val Thr Ile Thr Leu Thr Ala<br>110 115 120 | | 687 |
| cga act gcc cct aca gtg gtc cgt gga ctg caa ctg cat agc act ggg<br>Arg Thr Ala Pro Thr Val Val Arg Gly Leu Gln Leu His Ser Thr Gly<br>125 130 135 140 | | 735 |
| agc cca gcc agc ctg gaa gcc tca tgg agc gat gcc tct ggg gat caa<br>Ser Pro Ala Ser Leu Glu Ala Ser Trp Ser Asp Ala Ser Gly Asp Gln<br>145 150 155 | | 783 |
| gac agc tat caa ctt ctc ctc tac cac ccg gaa tcc cac act ctg gca<br>Asp Ser Tyr Gln Leu Leu Leu Tyr His Pro Glu Ser His Thr Leu Ala<br>160 165 170 | | 831 |
| tgt aat gtc tct gtg tcc cct gac acc ctg tct tac aat ttt ggt gac<br>Cys Asn Val Ser Val Ser Pro Asp Thr Leu Ser Tyr Asn Phe Gly Asp<br>175 180 185 | | 879 |
| ctc ttg cca ggt agt cag tat gtc ttg gag gtt atc acc tgg gct ggc<br>Leu Leu Pro Gly Ser Gln Tyr Val Leu Glu Val Ile Thr Trp Ala Gly<br>190 195 200 | | 927 |
| agt ctc cat gcg aag act agc atc ctc caa tgg aca gag cct gtc cct<br>Ser Leu His Ala Lys Thr Ser Ile Leu Gln Trp Thr Glu Pro Val Pro<br>205 210 215 220 | | 975 |
| cct gat cac cta aca ctg cgt gcc ttg ggt acc agt agc ctg caa gcc<br>Pro Asp His Leu Thr Leu Arg Ala Leu Gly Thr Ser Ser Leu Gln Ala<br>225 230 235 | | 1023 |
| ttc tgg aac agc tct gaa ggg gcc acc tgg ttt cac ctg ata ctt aca<br>Phe Trp Asn Ser Ser Glu Gly Ala Thr Trp Phe His Leu Ile Leu Thr<br>240 245 250 | | 1071 |
| gac ctc cta gag ggt acc aac ctg acc aaa gtg gtc aga caa ggc atc<br>Asp Leu Leu Glu Gly Thr Asn Leu Thr Lys Val Val Arg Gln Gly Ile<br>255 260 265 | | 1119 |
| tca acc cac acc ttc ctt cgc ctg tct ccg ggt aca cct tac cag ctg<br>Ser Thr His Thr Phe Leu Arg Leu Ser Pro Gly Thr Pro Tyr Gln Leu<br>270 275 280 | | 1167 |
| aag atc tgt gct gct gct ggg ccc cac cag att tgg gga ccc aat gcc<br>Lys Ile Cys Ala Ala Ala Gly Pro His Gln Ile Trp Gly Pro Asn Ala<br>285 290 295 300 | | 1215 |
| act gag tgg acc tat ccc tct tac cca tct gac ctg gtg ctg acc ccc<br>Thr Glu Trp Thr Tyr Pro Ser Tyr Pro Ser Asp Leu Val Leu Thr Pro<br>305 310 315 | | 1263 |
| tta tgg aat gag ctc tgg gca agc tgg aag gca ggg cag gga gcc cgg<br>Leu Trp Asn Glu Leu Trp Ala Ser Trp Lys Ala Gly Gln Gly Ala Arg<br>320 325 330 | | 1311 |
| gat ggc tat gta ctg aag tta agt ggg cca gtg gag aat aca act act<br>Asp Gly Tyr Val Leu Lys Leu Ser Gly Pro Val Glu Asn Thr Thr Thr<br>335 340 345 | | 1359 |
| ctg ggt cct gag gag tgc aac gct gtc ttc cca ggg ccc ctg cct cca<br>Leu Gly Pro Glu Glu Cys Asn Ala Val Phe Pro Gly Pro Leu Pro Pro<br>350 355 360 | | 1407 |
| gga cac tac act ttg ggg ctg agg gtt cta gct gga cct tat gat gcc<br>Gly His Tyr Thr Leu Gly Leu Arg Val Leu Ala Gly Pro Tyr Asp Ala<br>365 370 375 380 | | 1455 |

```
tgg gta gag ggc agt atc tgg ctg gct gaa tct gct gct cgt ccc atg      1503
Trp Val Glu Gly Ser Ile Trp Leu Ala Glu Ser Ala Ala Arg Pro Met
                385                 390                 395 gag gtc cct ggt gcc aga ctg tgg cta gaa gga ctg gaa gct act aag      1551
Glu Val Pro Gly Ala Arg Leu Trp Leu Glu Gly Leu Glu Ala Thr Lys
            400                 405                 410 caa cct ggg aga cgg gcg ctg ctc tat tct gtt gat gcc cca ggc ctc      1599
Gln Pro Gly Arg Arg Ala Leu Leu Tyr Ser Val Asp Ala Pro Gly Leu
        415                 420                 425 cta ggg aac atc tct gtg tct tct ggt gcc act cat gtc acc ttc tgt      1647
Leu Gly Asn Ile Ser Val Ser Ser Gly Ala Thr His Val Thr Phe Cys
    430                 435                 440 ggc ttg gta ccc gga gcg cac tac agg gtg gac att gcc tca tcc atg      1695
Gly Leu Val Pro Gly Ala His Tyr Arg Val Asp Ile Ala Ser Ser Met
445                 450                 455                 460 gga gac atc act cag agc ctc aca ggc tac aca agt ccc ctg cca cca      1743
Gly Asp Ile Thr Gln Ser Leu Thr Gly Tyr Thr Ser Pro Leu Pro Pro
                465                 470                 475 cag tct ctg gag atc atc agc cgg aac agc cca tct gac ctg act atc      1791
Gln Ser Leu Glu Ile Ile Ser Arg Asn Ser Pro Ser Asp Leu Thr Ile
            480                 485                 490 ggt tgg gct cca gca cca ggg cag atg gaa ggt tat aag gtc acc tgg      1839
Gly Trp Ala Pro Ala Pro Gly Gln Met Glu Gly Tyr Lys Val Thr Trp
        495                 500                 505 cat cag gat ggc agc cag agg tca cct ggc gac ctt gtt gac ttg ggc      1887
His Gln Asp Gly Ser Gln Arg Ser Pro Gly Asp Leu Val Asp Leu Gly
    510                 515                 520 cct gac att tcg agc ctg act ctg aaa tct ctg gta cct ggt tcc tgc      1935
Pro Asp Ile Ser Ser Leu Thr Leu Lys Ser Leu Val Pro Gly Ser Cys
525                 530                 535                 540 tac acc gtg tca gca tgg gcc tgg tct ggg aac ctc agc tct gac tct      1983
Tyr Thr Val Ser Ala Trp Ala Trp Ser Gly Asn Leu Ser Ser Asp Ser
                545                 550                 555 cag aag att cac agt tgc acc cgt ccc gct cct ccc acc aac ctg agc      2031
Gln Lys Ile His Ser Cys Thr Arg Pro Ala Pro Pro Thr Asn Leu Ser
            560                 565                 570 ctg ggc ttt gcc cac cag cct gca aca ctg agg gct tcc tgg tgt cac      2079
Leu Gly Phe Ala His Gln Pro Ala Thr Leu Arg Ala Ser Trp Cys His
        575                 580                 585 cca ccg ggt ggc agg gat gcc ttt cag tta cgg ctt tac agg ctg agg      2127
Pro Pro Gly Gly Arg Asp Ala Phe Gln Leu Arg Leu Tyr Arg Leu Arg
    590                 595                 600 ccc ctg aca ctg gaa agt gag aag atc cta tcc cag gag gcc cag aac      2175
Pro Leu Thr Leu Glu Ser Glu Lys Ile Leu Ser Gln Glu Ala Gln Asn
605                 610                 615                 620 ttc tcc tgg gcc cag ctg cct gca ggc tat gaa ttc cag gta cag ctg      2223
Phe Ser Trp Ala Gln Leu Pro Ala Gly Tyr Glu Phe Gln Val Gln Leu
                625                 630                 635 tct acc ttg tgg ggg tcg gag gag agc ggc agt gcc aac acc aca ggc      2271
Ser Thr Leu Trp Gly Ser Glu Glu Ser Gly Ser Ala Asn Thr Thr Gly
            640                 645                 650 tgg aca ccc ccc tca gct cct aca ttg gta aat gtg acc agt gaa gcc      2319
Trp Thr Pro Pro Ser Ala Pro Thr Leu Val Asn Val Thr Ser Glu Ala
        655                 660                 665 ccc acc cag ctc cac gta tcc tgg gtc cac gct gct ggg gac cgg agc      2367
Pro Thr Gln Leu His Val Ser Trp Val His Ala Ala Gly Asp Arg Ser
    670                 675                 680 agc tac caa gtg acc cta tac cag gag agc act cgg aca gcc acc agc      2415
Ser Tyr Gln Val Thr Leu Tyr Gln Glu Ser Thr Arg Thr Ala Thr Ser
```

```
                685                  690                  695                  700
att gtg ggg ccc aag gca gac agc aca agc ttt tgg ggt ttg act cct       2463
Ile Val Gly Pro Lys Ala Asp Ser Thr Ser Phe Trp Gly Leu Thr Pro
                    705                  710                  715 ggc act aag tac aag gtg gaa gcc atc tcc tgg gct ggg ccc ctt tac       2511
Gly Thr Lys Tyr Lys Val Glu Ala Ile Ser Trp Ala Gly Pro Leu Tyr
        720                  725                  730 act gca gca gcc aac gtt tct gct tgg acc tac cca ctc aca ccc aat       2559
Thr Ala Ala Ala Asn Val Ser Ala Trp Thr Tyr Pro Leu Thr Pro Asn
            735                  740                  745 gag ctg ctc gcc tct atg cag gca ggc agt gct gtg gtt aac ctg gcc       2607
Glu Leu Leu Ala Ser Met Gln Ala Gly Ser Ala Val Val Asn Leu Ala
    750                  755                  760 tgg ccc agt ggt ccc ttg ggg caa ggg aca tgc cat gcc caa ctc tca       2655
Trp Pro Ser Gly Pro Leu Gly Gln Gly Thr Cys His Ala Gln Leu Ser
765                  770                  775                  780 gat gct gga cac ctt tca tgg gag caa ccg ctg tcg cta ggc caa gac       2703
Asp Ala Gly His Leu Ser Trp Glu Gln Pro Leu Ser Leu Gly Gln Asp
                    785                  790                  795 ctc ctc atg cta agg aat ctt ata cca gga cat acg gtt tca ttg tct       2751
Leu Leu Met Leu Arg Asn Leu Ile Pro Gly His Thr Val Ser Leu Ser
        800                  805                  810 gtg aag tgt cgg gca gga cca ctc cag gcc tcc act cac ccc ctg gtg       2799
Val Lys Cys Arg Ala Gly Pro Leu Gln Ala Ser Thr His Pro Leu Val
            815                  820                  825 ctg tct gta gag cct ggc cct gtg gaa gat gtg ttc tgt caa cct gag       2847
Leu Ser Val Glu Pro Gly Pro Val Glu Asp Val Phe Cys Gln Pro Glu
    830                  835                  840 gcc acc tac ctg tcc ctg aac tgg acg atg cct act gga gat gtg gct       2895
Ala Thr Tyr Leu Ser Leu Asn Trp Thr Met Pro Thr Gly Asp Val Ala
845                  850                  855                  860 gtc tgt ctg gtg gag gta gag cag ctg gtg cca gga ggg agc gct cat       2943
Val Cys Leu Val Glu Val Glu Gln Leu Val Pro Gly Gly Ser Ala His
                    865                  870                  875 ttt gtc ttc cag gtc aac acc tcg gag gat gca ctt ctg ctg ccc aac       2991
Phe Val Phe Gln Val Asn Thr Ser Glu Asp Ala Leu Leu Leu Pro Asn
        880                  885                  890 ttg acg ccc acc act tct tac cgc ctt agc ctc act gtg ctg ggt ggg       3039
Leu Thr Pro Thr Thr Ser Tyr Arg Leu Ser Leu Thr Val Leu Gly Gly
            895                  900                  905 aat cgc cag tgg agc cgg gcg gtt acc ctg gtg tgc act act tct gct       3087
Asn Arg Gln Trp Ser Arg Ala Val Thr Leu Val Cys Thr Thr Ser Ala
    910                  915                  920 gag gtt tgg cac ccc cca gag cta gct gag gcc ccc cag gtg gag ctg       3135
Glu Val Trp His Pro Pro Glu Leu Ala Glu Ala Pro Gln Val Glu Leu
925                  930                  935                  940 ggg aca ggg atg ggt gtg aca gtc aca cgt ggc atg ttt ggt aaa gat       3183
Gly Thr Gly Met Gly Val Thr Val Thr Arg Gly Met Phe Gly Lys Asp
                    945                  950                  955 gac ggg cag atc cag tgg tat ggc ata att gcc acc atc aac atg aca       3231
Asp Gly Gln Ile Gln Trp Tyr Gly Ile Ile Ala Thr Ile Asn Met Thr
        960                  965                  970 ctg gcc cag cct tcc cag gaa gcc atc aac cac aca tgg tat gac cac       3279
Leu Ala Gln Pro Ser Gln Glu Ala Ile Asn His Thr Trp Tyr Asp His
            975                  980                  985 tac tat aga gga cat gac tcc tac ctg gct ctc ctg    ttc cca aac ccc    3327
Tyr Tyr Arg Gly His Asp Ser Tyr Leu Ala Leu Leu    Phe Pro Asn Pro
    990                  995                 1000 ttc  tac cca gag cct tgg  gct gtg cca aga tcc  tgg aca gta cct         3372
```

-continued

| | | |
|---|---|---|
| Phe Tyr Pro Glu Pro Trp Ala Val Pro Arg Ser Trp Thr Val Pro<br>1005                                      1010                               1015 | | |
| gtg ggt aca gag gac tgt gac aac acc cag gag ata tgc aat ggg<br>Val Gly Thr Glu Asp Cys Asp Asn Thr Gln Glu Ile Cys Asn Gly<br>1020                        1025                            1030 | 3417 | |
| cat ctc aag cca ggc ttc cag tat agg ttc agc att gca gcc ttt<br>His Leu Lys Pro Gly Phe Gln Tyr Arg Phe Ser Ile Ala Ala Phe<br>1035                        1040                            1045 | 3462 | |
| agt agg ctc agc tct cca gag acc atc ctg gcc ttc tcc gcc ttc<br>Ser Arg Leu Ser Ser Pro Glu Thr Ile Leu Ala Phe Ser Ala Phe<br>1050                        1055                            1060 | 3507 | |
| tca gag cct cag gct agc atc tct ctg gtg gcc atg ccc ctg aca<br>Ser Glu Pro Gln Ala Ser Ile Ser Leu Val Ala Met Pro Leu Thr<br>1065                        1070                            1075 | 3552 | |
| gtt atg atg ggg act gtg gtg ggc tgc atc atc att gtg tgt gca<br>Val Met Met Gly Thr Val Val Gly Cys Ile Ile Ile Val Cys Ala<br>1080                        1085                            1090 | 3597 | |
| gtg cta tgc ttg ttg tgc cgg cgg cgc ctg aag gga cca agg tca<br>Val Leu Cys Leu Leu Cys Arg Arg Arg Leu Lys Gly Pro Arg Ser<br>1095                        1100                            1105 | 3642 | |
| gag aag aat ggc ttt tcc cag gag ttg atg cct tac aac ctg tgg<br>Glu Lys Asn Gly Phe Ser Gln Glu Leu Met Pro Tyr Asn Leu Trp<br>1110                        1115                            1120 | 3687 | |
| cgg acc cat cgg ccc atc ccc agc cat agc ttc cgg cag agc tat<br>Arg Thr His Arg Pro Ile Pro Ser His Ser Phe Arg Gln Ser Tyr<br>1125                        1130                            1135 | 3732 | |
| gag gcc aag agt gca cgt gca cac cag gcc ttc ttc cag gaa ttt<br>Glu Ala Lys Ser Ala Arg Ala His Gln Ala Phe Phe Gln Glu Phe<br>1140                        1145                            1150 | 3777 | |
| gag gag ctg aag gag gtg ggc aag gac cag ccc aga cta gag gct<br>Glu Glu Leu Lys Glu Val Gly Lys Asp Gln Pro Arg Leu Glu Ala<br>1155                        1160                            1165 | 3822 | |
| gag cat cct gcc aac atc acc aag aac cgg tac cca cac gtg cta<br>Glu His Pro Ala Asn Ile Thr Lys Asn Arg Tyr Pro His Val Leu<br>1170                        1175                            1180 | 3867 | |
| cct tat gac cac tcc agg gtc agg ctg acc cag cta tca gga gag<br>Pro Tyr Asp His Ser Arg Val Arg Leu Thr Gln Leu Ser Gly Glu<br>1185                        1190                            1195 | 3912 | |
| cct cat tct gac tac atc aat gcc aac ttc atc cca ggc tat agc<br>Pro His Ser Asp Tyr Ile Asn Ala Asn Phe Ile Pro Gly Tyr Ser<br>1200                        1205                            1210 | 3957 | |
| cac cca cag gag atc att gcc acc cag ggg cct ctc aaa aag acg<br>His Pro Gln Glu Ile Ile Ala Thr Gln Gly Pro Leu Lys Lys Thr<br>1215                        1220                            1225 | 4002 | |
| gtc gag gac ttc tgg cgg ttg gtg tgg gag caa caa gtc cac gtg<br>Val Glu Asp Phe Trp Arg Leu Val Trp Glu Gln Gln Val His Val<br>1230                        1235                            1240 | 4047 | |
| atc atc atg cta act gtg ggc atg gag aat ggg cgg gta ctg tgt<br>Ile Ile Met Leu Thr Val Gly Met Glu Asn Gly Arg Val Leu Cys<br>1245                        1250                            1255 | 4092 | |
| gag cac tac tgg cca gtc aac tcc acg cct gtc acc cac ggt cac<br>Glu His Tyr Trp Pro Val Asn Ser Thr Pro Val Thr His Gly His<br>1260                        1265                            1270 | 4137 | |
| atc acc acc cac ctc ctg gca gag gaa tct gag gac gag tgg acc<br>Ile Thr Thr His Leu Leu Ala Glu Glu Ser Glu Asp Glu Trp Thr<br>1275                        1280                            1285 | 4182 | |
| agg agg gaa ttc cag ctg cag cac ggt gca gag caa aaa cag agg<br>Arg Arg Glu Phe Gln Leu Gln His Gly Ala Glu Gln Lys Gln Arg<br>1290                        1295                            1300 | 4227 | |

-continued

| | | | | | | | | | | | | | | |
|---|---|---|---|---|---|---|---|---|---|---|---|---|---|---|
| cgc | gtg | aag | cag | ctg | cag | ttc | acg | acc | tgg | cca | gac | cac | agt | gtc | 4272 |
| Arg | Val | Lys | Gln | Leu | Gln | Phe | Thr | Thr | Trp | Pro | Asp | His | Ser | Val | |
| 1305 | | | | 1310 | | | | | 1315 | | | | | | |

| | | | | | | | | | | | | | | |
|---|---|---|---|---|---|---|---|---|---|---|---|---|---|---|
| ccc | gag | gct | ccc | agc | tct | ctg | ctc | gct | ttt | gtg | gaa | ctg | gtg | cag | 4317 |
| Pro | Glu | Ala | Pro | Ser | Ser | Leu | Leu | Ala | Phe | Val | Glu | Leu | Val | Gln | |
| 1320 | | | | 1325 | | | | | 1330 | | | | | | |

| | | | | | | | | | | | | | | |
|---|---|---|---|---|---|---|---|---|---|---|---|---|---|---|
| gag | gag | gtg | aag | gca | act | cag | ggc | aag | ggg | ccc | atc | ctg | gtg | cat | 4362 |
| Glu | Glu | Val | Lys | Ala | Thr | Gln | Gly | Lys | Gly | Pro | Ile | Leu | Val | His | |
| 1335 | | | | 1340 | | | | | 1345 | | | | | | |

| | | | | | | | | | | | | | | |
|---|---|---|---|---|---|---|---|---|---|---|---|---|---|---|
| tgc | agt | gcg | ggt | gtg | ggc | agg | aca | ggc | acc | ttt | gtg | gct | ctc | tta | 4407 |
| Cys | Ser | Ala | Gly | Val | Gly | Arg | Thr | Gly | Thr | Phe | Val | Ala | Leu | Leu | |
| 1350 | | | | 1355 | | | | | 1360 | | | | | | |

| | | | | | | | | | | | | | | |
|---|---|---|---|---|---|---|---|---|---|---|---|---|---|---|
| ccg | gct | gtt | cga | caa | cta | gag | gaa | gaa | cag | gtg | gtc | gat | gtg | ttc | 4452 |
| Pro | Ala | Val | Arg | Gln | Leu | Glu | Glu | Glu | Gln | Val | Val | Asp | Val | Phe | |
| 1365 | | | | 1370 | | | | | 1375 | | | | | | |

| | | | | | | | | | | | | | | |
|---|---|---|---|---|---|---|---|---|---|---|---|---|---|---|
| aac | act | gtg | tac | ata | ctc | cgg | ctg | cac | cgg | ccc | ctc | atg | atc | cag | 4497 |
| Asn | Thr | Val | Tyr | Ile | Leu | Arg | Leu | His | Arg | Pro | Leu | Met | Ile | Gln | |
| 1380 | | | | 1385 | | | | | 1390 | | | | | | |

| | | | | | | | | | | | | | | |
|---|---|---|---|---|---|---|---|---|---|---|---|---|---|---|
| acc | ttg | agt | caa | tac | atc | ttc | ctg | cac | agc | tgc | ctg | ctg | aac | aag | 4542 |
| Thr | Leu | Ser | Gln | Tyr | Ile | Phe | Leu | His | Ser | Cys | Leu | Leu | Asn | Lys | |
| 1395 | | | | 1400 | | | | | 1405 | | | | | | |

| | | | | | | | | | | | | | | |
|---|---|---|---|---|---|---|---|---|---|---|---|---|---|---|
| att | ctg | gaa | ggg | ccc | tct | gac | gcc | tca | gac | tcc | ggc | ccc | atc | cct | 4587 |
| Ile | Leu | Glu | Gly | Pro | Ser | Asp | Ala | Ser | Asp | Ser | Gly | Pro | Ile | Pro | |
| 1410 | | | | 1415 | | | | | 1420 | | | | | | |

| | | | | | | | | | | | | | | |
|---|---|---|---|---|---|---|---|---|---|---|---|---|---|---|
| gtg | atg | aat | ttt | gca | caa | gct | tgt | gcc | aag | agg | gca | gcc | aat | gcc | 4632 |
| Val | Met | Asn | Phe | Ala | Gln | Ala | Cys | Ala | Lys | Arg | Ala | Ala | Asn | Ala | |
| 1425 | | | | 1430 | | | | | 1435 | | | | | | |

| | | | | | | | | | | | | | | |
|---|---|---|---|---|---|---|---|---|---|---|---|---|---|---|
| aat | gcc | ggt | ttc | ttg | aag | gag | tac | agg | ctc | ctg | aag | cag | gcc | atc | 4677 |
| Asn | Ala | Gly | Phe | Leu | Lys | Glu | Tyr | Arg | Leu | Leu | Lys | Gln | Ala | Ile | |
| 1440 | | | | 1445 | | | | | 1450 | | | | | | |

| | | | | | | | | | | | | | | |
|---|---|---|---|---|---|---|---|---|---|---|---|---|---|---|
| aag | gat | gag | act | ggc | tct | ctg | ctg | ccc | tct | cct | gac | tat | aat | cag | 4722 |
| Lys | Asp | Glu | Thr | Gly | Ser | Leu | Leu | Pro | Ser | Pro | Asp | Tyr | Asn | Gln | |
| 1455 | | | | 1460 | | | | | 1465 | | | | | | |

| | | | | | | | | | | | | | | |
|---|---|---|---|---|---|---|---|---|---|---|---|---|---|---|
| aac | agc | atc | gcc | tcc | tgt | cat | cat | tct | cag | gag | cag | ttg | gcc | ctg | 4767 |
| Asn | Ser | Ile | Ala | Ser | Cys | His | His | Ser | Gln | Glu | Gln | Leu | Ala | Leu | |
| 1470 | | | | 1475 | | | | | 1480 | | | | | | |

| | | | | | | | | | | | | | | |
|---|---|---|---|---|---|---|---|---|---|---|---|---|---|---|
| gtg | gag | gag | agc | cct | gct | gat | aac | atg | ctg | gca | gcc | tcg | ctc | ttc | 4812 |
| Val | Glu | Glu | Ser | Pro | Ala | Asp | Asn | Met | Leu | Ala | Ala | Ser | Leu | Phe | |
| 1485 | | | | 1490 | | | | | 1495 | | | | | | |

| | | | | | | | | | | | | | | |
|---|---|---|---|---|---|---|---|---|---|---|---|---|---|---|
| cct | ggt | ggg | ccg | tct | ggt | cgc | gac | cat | gtg | gtg | ctg | act | ggc | tcg | 4857 |
| Pro | Gly | Gly | Pro | Ser | Gly | Arg | Asp | His | Val | Val | Leu | Thr | Gly | Ser | |
| 1500 | | | | 1505 | | | | | 1510 | | | | | | |

| | | | | | | | | | | | | | | |
|---|---|---|---|---|---|---|---|---|---|---|---|---|---|---|
| gcc | gga | cca | aag | gaa | ctc | tgg | gaa | atg | gtg | tgg | gaa | cat | ggc | gcc | 4902 |
| Ala | Gly | Pro | Lys | Glu | Leu | Trp | Glu | Met | Val | Trp | Glu | His | Gly | Ala | |
| 1515 | | | | 1520 | | | | | 1525 | | | | | | |

| | | | | | | | | | | | | | | |
|---|---|---|---|---|---|---|---|---|---|---|---|---|---|---|
| tat | gtg | ctt | gtc | tcc | ctg | ggt | ctg | cct | gat | acc | aag | gag | aag | cca | 4947 |
| Tyr | Val | Leu | Val | Ser | Leu | Gly | Leu | Pro | Asp | Thr | Lys | Glu | Lys | Pro | |
| 1530 | | | | 1535 | | | | | 1540 | | | | | | |

| | | | | | | | | | | | | | | |
|---|---|---|---|---|---|---|---|---|---|---|---|---|---|---|
| caa | gac | atc | tgg | cca | atg | gag | atg | cag | cct | att | gtc | aca | gac | atg | 4992 |
| Gln | Asp | Ile | Trp | Pro | Met | Glu | Met | Gln | Pro | Ile | Val | Thr | Asp | Met | |
| 1545 | | | | 1550 | | | | | 1555 | | | | | | |

| | | | | | | | | | | | | | | |
|---|---|---|---|---|---|---|---|---|---|---|---|---|---|---|
| gtg | aca | gtg | cac | aga | gtg | gct | gag | agc | aac | aca | gct | ggc | tgg | ccc | 5037 |
| Val | Thr | Val | His | Arg | Val | Ala | Glu | Ser | Asn | Thr | Ala | Gly | Trp | Pro | |
| 1560 | | | | 1565 | | | | | 1570 | | | | | | |

| | | | | | | | | | | | | | | |
|---|---|---|---|---|---|---|---|---|---|---|---|---|---|---|
| agt | acc | ctc | atc | aga | gtt | ata | cat | ggg | gac | agt | ggg | acg | gaa | agg | 5082 |
| Ser | Thr | Leu | Ile | Arg | Val | Ile | His | Gly | Asp | Ser | Gly | Thr | Glu | Arg | |
| 1575 | | | | 1580 | | | | | 1585 | | | | | | |

| | | | | | | | | | | | | | | |
|---|---|---|---|---|---|---|---|---|---|---|---|---|---|---|
| cag | gtt | caa | tgc | ctg | cag | ttt | cca | cac | tgc | gag | act | ggg | agt | gag | 5127 |
| Gln | Val | Gln | Cys | Leu | Gln | Phe | Pro | His | Cys | Glu | Thr | Gly | Ser | Glu | |
| 1590 | | | | 1595 | | | | | 1600 | | | | | | |

```
ctc cca gct aac acc cta ctg acc ttc ctt gat gct gtg ggc cag      5172
Leu Pro Ala Asn Thr Leu Leu Thr Phe Leu Asp Ala Val Gly Gln
1605                1610                1615 tgc tgc tcc cgg ggc aat agc aag aag cca ggg acc ctg ctc agt      5217
Cys Cys Ser Arg Gly Asn Ser Lys Lys Pro Gly Thr Leu Leu Ser
1620                1625                1630 cac tcc agc aag gtc aca aac cag ctg agc acc ttc ttg gct atg      5262
His Ser Ser Lys Val Thr Asn Gln Leu Ser Thr Phe Leu Ala Met
1635                1640                1645 gaa cag ctg cta cag caa gca ggg acc gag cgc aca gtg gat gtc      5307
Glu Gln Leu Leu Gln Gln Ala Gly Thr Glu Arg Thr Val Asp Val
1650                1655                1660 ttc agt gtg gcc ctg aag cag aca cag gcc tgt ggc ctt aag acc      5352
Phe Ser Val Ala Leu Lys Gln Thr Gln Ala Cys Gly Leu Lys Thr
1665                1670                1675 cca acg ctg gag cag tat atc tac ctc tac aac tgt ctg aac agc      5397
Pro Thr Leu Glu Gln Tyr Ile Tyr Leu Tyr Asn Cys Leu Asn Ser
1680                1685                1690 gca ttg agg aac agg ctg ccc cga gct agg aag tgaccttgcc           5440
Ala Leu Arg Asn Arg Leu Pro Arg Ala Arg Lys
1695                1700                1705 ctgctaggca tcacgttcca gcaatccacc caggcctggc ttccccagga gaacagatct    5500
attcggcctc acgctgtcaa agggcagagt ctgggaataa aggtaaatc tcgag          5555

<210> SEQ ID NO 19
<211> LENGTH: 1705
<212> TYPE: PRT
<213> ORGANISM: mus musculus

<400> SEQUENCE: 19

Met Arg Pro Leu Ile Leu Ala Ala Leu Leu Trp Leu Gln Asp Ser
1               5                   10                  15

Leu Ala Gln Glu Asp Val Cys Ser Ser Leu Asp Gly Ser Pro Asp Arg
                20                  25                  30

Gln Gly Gly Gly Pro Pro Leu Ser Val Asn Val Ser Ser Arg Gly Lys
            35                  40                  45

Pro Thr Ser Leu Phe Leu Ser Trp Val Ala Ala Glu Pro Gly Gly Phe
        50                  55                  60

Asp Tyr Ala Leu Cys Leu Arg Ala Met Asn Leu Ser Gly Phe Pro Glu
65                  70                  75                  80

Gly Gln Gln Leu Gln Ala His Thr Asn Glu Ser Ser Phe Glu Phe His
                85                  90                  95

Gly Leu Val Pro Gly Ser Arg Tyr Gln Leu Glu Leu Thr Val Leu Arg
            100                 105                 110

Pro Cys Trp Gln Asn Val Thr Ile Thr Leu Thr Ala Arg Thr Ala Pro
        115                 120                 125

Thr Val Val Arg Gly Leu Gln Leu His Ser Thr Gly Ser Pro Ala Ser
    130                 135                 140

Leu Glu Ala Ser Trp Ser Asp Ala Ser Gly Asp Gln Asp Ser Tyr Gln
145                 150                 155                 160

Leu Leu Leu Tyr His Pro Glu Ser His Thr Leu Ala Cys Asn Val Ser
                165                 170                 175

Val Ser Pro Asp Thr Leu Ser Tyr Asn Phe Gly Asp Leu Leu Pro Gly
            180                 185                 190

Ser Gln Tyr Val Leu Glu Val Ile Thr Trp Ala Gly Ser Leu His Ala
        195                 200                 205
```

```
Lys Thr Ser Ile Leu Gln Trp Thr Glu Pro Val Pro Pro Asp His Leu
    210                 215                 220

Thr Leu Arg Ala Leu Gly Thr Ser Ser Leu Gln Ala Phe Trp Asn Ser
225                 230                 235                 240

Ser Glu Gly Ala Thr Trp Phe His Leu Ile Leu Thr Asp Leu Leu Glu
                245                 250                 255

Gly Thr Asn Leu Thr Lys Val Val Arg Gln Gly Ile Ser Thr His Thr
                    260                 265                 270

Phe Leu Arg Leu Ser Pro Gly Thr Pro Tyr Gln Leu Lys Ile Cys Ala
                275                 280                 285

Ala Ala Gly Pro His Gln Ile Trp Gly Pro Asn Ala Thr Glu Trp Thr
290                 295                 300

Tyr Pro Ser Tyr Pro Ser Asp Leu Val Leu Thr Pro Leu Trp Asn Glu
305                 310                 315                 320

Leu Trp Ala Ser Trp Lys Ala Gly Gln Gly Ala Arg Asp Gly Tyr Val
                    325                 330                 335

Leu Lys Leu Ser Gly Pro Val Glu Asn Thr Thr Thr Leu Gly Pro Glu
                340                 345                 350

Glu Cys Asn Ala Val Phe Pro Gly Pro Leu Pro Pro Gly His Tyr Thr
            355                 360                 365

Leu Gly Leu Arg Val Leu Ala Gly Pro Tyr Asp Ala Trp Val Glu Gly
370                 375                 380

Ser Ile Trp Leu Ala Glu Ser Ala Ala Arg Pro Met Glu Val Pro Gly
385                 390                 395                 400

Ala Arg Leu Trp Leu Glu Gly Leu Glu Ala Thr Lys Gln Pro Gly Arg
                    405                 410                 415

Arg Ala Leu Leu Tyr Ser Val Asp Ala Pro Gly Leu Leu Gly Asn Ile
                420                 425                 430

Ser Val Ser Ser Gly Ala Thr His Val Thr Phe Cys Gly Leu Val Pro
                435                 440                 445

Gly Ala His Tyr Arg Val Asp Ile Ala Ser Ser Met Gly Asp Ile Thr
            450                 455                 460

Gln Ser Leu Thr Gly Tyr Thr Ser Pro Leu Pro Pro Gln Ser Leu Glu
465                 470                 475                 480

Ile Ile Ser Arg Asn Ser Pro Ser Asp Leu Thr Ile Gly Trp Ala Pro
                485                 490                 495

Ala Pro Gly Gln Met Glu Gly Tyr Lys Val Thr Trp His Gln Asp Gly
                500                 505                 510

Ser Gln Arg Ser Pro Gly Asp Leu Val Asp Leu Gly Pro Asp Ile Ser
            515                 520                 525

Ser Leu Thr Leu Lys Ser Leu Val Pro Gly Ser Cys Tyr Thr Val Ser
530                 535                 540

Ala Trp Ala Trp Ser Gly Asn Leu Ser Ser Asp Ser Gln Lys Ile His
545                 550                 555                 560

Ser Cys Thr Arg Pro Ala Pro Pro Thr Asn Leu Ser Leu Gly Phe Ala
                565                 570                 575

His Gln Pro Ala Thr Leu Arg Ala Ser Trp Cys His Pro Pro Gly Gly
            580                 585                 590

Arg Asp Ala Phe Gln Leu Arg Leu Tyr Arg Leu Arg Pro Leu Thr Leu
                595                 600                 605

Glu Ser Glu Lys Ile Leu Ser Gln Glu Ala Gln Asn Phe Ser Trp Ala
610                 615                 620
```

```
Gln Leu Pro Ala Gly Tyr Glu Phe Gln Val Gln Leu Ser Thr Leu Trp
625                 630                 635                 640

Gly Ser Glu Glu Ser Gly Ser Ala Asn Thr Thr Gly Trp Thr Pro Pro
            645                 650                 655

Ser Ala Pro Thr Leu Val Asn Val Thr Ser Glu Ala Pro Thr Gln Leu
            660                 665                 670

His Val Ser Trp Val His Ala Ala Gly Asp Arg Ser Ser Tyr Gln Val
            675                 680                 685

Thr Leu Tyr Gln Glu Ser Thr Arg Thr Ala Thr Ser Ile Val Gly Pro
690                 695                 700

Lys Ala Asp Ser Thr Ser Phe Trp Gly Leu Thr Pro Gly Thr Lys Tyr
705                 710                 715                 720

Lys Val Glu Ala Ile Ser Trp Ala Gly Pro Leu Tyr Thr Ala Ala Ala
                725                 730                 735

Asn Val Ser Ala Trp Thr Tyr Pro Leu Thr Pro Asn Glu Leu Leu Ala
            740                 745                 750

Ser Met Gln Ala Gly Ser Ala Val Val Asn Leu Ala Trp Pro Ser Gly
            755                 760                 765

Pro Leu Gly Gln Gly Thr Cys His Ala Gln Leu Ser Asp Ala Gly His
770                 775                 780

Leu Ser Trp Glu Gln Pro Leu Ser Leu Gly Gln Asp Leu Leu Met Leu
785                 790                 795                 800

Arg Asn Leu Ile Pro Gly His Thr Val Ser Leu Ser Val Lys Cys Arg
                805                 810                 815

Ala Gly Pro Leu Gln Ala Ser Thr His Pro Leu Val Leu Ser Val Glu
            820                 825                 830

Pro Gly Pro Val Glu Asp Val Phe Cys Gln Pro Glu Ala Thr Tyr Leu
835                 840                 845

Ser Leu Asn Trp Thr Met Pro Thr Gly Asp Val Ala Val Cys Leu Val
850                 855                 860

Glu Val Glu Gln Leu Val Pro Gly Gly Ser Ala His Phe Val Phe Gln
865                 870                 875                 880

Val Asn Thr Ser Glu Asp Ala Leu Leu Leu Pro Asn Leu Thr Pro Thr
            885                 890                 895

Thr Ser Tyr Arg Leu Ser Leu Thr Val Leu Gly Gly Asn Arg Gln Trp
            900                 905                 910

Ser Arg Ala Val Thr Leu Val Cys Thr Thr Ser Ala Glu Val Trp His
            915                 920                 925

Pro Pro Glu Leu Ala Glu Ala Pro Gln Val Glu Leu Gly Thr Gly Met
930                 935                 940

Gly Val Thr Val Thr Arg Gly Met Phe Gly Lys Asp Asp Gly Gln Ile
945                 950                 955                 960

Gln Trp Tyr Gly Ile Ile Ala Thr Ile Asn Met Thr Leu Ala Gln Pro
                965                 970                 975

Ser Gln Glu Ala Ile Asn His Thr Trp Tyr Asp His Tyr Arg Gly
            980                 985                 990

His Asp Ser Tyr Leu Ala Leu Leu Phe Pro Asn Pro Phe Tyr Pro Glu
            995                 1000                1005

Pro Trp Ala Val Pro Arg Ser Trp Thr Val Pro Val Gly Thr Glu
        1010                1015                1020

Asp Cys Asp Asn Thr Gln Glu Ile Cys Asn Gly His Leu Lys Pro
        1025                1030                1035

Gly Phe Gln Tyr Arg Phe Ser Ile Ala Ala Phe Ser Arg Leu Ser
```

-continued

```
                1040                1045                1050
Ser Pro Glu Thr Ile Leu Ala Phe Ser Ala Phe Ser Glu Pro Gln
                1055                1060                1065
Ala Ser Ile Ser Leu Val Ala Met Pro Leu Thr Val Met Met Gly
                1070                1075                1080
Thr Val Val Gly Cys Ile Ile Ile Val Cys Ala Val Leu Cys Leu
                1085                1090                1095
Leu Cys Arg Arg Arg Leu Lys Gly Pro Arg Ser Glu Lys Asn Gly
                1100                1105                1110
Phe Ser Gln Glu Leu Met Pro Tyr Asn Leu Trp Arg Thr His Arg
                1115                1120                1125
Pro Ile Pro Ser His Ser Phe Arg Gln Ser Tyr Glu Ala Lys Ser
                1130                1135                1140
Ala Arg Ala His Gln Ala Phe Phe Gln Glu Phe Glu Glu Leu Lys
                1145                1150                1155
Glu Val Gly Lys Asp Gln Pro Arg Leu Glu Ala Glu His Pro Ala
                1160                1165                1170
Asn Ile Thr Lys Asn Arg Tyr Pro His Val Leu Pro Tyr Asp His
                1175                1180                1185
Ser Arg Val Arg Leu Thr Gln Leu Ser Gly Glu Pro His Ser Asp
                1190                1195                1200
Tyr Ile Asn Ala Asn Phe Ile Pro Gly Tyr Ser His Pro Gln Glu
                1205                1210                1215
Ile Ile Ala Thr Gln Gly Pro Leu Lys Lys Thr Val Glu Asp Phe
                1220                1225                1230
Trp Arg Leu Val Trp Glu Gln Gln Val His Val Ile Ile Met Leu
                1235                1240                1245
Thr Val Gly Met Glu Asn Gly Arg Val Leu Cys Glu His Tyr Trp
                1250                1255                1260
Pro Val Asn Ser Thr Pro Val Thr His Gly His Ile Thr Thr His
                1265                1270                1275
Leu Leu Ala Glu Glu Ser Glu Asp Glu Trp Thr Arg Arg Glu Phe
                1280                1285                1290
Gln Leu Gln His Gly Ala Glu Gln Lys Gln Arg Arg Val Lys Gln
                1295                1300                1305
Leu Gln Phe Thr Thr Trp Pro Asp His Ser Val Pro Glu Ala Pro
                1310                1315                1320
Ser Ser Leu Leu Ala Phe Val Glu Leu Val Gln Glu Glu Val Lys
                1325                1330                1335
Ala Thr Gln Gly Lys Gly Pro Ile Leu Val His Cys Ser Ala Gly
                1340                1345                1350
Val Gly Arg Thr Gly Thr Phe Val Ala Leu Leu Pro Ala Val Arg
                1355                1360                1365
Gln Leu Glu Glu Glu Gln Val Val Asp Val Phe Asn Thr Val Tyr
                1370                1375                1380
Ile Leu Arg Leu His Arg Pro Leu Met Ile Gln Thr Leu Ser Gln
                1385                1390                1395
Tyr Ile Phe Leu His Ser Cys Leu Leu Asn Lys Ile Leu Glu Gly
                1400                1405                1410
Pro Ser Asp Ala Ser Asp Ser Gly Pro Ile Pro Val Met Asn Phe
                1415                1420                1425
Ala Gln Ala Cys Ala Lys Arg Ala Ala Asn Ala Asn Ala Gly Phe
                1430                1435                1440
```

-continued

```
Leu Lys Glu Tyr Arg Leu Leu Lys Gln Ala Ile Lys Asp Glu Thr
    1445                1450                1455

Gly Ser Leu Leu Pro Ser Pro Asp Tyr Asn Gln Asn Ser Ile Ala
    1460                1465                1470

Ser Cys His His Ser Gln Glu Gln Leu Ala Leu Val Glu Glu Ser
    1475                1480                1485

Pro Ala Asp Asn Met Leu Ala Ala Ser Leu Phe Pro Gly Gly Pro
    1490                1495                1500

Ser Gly Arg Asp His Val Val Leu Thr Gly Ser Ala Gly Pro Lys
    1505                1510                1515

Glu Leu Trp Glu Met Val Trp Glu His Gly Ala Tyr Val Leu Val
    1520                1525                1530

Ser Leu Gly Leu Pro Asp Thr Lys Glu Lys Pro Gln Asp Ile Trp
    1535                1540                1545

Pro Met Glu Met Gln Pro Ile Val Thr Asp Met Val Thr Val His
    1550                1555                1560

Arg Val Ala Glu Ser Asn Thr Ala Gly Trp Pro Ser Thr Leu Ile
    1565                1570                1575

Arg Val Ile His Gly Asp Ser Gly Thr Glu Arg Gln Val Gln Cys
    1580                1585                1590

Leu Gln Phe Pro His Cys Glu Thr Gly Ser Glu Leu Pro Ala Asn
    1595                1600                1605

Thr Leu Leu Thr Phe Leu Asp Ala Val Gly Gln Cys Cys Ser Arg
    1610                1615                1620

Gly Asn Ser Lys Lys Pro Gly Thr Leu Leu Ser His Ser Ser Lys
    1625                1630                1635

Val Thr Asn Gln Leu Ser Thr Phe Leu Ala Met Glu Gln Leu Leu
    1640                1645                1650

Gln Gln Ala Gly Thr Glu Arg Thr Val Asp Val Phe Ser Val Ala
    1655                1660                1665

Leu Lys Gln Thr Gln Ala Cys Gly Leu Lys Thr Pro Thr Leu Glu
    1670                1675                1680

Gln Tyr Ile Tyr Leu Tyr Asn Cys Leu Asn Ser Ala Leu Arg Asn
    1685                1690                1695

Arg Leu Pro Arg Ala Arg Lys
    1700                1705

<210> SEQ ID NO 20
<211> LENGTH: 3078
<212> TYPE: DNA
<213> ORGANISM: Escherichia coli
<220> FEATURE:
<221> NAME/KEY: CDS
<222> LOCATION: (1)..(3078)

<400> SEQUENCE: 20 acc atg att acg gat tca ctg gcc gtc gtt tta caa cgt cgt gac tgg      48
Thr Met Ile Thr Asp Ser Leu Ala Val Val Leu Gln Arg Arg Asp Trp
  1               5                  10                  15 gaa aac cct ggc gtt acc caa ctt aat cgc ctt gca gca cat ccc cct      96
Glu Asn Pro Gly Val Thr Gln Leu Asn Arg Leu Ala Ala His Pro Pro
             20                  25                  30 ttc gcc agc tgg cgt aat agc gaa gag gcc cgc acc gat cgc cct tcc     144
Phe Ala Ser Trp Arg Asn Ser Glu Glu Ala Arg Thr Asp Arg Pro Ser
         35                  40                  45 caa cag ttg cgc agc ctg aat ggc gaa tgg cgc ttt gcc tgg ttt ccg     192
```

```
Gln Gln Leu Arg Ser Leu Asn Gly Glu Trp Arg Phe Ala Trp Phe Pro
    50              55                  60 gca cca gaa gcg gtg ccg gaa agc tgg ctg gag tgc gat ctt cct gag        240
Ala Pro Glu Ala Val Pro Glu Ser Trp Leu Glu Cys Asp Leu Pro Glu
65              70                  75                  80 gcc gat act gtc gtc gtc ccc tca aac tgg cag atg cac ggt tac gat        288
Ala Asp Thr Val Val Val Pro Ser Asn Trp Gln Met His Gly Tyr Asp
                85                  90                  95 gcg ccc atc tac acc aac gta acc tat ccc att acg gtc aat ccg ccg        336
Ala Pro Ile Tyr Thr Asn Val Thr Tyr Pro Ile Thr Val Asn Pro Pro
            100                 105                 110 ttt gtt ccc acg gag aat ccg acg ggt tgt tac tcg ctc aca ttt aat        384
Phe Val Pro Thr Glu Asn Pro Thr Gly Cys Tyr Ser Leu Thr Phe Asn
        115                 120                 125 gtt gat gaa agc tgg cta cag gaa ggc cag acg cga att att ttt gat        432
Val Asp Glu Ser Trp Leu Gln Glu Gly Gln Thr Arg Ile Ile Phe Asp
130                 135                 140 ggc gtt aac tcg gcg ttt cat ctg tgg tgc aac ggg cgc tgg gtc ggt        480
Gly Val Asn Ser Ala Phe His Leu Trp Cys Asn Gly Arg Trp Val Gly
145                 150                 155                 160 tac ggc cag gac agt cgt ttg ccg tct gaa ttt gac ctg agc gca ttt        528
Tyr Gly Gln Asp Ser Arg Leu Pro Ser Glu Phe Asp Leu Ser Ala Phe
                165                 170                 175 tta cgc gcc gga gaa aac cgc ctc gcg gtg atg gtg ctg cgt tgg agt        576
Leu Arg Ala Gly Glu Asn Arg Leu Ala Val Met Val Leu Arg Trp Ser
            180                 185                 190 gac ggc agt tat ctg gaa gat cag gat atg tgg cgg atg agc ggc att        624
Asp Gly Ser Tyr Leu Glu Asp Gln Asp Met Trp Arg Met Ser Gly Ile
        195                 200                 205 ttc cgt gac gtc tcg ttg ctg cat aaa ccg act aca caa atc agc gat        672
Phe Arg Asp Val Ser Leu Leu His Lys Pro Thr Thr Gln Ile Ser Asp
210                 215                 220 ttc cat gtt gcc act cgc ttt aat gat gat ttc agc cgc gct gta ctg        720
Phe His Val Ala Thr Arg Phe Asn Asp Asp Phe Ser Arg Ala Val Leu
225                 230                 235                 240 gag gct gaa gtt cag atg tgc ggc gag ttg cgt gac tac cta cgg gta        768
Glu Ala Glu Val Gln Met Cys Gly Glu Leu Arg Asp Tyr Leu Arg Val
                245                 250                 255 aca gtt tct tta tgg cag ggt gaa acg cag gtc gcc agc ggc acc gcg        816
Thr Val Ser Leu Trp Gln Gly Glu Thr Gln Val Ala Ser Gly Thr Ala
            260                 265                 270 cct ttc ggc ggt gaa att atc gat gag cgt ggt ggt tat gcc gat cgc        864
Pro Phe Gly Gly Glu Ile Ile Asp Glu Arg Gly Gly Tyr Ala Asp Arg
        275                 280                 285 gtc aca cta cgt ctg aac gtc gaa aac ccg aaa ctg tgg agc gcc gaa        912
Val Thr Leu Arg Leu Asn Val Glu Asn Pro Lys Leu Trp Ser Ala Glu
290                 295                 300 atc ccg aat ctc tat cgt gcg gtg gtt gaa ctg cac acc gcc gac ggc        960
Ile Pro Asn Leu Tyr Arg Ala Val Val Glu Leu His Thr Ala Asp Gly
305                 310                 315                 320 acg ctg att gaa gca gaa gcc tgc gat gtc ggt ttc cgc gag gtg cgg       1008
Thr Leu Ile Glu Ala Glu Ala Cys Asp Val Gly Phe Arg Glu Val Arg
                325                 330                 335 att gaa aat ggt ctg ctg ctg ctg aac ggc aag ccg ttg ctg att cga       1056
Ile Glu Asn Gly Leu Leu Leu Leu Asn Gly Lys Pro Leu Leu Ile Arg
            340                 345                 350 ggc gtt aac cgt cac gag cat cat cct ctg cat ggt cag gtc atg gat       1104
Gly Val Asn Arg His Glu His His Pro Leu His Gly Gln Val Met Asp
        355                 360                 365
```

```
gag cag acg atg gtg cag gat atc ctg ctg atg aag cag aac aac ttt    1152
Glu Gln Thr Met Val Gln Asp Ile Leu Leu Met Lys Gln Asn Asn Phe
    370                 375                 380 aac gcc gtg cgc tgt tcg cat tat ccg aac cat ccg ctg tgg tac acg    1200
Asn Ala Val Arg Cys Ser His Tyr Pro Asn His Pro Leu Trp Tyr Thr
385                 390                 395                 400 ctg tgc gac cgc tac ggc ctg tat gtg gtg gat gaa gcc aat att gaa    1248
Leu Cys Asp Arg Tyr Gly Leu Tyr Val Val Asp Glu Ala Asn Ile Glu
                405                 410                 415 acc cac ggc atg gtg cca atg aat cgt ctg acc gat gat ccg cgc tgg    1296
Thr His Gly Met Val Pro Met Asn Arg Leu Thr Asp Asp Pro Arg Trp
            420                 425                 430 cta ccg gcg atg agc gaa cgc gta acg cga atg gtg cag cgc gat cgt    1344
Leu Pro Ala Met Ser Glu Arg Val Thr Arg Met Val Gln Arg Asp Arg
        435                 440                 445 aat cac ccg agt gtg atc atc tgg tcg ctg ggg aat gaa tca ggc cac    1392
Asn His Pro Ser Val Ile Ile Trp Ser Leu Gly Asn Glu Ser Gly His
    450                 455                 460 ggc gct aat cac gac gcg ctg tat cgc tgg atc aaa tct gtc gat cct    1440
Gly Ala Asn His Asp Ala Leu Tyr Arg Trp Ile Lys Ser Val Asp Pro
465                 470                 475                 480 tcc cgc ccg gtg cag tat gaa ggc ggc gga gcc gac acc acg gcc acc    1488
Ser Arg Pro Val Gln Tyr Glu Gly Gly Gly Ala Asp Thr Thr Ala Thr
                485                 490                 495 gat att att tgc ccg atg tac gcg cgc gtg gat gaa gac cag ccc ttc    1536
Asp Ile Ile Cys Pro Met Tyr Ala Arg Val Asp Glu Asp Gln Pro Phe
                500                 505                 510 ccg gct gtg ccg aaa tgg tcc atc aaa aaa tgg ctt tcg cta cct gga    1584
Pro Ala Val Pro Lys Trp Ser Ile Lys Lys Trp Leu Ser Leu Pro Gly
            515                 520                 525 gag acg cgc ccg ctg atc ctt tgc gaa tac gcc cac gcg atg ggt aac    1632
Glu Thr Arg Pro Leu Ile Leu Cys Glu Tyr Ala His Ala Met Gly Asn
        530                 535                 540 agt ctt ggc ggt ttc gct aaa tac tgg cag gcg ttt cgt cag tat ccc    1680
Ser Leu Gly Gly Phe Ala Lys Tyr Trp Gln Ala Phe Arg Gln Tyr Pro
545                 550                 555                 560 cgt tta cag ggc ggc ttc gtc tgg gac tgg gtg gat cag tcg ctg att    1728
Arg Leu Gln Gly Gly Phe Val Trp Asp Trp Val Asp Gln Ser Leu Ile
                565                 570                 575 aaa tat gat gaa aac ggc aac ccg tgg tcg gct tac ggc ggt gat ttt    1776
Lys Tyr Asp Glu Asn Gly Asn Pro Trp Ser Ala Tyr Gly Gly Asp Phe
                580                 585                 590 ggc gat acg ccg aac gat cgc cag ttc tgt atg aac ggt ctg gtc ttt    1824
Gly Asp Thr Pro Asn Asp Arg Gln Phe Cys Met Asn Gly Leu Val Phe
            595                 600                 605 gcc gac cgc acg ccg cat cca gcg ctg acg gaa gca aaa cac cag cag    1872
Ala Asp Arg Thr Pro His Pro Ala Leu Thr Glu Ala Lys His Gln Gln
        610                 615                 620 cag ttt ttc cag ttc cgt tta tcc ggg caa acc atc gaa gtg acc agc    1920
Gln Phe Phe Gln Phe Arg Leu Ser Gly Gln Thr Ile Glu Val Thr Ser
625                 630                 635                 640 gaa tac ctg ttc cgt cat agc gat aac gag ctc ctg cac tgg atg gtg    1968
Glu Tyr Leu Phe Arg His Ser Asp Asn Glu Leu Leu His Trp Met Val
                645                 650                 655 gcg ctg gat ggt aag ccg ctg gca agc ggt gaa gtg cct ctg gat gtc    2016
Ala Leu Asp Gly Lys Pro Leu Ala Ser Gly Glu Val Pro Leu Asp Val
                660                 665                 670 gct cca caa ggt aaa cag ttg att gaa ctg cct gaa cta ccg cag ccg    2064
Ala Pro Gln Gly Lys Gln Leu Ile Glu Leu Pro Glu Leu Pro Gln Pro
            675                 680                 685
```

```
gag agc gcc ggg caa ctc tgg ctc aca gta cgc gta gtg caa ccg aac     2112
Glu Ser Ala Gly Gln Leu Trp Leu Thr Val Arg Val Val Gln Pro Asn
    690                 695                 700 gcg acc gca tgg tca gaa gcc ggg cac atc agc gcc tgg cag cag tgg     2160
Ala Thr Ala Trp Ser Glu Ala Gly His Ile Ser Ala Trp Gln Gln Trp
705                 710                 715                 720 cgt ctg gcg gaa aac ctc agt gtg acg ctc ccc gcc gcg tcc cac gcc     2208
Arg Leu Ala Glu Asn Leu Ser Val Thr Leu Pro Ala Ala Ser His Ala
                725                 730                 735 atc ccg cat ctg acc acc agc gaa atg gat ttt tgc atc gag ctg ggt     2256
Ile Pro His Leu Thr Thr Ser Glu Met Asp Phe Cys Ile Glu Leu Gly
            740                 745                 750 aat aag cgt tgg caa ttt aac cgc cag tca ggc ttt ctt tca cag atg     2304
Asn Lys Arg Trp Gln Phe Asn Arg Gln Ser Gly Phe Leu Ser Gln Met
        755                 760                 765 tgg att ggc gat aaa aaa caa ctg ctg acg ccg ctg cgc gat cag ttc     2352
Trp Ile Gly Asp Lys Lys Gln Leu Leu Thr Pro Leu Arg Asp Gln Phe
    770                 775                 780 acc cgt gca ccg ctg gat aac gac att ggc gta agt gaa gcg acc cgc     2400
Thr Arg Ala Pro Leu Asp Asn Asp Ile Gly Val Ser Glu Ala Thr Arg
785                 790                 795                 800 att gac cct aac gcc tgg gtc gaa cgc tgg aag gcg gcg ggc cat tac     2448
Ile Asp Pro Asn Ala Trp Val Glu Arg Trp Lys Ala Ala Gly His Tyr
                805                 810                 815 cag gcc gaa gca gcg ttg ttg cag tgc acg gca gat aca ctt gct gat     2496
Gln Ala Glu Ala Ala Leu Leu Gln Cys Thr Ala Asp Thr Leu Ala Asp
            820                 825                 830 gcg gtg ctg att acg acc gct cac gcg tgg cag cat cag ggg aaa acc     2544
Ala Val Leu Ile Thr Thr Ala His Ala Trp Gln His Gln Gly Lys Thr
        835                 840                 845 tta ttt atc agc cgg aaa acc tac cgg att gat ggt agt ggt caa atg     2592
Leu Phe Ile Ser Arg Lys Thr Tyr Arg Ile Asp Gly Ser Gly Gln Met
    850                 855                 860 gcg att acc gtt gat gtt gaa gtg gcg agc gat aca ccg cat ccg gcg     2640
Ala Ile Thr Val Asp Val Glu Val Ala Ser Asp Thr Pro His Pro Ala
865                 870                 875                 880 cgg att ggc ctg aac tgc cag ctg gcg cag gta gca gag cgg gta aac     2688
Arg Ile Gly Leu Asn Cys Gln Leu Ala Gln Val Ala Glu Arg Val Asn
                885                 890                 895 tgg ctc gga tta ggg ccg caa gaa aac tat ccc gac cgc ctt act gcc     2736
Trp Leu Gly Leu Gly Pro Gln Glu Asn Tyr Pro Asp Arg Leu Thr Ala
            900                 905                 910 gcc tgt ttt gac cgc tgg gat ctg cca ttg tca gac atg tat acc ccg     2784
Ala Cys Phe Asp Arg Trp Asp Leu Pro Leu Ser Asp Met Tyr Thr Pro
        915                 920                 925 tac gtc ttc ccg agc gaa aac ggt ctg cgc tgc ggg acg cgc gaa ttg     2832
Tyr Val Phe Pro Ser Glu Asn Gly Leu Arg Cys Gly Thr Arg Glu Leu
    930                 935                 940 aat tat ggc cca cac cag tgg cgc ggc gac ttc cag ttc aac atc agc     2880
Asn Tyr Gly Pro His Gln Trp Arg Gly Asp Phe Gln Phe Asn Ile Ser
945                 950                 955                 960 cgc tac agt caa cag caa ctg atg gaa acc agc cat cgc cat ctg ctg     2928
Arg Tyr Ser Gln Gln Gln Leu Met Glu Thr Ser His Arg His Leu Leu
                965                 970                 975 cac gcg gaa gaa ggc aca tgg ctg aat atc gac ggt ttc cat atg ggg     2976
His Ala Glu Glu Gly Thr Trp Leu Asn Ile Asp Gly Phe His Met Gly
            980                 985                 990 att ggt ggc gac gac tcc tgg agc  ccg tca gta tcg gcg  gaa ttc cag    3024
Ile Gly Gly Asp Asp Ser Trp Ser  Pro Ser Val Ser Ala  Glu Phe Gln
```

-continued

```
              995                  1000                 1005
    ctg agc  gcc ggt  cgc tac  cat  tac cag  ttg gtc  tgg tgt  caa aaa      3069
    Leu Ser  Ala Gly  Arg Tyr  His  Tyr Gln  Leu Val  Trp Cys  Gln Lys
       1010          1015                   1020 taa taa taa                                                              3078
```

<210> SEQ ID NO 21
<211> LENGTH: 1023
<212> TYPE: PRT
<213> ORGANISM: Escherichia coli

<400> SEQUENCE: 21

| | | | | | | | | | | | | | | |
|---|---|---|---|---|---|---|---|---|---|---|---|---|---|---|
| Thr | Met | Ile | Thr | Asp | Ser | Leu | Ala | Val | Val | Leu | Gln | Arg | Arg | Asp | Trp |
| 1 | | | | 5 | | | | | 10 | | | | | 15 | |
| Glu | Asn | Pro | Gly | Val | Thr | Gln | Leu | Asn | Arg | Leu | Ala | Ala | His | Pro | Pro |
| | | | 20 | | | | | 25 | | | | | 30 | | |
| Phe | Ala | Ser | Trp | Arg | Asn | Ser | Glu | Glu | Ala | Arg | Thr | Asp | Arg | Pro | Ser |
| | | 35 | | | | | 40 | | | | | 45 | | | |
| Gln | Gln | Leu | Arg | Ser | Leu | Asn | Gly | Glu | Trp | Arg | Phe | Ala | Trp | Phe | Pro |
| | 50 | | | | | 55 | | | | | 60 | | | | |
| Ala | Pro | Glu | Ala | Val | Pro | Glu | Ser | Trp | Leu | Glu | Cys | Asp | Leu | Pro | Glu |
| 65 | | | | | 70 | | | | | 75 | | | | | 80 |
| Ala | Asp | Thr | Val | Val | Pro | Ser | Asn | Trp | Gln | Met | His | Gly | Tyr | Asp |
| | | | | 85 | | | | | 90 | | | | | 95 |
| Ala | Pro | Ile | Tyr | Thr | Asn | Val | Thr | Tyr | Pro | Ile | Thr | Val | Asn | Pro | Pro |
| | | | 100 | | | | | 105 | | | | | 110 | | |
| Phe | Val | Pro | Thr | Glu | Asn | Pro | Thr | Gly | Cys | Tyr | Ser | Leu | Thr | Phe | Asn |
| | | | 115 | | | | | 120 | | | | | 125 | | |
| Val | Asp | Glu | Ser | Trp | Leu | Gln | Glu | Gly | Gln | Thr | Arg | Ile | Ile | Phe | Asp |
| | 130 | | | | | 135 | | | | | 140 | | | | |
| Gly | Val | Asn | Ser | Ala | Phe | His | Leu | Trp | Cys | Asn | Gly | Arg | Trp | Val | Gly |
| 145 | | | | | 150 | | | | | 155 | | | | | 160 |
| Tyr | Gly | Gln | Asp | Ser | Arg | Leu | Pro | Ser | Glu | Phe | Asp | Leu | Ser | Ala | Phe |
| | | | 165 | | | | | 170 | | | | | 175 | | |
| Leu | Arg | Ala | Gly | Glu | Asn | Arg | Leu | Ala | Val | Met | Val | Leu | Arg | Trp | Ser |
| | | | 180 | | | | | 185 | | | | | 190 | | |
| Asp | Gly | Ser | Tyr | Leu | Glu | Asp | Gln | Asp | Met | Trp | Arg | Met | Ser | Gly | Ile |
| | | | 195 | | | | | 200 | | | | | 205 | | |
| Phe | Arg | Asp | Val | Ser | Leu | Leu | His | Lys | Pro | Thr | Thr | Gln | Ile | Ser | Asp |
| | | 210 | | | | | 215 | | | | | 220 | | | |
| Phe | His | Val | Ala | Thr | Arg | Phe | Asn | Asp | Asp | Phe | Ser | Arg | Ala | Val | Leu |
| 225 | | | | | 230 | | | | | 235 | | | | | 240 |
| Glu | Ala | Glu | Val | Gln | Met | Cys | Gly | Glu | Leu | Arg | Asp | Tyr | Leu | Arg | Val |
| | | | | 245 | | | | | 250 | | | | | 255 | |
| Thr | Val | Ser | Leu | Trp | Gln | Gly | Glu | Thr | Gln | Val | Ala | Ser | Gly | Thr | Ala |
| | | | | 260 | | | | | 265 | | | | | 270 | |
| Pro | Phe | Gly | Gly | Glu | Ile | Ile | Asp | Glu | Arg | Gly | Gly | Tyr | Ala | Asp | Arg |
| | | | 275 | | | | | 280 | | | | | 285 | | |
| Val | Thr | Leu | Arg | Leu | Asn | Val | Glu | Asn | Pro | Lys | Leu | Trp | Ser | Ala | Glu |
| | | | 290 | | | | | 295 | | | | | 300 | | |
| Ile | Pro | Asn | Leu | Tyr | Arg | Ala | Val | Val | Glu | Leu | His | Thr | Ala | Asp | Gly |
| 305 | | | | | 310 | | | | | 315 | | | | | 320 |
| Thr | Leu | Ile | Glu | Ala | Glu | Ala | Cys | Asp | Val | Gly | Phe | Arg | Glu | Val | Arg |
| | | | | 325 | | | | | 330 | | | | | 335 | |

-continued

```
Ile Glu Asn Gly Leu Leu Leu Asn Gly Lys Pro Leu Leu Ile Arg
            340                 345                 350

Gly Val Asn Arg His Glu His His Pro Leu His Gly Gln Val Met Asp
            355                 360                 365

Glu Gln Thr Met Val Gln Asp Ile Leu Leu Met Lys Gln Asn Asn Phe
370                 375                 380

Asn Ala Val Arg Cys Ser His Tyr Pro Asn His Pro Leu Trp Tyr Thr
385                 390                 395                 400

Leu Cys Asp Arg Tyr Gly Leu Tyr Val Val Asp Glu Ala Asn Ile Glu
                405                 410                 415

Thr His Gly Met Val Pro Met Asn Arg Leu Thr Asp Asp Pro Arg Trp
            420                 425                 430

Leu Pro Ala Met Ser Glu Arg Val Thr Arg Met Val Gln Arg Asp Arg
            435                 440                 445

Asn His Pro Ser Val Ile Ile Trp Ser Leu Gly Asn Glu Ser Gly His
            450                 455                 460

Gly Ala Asn His Asp Ala Leu Tyr Arg Trp Ile Lys Ser Val Asp Pro
465                 470                 475                 480

Ser Arg Pro Val Gln Tyr Glu Gly Gly Ala Asp Thr Thr Ala Thr
                485                 490                 495

Asp Ile Ile Cys Pro Met Tyr Ala Arg Val Asp Glu Asp Gln Pro Phe
                500                 505                 510

Pro Ala Val Pro Lys Trp Ser Ile Lys Lys Trp Leu Ser Leu Pro Gly
            515                 520                 525

Glu Thr Arg Pro Leu Ile Leu Cys Glu Tyr Ala His Ala Met Gly Asn
530                 535                 540

Ser Leu Gly Gly Phe Ala Lys Tyr Trp Gln Ala Phe Arg Gln Tyr Pro
545                 550                 555                 560

Arg Leu Gln Gly Gly Phe Val Trp Asp Trp Val Asp Gln Ser Leu Ile
                565                 570                 575

Lys Tyr Asp Glu Asn Gly Asn Pro Trp Ser Ala Tyr Gly Gly Asp Phe
            580                 585                 590

Gly Asp Thr Pro Asn Asp Arg Gln Phe Cys Met Asn Gly Leu Val Phe
            595                 600                 605

Ala Asp Arg Thr Pro His Pro Ala Leu Thr Glu Ala Lys His Gln Gln
            610                 615                 620

Gln Phe Phe Gln Phe Arg Leu Ser Gly Gln Thr Ile Glu Val Thr Ser
625                 630                 635                 640

Glu Tyr Leu Phe Arg His Ser Asp Asn Glu Leu Leu His Trp Met Val
                645                 650                 655

Ala Leu Asp Gly Lys Pro Leu Ala Ser Gly Glu Val Pro Leu Asp Val
            660                 665                 670

Ala Pro Gln Gly Lys Gln Leu Ile Glu Leu Pro Glu Leu Pro Gln Pro
            675                 680                 685

Glu Ser Ala Gly Gln Leu Trp Leu Thr Val Arg Val Val Gln Pro Asn
690                 695                 700

Ala Thr Ala Trp Ser Glu Ala Gly His Ile Ser Ala Trp Gln Gln Trp
705                 710                 715                 720

Arg Leu Ala Glu Asn Leu Ser Val Thr Leu Pro Ala Ala Ser His Ala
                725                 730                 735

Ile Pro His Leu Thr Thr Ser Glu Met Asp Phe Cys Ile Glu Leu Gly
            740                 745                 750

Asn Lys Arg Trp Gln Phe Asn Arg Gln Ser Gly Phe Leu Ser Gln Met
```

```
                     755                 760                 765

Trp Ile Gly Asp Lys Lys Gln Leu Leu Thr Pro Leu Arg Asp Gln Phe
    770                 775                 780

Thr Arg Ala Pro Leu Asp Asn Asp Ile Gly Val Ser Glu Ala Thr Arg
785                 790                 795                 800

Ile Asp Pro Asn Ala Trp Val Glu Arg Trp Lys Ala Ala Gly His Tyr
                805                 810                 815

Gln Ala Glu Ala Ala Leu Leu Gln Cys Thr Ala Asp Thr Leu Ala Asp
            820                 825                 830

Ala Val Leu Ile Thr Thr Ala His Ala Trp Gln His Gln Gly Lys Thr
        835                 840                 845

Leu Phe Ile Ser Arg Lys Thr Tyr Arg Ile Asp Gly Ser Gly Gln Met
    850                 855                 860

Ala Ile Thr Val Asp Val Glu Val Ala Ser Asp Thr Pro His Pro Ala
865                 870                 875                 880

Arg Ile Gly Leu Asn Cys Gln Leu Ala Gln Val Ala Glu Arg Val Asn
                885                 890                 895

Trp Leu Gly Leu Gly Pro Gln Glu Asn Tyr Pro Asp Arg Leu Thr Ala
            900                 905                 910

Ala Cys Phe Asp Arg Trp Asp Leu Pro Leu Ser Asp Met Tyr Thr Pro
        915                 920                 925

Tyr Val Phe Pro Ser Glu Asn Gly Leu Arg Cys Gly Thr Arg Glu Leu
    930                 935                 940

Asn Tyr Gly Pro His Gln Trp Arg Gly Asp Phe Gln Phe Asn Ile Ser
945                 950                 955                 960

Arg Tyr Ser Gln Gln Gln Leu Met Glu Thr Ser His Arg His Leu Leu
                965                 970                 975

His Ala Glu Glu Gly Thr Trp Leu Asn Ile Asp Gly Phe His Met Gly
            980                 985                 990

Ile Gly Gly Asp Asp Ser Trp Ser Pro Ser Val Ser Ala Glu Phe Gln
        995                1000                1005

Leu Ser Ala Gly Arg Tyr His Tyr Gln Leu Val Trp Cys Gln Lys
    1010                1015                1020

<210> SEQ ID NO 22
<211> LENGTH: 49
<212> TYPE: PRT
<213> ORGANISM: homo sapiens

<400> SEQUENCE: 22

Tyr Leu Tyr Gln Trp Leu Gly Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 23
<211> LENGTH: 49
<212> TYPE: PRT
<213> ORGANISM: homo sapiens
<220> FEATURE:
<221> NAME/KEY: VARIANT
<222> LOCATION: (17)..(17)
<223> OTHER INFORMATION: Xaa can be any amino acid.
<220> FEATURE:
```

```
<221> NAME/KEY: VARIANT
<222> LOCATION: (17)..(17)
<223> OTHER INFORMATION: If Xaa at positions 17, 21, and 24 are all
      Glu, then Glu17 is not carboxylated, or less than 50% of Glu21 is
      carboxylated, and/or less than 50% of Glu24 is carboxylated, or 1
      to 7 positions other than 17, 21, and 24 are any aa other than the
      specified aa.
<220> FEATURE:
<221> NAME/KEY: VARIANT
<222> LOCATION: (21)..(21)
<223> OTHER INFORMATION: Xaa can be any amino acid.
<220> FEATURE:
<221> NAME/KEY: VARIANT
<222> LOCATION: (21)..(21)
<223> OTHER INFORMATION: If Xaa at positions 17, 21, and 24 are all Glu,
      then Glu17 is not carboxylated, or less than 50% of Glu21 is
      carboxylated, and/or less than 50% of Glu24 is carboxylated, or 1
      to 7 positions other than 17, 21, and 24 are any aa other than the
      specified aa.
<220> FEATURE:
<221> NAME/KEY: VARIANT
<222> LOCATION: (24)..(24)
<223> OTHER INFORMATION: Xaa can be any amino acid.
<220> FEATURE:
<221> NAME/KEY: VARIANT
<222> LOCATION: (24)..(24)
<223> OTHER INFORMATION: If Xaa at positions 17, 21, and 24 are all Glu,
      then Glu17 is not carboxylated, or less than 50% of Glu21 is
      carboxylated, and/or less than 50% of Glu24 is carboxylated, or 1
      to 7 positions other than 17, 21, and 24 are any aa other than the
      specified aa.

<400> SEQUENCE: 23

Tyr Leu Tyr Gln Trp Leu Gly Ala Pro Val Pro Tyr Pro Asp Pro Leu
1               5                   10                  15

Xaa Pro Arg Arg Xaa Val Cys Xaa Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 24
<211> LENGTH: 5136
<212> TYPE: DNA
<213> ORGANISM: Rattus norvegicus
<220> FEATURE:
<221> NAME/KEY: CDS
<222> LOCATION: (1)..(5136)

<400> SEQUENCE: 24 atg agg ccc ctg att ctg tta gct gcc ctc ctc tgg ctc cag ggc ttt      48
Met Arg Pro Leu Ile Leu Leu Ala Ala Leu Leu Trp Leu Gln Gly Phe
1               5                   10                  15 ttg gcc gag gac gac gca tgc tca tcc ttg gaa ggg agc cca gac agg      96
Leu Ala Glu Asp Asp Ala Cys Ser Ser Leu Glu Gly Ser Pro Asp Arg
            20                  25                  30 cag ggt gga ggt cca ctt ctg agt gtg aac gtc agt agc cat gga aag     144
Gln Gly Gly Gly Pro Leu Leu Ser Val Asn Val Ser Ser His Gly Lys
        35                  40                  45 tct acc agc ctg ttt ctg agc tgg gta gct gca gag ctg ggc gga ttt     192
Ser Thr Ser Leu Phe Leu Ser Trp Val Ala Ala Glu Leu Gly Gly Phe
    50                  55                  60 gac tat gcc ctc agc ctc agg agt gtg aac tcc tca ggt tct cca gaa     240
Asp Tyr Ala Leu Ser Leu Arg Ser Val Asn Ser Ser Gly Ser Pro Glu
65                  70                  75                  80 ggg caa cag ctc cag gct cac aca aat gag tcc ggc ttt gag ttc cat     288
Gly Gln Gln Leu Gln Ala His Thr Asn Glu Ser Gly Phe Glu Phe His
                85                  90                  95
```

| | | | | | | | | | | | | | | | | |
|---|---|---|---|---|---|---|---|---|---|---|---|---|---|---|---|---|
| ggc | ctg | gtg | cca | ggg | agt | cgc | tac | cag | cta | aaa | ctg | act | gtc | cta | aga | 336 |
| Gly | Leu | Val | Pro | Gly | Ser | Arg | Tyr | Gln | Leu | Lys | Leu | Thr | Val | Leu | Arg | |
| | | | 100 | | | | | 105 | | | | | 110 | | | |
| ccc | tgt | tgg | cag | aat | gtc | aca | att | acc | ctc | act | gcc | cga | act | gcc | ccg | 384 |
| Pro | Cys | Trp | Gln | Asn | Val | Thr | Ile | Thr | Leu | Thr | Ala | Arg | Thr | Ala | Pro | |
| | | 115 | | | | | 120 | | | | | 125 | | | | |
| aca | gtg | gtc | cgt | gga | ctg | cag | ctg | cat | agc | gct | ggg | agc | cca | gcc | agg | 432 |
| Thr | Val | Val | Arg | Gly | Leu | Gln | Leu | His | Ser | Ala | Gly | Ser | Pro | Ala | Arg | |
| | 130 | | | | | 135 | | | | | 140 | | | | | |
| ctg | gaa | gcc | tcg | tgg | agt | gat | gcc | cct | gga | gat | caa | gac | agc | tac | caa | 480 |
| Leu | Glu | Ala | Ser | Trp | Ser | Asp | Ala | Pro | Gly | Asp | Gln | Asp | Ser | Tyr | Gln | |
| 145 | | | | | 150 | | | | | 155 | | | | | 160 | |
| ctt | ctc | ctc | tac | cac | ctg | gaa | tcc | caa | act | ctg | gca | tgc | aat | gtc | tct | 528 |
| Leu | Leu | Leu | Tyr | His | Leu | Glu | Ser | Gln | Thr | Leu | Ala | Cys | Asn | Val | Ser | |
| | | | | 165 | | | | | 170 | | | | | 175 | | |
| gtg | tcc | cct | gac | acc | ctg | tct | tac | agt | ttt | ggc | gac | ctt | ttg | cca | ggt | 576 |
| Val | Ser | Pro | Asp | Thr | Leu | Ser | Tyr | Ser | Phe | Gly | Asp | Leu | Leu | Pro | Gly | |
| | | | | 180 | | | | | 185 | | | | | 190 | | |
| act | cag | tat | gtc | ttg | gag | gtt | atc | acc | tgg | gct | ggc | agt | ctc | cat | gcg | 624 |
| Thr | Gln | Tyr | Val | Leu | Glu | Val | Ile | Thr | Trp | Ala | Gly | Ser | Leu | His | Ala | |
| | | | 195 | | | | | 200 | | | | | 205 | | | |
| aag | act | agt | atc | ctc | cag | tgg | aca | gag | cct | gtc | cct | cct | gat | cac | cta | 672 |
| Lys | Thr | Ser | Ile | Leu | Gln | Trp | Thr | Glu | Pro | Val | Pro | Pro | Asp | His | Leu | |
| | 210 | | | | | 215 | | | | | 220 | | | | | |
| gca | cta | cgt | gcc | ttg | ggt | acc | agt | agc | ctg | caa | gcc | ttc | tgg | aac | agc | 720 |
| Ala | Leu | Arg | Ala | Leu | Gly | Thr | Ser | Ser | Leu | Gln | Ala | Phe | Trp | Asn | Ser | |
| 225 | | | | | 230 | | | | | 235 | | | | | 240 | |
| tct | gaa | ggg | gcc | acc | tcg | ttt | cac | ctg | atg | ctc | aca | gac | ctc | ctc | ggg | 768 |
| Ser | Glu | Gly | Ala | Thr | Ser | Phe | His | Leu | Met | Leu | Thr | Asp | Leu | Leu | Gly | |
| | | | | 245 | | | | | 250 | | | | | 255 | | |
| ggc | acc | aac | acg | act | gcg | gtg | atc | aga | caa | ggg | gtc | tcg | acc | cac | acc | 816 |
| Gly | Thr | Asn | Thr | Thr | Ala | Val | Ile | Arg | Gln | Gly | Val | Ser | Thr | His | Thr | |
| | | | | 260 | | | | | 265 | | | | | 270 | | |
| ttt | ctt | cac | cta | tct | ccg | ggt | aca | cct | cat | gag | ctg | aag | att | tgt | gct | 864 |
| Phe | Leu | His | Leu | Ser | Pro | Gly | Thr | Pro | His | Glu | Leu | Lys | Ile | Cys | Ala | |
| | | | 275 | | | | | 280 | | | | | 285 | | | |
| tct | gct | ggg | ccc | cac | cag | atc | tgg | gga | ccc | agt | gcc | acc | gag | tgg | acc | 912 |
| Ser | Ala | Gly | Pro | His | Gln | Ile | Trp | Gly | Pro | Ser | Ala | Thr | Glu | Trp | Thr | |
| | 290 | | | | | 295 | | | | | 300 | | | | | |
| tat | ccc | tct | tac | cca | tct | gac | ctg | gtg | ctg | act | ccc | tta | cgg | aat | gag | 960 |
| Tyr | Pro | Ser | Tyr | Pro | Ser | Asp | Leu | Val | Leu | Thr | Pro | Leu | Arg | Asn | Glu | |
| 305 | | | | | 310 | | | | | 315 | | | | | 320 | |
| ctc | tgg | gcc | agc | tgg | aag | gca | ggg | ctg | gga | gcc | cgg | gac | ggc | tat | gta | 1008 |
| Leu | Trp | Ala | Ser | Trp | Lys | Ala | Gly | Leu | Gly | Ala | Arg | Asp | Gly | Tyr | Val | |
| | | | | 325 | | | | | 330 | | | | | 335 | | |
| ctg | aag | tta | agt | ggg | cca | atg | gag | agt | acg | tct | acc | ctg | ggc | ccg | gaa | 1056 |
| Leu | Lys | Leu | Ser | Gly | Pro | Met | Glu | Ser | Thr | Ser | Thr | Leu | Gly | Pro | Glu | |
| | | | | 340 | | | | | 345 | | | | | 350 | | |
| gag | tgc | aat | gca | gtc | ttc | cca | ggg | ccc | ctg | cct | ccg | gga | cac | tac | act | 1104 |
| Glu | Cys | Asn | Ala | Val | Phe | Pro | Gly | Pro | Leu | Pro | Pro | Gly | His | Tyr | Thr | |
| | | | 355 | | | | | 360 | | | | | 365 | | | |
| ttg | cag | ctg | aag | gtt | cta | gct | gga | cct | tat | gat | gcc | tgg | gtg | gag | ggc | 1152 |
| Leu | Gln | Leu | Lys | Val | Leu | Ala | Gly | Pro | Tyr | Asp | Ala | Trp | Val | Glu | Gly | |
| | 370 | | | | | 375 | | | | | 380 | | | | | |
| agt | acc | tgg | ctg | gct | gaa | tct | gct | gcc | ctt | ccc | agg | gag | gtc | cct | ggt | 1200 |
| Ser | Thr | Trp | Leu | Ala | Glu | Ser | Ala | Ala | Leu | Pro | Arg | Glu | Val | Pro | Gly | |
| 385 | | | | | 390 | | | | | 395 | | | | | 400 | |
| gcc | aga | ctg | tgg | cta | gat | gga | ctg | gaa | gct | tcc | aag | cag | cct | ggg | aga | 1248 |
| Ala | Arg | Leu | Trp | Leu | Asp | Gly | Leu | Glu | Ala | Ser | Lys | Gln | Pro | Gly | Arg | |

-continued

|  | 405 |  |  |  |  |  | 410 |  |  |  |  |  | 415 |  |  |
|---|---|---|---|---|---|---|---|---|---|---|---|---|---|---|---|
| cgg | gcg | cta | ctc | tat | tct | gac | gat | gcc | cca | ggc | tcc | cta | ggg | aac | atc | 1296 |
| Arg | Ala | Leu | Leu | Tyr | Ser | Asp | Asp | Ala | Pro | Gly | Ser | Leu | Gly | Asn | Ile |
|  |  | 420 |  |  |  |  | 425 |  |  |  |  | 430 |  |  |  |

| tct | gtg | ccc | tct | ggt | gcc | act | cac | gtc | att | ttc | tgt | ggc | ctg | gta | cct | 1344 |
| Ser | Val | Pro | Ser | Gly | Ala | Thr | His | Val | Ile | Phe | Cys | Gly | Leu | Val | Pro |
|  |  |  | 435 |  |  |  |  | 440 |  |  |  |  | 445 |  |  |

| gga | gcc | cac | tat | agg | gtg | gac | att | gcc | tca | tcc | acg | ggg | gac | atc | tct | 1392 |
| Gly | Ala | His | Tyr | Arg | Val | Asp | Ile | Ala | Ser | Ser | Thr | Gly | Asp | Ile | Ser |
|  | 450 |  |  |  |  | 455 |  |  |  |  | 460 |  |  |  |  |

| cag | agc | atc | tca | ggc | tat | aca | agt | ccc | ctg | cca | ccg | cag | tca | ctg | gag | 1440 |
| Gln | Ser | Ile | Ser | Gly | Tyr | Thr | Ser | Pro | Leu | Pro | Pro | Gln | Ser | Leu | Glu |
| 465 |  |  |  |  | 470 |  |  |  |  | 475 |  |  |  |  | 480 |

| gtc | atc | agc | agg | agc | agc | cca | tct | gac | ctg | act | att | gct | tgg | ggt | cca | 1488 |
| Val | Ile | Ser | Arg | Ser | Ser | Pro | Ser | Asp | Leu | Thr | Ile | Ala | Trp | Gly | Pro |
|  |  |  |  | 485 |  |  |  |  | 490 |  |  |  |  | 495 |  |

| gca | cca | ggg | cag | ctg | gaa | ggt | tat | aag | gtt | acc | tgg | cat | cag | gat | ggc | 1536 |
| Ala | Pro | Gly | Gln | Leu | Glu | Gly | Tyr | Lys | Val | Thr | Trp | His | Gln | Asp | Gly |
|  |  |  | 500 |  |  |  |  | 505 |  |  |  |  | 510 |  |  |

| agc | cag | agg | tct | cct | ggc | gac | ctt | gtt | gac | ttg | ggc | cct | gac | act | ttg | 1584 |
| Ser | Gln | Arg | Ser | Pro | Gly | Asp | Leu | Val | Asp | Leu | Gly | Pro | Asp | Thr | Leu |
|  |  | 515 |  |  |  |  | 520 |  |  |  |  | 525 |  |  |  |

| agc | ctg | act | ctg | aaa | tct | ctg | gta | ccc | ggc | tcc | tgc | tac | acc | gtg | tca | 1632 |
| Ser | Leu | Thr | Leu | Lys | Ser | Leu | Val | Pro | Gly | Ser | Cys | Tyr | Thr | Val | Ser |
| 530 |  |  |  |  | 535 |  |  |  |  | 540 |  |  |  |  |  |

| gca | tgg | gcc | tgg | gcc | ggg | aac | ctc | gac | tct | gac | tct | cag | aag | att | cac | 1680 |
| Ala | Trp | Ala | Trp | Ala | Gly | Asn | Leu | Asp | Ser | Asp | Ser | Gln | Lys | Ile | His |
| 545 |  |  |  |  | 550 |  |  |  |  | 555 |  |  |  |  | 560 |

| agc | tgc | acc | cgc | ccc | gct | cct | ccc | acc | aac | ctg | agt | ctg | ggc | ttt | gcc | 1728 |
| Ser | Cys | Thr | Arg | Pro | Ala | Pro | Pro | Thr | Asn | Leu | Ser | Leu | Gly | Phe | Ala |
|  |  |  | 565 |  |  |  |  | 570 |  |  |  |  | 575 |  |  |

| cac | cag | cct | gcg | gca | ctg | aag | gct | tcc | tgg | tat | cac | cca | ccg | ggt | ggc | 1776 |
| His | Gln | Pro | Ala | Ala | Leu | Lys | Ala | Ser | Trp | Tyr | His | Pro | Pro | Gly | Gly |
|  |  | 580 |  |  |  |  | 585 |  |  |  |  | 590 |  |  |  |

| agg | gat | gcc | ttt | cac | tta | cgg | ctt | tac | agg | ctg | agg | cct | ctg | aca | ctg | 1824 |
| Arg | Asp | Ala | Phe | His | Leu | Arg | Leu | Tyr | Arg | Leu | Arg | Pro | Leu | Thr | Leu |
|  |  | 595 |  |  |  |  | 600 |  |  |  |  | 605 |  |  |  |

| gaa | agt | gag | aag | gtc | cta | cct | cgg | gag | gcc | cag | aac | ttc | tcc | tgg | gcc | 1872 |
| Glu | Ser | Glu | Lys | Val | Leu | Pro | Arg | Glu | Ala | Gln | Asn | Phe | Ser | Trp | Ala |
| 610 |  |  |  |  | 615 |  |  |  |  | 620 |  |  |  |  |  |

| cag | ctg | act | gca | ggc | tgt | gag | ttc | cag | gta | cag | ctg | tct | acc | ttg | tgg | 1920 |
| Gln | Leu | Thr | Ala | Gly | Cys | Glu | Phe | Gln | Val | Gln | Leu | Ser | Thr | Leu | Trp |
| 625 |  |  |  |  | 630 |  |  |  |  | 635 |  |  |  |  | 640 |

| ggg | tct | gag | aga | agc | agc | agt | gcc | aac | gcc | aca | ggc | tgg | aca | ccc | cct | 1968 |
| Gly | Ser | Glu | Arg | Ser | Ser | Ser | Ala | Asn | Ala | Thr | Gly | Trp | Thr | Pro | Pro |
|  |  |  |  | 645 |  |  |  |  | 650 |  |  |  |  | 655 |  |

| tca | gct | cct | aca | ctg | gta | aac | gtg | acc | agc | gat | gct | cct | acc | cag | ctc | 2016 |
| Ser | Ala | Pro | Thr | Leu | Val | Asn | Val | Thr | Ser | Asp | Ala | Pro | Thr | Gln | Leu |
|  |  |  | 660 |  |  |  |  | 665 |  |  |  |  | 670 |  |  |

| caa | gta | tcc | tgg | gcc | cac | gtt | cct | ggg | ggc | cgg | agc | cgc | tac | caa | gtg | 2064 |
| Gln | Val | Ser | Trp | Ala | His | Val | Pro | Gly | Gly | Arg | Ser | Arg | Tyr | Gln | Val |
|  |  | 675 |  |  |  |  | 680 |  |  |  |  | 685 |  |  |  |

| acc | cta | tac | cag | gag | agt | acc | cgg | aca | gcc | acc | agc | atc | atg | ggg | ccc | 2112 |
| Thr | Leu | Tyr | Gln | Glu | Ser | Thr | Arg | Thr | Ala | Thr | Ser | Ile | Met | Gly | Pro |
|  | 690 |  |  |  |  | 695 |  |  |  |  | 700 |  |  |  |  |

| aag | gaa | gat | ggc | acg | agc | ttt | ttg | ggt | ttg | act | cct | ggc | act | aag | tac | 2160 |
| Lys | Glu | Asp | Gly | Thr | Ser | Phe | Leu | Gly | Leu | Thr | Pro | Gly | Thr | Lys | Tyr |
| 705 |  |  |  |  | 710 |  |  |  |  | 715 |  |  |  |  | 720 |

| aag | gtg | gaa | gtc | atc | tcc | tgg | gct | ggg | ccc | ctc | tac | act | gca | gca | gcc | 2208 |

```
                Lys Val Glu Val Ile Ser Trp Ala Gly Pro Leu Tyr Thr Ala Ala Ala
                                725                 730                 735 aac gtt tct gcc tgg acc tac cca ctc ata ccc aat gag ctg ctc gtg              2256
Asn Val Ser Ala Trp Thr Tyr Pro Leu Ile Pro Asn Glu Leu Leu Val
            740                 745                 750 tca atg cag gca ggc agt gct gtg gtt aac ctg gcc tgg ccc agt ggt              2304
Ser Met Gln Ala Gly Ser Ala Val Val Asn Leu Ala Trp Pro Ser Gly
        755                 760                 765 ccc ctg ggg caa ggg gca tgc cac gcc caa ctc tca gat gct gga cac              2352
Pro Leu Gly Gln Gly Ala Cys His Ala Gln Leu Ser Asp Ala Gly His
    770                 775                 780 ctc tca tgg gag caa ccc ctg aaa cta ggc caa gag ctc ttc atg cta              2400
Leu Ser Trp Glu Gln Pro Leu Lys Leu Gly Gln Glu Leu Phe Met Leu
785                 790                 795                 800 agg gat ctc aca cca gga cat acc atc tcg atg tca gtg agg tgt cgg              2448
Arg Asp Leu Thr Pro Gly His Thr Ile Ser Met Ser Val Arg Cys Arg
                805                 810                 815 gca ggg ccg ctc cag gcc tct acg cac ctt gtg gtg ctg tct gtg gag              2496
Ala Gly Pro Leu Gln Ala Ser Thr His Leu Val Val Leu Ser Val Glu
            820                 825                 830 cct ggc cct gtg gaa gat gtg ctc tgt cat cca gag gcc acc tac ctg              2544
Pro Gly Pro Val Glu Asp Val Leu Cys His Pro Glu Ala Thr Tyr Leu
        835                 840                 845 gcc ctg aac tgg acg atg cct gct gga gac gtg gat gtc tgt ctg gtg              2592
Ala Leu Asn Trp Thr Met Pro Ala Gly Asp Val Asp Val Cys Leu Val
    850                 855                 860 gtg gta gag cgg ctg gtg ccg gga ggg ggc act cat ttt gtc ttc cag              2640
Val Val Glu Arg Leu Val Pro Gly Gly Gly Thr His Phe Val Phe Gln
865                 870                 875                 880 gtc aac acc tca ggg gat gct ctt ctg ttg ccc aac ttg atg ccc acc              2688
Val Asn Thr Ser Gly Asp Ala Leu Leu Leu Pro Asn Leu Met Pro Thr
                885                 890                 895 act tct tac cgc ctt agc ctc acc gtt ctg ggc agg aat agt cgg tgg              2736
Thr Ser Tyr Arg Leu Ser Leu Thr Val Leu Gly Arg Asn Ser Arg Trp
            900                 905                 910 agc cgg gcg gtt tcc ctg gtg tgc agt act tct gct gag gct tgg cac              2784
Ser Arg Ala Val Ser Leu Val Cys Ser Thr Ser Ala Glu Ala Trp His
        915                 920                 925 ccc cca gag cta gct gag ccc ccc cag gtg gag ctg ggg aca ggg atg              2832
Pro Pro Glu Leu Ala Glu Pro Pro Gln Val Glu Leu Gly Thr Gly Met
    930                 935                 940 ggt gtg aca gtc atg cgt ggc atg ttt ggt aaa gat gac ggg cag atc              2880
Gly Val Thr Val Met Arg Gly Met Phe Gly Lys Asp Asp Gly Gln Ile
945                 950                 955                 960 cag tgg tat ggc ata att gcc acc atc aac atg acg ctg gcc cag cct              2928
Gln Trp Tyr Gly Ile Ile Ala Thr Ile Asn Met Thr Leu Ala Gln Pro
                965                 970                 975 tcc cgg gaa gcc atc aat tac aca tgg tat gac cac tac tat aga gga              2976
Ser Arg Glu Ala Ile Asn Tyr Thr Trp Tyr Asp His Tyr Tyr Arg Gly
            980                 985                 990 tgt gag tcc ttc ctg gct ctc ctg  ttc cca aac ccc ttc  tac cca gag            3024
Cys Glu Ser Phe Leu Ala Leu Leu Phe Pro Asn Pro Phe Tyr Pro Glu
        995                 1000                 1005 cct tgg  gct ggg cca aga tcc  tgg aca gta cct gtg  ggt act gag              3069
Pro Trp Ala Gly Pro Arg Ser Trp Thr Val Pro Val Gly Thr Glu
    1010                 1015                 1020 gac tgt  gac aac acc caa gag  ata tgc aat ggg cgt  ctc aag tca              3114
Asp Cys Asp Asn Thr Gln Glu Ile Cys Asn Gly Arg Leu Lys Ser
    1025                 1030                 1035
```

| | | | | | | | | | | |
|---|---|---|---|---|---|---|---|---|---|---|
| ggc | ttc | cag | tat | agg | ttc | agc | gtt | gtg | gcc | ttt | agt | agg | ctc | aac | 3159 |
| Gly | Phe | Gln | Tyr | Arg | Phe | Ser | Val | Val | Ala | Phe | Ser | Arg | Leu | Asn | |
| 1040 | | | | | 1045 | | | | | 1050 | | | | | |

| | | | | | | | | | | |
|---|---|---|---|---|---|---|---|---|---|---|
| act | cca | gag | acc | atc | ctc | gcc | ttc | tcg | gcc | ttc | tca | gag | ccc | cgg | 3204 |
| Thr | Pro | Glu | Thr | Ile | Leu | Ala | Phe | Ser | Ala | Phe | Ser | Glu | Pro | Arg | |
| 1055 | | | | | 1060 | | | | | 1065 | | | | | |

| | | | | | | | | | | |
|---|---|---|---|---|---|---|---|---|---|---|
| gcc | agc | atc | tct | ctg | gcg | atc | att | ccc | ctg | aca | gtt | atg | ctg | ggg | 3249 |
| Ala | Ser | Ile | Ser | Leu | Ala | Ile | Ile | Pro | Leu | Thr | Val | Met | Leu | Gly | |
| 1070 | | | | | 1075 | | | | | 1080 | | | | | |

| | | | | | | | | | | |
|---|---|---|---|---|---|---|---|---|---|---|
| gct | gtg | gtg | ggc | agc | att | gtc | att | gtg | tgt | gca | gtg | cta | tgc | ttg | 3294 |
| Ala | Val | Val | Gly | Ser | Ile | Val | Ile | Val | Cys | Ala | Val | Leu | Cys | Leu | |
| 1085 | | | | | 1090 | | | | | 1095 | | | | | |

| | | | | | | | | | | |
|---|---|---|---|---|---|---|---|---|---|---|
| ctc | cgc | tgg | cgg | tgc | ctg | aag | gga | cca | aga | tca | gag | aag | gat | ggc | 3339 |
| Leu | Arg | Trp | Arg | Cys | Leu | Lys | Gly | Pro | Arg | Ser | Glu | Lys | Asp | Gly | |
| 1100 | | | | | 1105 | | | | | 1110 | | | | | |

| | | | | | | | | | | |
|---|---|---|---|---|---|---|---|---|---|---|
| ttt | tcc | aag | gag | ctg | atg | cct | tac | aac | ctg | tgg | cgg | acc | cat | cgg | 3384 |
| Phe | Ser | Lys | Glu | Leu | Met | Pro | Tyr | Asn | Leu | Trp | Arg | Thr | His | Arg | |
| 1115 | | | | | 1120 | | | | | 1125 | | | | | |

| | | | | | | | | | | |
|---|---|---|---|---|---|---|---|---|---|---|
| cct | atc | ccc | atc | cat | agc | ttc | cgg | cag | agc | tat | gag | gcc | aag | agc | 3429 |
| Pro | Ile | Pro | Ile | His | Ser | Phe | Arg | Gln | Ser | Tyr | Glu | Ala | Lys | Ser | |
| 1130 | | | | | 1135 | | | | | 1140 | | | | | |

| | | | | | | | | | | |
|---|---|---|---|---|---|---|---|---|---|---|
| gca | cat | gca | cac | cag | acc | ttc | ttc | cag | gaa | ttt | gag | gag | ttg | aag | 3474 |
| Ala | His | Ala | His | Gln | Thr | Phe | Phe | Gln | Glu | Phe | Glu | Glu | Leu | Lys | |
| 1145 | | | | | 1150 | | | | | 1155 | | | | | |

| | | | | | | | | | | |
|---|---|---|---|---|---|---|---|---|---|---|
| gag | gta | ggc | aag | gac | cag | ccc | cga | cta | gag | gct | gag | cat | ccg | gac | 3519 |
| Glu | Val | Gly | Lys | Asp | Gln | Pro | Arg | Leu | Glu | Ala | Glu | His | Pro | Asp | |
| 1160 | | | | | 1165 | | | | | 1170 | | | | | |

| | | | | | | | | | | |
|---|---|---|---|---|---|---|---|---|---|---|
| aac | atc | atc | aag | aac | cgg | tac | cca | cac | gtg | ctg | ccc | tat | gac | cac | 3564 |
| Asn | Ile | Ile | Lys | Asn | Arg | Tyr | Pro | His | Val | Leu | Pro | Tyr | Asp | His | |
| 1175 | | | | | 1180 | | | | | 1185 | | | | | |

| | | | | | | | | | | |
|---|---|---|---|---|---|---|---|---|---|---|
| tcc | agg | gtc | agg | ctg | acc | cag | cta | cca | gga | gag | cct | cat | tct | gac | 3609 |
| Ser | Arg | Val | Arg | Leu | Thr | Gln | Leu | Pro | Gly | Glu | Pro | His | Ser | Asp | |
| 1190 | | | | | 1195 | | | | | 1200 | | | | | |

| | | | | | | | | | | |
|---|---|---|---|---|---|---|---|---|---|---|
| tac | atc | aat | gcc | aac | ttc | atc | cca | ggc | tat | agc | cac | aca | cag | gag | 3654 |
| Tyr | Ile | Asn | Ala | Asn | Phe | Ile | Pro | Gly | Tyr | Ser | His | Thr | Gln | Glu | |
| 1205 | | | | | 1210 | | | | | 1215 | | | | | |

| | | | | | | | | | | |
|---|---|---|---|---|---|---|---|---|---|---|
| atc | att | gcc | acc | cag | ggg | cct | ctc | aaa | aag | acg | cta | gag | gac | ttc | 3699 |
| Ile | Ile | Ala | Thr | Gln | Gly | Pro | Leu | Lys | Lys | Thr | Leu | Glu | Asp | Phe | |
| 1220 | | | | | 1225 | | | | | 1230 | | | | | |

| | | | | | | | | | | |
|---|---|---|---|---|---|---|---|---|---|---|
| tgg | cgg | ttg | gta | tgg | gag | cag | caa | gtc | cac | gtg | atc | atc | atg | ctg | 3744 |
| Trp | Arg | Leu | Val | Trp | Glu | Gln | Gln | Val | His | Val | Ile | Ile | Met | Leu | |
| 1235 | | | | | 1240 | | | | | 1245 | | | | | |

| | | | | | | | | | | |
|---|---|---|---|---|---|---|---|---|---|---|
| act | gta | ggc | atg | gag | aac | ggg | cgg | gta | ctg | tgt | gag | cac | tac | tgg | 3789 |
| Thr | Val | Gly | Met | Glu | Asn | Gly | Arg | Val | Leu | Cys | Glu | His | Tyr | Trp | |
| 1250 | | | | | 1255 | | | | | 1260 | | | | | |

| | | | | | | | | | | |
|---|---|---|---|---|---|---|---|---|---|---|
| cca | gcc | aac | tcc | acg | cct | gtt | act | cac | ggt | cac | atc | acc | atc | cac | 3834 |
| Pro | Ala | Asn | Ser | Thr | Pro | Val | Thr | His | Gly | His | Ile | Thr | Ile | His | |
| 1265 | | | | | 1270 | | | | | 1275 | | | | | |

| | | | | | | | | | | |
|---|---|---|---|---|---|---|---|---|---|---|
| ctc | ctg | gca | gag | gag | cct | gag | gat | gag | tgg | acc | agg | agg | gaa | ttc | 3879 |
| Leu | Leu | Ala | Glu | Glu | Pro | Glu | Asp | Glu | Trp | Thr | Arg | Arg | Glu | Phe | |
| 1280 | | | | | 1285 | | | | | 1290 | | | | | |

| | | | | | | | | | | |
|---|---|---|---|---|---|---|---|---|---|---|
| cag | ctg | cag | cac | ggt | acc | gag | caa | aaa | cag | agg | cga | gtg | aag | cag | 3924 |
| Gln | Leu | Gln | His | Gly | Thr | Glu | Gln | Lys | Gln | Arg | Arg | Val | Lys | Gln | |
| 1295 | | | | | 1300 | | | | | 1305 | | | | | |

| | | | | | | | | | | |
|---|---|---|---|---|---|---|---|---|---|---|
| ctg | cag | ttc | act | acc | tgg | cca | gac | cac | agt | gtc | ccg | gag | gct | ccc | 3969 |
| Leu | Gln | Phe | Thr | Thr | Trp | Pro | Asp | His | Ser | Val | Pro | Glu | Ala | Pro | |
| 1310 | | | | | 1315 | | | | | 1320 | | | | | |

| | | | | | | | | | | |
|---|---|---|---|---|---|---|---|---|---|---|
| agc | tct | ctg | ctc | gct | ttt | gta | gaa | ctg | gta | cag | gag | cag | gtg | cag | 4014 |
| Ser | Ser | Leu | Leu | Ala | Phe | Val | Glu | Leu | Val | Gln | Glu | Gln | Val | Gln | |
| 1325 | | | | | 1330 | | | | | 1335 | | | | | |

| | | | | | | | | | | |
|---|---|---|---|---|---|---|---|---|---|---|
| gcc | act | cag | ggc | aag | gga | ccc | atc | ctg | gtg | cat | tgc | agt | gct | ggc | 4059 |
| Ala | Thr | Gln | Gly | Lys | Gly | Pro | Ile | Leu | Val | His | Cys | Ser | Ala | Gly | |
| | 1340 | | | | 1345 | | | | | 1350 | | | | | |

```
gcc act cag ggc aag gga ccc atc ctg gtg cat tgc agt gct ggc      4059
Ala Thr Gln Gly Lys Gly Pro Ile Leu Val His Cys Ser Ala Gly
    1340            1345                1350 gtg ggg agg aca ggc acc ttt gtg gct ctc ttg cgg cta ctg cga      4104
Val Gly Arg Thr Gly Thr Phe Val Ala Leu Leu Arg Leu Leu Arg
1355            1360                1365 caa cta gag gaa gag aag gtg gcc gat gtg ttc aac act gtg tac      4149
Gln Leu Glu Glu Glu Lys Val Ala Asp Val Phe Asn Thr Val Tyr
    1370            1375                1380 ata ctc cgg ttg cac cgg ccc ctc atg atc cag acc ctg agt caa      4194
Ile Leu Arg Leu His Arg Pro Leu Met Ile Gln Thr Leu Ser Gln
1385            1390                1395 tac atc ttc ctg cac agt tgc ctg ctg aac aag att ctg gaa ggg      4239
Tyr Ile Phe Leu His Ser Cys Leu Leu Asn Lys Ile Leu Glu Gly
    1400            1405                1410 ccc cct gac agc tcc gac tcc ggc ccc atc tct gtg atg gat ttt      4284
Pro Pro Asp Ser Ser Asp Ser Gly Pro Ile Ser Val Met Asp Phe
1415            1420                1425 gca cag gct tgt gcc aag agg gca gcc aac gcc aat gct ggt ttc      4329
Ala Gln Ala Cys Ala Lys Arg Ala Ala Asn Ala Asn Ala Gly Phe
    1430            1435                1440 ttg aag gag tac aag ctc ctg aag cag gcc atc aag gat ggg act      4374
Leu Lys Glu Tyr Lys Leu Leu Lys Gln Ala Ile Lys Asp Gly Thr
1445            1450                1455 ggc tct ctg ctg ccc cct cct gac tac aat cag aac agc att gtc      4419
Gly Ser Leu Leu Pro Pro Pro Asp Tyr Asn Gln Asn Ser Ile Val
    1460            1465                1470 tcc cgt cgt cat tct cag gag cag ttc gcc ctg gtg gag gag tgc      4464
Ser Arg Arg His Ser Gln Glu Gln Phe Ala Leu Val Glu Glu Cys
1475            1480                1485 cct gag gat agc atg ctg gaa gcc tca ctc ttc cct ggt ggt ccg      4509
Pro Glu Asp Ser Met Leu Glu Ala Ser Leu Phe Pro Gly Gly Pro
    1490            1495                1500 tct ggt tgt gat cat gtg gtg ctg act ggc tca gcc gga cca aag      4554
Ser Gly Cys Asp His Val Val Leu Thr Gly Ser Ala Gly Pro Lys
1505            1510                1515 gaa ctc tgg gaa atg gtg tgg gag cat gat gcc cat gtg ctc gtc      4599
Glu Leu Trp Glu Met Val Trp Glu His Asp Ala His Val Leu Val
    1520            1525                1530 tcc ctg ggc ctg cct gat acc aag gag aag cca cca gac atc tgg      4644
Ser Leu Gly Leu Pro Asp Thr Lys Glu Lys Pro Pro Asp Ile Trp
1535            1540                1545 cca gtg gag atg cag cct att gtc aca gac atg gtg aca gtg cac      4689
Pro Val Glu Met Gln Pro Ile Val Thr Asp Met Val Thr Val His
    1550            1555                1560 aga gtg tct gag agc aac aca aca act ggc tgg ccc agc acc ctc      4734
Arg Val Ser Glu Ser Asn Thr Thr Thr Gly Trp Pro Ser Thr Leu
1565            1570                1575 ttc aga gtc ata cac ggg gag agt gga aag gaa agg cag gtt caa      4779
Phe Arg Val Ile His Gly Glu Ser Gly Lys Glu Arg Gln Val Gln
    1580            1585                1590 tgc ctg caa ttt cca tgc tct gag tct ggg tgt gag ctc cca gct      4824
Cys Leu Gln Phe Pro Cys Ser Glu Ser Gly Cys Glu Leu Pro Ala
1595            1600                1605 aac acc cta ctg acc ttc ctt gat gct gtg ggc cag tgc tgc ttc      4869
Asn Thr Leu Leu Thr Phe Leu Asp Ala Val Gly Gln Cys Cys Phe
    1610            1615                1620 cgg ggc aag agc aag aag cca ggg acc ctg ctc agc cac tcc agc      4914
Arg Gly Lys Ser Lys Lys Pro Gly Thr Leu Leu Ser His Ser Ser
1625
```

-continued

```
                1625                1630                1635
aaa aac aca aac cag ctg ggc acc ttc ttg gct atg gaa cag ctg        4959
Lys Asn Thr Asn Gln Leu Gly Thr Phe Leu Ala Met Glu Gln Leu
    1640                1645                1650 tta cag caa gca ggg aca gag cgc aca gtg gac gtc ttc aat gtg        5004
Leu Gln Gln Ala Gly Thr Glu Arg Thr Val Asp Val Phe Asn Val
    1655                1660                1665 gcc ctg aag cag tca cag gcc tgc ggc ctt atg acc cca aca ctg        5049
Ala Leu Lys Gln Ser Gln Ala Cys Gly Leu Met Thr Pro Thr Leu
    1670                1675                1680 gag cag tat atc tac ctc tac aac tgt ctg aac agc gca ctg ctg        5094
Glu Gln Tyr Ile Tyr Leu Tyr Asn Cys Leu Asn Ser Ala Leu Leu
    1685                1690                1695 aac ggg ctg ccc aga gct ggg aag tgg cct gcg ccc tgc tag            5136
Asn Gly Leu Pro Arg Ala Gly Lys Trp Pro Ala Pro Cys
    1700                1705                1710
```

<210> SEQ ID NO 25
<211> LENGTH: 1711
<212> TYPE: PRT
<213> ORGANISM: Rattus norvegicus

<400> SEQUENCE: 25

```
Met Arg Pro Leu Ile Leu Leu Ala Ala Leu Leu Trp Leu Gln Gly Phe
1               5                   10                  15

Leu Ala Glu Asp Asp Ala Cys Ser Ser Leu Glu Gly Ser Pro Asp Arg
            20                  25                  30

Gln Gly Gly Gly Pro Leu Leu Ser Val Asn Val Ser Ser His Gly Lys
        35                  40                  45

Ser Thr Ser Leu Phe Leu Ser Trp Val Ala Ala Glu Leu Gly Gly Phe
    50                  55                  60

Asp Tyr Ala Leu Ser Leu Arg Ser Val Asn Ser Ser Gly Ser Pro Glu
65                  70                  75                  80

Gly Gln Gln Leu Gln Ala His Thr Asn Glu Ser Gly Phe Glu Phe His
                85                  90                  95

Gly Leu Val Pro Gly Ser Arg Tyr Gln Leu Lys Leu Thr Val Leu Arg
            100                 105                 110

Pro Cys Trp Gln Asn Val Thr Ile Thr Leu Thr Ala Arg Thr Ala Pro
        115                 120                 125

Thr Val Val Arg Gly Leu Gln Leu His Ser Ala Gly Ser Pro Ala Arg
    130                 135                 140

Leu Glu Ala Ser Trp Ser Asp Ala Pro Gly Asp Gln Asp Ser Tyr Gln
145                 150                 155                 160

Leu Leu Leu Tyr His Leu Glu Ser Gln Thr Leu Ala Cys Asn Val Ser
                165                 170                 175

Val Ser Pro Asp Thr Leu Ser Tyr Ser Phe Gly Asp Leu Leu Pro Gly
            180                 185                 190

Thr Gln Tyr Val Leu Glu Val Ile Thr Trp Ala Gly Ser Leu His Ala
        195                 200                 205

Lys Thr Ser Ile Leu Gln Trp Thr Glu Pro Val Pro Pro Asp His Leu
    210                 215                 220

Ala Leu Arg Ala Leu Gly Thr Ser Ser Leu Gln Ala Phe Trp Asn Ser
225                 230                 235                 240

Ser Glu Gly Ala Thr Ser Phe His Leu Met Leu Thr Asp Leu Leu Gly
                245                 250                 255

Gly Thr Asn Thr Thr Ala Val Ile Arg Gln Gly Val Ser Thr His Thr
```

-continued

```
                260                 265                 270
Phe Leu His Leu Ser Pro Gly Thr Pro His Glu Leu Lys Ile Cys Ala
            275                 280                 285
Ser Ala Gly Pro His Gln Ile Trp Gly Pro Ser Ala Thr Glu Trp Thr
        290                 295                 300
Tyr Pro Ser Tyr Pro Ser Asp Leu Val Leu Thr Pro Leu Arg Asn Glu
305                 310                 315                 320
Leu Trp Ala Ser Trp Lys Ala Gly Leu Gly Ala Arg Asp Gly Tyr Val
                325                 330                 335
Leu Lys Leu Ser Gly Pro Met Glu Ser Thr Ser Thr Leu Gly Pro Glu
            340                 345                 350
Glu Cys Asn Ala Val Phe Pro Gly Pro Leu Pro Pro Gly His Tyr Thr
        355                 360                 365
Leu Gln Leu Lys Val Leu Ala Gly Pro Tyr Asp Ala Trp Val Glu Gly
    370                 375                 380
Ser Thr Trp Leu Ala Glu Ser Ala Ala Leu Pro Arg Glu Val Pro Gly
385                 390                 395                 400
Ala Arg Leu Trp Leu Asp Gly Leu Glu Ala Ser Lys Gln Pro Gly Arg
                405                 410                 415
Arg Ala Leu Leu Tyr Ser Asp Asp Ala Pro Gly Ser Leu Gly Asn Ile
            420                 425                 430
Ser Val Pro Ser Gly Ala Thr His Val Ile Phe Cys Gly Leu Val Pro
        435                 440                 445
Gly Ala His Tyr Arg Val Asp Ile Ala Ser Ser Thr Gly Asp Ile Ser
    450                 455                 460
Gln Ser Ile Ser Gly Tyr Thr Ser Pro Leu Pro Pro Gln Ser Leu Glu
465                 470                 475                 480
Val Ile Ser Arg Ser Ser Pro Ser Asp Leu Thr Ile Ala Trp Gly Pro
                485                 490                 495
Ala Pro Gly Gln Leu Glu Gly Tyr Lys Val Thr Trp His Gln Asp Gly
            500                 505                 510
Ser Gln Arg Ser Pro Gly Asp Leu Val Asp Leu Gly Pro Asp Thr Leu
        515                 520                 525
Ser Leu Thr Leu Lys Ser Leu Val Pro Gly Ser Cys Tyr Thr Val Ser
    530                 535                 540
Ala Trp Ala Trp Ala Gly Asn Leu Asp Ser Asp Ser Gln Lys Ile His
545                 550                 555                 560
Ser Cys Thr Arg Pro Ala Pro Pro Thr Asn Leu Ser Leu Gly Phe Ala
                565                 570                 575
His Gln Pro Ala Ala Leu Lys Ala Ser Trp Tyr His Pro Pro Gly Gly
            580                 585                 590
Arg Asp Ala Phe His Leu Arg Leu Tyr Arg Leu Arg Pro Leu Thr Leu
        595                 600                 605
Glu Ser Glu Lys Val Leu Pro Arg Glu Ala Gln Asn Phe Ser Trp Ala
    610                 615                 620
Gln Leu Thr Ala Gly Cys Glu Phe Gln Val Gln Leu Ser Thr Leu Trp
625                 630                 635                 640
Gly Ser Glu Arg Ser Ser Asn Ala Thr Gly Trp Thr Pro Pro
                645                 650                 655
Ser Ala Pro Thr Leu Val Asn Val Thr Ser Asp Ala Pro Thr Gln Leu
            660                 665                 670
Gln Val Ser Trp Ala His Val Pro Gly Gly Arg Ser Arg Tyr Gln Val
        675                 680                 685
```

```
Thr Leu Tyr Gln Glu Ser Thr Arg Thr Ala Thr Ser Ile Met Gly Pro
    690                 695                 700

Lys Glu Asp Gly Thr Ser Phe Leu Gly Leu Thr Pro Gly Thr Lys Tyr
705                 710                 715                 720

Lys Val Glu Val Ile Ser Trp Ala Gly Pro Leu Tyr Thr Ala Ala Ala
                725                 730                 735

Asn Val Ser Ala Trp Thr Tyr Pro Leu Ile Pro Asn Glu Leu Leu Val
                740                 745                 750

Ser Met Gln Ala Gly Ser Ala Val Val Asn Leu Ala Trp Pro Ser Gly
            755                 760                 765

Pro Leu Gly Gln Gly Ala Cys His Ala Gln Leu Ser Asp Ala Gly His
        770                 775                 780

Leu Ser Trp Glu Gln Pro Leu Lys Leu Gly Gln Glu Leu Phe Met Leu
785                 790                 795                 800

Arg Asp Leu Thr Pro Gly His Thr Ile Ser Met Ser Val Arg Cys Arg
                805                 810                 815

Ala Gly Pro Leu Gln Ala Ser Thr His Leu Val Val Leu Ser Val Glu
                820                 825                 830

Pro Gly Pro Val Glu Asp Val Leu Cys His Pro Glu Ala Thr Tyr Leu
            835                 840                 845

Ala Leu Asn Trp Thr Met Pro Ala Gly Asp Val Asp Val Cys Leu Val
        850                 855                 860

Val Val Glu Arg Leu Val Pro Gly Gly Gly Thr His Phe Val Phe Gln
865                 870                 875                 880

Val Asn Thr Ser Gly Asp Ala Leu Leu Leu Pro Asn Leu Met Pro Thr
                885                 890                 895

Thr Ser Tyr Arg Leu Ser Leu Thr Val Leu Gly Arg Asn Ser Arg Trp
            900                 905                 910

Ser Arg Ala Val Ser Leu Val Cys Ser Thr Ser Ala Glu Ala Trp His
        915                 920                 925

Pro Pro Glu Leu Ala Glu Pro Pro Gln Val Glu Leu Gly Thr Gly Met
930                 935                 940

Gly Val Thr Val Met Arg Gly Met Phe Gly Lys Asp Asp Gly Gln Ile
945                 950                 955                 960

Gln Trp Tyr Gly Ile Ile Ala Thr Ile Asn Met Thr Leu Ala Gln Pro
                965                 970                 975

Ser Arg Glu Ala Ile Asn Tyr Thr Trp Tyr Asp His Tyr Tyr Arg Gly
                980                 985                 990

Cys Glu Ser Phe Leu Ala Leu Leu Phe Pro Asn Pro Phe Tyr Pro Glu
            995                 1000                1005

Pro Trp Ala Gly Pro Arg Ser Trp Thr Val Pro Val Gly Thr Glu
    1010                1015                1020

Asp Cys Asp Asn Thr Gln Glu Ile Cys Asn Gly Arg Leu Lys Ser
    1025                1030                1035

Gly Phe Gln Tyr Arg Phe Ser Val Val Ala Phe Ser Arg Leu Asn
    1040                1045                1050

Thr Pro Glu Thr Ile Leu Ala Phe Ser Ala Phe Ser Glu Pro Arg
    1055                1060                1065

Ala Ser Ile Ser Leu Ala Ile Ile Pro Leu Thr Val Met Leu Gly
    1070                1075                1080

Ala Val Val Gly Ser Ile Val Ile Val Cys Ala Val Leu Cys Leu
    1085                1090                1095
```

-continued

```
Leu Arg Trp Arg Cys Leu Lys Gly Pro Arg Ser Glu Lys Asp Gly
    1100                1105                1110
Phe Ser Lys Glu Leu Met Pro Tyr Asn Leu Trp Arg Thr His Arg
    1115                1120                1125
Pro Ile Pro Ile His Ser Phe Arg Gln Ser Tyr Glu Ala Lys Ser
    1130                1135                1140
Ala His Ala His Gln Thr Phe Phe Gln Glu Phe Glu Glu Leu Lys
    1145                1150                1155
Glu Val Gly Lys Asp Gln Pro Arg Leu Glu Ala Glu His Pro Asp
    1160                1165                1170
Asn Ile Ile Lys Asn Arg Tyr Pro His Val Leu Pro Tyr Asp His
    1175                1180                1185
Ser Arg Val Arg Leu Thr Gln Leu Pro Gly Glu Pro His Ser Asp
    1190                1195                1200
Tyr Ile Asn Ala Asn Phe Ile Pro Gly Tyr Ser His Thr Gln Glu
    1205                1210                1215
Ile Ile Ala Thr Gln Gly Pro Leu Lys Lys Thr Leu Glu Asp Phe
    1220                1225                1230
Trp Arg Leu Val Trp Glu Gln Val His Val Ile Ile Met Leu
    1235                1240                1245
Thr Val Gly Met Glu Asn Gly Arg Val Leu Cys Glu His Tyr Trp
    1250                1255                1260
Pro Ala Asn Ser Thr Pro Val Thr His Gly His Ile Thr Ile His
    1265                1270                1275
Leu Leu Ala Glu Glu Pro Glu Asp Glu Trp Thr Arg Arg Glu Phe
    1280                1285                1290
Gln Leu Gln His Gly Thr Glu Gln Lys Gln Arg Arg Val Lys Gln
    1295                1300                1305
Leu Gln Phe Thr Thr Trp Pro Asp His Ser Val Pro Glu Ala Pro
    1310                1315                1320
Ser Ser Leu Leu Ala Phe Val Glu Leu Val Gln Glu Gln Val Gln
    1325                1330                1335
Ala Thr Gln Gly Lys Gly Pro Ile Leu Val His Cys Ser Ala Gly
    1340                1345                1350
Val Gly Arg Thr Gly Thr Phe Val Ala Leu Leu Arg Leu Leu Arg
    1355                1360                1365
Gln Leu Glu Glu Glu Lys Val Ala Asp Val Phe Asn Thr Val Tyr
    1370                1375                1380
Ile Leu Arg Leu His Arg Pro Leu Met Ile Gln Thr Leu Ser Gln
    1385                1390                1395
Tyr Ile Phe Leu His Ser Cys Leu Leu Asn Lys Ile Leu Glu Gly
    1400                1405                1410
Pro Pro Asp Ser Ser Asp Ser Gly Pro Ile Ser Val Met Asp Phe
    1415                1420                1425
Ala Gln Ala Cys Ala Lys Arg Ala Ala Asn Ala Asn Ala Gly Phe
    1430                1435                1440
Leu Lys Glu Tyr Lys Leu Leu Lys Gln Ala Ile Lys Asp Gly Thr
    1445                1450                1455
Gly Ser Leu Leu Pro Pro Asp Tyr Asn Gln Asn Ser Ile Val
    1460                1465                1470
Ser Arg Arg His Ser Gln Glu Gln Phe Ala Leu Val Glu Glu Cys
    1475                1480                1485
Pro Glu Asp Ser Met Leu Glu Ala Ser Leu Phe Pro Gly Gly Pro
```

```
                    1490               1495               1500

Ser Gly Cys Asp His Val Val Leu Thr Gly Ser Ala Gly Pro Lys
    1505                1510                1515

Glu Leu Trp Glu Met Val Trp Glu His Asp Ala His Val Leu Val
    1520                1525                1530

Ser Leu Gly Leu Pro Asp Thr Lys Glu Lys Pro Pro Asp Ile Trp
    1535                1540                1545

Pro Val Glu Met Gln Pro Ile Val Thr Asp Met Val Thr Val His
    1550                1555                1560

Arg Val Ser Glu Ser Asn Thr Thr Thr Gly Trp Pro Ser Thr Leu
    1565                1570                1575

Phe Arg Val Ile His Gly Glu Ser Gly Lys Glu Arg Gln Val Gln
    1580                1585                1590

Cys Leu Gln Phe Pro Cys Ser Glu Ser Gly Cys Glu Leu Pro Ala
    1595                1600                1605

Asn Thr Leu Leu Thr Phe Leu Asp Ala Val Gly Gln Cys Cys Phe
    1610                1615                1620

Arg Gly Lys Ser Lys Lys Pro Gly Thr Leu Leu Ser His Ser Ser
    1625                1630                1635

Lys Asn Thr Asn Gln Leu Gly Thr Phe Leu Ala Met Glu Gln Leu
    1640                1645                1650

Leu Gln Gln Ala Gly Thr Glu Arg Thr Val Asp Val Phe Asn Val
    1655                1660                1665

Ala Leu Lys Gln Ser Gln Ala Cys Gly Leu Met Thr Pro Thr Leu
    1670                1675                1680

Glu Gln Tyr Ile Tyr Leu Tyr Asn Cys Leu Asn Ser Ala Leu Leu
    1685                1690                1695

Asn Gly Leu Pro Arg Ala Gly Lys Trp Pro Ala Pro Cys
    1700                1705                1710

<210> SEQ ID NO 26
<211> LENGTH: 49
<212> TYPE: PRT
<213> ORGANISM: Sus scrofa

<400> SEQUENCE: 26

Tyr Leu Asp His Gly Leu Gly Ala Pro Ala Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Ile
        35                  40                  45

Ala

<210> SEQ ID NO 27
<211> LENGTH: 49
<212> TYPE: PRT
<213> ORGANISM: Homo sapiens

<400> SEQUENCE: 27

Tyr Leu Tyr Gln Trp Leu Gly Ala Pro Ala Val Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45
```

Val

<210> SEQ ID NO 28
<211> LENGTH: 49
<212> TYPE: PRT
<213> ORGANISM: Macaca mulatta

<400> SEQUENCE: 28

Tyr Leu Tyr Gln Trp Leu Gly Ala Pro Ala Pro Tyr Pro Asp Pro Leu
1               5                   10                  15

Glu Pro Lys Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 29
<211> LENGTH: 49
<212> TYPE: PRT
<213> ORGANISM: Bos taurus

<400> SEQUENCE: 29

Tyr Leu Asp His Trp Leu Gly Ala Pro Ala Pro Tyr Pro Asp Pro Leu
1               5                   10                  15

Glu Pro Lys Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 30
<211> LENGTH: 49
<212> TYPE: PRT
<213> ORGANISM: Ovis aries

<400> SEQUENCE: 30

Tyr Leu Asp Pro Gly Leu Gly Ala Pro Ala Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 31
<211> LENGTH: 49
<212> TYPE: PRT
<213> ORGANISM: bat

<400> SEQUENCE: 31

Tyr Leu Asp Pro Gly Leu Gly Ala Pro Ala Pro Tyr Pro Asp Pro Leu
1               5                   10                  15

Glu Pro Lys Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 32
<211> LENGTH: 49
<212> TYPE: PRT
<213> ORGANISM: Canis lupus

<400> SEQUENCE: 32

Tyr Leu Asp Ser Gly Leu Gly Ala Pro Val Pro Tyr Pro Asp Pro Leu
1               5                   10                  15

Glu Pro Lys Arg Glu Val Cys Glu Leu Asn Pro Asp Cys Asp Glu Leu
            20                  25                  30

Ala Asp His Ile Gly Phe Gln Glu Ala Tyr Gln Arg Phe Tyr Gly Pro
        35                  40                  45

Val

<210> SEQ ID NO 33
<211> LENGTH: 49
<212> TYPE: PRT
<213> ORGANISM: Felis catus

<400> SEQUENCE: 33

Tyr Leu Ala Pro Gly Leu Gly Phe Pro Ala Pro Tyr Pro Asp Pro Leu
1               5                   10                  15

Glu Pro Lys Arg Glu Ile Cys Glu Leu Asn Pro Asp Cys Asp Glu Leu
            20                  25                  30

Ala Asp His Ile Gly Phe Gln Asp Ala Tyr Arg Arg Phe Tyr Gly Thr
        35                  40                  45

Val

<210> SEQ ID NO 34
<211> LENGTH: 49
<212> TYPE: PRT
<213> ORGANISM: Oryctolagus cuniculus

<400> SEQUENCE: 34

Gln Leu Ile Asn Gly Gln Gly Ala Pro Ala Pro Tyr Pro Asp Pro Leu
1               5                   10                  15

Glu Pro Lys Arg Glu Val Cys Glu Leu Asn Pro Asp Cys Asp Glu Leu
            20                  25                  30

Ala Asp Gln Val Gly Leu Gln Asp Ala Tyr Gln Arg Phe Tyr Gly Pro
        35                  40                  45

Val

<210> SEQ ID NO 35
<211> LENGTH: 49
<212> TYPE: PRT
<213> ORGANISM: wallaby

<400> SEQUENCE: 35

Tyr Leu Tyr Gln Thr Leu Gly Ala Pro Phe Pro Tyr Pro Asp Pro Gln
1               5                   10                  15

Glu Asn Lys Arg Glu Val Cys Glu Leu Asn Pro Asp Cys Asp Glu Leu
            20                  25                  30

Ala Asp His Ile Gly Phe Ser Glu Ala Tyr Arg Arg Phe Tyr Gly Thr
        35                  40                  45

Ala

<210> SEQ ID NO 36
<211> LENGTH: 50

```
<212> TYPE: PRT
<213> ORGANISM: Rattus norvegicus

<400> SEQUENCE: 36

Tyr Leu Asn Asn Gly Leu Gly Ala Pro Ala Pro Tyr Pro Asp Pro Leu
1               5                   10                  15

Glu Pro His Arg Glu Val Cys Glu Leu Asn Pro Asn Cys Asp Glu Leu
            20                  25                  30

Ala Asp His Ile Gly Phe Gln Asp Ala Tyr Lys Arg Ile Tyr Gly Thr
        35                  40                  45

Thr Val
    50

<210> SEQ ID NO 37
<211> LENGTH: 46
<212> TYPE: PRT
<213> ORGANISM: Mus musculus

<400> SEQUENCE: 37

Tyr Leu Gly Ala Ser Val Pro Ser Pro Asp Pro Leu Glu Pro Thr Arg
1               5                   10                  15

Glu Gln Cys Glu Leu Asn Pro Ala Cys Asp Glu Leu Ser Asp Gln Tyr
            20                  25                  30

Gly Leu Lys Thr Ala Tyr Lys Arg Ile Tyr Gly Ile Thr Ile
        35                  40                  45

<210> SEQ ID NO 38
<211> LENGTH: 49
<212> TYPE: PRT
<213> ORGANISM: Xenopus laevis

<400> SEQUENCE: 38

Ser Tyr Gly Asn Asn Val Gly Gln Gly Ala Ala Val Gly Ser Pro Leu
1               5                   10                  15

Glu Ser Gln Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 39
<211> LENGTH: 48
<212> TYPE: PRT
<213> ORGANISM: Dromaius novaehollandiae

<400> SEQUENCE: 39

Ser Phe Ala Val Gly Ser Ser Tyr Gly Ala Ala Pro Asp Pro Leu Glu
1               5                   10                  15

Ala Gln Arg Glu Val Cys Glu Leu Asn Pro Asp Cys Asp Glu Leu Ala
            20                  25                  30

Asp His Ile Gly Phe Gln Glu Ala Tyr Arg Arg Phe Tyr Gly Pro Val
        35                  40                  45

<210> SEQ ID NO 40
<211> LENGTH: 50
<212> TYPE: PRT
<213> ORGANISM: Gallus gallus

<400> SEQUENCE: 40

His Tyr Ala Gln Asp Ser Gly Val Ala Gly Ala Pro Tyr Pro Asp Pro
```

-continued

```
                1               5                  10                  15
Leu Glu Pro Lys Arg Glu Val Cys Glu Leu Asn Pro Asp Cys Asp Glu
                20                  25                  30

Leu Ala Asp His Ile Gly Phe Gln Glu Ala Tyr Arg Arg Phe Tyr Gly
        35                  40                  45

Pro Val
    50

<210> SEQ ID NO 41
<211> LENGTH: 48
<212> TYPE: PRT
<213> ORGANISM: Cyprinus carpio

<400> SEQUENCE: 41

Ala Gly Thr Ala Pro Ala Asp Leu Thr Val Ala Gln Leu Glu Ser Leu
1               5                   10                  15

Lys Glu Val Cys Glu Ala Asn Leu Ala Cys Glu His Met Met Asp Val
                20                  25                  30

Ser Gly Ile Ile Ala Ala Tyr Thr Ala Tyr Tyr Gly Pro Ile Pro Tyr
        35                  40                  45

<210> SEQ ID NO 42
<211> LENGTH: 45
<212> TYPE: PRT
<213> ORGANISM: Tetraodon nigroviridis

<400> SEQUENCE: 42

Ala Ala Gly Glu Pro Thr Leu Gln Gln Leu Glu Ser Leu Arg Glu Val
1               5                   10                  15

Cys Glu Leu Asn Ile Ala Cys Asp Glu Met Ala Asp Pro Ala Gly Ile
                20                  25                  30

Val Ala Ala Tyr Ala Ala Tyr Tyr Gly Pro Pro Thr Phe
        35                  40                  45

<210> SEQ ID NO 43
<211> LENGTH: 45
<212> TYPE: PRT
<213> ORGANISM: Takifugu rubripes

<400> SEQUENCE: 43

Ala Pro Gly Glu Pro Thr Pro Gln Gln Leu Glu Ser Leu Arg Glu Val
1               5                   10                  15

Cys Glu Leu Asn Ile Ala Cys Asp Glu Met Ala Asp Thr Ala Gly Ile
                20                  25                  30

Val Ala Ala Tyr Ala Ala Tyr Tyr Gly Pro Pro Pro Phe
        35                  40                  45

<210> SEQ ID NO 44
<211> LENGTH: 45
<212> TYPE: PRT
<213> ORGANISM: Lepomis macrochirus

<400> SEQUENCE: 44

Ala Ala Gly Glu Leu Thr Leu Thr Gln Leu Glu Ser Leu Arg Glu Val
1               5                   10                  15

Cys Glu Ala Asn Leu Ala Cys Glu Asp Met Met Asp Ala Gln Gly Ile
                20                  25                  30

Ile Ala Ala Tyr Thr Ala Tyr Tyr Gly Pro Ile Pro Tyr
        35                  40                  45
```

```
<210> SEQ ID NO 45
<211> LENGTH: 45
<212> TYPE: PRT
<213> ORGANISM: Sparus aurata

<400> SEQUENCE: 45

Ala Ala Gly Gln Leu Ser Leu Thr Gln Leu Glu Ser Leu Arg Glu Val
1               5                   10                  15

Cys Glu Leu Asn Leu Ala Cys Glu His Met Met Asp Thr Glu Gly Ile
            20                  25                  30

Ile Ala Ala Tyr Thr Ala Tyr Tyr Gly Pro Ile Pro Tyr
        35                  40                  45

<210> SEQ ID NO 46
<211> LENGTH: 47
<212> TYPE: PRT
<213> ORGANISM: Xiphias gladius

<400> SEQUENCE: 46

Ala Thr Arg Ala Gly Asp Leu Thr Pro Leu Gln Leu Glu Ser Leu Arg
1               5                   10                  15

Glu Val Cys Glu Leu Asn Val Ser Cys Asp Glu Met Ala Asp Thr Ala
            20                  25                  30

Gly Ile Val Ala Ala Tyr Ile Ala Tyr Tyr Gly Pro Ile Gln Phe
        35                  40                  45

<210> SEQ ID NO 47
<211> LENGTH: 13
<212> TYPE: PRT
<213> ORGANISM: Artificial Sequence
<220> FEATURE:
<223> OTHER INFORMATION: Exemplary sequence

<400> SEQUENCE: 47

Ala Gly Leu Tyr Ser Thr Val Leu Met Gly Arg Pro Ser
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Examplary sequence

<400> SEQUENCE: 48

Gly Leu Val Ser Thr Val Leu Met Gly Asn
1               5                   10
```